United States Patent [19]

St. George-Hyslop et al.

[11] Patent Number: 6,020,143

[45] Date of Patent: Feb. 1, 2000

[54] METHOD FOR IDENTIFYING SUBSTANCES THAT AFFECT THE INTERACTION OF A PRESENILIN-1-INTERACTING PROTEIN WITH A MAMMALIAN PRESENILIN-1 PROTEIN

[75] Inventors: Peter H. St. George-Hyslop; Johanna M. Rommens; Paul E. Fraser, all of Toronto, Canada

[73] Assignee: Research and Development Limited Partnership, Toronto, Canada

[21] Appl. No.: 08/888,077

[22] Filed: Jul. 3, 1997

Related U.S. Application Data

[63] Continuation-in-part of application No. 08/592,541, Jan. 26, 1996

[60] Provisional application No. 60/021,673, Jul. 5, 1996, provisional application No. 60/021,700, Jul. 12, 1996, provisional application No. 60/029,895, Nov. 8, 1996, and provisional application No. 60/034,590, Jan. 2, 1997.

[51] Int. Cl.⁷ ............................. C12Q 1/00; C07K 14/00
[52] U.S. Cl. .............................................. 435/7.1; 530/350
[58] Field of Search ............................... 435/7.1; 530/350

[56] References Cited

U.S. PATENT DOCUMENTS

| | | | |
|---|---|---|---|
| 5,262,332 | 11/1993 | Selkoe | 436/518 |
| 5,297,562 | 3/1994 | Potter | 128/898 |
| 5,449,604 | 9/1995 | Schellenberg et al. | 435/6 |
| 5,668,006 | 9/1997 | Hadcock et al. | 435/252.3 |

FOREIGN PATENT DOCUMENTS

| | | |
|---|---|---|
| 2054302 | 4/1992 | Canada . |
| 2071105 | 12/1992 | Canada . |
| 2096911 | 11/1993 | Canada . |
| WO 91/19810 | 12/1991 | WIPO . |
| WO 94/00569 | 1/1994 | WIPO . |
| 94/10569 | 5/1994 | WIPO . |
| 94/23049 | 10/1994 | WIPO . |
| WO 96/34099 | 10/1996 | WIPO . |
| WO 97/03086 | 1/1997 | WIPO . |
| WO 97/03192 | 1/1997 | WIPO . |
| WO 97/03999 | 2/1997 | WIPO . |
| WO 97/08319 | 3/1997 | WIPO . |
| WO 97/46678 | 12/1997 | WIPO . |

*Primary Examiner*—Karen Cochrane Carlson
*Attorney, Agent, or Firm*—Darby & Darby

[57] ABSTRACT

The identification, isolation, sequencing and characterization of two human presenilin genes, PS-1 and PS-2, mutations in which lead to Familial Alzheimer's Disease, are disclosed. Presenilin gene homologs in mice, *C. elegans* and *D. melanogaster* are also disclosed. Use of the nucleic acids and proteins comprising or derived from the presenilins in screening and diagnosing Alzheimer's Disease, identifying and developing therapeutics for treatment of Alzheimer's Disease, in producing cell lines and transgenic animals useful as models of Alzheimer's Disease. Methods for identifying substances that bind to, or modulate the activity of, a presenilin protein, functional fragment or variant thereof, or a mutein thereof, and methods for identifying substances that affect the interaction of a presenilin-interacting protein with a presenilin protein, functional fragment or variant thereof, or a mutein thereof, are further disclosed.

7 Claims, 9 Drawing Sheets

FIG. 3A

```
hPS1  MTELPAPLSYFQNAQMSEDNHLSNTVRSQNDNRERQEHNDRRSLGHPE    48
      |||||||||||||||||| ||| |||  | ||||||||  ||| |||
mPS1  MTEIPAPLSYFQNAQMSEDSHSSSAIRSQNDSQERQQQHDRQRLDNPE    48 hPS1  PLSNGRPQGNSRQVVEQDEEEDEELTLKYGAKHVIMLFVPVTLCMVVV    96
      |||||||| ||||||||||||||||||||||||||||||||||||||
mPS1  PISNGRPQSNSRQVVEQDEEEDEELTLKYGAKHVIMLFVPVTLCMVVV    96 hPS1  VATIKSVSFYTRKDGQLIYTPFTEDTETVGQRALHSILNAAIMISVIV   144
      ||||||||||||||||||||||||||||||||||||||||||||||||
mPS1  VATIKSVSFYTRKDGQLIYTPFTEDTETVGQRALHSILNAAIMISVIV   144 hPS1  VMTILLVVLYKYRCYKVIHAWLIISSLLLLFFFSFIYLGEVFKTYNVA   192
       ||||||||||||||||||||||||||||||||||||||||||||||
mPS1  IMTILLVVLYKYRCYKVIHAWLIISSLLLLFFFSFIYLGEVFKTYNVA   192 hPS1  VDYITVALLIWNFGVVGMISIHWKGPLRLQQAYLIMISALMALVFIKY   240
      ||| ||||||||||||||| ||||||||||||||||||||||||||||
mPS1  VDYVTVALLIWNFGVVGMIAIHWKGPLRLQQAYLIMISALMALVFIKY   240
```

FIG. 3B

```
hPS1  LPEWTAWLILAVISVYDLVAVLCPKGPLRMLVETAQERNETLFPALIY   288
      ||||||||||||||||||||||||||||||||||||||||||||||||
mPS1  LPEWTAWLILAVISVYDLVAVLCPKGPLRMLVETAQERNETLFPALIY   288 hPS1  SSTMVWLVNMAEGDPEAQRRRVSKNSKYNAESTERESQDTVAENDDGGF   336
      |||||||||||||||||||||   |||  |||||  |   |||||||
mPS1  SSTMVWLVNMAEGDPEAQRRVPKNPKYNTQRAERETQDSGSGNDDGGF   336 hPS1  SEEWEAQRDSHLGPHRSTPESRAAVQELSSSILAGEDPEERGVKLGLG   384
      |||||||||||||||||||||||||||||| ||  |||||||||||||
mPS1  SEEWEAQRDSHLGPHRSTPESRAAVQELSGSILTSEDPEERGVKLGLG   384 hPS1  DFIFYSVLVGKASATASGDWNTTIACFVAILIGLCLTLLLLAIFKKAL   432
      ||||||||||||||||||||||||||||||||||||||||||||||||
mPS1  DFIFYSVLVGKASATASGDWNTTIACFVAILIGLCLTLLLLAIFKKAL   432 hPS1  PALPISITFGLVFYFATDYLVQPFMDQLAFHQFYI   467
      ||||||||||||||||||||||||||||||||||
mPS1  PALPISITFGLVFYFATDYLVQPFMDQLAFHQFYI   467
```

FIG. 4A

```
hPS1  ------------------------MT-ELPAPLSYFQNA-QMSEDNHLSNTV                    26
                                || |||| ||  |
hPS2  MLTFMASDSEEEVCDERTSLMSAESPTPRSC-QEGRQPEDGE--NTA                          45 hPS1  --RSQ-N--DNREREQEHNDRR--SLGHPEPLSNGRPQGNSRQVVEQDE                         67
        |||  |   |||             |  ||
hPS2  QWRSQENEEDG-E--EDPDRYVCS-GVP-----GRPPGL----E---                           76 hPS1  EEDEELTLKYGAKHVIMLFVPVTLCMVVVVATIKSVSFYTRKDGQLIY                          115
         |||||||||||||||||||||||||||||||||  |||| |  |||||
hPS2  ---EELTLKYGAKHVIMLFVPVTLCMIVVVATIKSVRFYTEKNGQLIY                          121 hPS1  TPFTEDTETVGQRALHSILNAAIMISVIVVMTILLVVLYKYRCYKVIH                          163
      ||||||| |||| ||| ||  |||||||||||| |||||||||| ||
hPS2  TPFTEDTPSVGQRLLNSVLNTLIMISVIVVMTIFLVVLYKYRCYKFIH                          169 hPS1  AWLIISSLLLLFFFSFIYLGEVFKTYNVAVDYITVALLI-WNFGVVGM                          210
      |||| ||  |||  || | |||||||||  ||  |||| ||||| ||
hPS2  GWLIMSSLMLLFLFTYIYLGEVLKTYNVAMDYPTL-LLTVWNFEGAVGM                         216 hPS1  ISIHWKGPLRLQQAYLIMISALMALVFIKYLPEWTAWLIL-AVISVYD                          257
```

```
hPS2   VCIHWKGPLVLQQAYLIMISALMALVFIKYLPEWSAWVILGA-ISVYD           263
            |||||| ||||||||||||||||||||||||||||||||||||
hPS1   LVAVLCPKGPLRMLVETAQERNETLFPALIYSSTMVWLVNMAEGDPEA          305
       ||||||||||||||||||||||||||||||||
hPS2   LVAVLCPKGPLRMLVETAQERNEPIFPALIYSSAMVWTVGMAKLDP--          309 hPS1   QRRVSKNSKYNAESTERESQDTVAENDDGGFSE-EWEAQRDSHLG-PH          351
            |     |       |      |
hPS2   ----S--SQGAL------QLPY---DP----EME-EDSYDSF-GEP-          334 hPS1   RSTPESRAAVQE--LSSSILAGEDP---EERGVKLGLGDFIFYSVLVG          394
                                    |||||||||||||||||||||
hPS2   -SYPE----VFEPPLTGYP--GEELEEEERGVKLGLGDFIFYSVLVG          375 hPS1   KASATASGDWNTTIACFVAILIGLCLTLLLLAIFKKALPALPISITFG          442
       || || |||||||| ||||||||||||||||| |||||||||||||||
hPS2   KAAATGSGDWNTTLACFVAILIGLCLTLLLLAVFKKALPALPISITFG          423 hPS1   LVFYFATDYLVQPFMDQLAFHQFYI                                 467
       | ||| || || |||| | ||
hPS2   LIFYFSTDNLVRPFMDTLASHQLYI                                 448
```

METHOD FOR IDENTIFYING SUBSTANCES THAT AFFECT THE INTERACTION OF A PRESENILIN-1-INTERACTING PROTEIN WITH A MAMMALIAN PRESENILIN-1 PROTEIN

CROSS REFERENCE TO RELATED APPLICATIONS

This application is a Continuation-in-Part of U.S. application Ser. No. 08/592,541, filed Jan. 26, 1996, and claims benefit of U.S. Provisional Application Ser. No. 60/021,673, filed Jul. 5, 1996, U.S. Provisional Application Ser. No. 60/021,700, filed Jul. 12, 1996, U.S. Provisional Application Ser. No. 60/029,895, filed Nov. 8, 1996, and U.S. Provisional Application Ser. No. 60/034,590, filed Jan. 2, 1997, and all of which are incorporated by reference herein.

FIELD OF THE INVENTION

The present invention relates generally to the field of neurological and physiological dysfunctions associated with Alzheimer's Disease. More particularly, the invention is concerned with the identification, isolation and cloning of genes which are associated with Alzheimer's Disease, as well as their transcripts, gene products, associated sequence information, and related genes. The present invention also relates to methods for detecting and diagnosing carriers of normal and mutant alleles of these genes, to methods for detecting and diagnosing Alzheimer's Disease, to methods of identifying genes and proteins related to or interacting with the Alzheimer's genes and proteins, to methods of screening for potential therapeutics for Alzheimer's Disease, to methods of treatment for Alzheimer's Disease, and to cell lines and animal models useful in screening for and evaluating potentially useful therapies for Alzheimer's Disease.

BACKGROUND OF THE INVENTION

Alzheimer's Disease (AD) is a degenerative disorder of the human central nervous system characterized by progressive memory impairment and cognitive and intellectual decline during mid to late adult life (Katzman (1986) *N. Eng. J. Med.* 314:964–973). The disease is accompanied by a constellation of neuropathologic features principal amongst which are the presence of extracellular amyloid or senile plaques and the neurofibrillary degeneration of neurons. The etiology of this disease is complex, although in some families it appears to be inherited as an autosomal dominant trait. However, even amongst these inherited forms of AD, there are at least three different genes which confer inherited susceptibility to this disease (St. George-Hyslop et al. (1990) *Nature* 347:194–197). The ε4 (C112R) allelic polymorphism of the Apolipoprotein E (ApoE) gene has been associated with AD in a significant proportion of cases with onset late in life (Saunders et al. (1993) *Neurology* 43:1467–1472; Strittmatter et al. (1993) *Proc. Natl. Acad. Sci. (USA)* 90:1977–1981). Similarly, a very small proportion of familial cases with onset before age 65 years have been associated with mutations in the β-amyloid precursor protein (APP) gene (Chartier-Harlin et al. (1991) *Nature* 353:844–846; Goate et al. (1991) *Nature* 349:704–706; Murrell et al. (1991) *Science* 254:97–99; Karlinsky et al. (1992) *Neurology* 42:1445–1453; Mullan et al. (1992) *Nature Genetics* 1:345–347). A third locus (AD3) associated with a larger proportion of cases with early onset AD has recently been mapped to chromosome 14q24.3 (Schellenberg et al. (1992) *Science* 258:668–670; St. George-Hyslop et al., (1992) *Nature Genetics* 2:330–334; Van Broeckhoven et al. (1992) *Nature Genetics* 2:335–339).

Although the chromosome 14q region carries several genes which could be regarded as candidate genes for the site of mutations associated with AD3 (e.g., cFOS, alpha-1-antichymotrypsin, and cathepsin G), most of these candidate genes have been excluded on the basis of their physical location outside the AD3 region and/or the absence of mutations in their respective open reading frames (Schellenberg et al. (1992) *Science* 258:668–670; Van Broeckhoven et al. (1992) *Nature Genetics* 2:335–339; Rogaev et al. (1993) *Neurology* 43:2275–2279; Wong et al. (1993) *Neurosci. Lett.* 152:96–98).

There have been several developments and commercial directions or strategies in respect of treatment of Alzheimer's Disease and diagnosis thereof Published PCT application WO/94 23049 describes transfection of high molecular weight YAC DNA into specific mouse cells. This method may be used to analyze large gene complexes. For example, the transgenic mice may have increased APP gene dosage, which mimics the trisomic condition that prevails in Down's Syndrome, and allows the generation of animal models with β-amyloidosis similar to that prevalent in individuals with Alzheimer's Disease. Published International Patent Application No. WO 94/00569 describes transgenic non-human animals harboring large transgenes such as the transgene comprising a human APP gene. Such animal models can provide useful models of human genetic diseases such as Alzheimer's Disease.

Canadian Patent Application No. 2,096,911 describes a nucleic acid coding for an APP-cleaving protease, which is associated with Alzheimer's Disease and Down's syndrome. The genetic information, which was isolated from chromosome 19, may be used to diagnose Alzheimer's Disease. Canadian Patent Application No. 2,071,105, describes detection and treatment of inherited or acquired Alzheimer's Disease by the use of YAC nucleotide sequences. The YACs are identified by the numbers 23CB10, 28CA12 and 26FF3.

U.S. Pat. No. 5,297,562, describes detection of Alzheimer's Disease associated with trisomy of chromosome 21. Treatment involves methods for reducing the proliferation of chromosome 21 trisomy. Canadian Patent application No. 2054302 describes monoclonal antibodies which recognize a human brain cell nucleus protein encoded by chromosome 21 and are used to detect changes of expression due to Alzheimer's Disease or Down's Syndrome. The monoclonal antibody is specific to a protein encoded by human chromosome 21 and is found in large pyramidal cells of human brain tissue.

SUMMARY OF THE INVENTION

The present invention is based, in part, upon the identification, isolation, cloning and sequencing of two mammalian genes which have been designated presenilin-1 (PS 1) and presenilin-2 (PS2). These two genes, and their corresponding protein products, are members of a highly conserved family of genes, the presenilins, with homologues or orthologues in other mammalian species (e.g., mice, rats) as well as orthologues in invertebrate species (e.g., *C. elegans, D. melanogaster*). Mutations in these genes have been linked to the development in humans of forms of Familial Alzheimer's Disease and may be causative of other disorders as well (e.g., other cognitive, intellectual, neurological or psychological disorders such as cerebral hemorrhage, schizophrenia, depression, mental retardation and epilepsy). The present disclosure provides genomic and cDNA nucleotide sequences for human PS1 (hPS1) and human PS2 (hPS2) genes, a murine PS1 homologue (mPS1), and related genes from *C. elegans* (sel-12, SPE-4) and *D. melanogaster* (DmPS). The disclosure also provides the predicted amino acid sequences of the presenilin proteins encoded by these genes and a structural characterization of the presenilins, including putative functional domains and antigenic determinants. A number of mutations in the presenilins which are causative of Alzheimer's Disease (AD) in humans are also disclosed and related to the functional domains of the proteins.

Thus, in one series of embodiments, the present invention provides isolated nucleic acids including nucleotide sequences comprising or derived from the presenilin genes and/or encoding polypeptides comprising or derived from the presenilin proteins. The presenilin sequences of the invention include the specifically disclosed sequences, splice variants of these sequences, allelic variants of these sequences, synonymous sequences, and homologous or orthologous variants of these sequences. Thus, for example, the invention provides genomic and cDNA sequences from the hPS1 gene, the hPS2 gene, the mPS1 gene, and the DmPS gene. The present invention also provides allelic variants and homologous or orthologous sequences by providing methods by which such variants may be routinely obtained. The present invention also specifically provides for mutant or disease-causing variants of the presenilins by disclosing a number of specific mutant sequences and by providing methods by which other such variants may be routinely obtained. Because the nucleic acids of the invention may be used in a variety of diagnostic, therapeutic and recombinant applications, various subsets of the presenilin sequences and combinations of the presenilin sequences with heterologous sequences are also provided. For example, for use in allele specific hybridization screening or PCR amplification techniques, subsets of the presenilin sequences, including both sense and antisense sequences, and both normal and mutant sequences, as well as intronic, exonic and untranslated sequences, are provided. Such sequences may comprise a small number of consecutive nucleotides from the sequences which are disclosed or otherwise enabled herein but preferably include at least 8–10, and more preferably 9–25, consecutive nucleotides from a presenilin sequence. Other preferred subsets of the presenilin sequences include those encoding one or more of the functional domains or antigenic determinants of the presenilin proteins and, in particular, may include either normal (wild-type) or mutant sequences. The invention also provides for various nucleic acid constructs in which presenilin sequences, either complete or subsets, are operably joined to exogenous sequences to form cloning vectors, expression vectors, fusion vectors, transgenic constructs, and the like. Thus, in accordance with another aspect of the invention, a recombinant vector for transforming a mammalian or invertebrate tissue cell to express a normal or mutant presenilin sequence in the cells is provided.

In another series of embodiments, the present invention provides for host cells which have been transfected or otherwise transformed with one of the nucleic acids of the invention. The cells may be transformed merely for purposes of propagating the nucleic acid constructs of the invention, or may be transformed so as to express the presenilin sequences. The transformed cells of the invention may be used in assays to identify proteins and/or other compounds which affect normal or mutant presenilin expression, which interact with the normal or mutant presenilin proteins, and/or which modulate the function or effects of the normal or mutant proteins, or to produce the presenilin proteins, fusion proteins, functional domains, antigenic determinants, and/or antibodies of the invention. Transformed cells may also be implanted into hosts, including humans, for therapeutic or other reasons. Preferred host cells include mammalian cells from neuronal, fibroblast, bone marrow, spleen, organotypic or mixed cell cultures, as well as bacterial, yeast, nematode, insect and other invertebrate cells. For uses as described below, preferred cells also include embryonic stem cells, zygotes, gametes, and germ line cells.

In another series of embodiments, the present invention provides transgenic animal models for AD and other diseases or disorders associated with mutations in the presenilin genes. The animal may be essentially any mammal, including rats, mice, hamsters, guinea pigs, rabbits, dogs, cats, goats, sheep, pigs, and non-human primates. In addition, invertebrate models, including nematodes and insects, may be used for certain applications. The animal models are produced by standard transgenic methods including microinjection, transfection, or by other forms of transformation of embryonic stem cells, zygotes, gametes, and germ line cells with vectors including genomic or cDNA fragments, minigenes, homologous recombination vectors, viral insertion vectors and the like. Suitable vectors include vaccinia virus, adenovirus, adeno associated virus, retrovirus, liposome transport, neuraltropic viruses, and Herpes simplex virus. The animal models may include transgenic sequences comprising or derived from the presenilins, including normal and mutant sequences, intronic, exonic and untranslated sequences, and sequences encoding subsets of the presenilins such as functional domains. The major types of animal models provided include: (1) Animals in which a normal human presenilin gene has been recombinantly introduced into the genome of the animal as an additional gene, under the regulation of either an exogenous or an endogenous promoter element, and as either a minigene or a large genomic fragment; in which a normal human presenilin gene has been recombinantly substituted for one or both copies of the animal's homologous presenilin gene by homologous recombination or gene targeting; and/or in which one or both copies of one of the animal's homologous presenilin genes have been recombinantly "humanized" by the partial substitution of sequences encoding the human homologue by homologous recombination or gene targeting. (2) Animals in which a mutant human presenilin gene has been recombinantly introduced into the genome of the animal as an additional gene, under the regulation of either an exogenous or an endogenous promoter element, and as either a minigene or a large genomic fragment; in which a mutant human presenilin gene has been recombinantly substituted for one or both copies of the animal's homologous presenilin gene by homologous recombination or gene targeting; and/or in which one or both copies of one of the animal's homologous presenilin genes have been recombinantly "humanized" by the partial substitution of sequences encoding a mutant human homologue by homologous recombination or gene targeting. (3) Animals in which a mutant version of one of that animal's presenilin genes has been recombinantly introduced into the genome of the animal as an additional gene, under the regulation of either an exogenous or an endogenous promoter element, and as either a minigene or a large genomic fragment; and/or in which a mutant version of one of that animal's presenilin genes has been recombinantly substituted for one or both copies of the animal's homologous presenilin gene by homologous recombination or gene targeting. (4) "Knock-out" animals in which one or both copies of one of the animal's presenilin genes have been partially or completely deleted by homologous recombination or gene targeting, or have been inactivated by the insertion or substitution by homologous recombination or gene targeting of exogenous sequences. In preferred embodiments, a transgenic mouse model for AD has a transgene encoding a normal human PS1 or PS2 protein, a mutant human or murine PS1 or PS2 protein, or a humanized normal or mutant murine PS1 or PS2 protein generated by homologous recombination or gene targeting.

In another series of embodiments, the present invention provides for substantially pure protein preparations including polypeptides comprising or derived from the presenilins proteins. The presenilin protein sequences of the invention include the specifically disclosed sequences, variants of these sequences resulting from alternative mRNA splicing, allelic variants of these sequences, muteins of these sequences and homologous or orthologous variants of these sequences. Thus, for example, the invention provides amino acid sequences from the hPS1 protein, the hPS2 protein, the mPS1 protein, and the DmPS protein. The present invention also provides allelic variants and homologous or orthologous proteins by providing methods by which such variants may be routinely obtained. The present invention also specifically provides for mutant or disease-causing variants of the presenilins by disclosing a number of specific mutant sequences and by providing methods by which other such variants may be routinely obtained. Because the proteins of the invention may be used in a variety of diagnostic, therapeutic and recombinant applications, various subsets of the presenilin protein sequences and combinations of the presenilin protein sequences with heterologous sequences are also provided. For example, for use as immunogens or in binding assays, subsets of the presenilin protein sequences, including both normal and mutant sequences, are provided. Such protein sequences may comprise a small number of consecutive amino acid residues from the sequences which are disclosed or otherwise enabled herein but preferably include at least 4–8, and preferably at least 9–15 consecutive amino acid residues from a presenilin sequence. Other preferred subsets of the presenilin protein sequences include those corresponding to one or more of the functional domains or antigenic determinants of the presenilin proteins and, in particular, may include either normal (wild-type) or mutant sequences. The invention also provides for various protein constructs in which presenilin sequences, either complete or subsets, are joined to exogenous sequences to form fusion proteins and the like. In accordance with these embodiments, the present invention also provides for methods of producing all of the above described proteins which comprise, or are derived from, the presenilins.

In another series of embodiments, the present invention provides for the production and use of polyclonal and monoclonal antibodies, including antibody fragments, including Fab fragments, F(ab')$_2$, and single chain antibody fragments, which selectively bind to the presenilins, or to specific antigenic determinants of the presenilins. The antibodies may be raised in mouse, rabbit, goat or other suitable animals, or may be produced recombinantly in cultured cells such as hybridoma cell lines. Preferably, the antibodies are raised against presenilin sequences comprising at least 4–8, and preferably at least 9–15 consecutive amino acid residues from a presenilin sequence. The antibodies of the invention may be used in the various diagnostic, therapeutic and technical applications described herein.

In another series of embodiments, the present invention provides methods of screening or identifying proteins, small molecules or other compounds which are capable of inducing or inhibiting the expression of the presenilin genes and proteins (e.g., PS1 or PS2). The assays may be performed in vitro using transformed or non-transformed cells, immortalized cell lines, or in vivo using the transgenic animal models or human subjects enabled herein. In particular, the assays may detect the presence of increased or decreased expression of PS1, PS2 or other presenilin-related genes or proteins on the basis of increased or decreased mRNA expression, increased or decreased levels of presenilin-related protein products, or increased or decreased levels of expression of a marker gene (e.g., β-galactosidase, green fluorescent protein, alkaline phosphatase or luciferase) operably joined to a presenilin 5' regulatory region in a recombinant construct. Cells known to express a particular presenilin, or transformed to express a particular presenilin, are incubated and one or more test compounds are added to the medium. After allowing a sufficient period of time (e.g., 0–72 hours) for the compound to induce or inhibit the expression of the presenilin, any change in levels of expression from an established baseline may be detected using any of the techniques described above. In particularly preferred embodiments, the cells are from an immortalized cell line such as a human neuroblastoma, glioblastoma or a hybridoma cell line, or are transformed cells of the invention.

In another series of embodiments, the present invention provides methods for identifying proteins and other compounds which bind to, or otherwise directly interact with, the presenilins. The proteins and compounds will include endogenous cellular components which interact with the presenilins in vivo and which, therefore, provide new targets for pharmaceutical and therapeutic interventions, as well as recombinant, synthetic and otherwise exogenous compounds which may have presenilin binding capacity and, therefore, may be candidates for pharmaceutical agents. Thus, in one series of embodiments, cell lysates or tissue homogenates (e.g., human brain homogenates, lymphocyte lysates) may be screened for proteins or other compounds which bind to one of the normal or mutant presenilins. Alternatively, any of a variety of exogenous compounds, both naturally occurring and/or synthetic (e.g., libraries of small molecules or peptides), may be screened for presenilin binding capacity. In each of these embodiments, an assay is conducted to detect binding between a "presenilin component" and some other moiety. The "presenilin component" in these assays may be any polypeptide comprising or derived from a normal or mutant presenilin protein, including functional domains or antigenic determinants of the presenilins, or presenilin fusion proteins. Binding may be detected by non-specific measures (e.g., changes in intracellular $Ca^{2+}$, $Na^+$, $K^+$, or GTP/GDP ratio, changes in apoptosis or microtubule associated protein phosphorylation, changes in Aβ peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of presenilin components and bound proteins or other compounds by immunoprecipitation; (3) BIAcore analysis; and (4) the yeast two-hybrid systems.

In another series of embodiments, the present invention provides for methods of identifying proteins, small molecules and other compounds capable of modulating the activity of normal or mutant presenilins. Using normal cells or animals, the transformed cells and animal models of the present invention, or cells obtained from subjects bearing normal or mutant presenilin genes, the present invention provides methods of identifying such compounds on the basis of their ability to affect the expression of the presenilins, the intracellular localization of the presenilins, changes in intracellular $Ca^{2+}$, $Na^+$, $K^+$, or GTP/GDP ratios, or other ion levels or metabolic measures, the occurrence or rate of apoptosis or cell death, the levels or pattern of Aβ peptide production, the presence or levels of phosphorylation of microtubule associated proteins, or other biochemical, histological, or physiological markers which distinguish cells bearing normal and mutant presenilin sequences. Using the animal models of the invention, methods of identifying such compounds are also provided on the basis of the ability of the compounds to affect behavioral, physiological or histological phenotypes associated with mutations in the presenilins.

In another series of embodiments, the present invention provides methods for screening for carriers of presenilin alleles associated with AD, for diagnosis of victims of AD, and for the screening and diagnosis of related presenile and senile dementias, psychiatric diseases such as schizophrenia and depression, and neurologic diseases such as stroke and cerebral hemorrhage, which associated with mutations in the PS1 or PS2 genes. Screening and/or diagnosis can be accomplished by methods based upon the nucleic acids (including genomic and mRNA/cDNA sequences), proteins, and/or antibodies disclosed and enabled herein, including functional assays designed to detect failure or augmentation of the normal presenilin activity and/or the presence of specific new activities conferred by the mutant presenilins. Thus, screens and diagnostics based upon presenilin proteins are provided which detect differences between mutant and normal presenilins in electrophoretic mobility, in proteolytic cleavage patterns, in molar ratios of the various amino acid residues, in ability to bind specific antibodies. In addition, screens and diagnostics based upon nucleic acids (gDNA, cDNA or mRNA) are provided which detect differences in nucleotide sequences by direct nucleotide sequencing, hybridization using allele specific oligonucleotides, restriction enzyme digest and mapping (e.g., RFLP, REF-SSCP), electrophoretic mobility (e.g., SSCP, DGGE), PCR mapping, RNase protection, chemical mismatch cleavage, ligase-mediated detection, and various other methods. Other methods are also provided which detect abnormal processing of PS1, PS2, APP, or proteins reacting with PS1, PS2, or APP (e.g., abnormal phosphorylation, glycosylation, glycation amidation or proteolytic cleavage) alterations in presenilin transcription, translation, and post-translational modification; alterations in the intracellular and extracellular trafficking of presenilin gene products; or abnormal intracellular localization of the presenilins. In accordance with these embodiments, diagnostic kits are also provided which will include the reagents necessary for the above-described diagnostic screens.

In another series of embodiments, the present invention provides methods and pharmaceutical preparations for use in the treatment of presenilin-associated diseases such as AD. These methods and pharmaceuticals are based upon (1) administration of normal PS1 or PS2 proteins, (2) gene therapy with normal PS1 or PS2 genes to compensate for or replace the mutant genes, (3) gene therapy based upon antisense sequences to mutant PS1 or PS2 genes or which "knock-out" the mutant genes, (4) gene therapy based upon sequences which encode a protein which blocks or corrects the deleterious effects of PS1 or PS2 mutants, (5) immunotherapy based upon antibodies to normal and/or mutant PS1 or PS2 proteins, or (6) small molecules (drugs) which alter PS1 or PS2 expression, block abnormal interactions between mutant forms of PS1 or PS2 and other proteins or ligands, or which otherwise block the aberrant function of mutant PS1 or PS2 proteins by altering the structure of the mutant proteins, by enhancing their metabolic clearance, or by inhibiting their function.

The present disclosure also identifies and partially characterizes a number of human cellular proteins which interact with the presenilins under physiological conditions, including the S5a subunit of the 26S proteasome, the GT24 protein and Rab11. These presenilin-interacting proteins form the basis of additional embodiments directed to the investigation, diagnosis and treatment of Alzheimer's Disease. In particular, the present invention provides isolated nucleic acids encoding these presenilin-interacting proteins, their functional domains, or subsequences useful as probes or primers. These nucleic acids may be incorporated into a variety of recombinant DNA constructs, including vectors encoding fusion proteins and vectors for the transfection or transformation of cell lines and the production of animal models. Thus, the present invention also provides transformed cell lines and transgenic animals bearing these nucleic acids which encode at least a functional domain of a presenilin-interacting protein. Using the cell lines and animal models of the invention, one is enabled to produce substantially pure peptides or proteins corresponding to these presenilin-interacting proteins, their functional domains, or at least their antigenic determinants. In addition, using these recombinantly produced proteins, or naturally produced but substantially purified presenilin-interacting peptides, one is enabled to produce antibodies to these presenilin-interacting proteins which will have utility in the assays described herein. In another series of embodiments, the present invention provides for assays for compounds which modulate the interaction between the presenilins and the presenilin-interacting proteins. In preferred embodiments, these assays are performed in a yeast two-hybrid system in which the interacting domains of a presenilin and a presenilin-interacting protein are expressed in the hybrid fusion proteins and candidate compounds are tested for their ability to modulate this interaction. In other embodiments, the ability of a compound to modulate these interactions may be tested using the transformed cell lines and transgenic animals of the invention or by in vitro means (e.g., competitive binding assays). Candidate compounds which have been shown to modulate these interactions may be produced in pharmaceutically useful quantities, be tested in the animal models of Alzheimer's Disease provided herein, and/or be tested in human clinical trials for their ability to provide therapeutic benefits. In another series of embodiments, diagnostic screens are provided for mutations in the presenilin-interacting proteins which may be causative of Alzheimer's Disease or related disorders. In addition, pharmaceutical compositions are provided, and methods of their use, for the treatment of Alzheimer's Disease and related disorders. These pharmaceuticals include compounds identified by the methods of the present invention which modulate the interactions between the presenilins and the presenilin-interacting proteins. Such pharmaceuticals also include peptide fragments of the interacting domains of both the presenilins and the presenilin-interacting proteins, as well as small molecule mimetics of these domains. These and other embodiments relating to the newly disclosed presenilin-interacting proteins will be readily apparent from the following disclosure.

In accordance with another aspect of the invention, the proteins of the invention can be used as starting points for rational drug design to provide ligands, therapeutic drugs or other types of small chemical molecules. Alternatively, small molecules or other compounds identified by the above-described screening assays may serve as "lead compounds" in rational drug design.

Particularly disclosed nucleotide and amino acid sequences of the present invention are numbered SEQ ID NOs: 1–41. In addition, under the terms of the Budapest Treaty, biological deposits of particular nucleic acids disclosed herein have made with the ATCC (Rockville, Md.). These deposits include Accession Number 97124 (deposited Apr. 28, 1995), Accession Number 97508 (deposited on Apr. 28, 1995), Accession Number 97214 (deposited on Jun. 28, 1995), and Accession Number 97428 (deposited Jan. 26, 1996).

BRIEF DESCRIPTION OF THE DRAWINGS

FIG. 3: This figure presents a sequence alignment of the hPS1 and mPS1 protein sequences. Vertical bars indicate identical amino acids.

FIG. 4: This figure presents a sequence alignment of the hPS1 and hPS2 protein sequences. Vertical bars indicate identical amino acids.

DETAILED DESCRIPTION OF THE INVENTION

I. Definitions

Figure 1A:
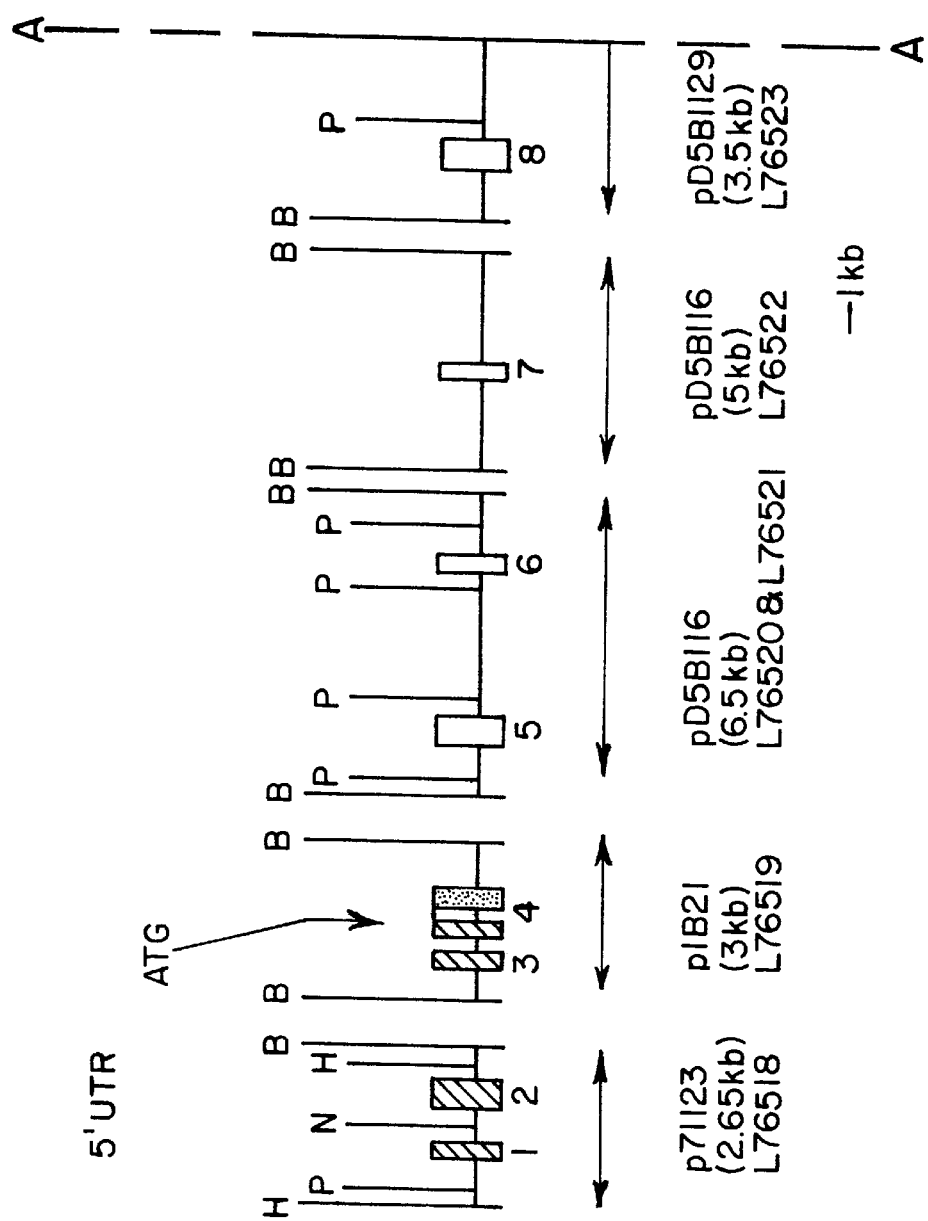
FIG. 1: This figure is a representation of the structural organization of the hPS1 genomic DNA. Non-coding exons are depicted by solid shaded boxes. Coding exons are depicted by open boxes or hatched boxes for alternatively spliced sequences. Restriction sites are: B=BamHI; E=EcoRI; H=HindIII; N=NotI; P=PstI; V=PvuII; X=XbaI. Discontinuities in the horizontal line between restriction sites represent undefined genomic sequences. Cloned genomic fragments containing each exon are depicted by double-ended horizontal arrows. The size of the genomic subclones and Accession number for each genomic sequence are provided.

In order to facilitate review of the various embodiments of the invention, and an understanding of the various elements and constituents used in making and using the invention, the following definitions are provided for particular terms used in the description and appended claims:

Presenilin. As used without further modification herein, the terms "presenilin" or "presenilins" mean the presenilin-1 (PS1) and/or the presenilin-2 (PS2) genes/proteins. In particular, the unmodified terms "presenilin" or "presenilins" refer to the mammalian PS1 and/or PS2 genes/proteins and, preferably, the human PS1 and/or PS2 genes/proteins.

Presenilin-1 gene. As used herein, the term "presenilin-1 gene" or "PS1 gene" means the mammalian gene first disclosed and described in U.S. application Ser. No. 08/431,048, filed on Apr. 28, 1995, and later described in Sherrington et al. (1995) *Nature* 375:754–760, including any allelic variants and heterospecific mammalian homologues. One human presenilin-1 (hPS1) cDNA sequence is disclosed herein as SEQ ID NO: 1. Another human cDNA sequence, resulting from alternative splicing of the hPS1 mRNA transcript, is disclosed as SEQ ID NO:3. Additional human splice variants, as described below, have also been found in which a region encoding thirty-three residues may be spliced-out in some transcripts. A cDNA of the murine homologue (mPS1) is disclosed as SEQ ID NO: 16. The term "presenilin-1 gene" or "PS1 gene" primarily relates to a coding sequence, but can also include some or all of the flanking regulatory regions and/or introns. The term "PS1 gene" specifically includes artificial or recombinant genes created from cDNA or genomic DNA, including recombinant genes based upon splice variants. The presenilin-1 gene has also been referred to as the S182 gene (e.g., Sherrington et al., 1995) or as the Alzheimer's Related Membrane Protein (ARMP) gene (e.g., U.S. application Ser. No. 08/431,048, filed on Apr. 28, 1995).

Presenilin-1 protein. As used herein, the term "presenilin-1 protein" or "PS1 protein" means a protein encoded by a PS1 gene, including allelic variants and heterospecific mammalian homologues. One human presenilin-1 (hPS 1) protein sequence is disclosed herein as SEQ ID NO:2. Another human PS1 protein sequence, resulting from alternative splicing of the hPS1 mRNA transcript, is disclosed as SEQ ID NO:4. Additional human splice variants, as described below, have also been found in which a region including thirty-three residues may be omitted due to variant mRNA splicing.. These variants are also embraced by the term presenilin-1 protein as used herein. A protein sequence of the murine homologue (mPS1) is disclosed as SEQ ID NO: 17. The protein may be produced by recombinant cells or organisms, may be substantially purified from natural tissues or cell lines, or may be synthesized chemically or enzymatically. Therefore, the term "presenilin-1 protein" or "PS1 protein" is intended to include the protein in glycosylated, partially glycosylated, or unglycosylated forms, as well as in phosphorylated, partially phosphorylated, unphosphorylated, sulphated, partially sulphated, or unsulphated forms. The term also includes allelic variants, other functional equivalents of the PS1 amino acid sequence, including biologically active proteolytic or other fragments, and physiological and pathological proteolytic cleavage products of PS1. This protein has also been referred to as the S182 protein (e.g., Sherrington et al., 1995) or as the Alzheimer's Related Membrane Protein (ARMP) (e.g., U.S. application Ser. No. 08/431,048, filed on Apr. 28, 1995).

hPS1 gene and/or protein. As used herein, the abbreviation "hPS1" refers to the human homologues and human allelic variants of the PS 1 gene and/or protein. Two cDNA sequences of the human PS1 gene are disclosed herein as SEQ ID NO: 1 and SEQ ID NO:3. The corresponding hPS1 protein sequences are disclosed herein as SEQ ID NO:2 and SEQ ID NO:4. Numerous allelic variants, including deleterious mutants, are disclosed and enabled throughout the description which follows.

mPS1 gene and/or protein. As used herein, the abbreviation "mPS1" refers to the murine homologues and murine allelic variants of the PS1 gene and/or protein. A cDNA sequence of one murine PS1 gene is disclosed herein as SEQ ID NO:16. The corresponding mPS1 protein sequence is disclosed herein as SEQ ID NO: 17. Allelic variants, including deleterious mutants, are enabled in the description which follows.

Presenilin-2 gene. As used herein, the term "presenilin-2 gene" or "PS2 gene" means the mammalian gene first disclosed and described in U.S. application Ser. No. 08/496,841, filed on Jun. 28, 1995, and later described in Rogaev et al. (1995) Nature 376:775–778 and Levy-Lahad et al. (1995) Science 269:970–973, including any allelic variants and heterospecific mammalian homologues. One human presenilin-2 (hPS2) cDNA sequence is disclosed herein as SEQ ID NO: 18. Additional human splice variants, as described below, have also been found in which a single codon or a region encoding thirty-three residues may be spliced-out in some transcripts. The term "presenilin-2 gene" or "PS2 gene" primarily relates to a coding sequence, but can also include some or all of the flanking regulatory regions and/or introns. The term "PS2 gene" specifically includes artificial or recombinant genes created from cDNA or genomic DNA, including recombinant genes based upon splice variants. The presenilin-2 gene has also been referred to as the E5-1 gene (e.g., Rogaev et al., 1995; U.S. application Ser. No. 08/496,841, filed on Jun. 28, 1995) or the STM2 gene (e.g., Levy-Lahad et al., 1995).

Presenilin-2 protein. As used herein, the term "presenilin-2 protein" or "PS2 protein" means a protein encoded by a PS2 gene, including allelic variants and heterospecific mammalian homologues. One human presenilin-2 (hPS2) protein sequence is disclosed herein as SEQ ID NO: 19. Additional human splice variants, as described below, have also been found in which a single residue or a region including thirty-three residues may be spliced-out in some transcripts. These variants are also embraced by the term presenilin-2 protein as used herein. The protein may be produced by recombinant cells or organisms, may be substantially purified from natural tissues or cell lines, or may be synthesized chemically or enzymatically. Therefore, the term "presenilin-2 protein" or "PS2 protein" is intended to include the protein in glycosylated, partially glycosylated, or unglycosylated forms, as well as in phosphorylated, partially phosphorylated, unphosphorylated, sulphated, partially sulphated, or unsulphated forms. The term also includes allelic variants, other functional equivalents of the PS2 amino acid sequence, including biologically active proteolytic or other fragments, and physiological and pathological proteolytic cleavage products of PS2. This protein has also been referred to as the E5-1 protein (e.g., Sherrington et al., 1995; U.S. application Ser. No. 08/496,841, filed on Jun. 28, 1995) or the STM2 protein (e.g., Levy-Lahad et al., 1995).

hPS2 gene and/or protein. As used herein, the abbreviation "hPS2" refers to the human homologue and human allelic variants of the PS2 gene and/or protein. One cDNA sequences of the human PS2 gene is disclosed herein as SEQ ID NO:18. The corresponding hPS2 protein sequence is disclosed herein as SEQ ID NO: 19. Numerous allelic variants, including deleterious mutants, are disclosed and enabled throughout the description which follows.

DmPS gene and/or protein. As used herein, the abbreviation "DMPS" refers to the Drosophila homologues and allelic variants of the PS1 and PS2 genes/proteins. This definition is understood to include nucleic acid and amino acid sequence polymorphisms wherein substitutions, insertions or deletions in the gene or protein sequence do not affect the essential function of the gene product. The nucleotide sequence of one cDNA of the DmPS gene is disclosed herein as SEQ ID NO:20 and the corresponding amino acid sequence is disclosed as SEQ ID NO:21. The term "DMPS gene" primarily relates to a coding sequence but can also include some or all of the flanking regulatory regions and/or introns.

Normal. As used herein with respect to genes, the term "normal" refers to a gene which encodes a normal protein. As used herein with respect to proteins, the term "normal" means a protein which performs its usual or normal physiological role and which is not associated with, or causative of, a pathogenic condition or state. Therefore, as used herein, the term "normal" is essentially synonymous with the usual meaning of the phrase "wild type." For any given gene, or corresponding protein, a multiplicity of normal allelic variants may exist, none of which is associated with the development of a pathogenic condition or state. Such normal allelic variants include, but are not limited to, variants in which one or more nucleotide substitutions do not result in a change in the encoded amino acid sequence.

Mutant. As used herein with respect to genes, the term "mutant" refers to a gene which encodes a mutant protein. As used herein with respect to proteins, the term "mutant" means a protein which does not perform its usual or normal physiological role and which is associated with, or causative of, a pathogenic condition or state. Therefore, as used herein, the term "mutant" is essentially synonymous with the terms "dysfunctional," "pathogenic," "disease-causing," and "deleterious." With respect to the presenilin genes and proteins of the present invention, the term "mutant" refers to presenilin genes/proteins bearing one or more nucleotide/amino acid substitutions, insertions and/or deletions which typically lead to the development of the symptoms of Alzheimer's Disease and/or other relevant inheritable phenotypes (e.g. cerebral hemorrhage, mental retardation, schizophrenia, psychosis, and depression) when expressed in humans. This definition is understood to include the various mutations that naturally exist, including but not limited to those disclosed herein, as well as synthetic or recombinant mutations produced by human intervention. The term "mutant," as applied to the presenilin genes, is not intended to embrace sequence variants which, due to the degeneracy of the genetic code, encode proteins identical to the normal sequences disclosed or otherwise enabled herein; nor is it intended to embrace sequence variants which, although they encode different proteins, encode proteins which are functionally equivalent to normal presenilin proteins.

Functional equivalent. As used herein in describing gene sequences and amino acid sequences, the term "functional equivalent" means that a recited sequence need not be identical to a particularly disclosed sequence of the SEQ ID NOs but need only provide a sequence which functions biologically and/or chemically as the equivalent of the disclosed sequence.

Substantially pure. As used herein with respect to proteins (including antibodies) or other preparations, the term "substantially pure" means a preparation which is at least 60% by weight (dry weight) the compound of interest. Preferably the preparation is at least 75%, more preferably at least 90%, and most preferably at least 99%, by weight the compound of interest. Purity can be measured by any appropriate method, e.g., column chromatography, gel electrophoresis, or HPLC analysis. With respect to proteins, including antibodies, if a preparation includes two or more different compounds of interest (e.g., two or more different antibodies, immunogens, functional domains, or other polypeptides of the invention), a "substantially pure" preparation means a preparation in which the total weight (dry weight) of all the compounds of interest is at least 60% of the total dry weight. Similarly, for such preparations containing two or more compounds of interest, it is preferred that the total weight of the compounds of interest be at least 75%, more preferably at least 90%, and most preferably at least 99%, of the total dry weight of the preparation. Finally, in the event that the protein of interest is mixed with one or more other proteins (e.g., serum albumin) or compounds (e.g., diluents, excipients, salts, polysaccharides, sugars, lipids) for purposes of administration, stability, storage, and the like, such other proteins or compounds may be ignored in calculation of the purity of the preparation.

Isolated nucleic acid. As used herein, an "isolated nucleic acid" is a ribonucleic acid, deoxyribonucleic acid, or nucleic acid analog comprising a polynucleotide sequence that has been isolated or separated from sequences that are immediately contiguous (one on the 5' end and one on the 3' end) in the naturally occurring genome of the organism from which it is derived. The term therefore includes, for example, a recombinant nucleic acid which is incorporated into a vector, into an autonomously replicating plasmid or virus, or into the genomic DNA of a prokaryote or eukaryote; or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequences and/or including exogenous regulatory elements.

Substantially identical sequence. As used herein, a "substantially identical" amino acid sequence is an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 85%, more preferably 90%, and most preferably 95% identical at the amino acid level to the sequence of the protein or peptide to which it is being compared. For nucleic acids, the length of comparison sequences will generally be at least 50 nucleotides, preferably at least 60 nucleotides, more preferably at least 75 nucleotides, and most preferably 110 nucleotides. A "substantially identical" nucleic acid sequence codes for a substantially identical amino acid sequence as defined above.

Transformed cell. As used herein, a "transformed cell" is a cell into which (or into an ancestor of which) has been introduced, by means of recombinant DNA techniques, a nucleic acid molecule of interest. The nucleic acid of interest will typically encode a peptide or protein. The transformed cell may express the sequence of interest or may be used only to propagate the sequence. The term "transformed" may be used herein to embrace any method of introducing exogenous nucleic acids including, but not limited to, transformation, transfection, electroporation, microinjection, viral-mediated transfection, and the like.

Operably joined. As used herein, a coding sequence and a regulatory region are said to be "operably joined" when they are covalently linked in such a way as to place the expression or transcription of the coding sequence under the influence or control of the regulatory region. If it is desired that the coding sequences be translated into a functional protein, two DNA sequences are said to be operably joined if induction of promoter function results in the transcription of the coding sequence and if the nature of the linkage between the two DNA sequences does not (1) result in the introduction of a frame-shift mutation, (2) interfere with the ability of the regulatory region to direct the transcription of the coding sequences, or (3) interfere with the ability of the corresponding RNA transcript to be translated into a protein. Thus, a regulatory region would be operably joined to a coding sequence if the regulatory region were capable of effecting transcription of that DNA sequence such that the resulting transcript might be translated into the desired protein or polypeptide.

Stringent hybridization conditions. Stringent hybridization conditions is a term of art understood by those of ordinary skill in the art. For any given nucleic acid sequence, stringent hybridization conditions are those conditions of temperature, chaotrophic acids, buffer, and ionic strength which will permit hybridization of that nucleic acid sequence to its complementary sequence and not to substantially different sequences. The exact conditions which constitute "stringent" conditions, depend upon the nature of the nucleic acid sequence, the length of the sequence, and the frequency of occurrence of subsets of that sequence within other non-identical sequences. By varying hybridization conditions from a level of stringency at which non-specific hybridization occurs to a level at which only specific hybridization is observed, one of ordinary skill in the art can, without undue experimentation, determine conditions which will allow a given sequence to hybridize only with complementary sequences. Suitable ranges of such stringency conditions are described in Krause and Aaronson (1991) *Methods in Enzymology,* 200:546–556. Hybridization conditions, depending upon the length and commonality of a sequence, may include temperatures of 20° C.–65° C. and ionic strengths from 5× to 0.1×SSC. Highly stringent hybridization conditions may include temperatures as low as 40–42° C. (when denaturants such as formamide are included) or up to 60–65° C. in ionic strengths as low as 0.1×SSC. These ranges, however, are only illustrative and, depending upon the nature of the target sequence, and possible future technological developments, may be more stringent than necessary. Less than stringent conditions are employed to isolate nucleic acid sequences which are substantially similar, allelic or homologous to any given sequence.

Selectively binds. As used herein with respect to antibodies, an antibody is said to "selectively bind" to a target if the antibody recognizes and binds the target of interest but does not substantially recognize and bind other molecules in a sample, e.g., a biological sample, which includes the target of interest.

II. The Presenilins

The present invention is based, in part, upon the discovery of a family of mammalian genes which, when mutated, are associated with the development of Alzheimer's Disease. The discovery of these genes, designated presenilin-1 and presenilin-2, as well as the characterization of these genes, their protein products, mutants, and possible functional roles, are described below. Invertebrate homologues of the presenilins are also discussed as they may shed light on the function of the presenilins and to the extent they may be useful in the various embodiments described below.

1. Isolation of the Human Presenilin-1 Gene

A. Genetic Mapping of the AD3 Region

The initial isolation and characterization of the PS1 gene, then referred to as the AD3 gene or S182 gene, was described in Sherrington et al., 1995. After the initial regional mapping of the AD3 gene locus to 14q24.3 near the anonymous microsatellite markers D14S43 and D14S53 (Schellenberg et al., 1992; St. George-Hyslop et al., 1992; Van Broeckhoven et al., 1992), twenty one pedigrees were used to segregate AD as a putative autosomal dominant trait (St. George-Hyslop et al., 1992) and to investigate the segregation of 18 additional genetic markers from the 14q24.3 region which had been organized into a high density genetic linkage map (Weissenbach et al. (1992) *Nature* 359:794–798; Gyapay et al. (1994) *Nature Genetics* 7:246–339). Previously published pairwise maximum likelihood analyses confirmed substantial cumulative evidence for linkage between familial Alzheimer's Disease (FAD) and all of these markers. However, much of the genetic data supporting linkage to these markers were derived from six large early onset pedigrees, FAD1 (Nee et al. (1983) *Arc. Neurol.* 40:203–208), FAD2 (Frommelt et al. (1991) *Alzheimer Dis. Assoc. Disorders* 5:36–43), FAD3 (Goudsmit et al. (1981) *J. Neurol. Sci.* 49:79–87; Pollen (1993) *Hannah's Heirs: The Quest for the Genetic Origins of Alzheimer's Disease,* Oxford University Press, Oxford), FAD4 (Foncin et al. (1985) *Rev. Neurol. (Paris)* 141:194–202), TOR1.1 (Bergamini et al. (1991) *Acta Neurol.* 13:534–538) and 603 (Pericak-Vance et al. (1988) *Exp. Neurol.* 102:271–279), each of which provides at least one anonymous genetic marker from 14q24.3 (St. George-Hyslop et al., 1992).

In order to define more precisely the location of the AD3 gene relative to the known locations of the genetic markers from 14q24.3, recombinational landmarks were sought by direct inspection of the raw haplotype data from those genotyped affected members of the six pedigrees showing definitive linkage to chromosome 14. This selective strategy in this particular instance necessarily discards data from the reconstructed genotypes of deceased affected members as well as from elderly asymptomatic members of the large pedigrees, and takes no account of the smaller pedigrees of uncertain linkage status. However, this strategy is very sound because it also avoids the acquisition of potentially misleading genotype data acquired either through errors in the reconstructed genotypes of deceased affected members arising from non-paternity or sampling errors or from the inclusion of unlinked pedigrees.

Upon inspection of the haplotype data for affected subjects, members of the six large pedigrees whose genotypes were directly determined revealed obligate recombinants at D14S48 and D14S53, and at D14S258 and D14S63. The single recombinant at D14S53, which depicts a telomeric boundary for the FAD region, occurred in the same AD affected subject of the FAD1 pedigree who had previously been found to be recombinant at several other markers located telomeric to D14S53, including D14S48 (St. George-Hyslop et al., 1992). Conversely, the single recombinant at D14S258, which marks a centromeric boundary of the FAD region, occurred in an affected member of the FAD3 pedigree who was also recombinant at several other markers centromeric to D14S258 including D14S63. Both recombinant subjects had unequivocal evidence of Alzheimer's Disease confirmed through standard clinical tests for the illness in other affected members of their families, and the genotype of both recombinant subjects was informative and co-segregating at multiple loci within the interval centromeric to D14S53 and telomeric to D14S258.

When the haplotype analyses were enlarged to include the reconstructed genotypes of deceased affected members of the six large pedigrees as well as data from the remaining fifteen pedigrees with probabilities for linkage of less than 0.95, several additional recombinants were detected at one or more marker loci within the interval between D14S53 and D14S258. Thus, one additional recombinant was detected in the reconstructed genotype of a deceased affected member of each of three of the larger FAD pedigrees (FAD1, FAD2 and other related families), and eight additional recombinants were detected in affected members of five smaller FAD pedigrees. However, while some of these recombinants might have correctly placed the AD3 gene within a more defined target region, it was necessary to regard these potentially closer "internal recombinants" as unreliable not only for the reasons discussed earlier, but also because they provided mutually inconsistent locations for the AD3 gene within the D14S53–D14S258 interval.

B. Construction of a Physical Contig Spanning the AD3 Region

As an initial step towards cloning the AD3 gene, a contig of overlapping genomic DNA fragments cloned into yeast artificial chromosome vectors, phage artificial chromosome vectors and cosmid vectors was constructed. FISH mapping studies using cosmids derived from the YAC clones 932c7 and 964f5 suggested that the interval most likely to carry the AD3 gene was at least five megabases in size. Because the large size of this minimal co-segregating region would make positional cloning strategies intractable, additional genetic pointers were sought which focused the search for the AD3 gene to one or more subregions within the interval flanked by D14S53 and D14S258. Haplotype analyses at the markers between D14S53 and D14S258 failed to detect statistically significant evidence for linkage disequilibrium and/or allelic association between the FAD trait and alleles at any of these markers, irrespective of whether the analyses were restricted to those pedigrees with early onset forms of FAD, or were generalized to include all pedigrees. This result was not unexpected given the diverse ethnic origins of our pedigrees. However, when pedigrees of similar ethnic descent were collated, direct inspection of the haplotypes observed on the disease-bearing chromosome segregating in different pedigrees of similar ethnic origin revealed two clusters of marker loci. The first of these clusters located centromeric to D14S77 (D14S786, D14S277 and D14S268) and spanned the 0.95 Mb physical interval contained in YAC 78842. The second cluster was located telomeric to D14S77 (D1443, D14S273, and D1476) and spanned the ~1 Mb physical interval included within the overlapping YAC clones 964c2, 74163, 797d11 and part of 854f5. Identical alleles were observed in at least two pedigrees from the same ethnic origin. As part of the strategy, it was reasoned that the presence of shared alleles at one of these groups of physically clustered marker loci might reflect the co-inheritance of a small physical region surrounding the PSI gene on the original founder chromosome in each ethnic population. Significantly, each of the shared extended haplotypes were rare in normal Caucasian populations and allele sharing was not observed at other groups of markers spanning similar genetic intervals elsewhere on chromosome 14q24.3.

C. Transcription Mapping and Analysis of Candidate Genes

To isolate expressed sequences encoded within both critical intervals, a direct selection strategy was used involving immobilized, cloned, human genomic DNA as the hybridization target to recover transcribed sequences from primary complementary DNA pools derived from human brain mRNA (Rommens et al. (1993) *Hum. Molec. Genet.* 2:901–907). Approximately 900 putative cDNA fragments of size 100 to 600 base pairs were recovered from these regions. These fragments were hybridized to Southern blots containing genomic DNAs from each of the overlapping YAC clones and genomic DNAs from humans and other mammals. This identified a subset of 151 clones which showed evidence for evolutionary conservation and/or for a complex structure which suggested that they were derived from spliced mRNA. The clones within this subset were collated on the basis of physical map location, cross-hybridization and nucleotide sequence, and were used to screen conventional human brain cDNA libraries for longer cDNAs. At least 19 independent cDNA clones over 1 kb in length were isolated and then aligned into a partial transcription map of the AD3 region. Only three of these transcripts corresponded to known characterized genes (cFOS, dihydrolipoamide succinyl transferase, and latent transforming growth factor binding protein 2).

D. Recovery of Candidate Genes

Each of the open reading frame portions of the candidate genes were recovered by RT-PCR from mRNA isolated from post-mortem brain tissue of normal control subjects and from either post-mortem brain tissue or cultured fibroblast cell lines of affected members of six pedigrees definitively linked to chromosome 14. The RT-PCR products were then screened for sequence differences using chemical cleavage and restriction endonuclease fingerprinting single-strand sequence conformational polymorphism methods (Saleeba and Cotton (1993) *Methods in Enzymology* 217:286–295; Liu and Sommer (1995) *Biotechniques* 18:470–477), and by direct nucleotide sequencing. With one exception, all of the genes examined, although of interest, did not contain alterations in sequences that were unique to affected subjects, or co-segregated with the disease. The single exception was the candidate gene represented by clone S182 which contained a series of nucleotide changes not observed in normal subjects, and which were predicted to alter the amino acid sequence in affected subjects. The gene corresponding to this clone has now been designated as presenilin-1 (PS1). Two PS1 cDNA sequences, representing alternative splice variants described below, are disclosed herein as SEQ ID NO: 1 and SEQ ID NO:3. The corresponding predicted amino acid sequences are disclosed as SEQ ID NO:2 and SEQ ID NO:4, respectively. Bluescript plasmids bearing clones of these cDNAs have been deposited at the ATCC, Rockville, Md., under ATCC Accession Numbers 97124 and 97508 on Apr. 28, 1995. Sequences corresponding to SEQ ID NO:1 and SEQ ID NO:2 have also been deposited in the GenBank database and may be retrieved through Accession #42110.

2. Isolation of the Murine Presenilin-1 Gene

A murine homologue (mPS1) of the human PS1 gene was recovered by screening a mouse cDNA library with a labeled human DNA probe from the hPS1 gene. In this manner, a 2 kb partial transcript (representing the 3' end of the gene) and several RT-PCR products representing the 5' end were recovered. Sequencing of the consensus cDNA transcript of the murine homologue revealed substantial amino acid identity with hPS1. Importantly, as detailed below, all of the amino acids that were mutated in the FAD pedigrees were conserved between the murine homologue and the normal human variant. This conservation of the PS1 gene indicates that an orthologous gene exists in the mouse (mPS1), and that it is now possible to clone other mammalian homologues or orthologues by screening genomic or cDNA libraries using human PS1 probes. Thus, a similar approach will make it possible to identify and characterize the PS1 gene in other species. The nucleic acid sequence of the mPS1 clone is disclosed herein as SEQ ID NO:16 and the corresponding amino acid sequence is disclosed as SEQ ID NO:17. Both sequences have been deposited in the GenBank database and may be retrieved through Accession #42177.

3. Isolation of the Human Presenilin-2 Gene

A second human gene, now designated presenilin-2 (PS2), has been isolated and demonstrated to share substantial nucleotide and amino acid homology with the PS1 gene. The initial isolation of this gene is described in detail in Rogaev et al. (1995). Isolation of the human PS2 gene (referred to as "STM2") by nearly identical methods is also reported in Levy-Lahad et al. (1995). Briefly, the PS2 gene was identified by using the nucleotide sequence of the cDNA for PS1 to search data bases using the BLASTN paradigm of Altschul et al. (1990) *J. Mol. Biol.* 215:403–410). Three expressed sequence tagged sites (ESTs) identified by Accession #s T03796, R14600, and R05907 were located which had substantial homology ($p<1.0$ $e^{-100}$, greater than 97% identity over at least 100 contiguous base pairs).

Oligonucleotide primers were produced from these sequences and used to generate PCR products by reverse transcriptase PCR (RT-PCR). These short RT-PCR products were partially sequenced to confirm their identity with the sequences within the data base and were then used as hybridization probes to screen full-length cDNA libraries. Several different cDNAs ranging in size from 1 kb to 2.3 kb were recovered from a cancer cell cDNA library (CaCo2) and from a human brain cDNA library (E5-1, G1-1, cc54, cc32). The nucleotide sequence of these clones confirmed that all were derivatives of the same transcript.

The gene encoding the transcript, the PS2 gene, mapped to human chromosome 1 using hybrid mapping panels to two clusters of CEPH Mega YAC clones which have been placed upon a physical contig map (YAC clones 750g7, 921d12 mapped by FISH to 1q41; and YAC clone 787g12 mapped to 1p36.1-p35). The nucleic acid sequence of the hPS2 clone is disclosed herein as SEQ ID NO:18 and the corresponding amino acid sequence is disclosed as SEQ ID NO:19. Both sequences have been deposited in the GenBank database and may be retrieved through Accession #L44577. The DNA sequence of the hPS2 clone also has been incorporated into a vector and deposited at the ATCC, Rockville, Md., under ATCC Accession Number 97214 on Jun. 28, 1995.

4. Identification of Homologues in *C. elegans* and *D. melanogaster*

A. SPE-4 of *C. elegans*

Comparison of the nucleic acid and predicted amino acid sequences of PS1 with available databases using the BLAST alignment paradigms revealed modest amino acid similarity with the *C. elegans* sperm integral membrane protein SPE-4 ($P=1.5e-25$, 24–37% identity over three groups of at least fifty residues) and weaker similarity to portions of several other membrane spanning proteins including mammalian chromogranin A and the alpha subunit of mammalian voltage dependent calcium channels (Altschul et al., 1990). Amino-acid sequence similarities across putative transmembrane domains may occasionally yield alignment that simply arises from the limited number of hydrophobic amino acids, but there is also extended sequence alignment between PS1 and SPE-4 at several hydrophilic domains. Both the putative PS1 protein and SPE-4 are predicted to be of comparable size (467 and 465 residues, respectively) and, as described more fully below, to contain at least seven transmembrane domains with a large acidic domain preceding the final predicted transmembrane domain. The PS1 protein does have a longer predicted hydrophilic region at the N terminus.

BLASTP alignment analyses also detected significant homology between PS2 and the *C. elegans* SPE-4 protein ($p=3.5e-26$; identity=20–63% over five domains of at least 22 residues), and weak homologies to brain sodium channels (alpha III subunit) and to the alpha subunit of voltage dependent calcium channels from a variety of species (p=0.02; identities 20–28% over two or more domains each of at least 35 residues) (Altschul, 1990). These alignments are similar to those described above for the PS1 gene.

B. Sel-12 of C. elegans

The 461 residue Sel-12 protein from *C. elegans* and S182 (SEQ ID NO:2) were found to share 48% sequence identity over 460 amino acids (Levitan and Greenwald (1995) *Nature* 377:351–354). The Sel-12 protein also is believed to have multiple transmembrane domains. The sel-12 gene (Accession number U35660) was identified by screening for suppressors of a lin-12 gain-of-function mutation, and was cloned by transformation rescue (Levitan and Greenwald, 1995).

C. DmPS of *D. melanogaster*

Redundant oligonucleotides coding for highly conserved regions of the presenilin/sel 12 proteins were prepared and used to identify relevant mRNAs from adult and embryonic *D. melanogaster*. These mRNAs were sequenced and shown to contain an open reading frame with a putative amino acid sequence highly homologous to that of the human presenilins. The DmPS cDNA is identified as SEQ ID NO:20.

This sequence encodes a polypeptide of 541 amino acids (SEQ ID NO:21) with about 52% identity to the human presenilins.

The structure of the *D. melanogaster* homologue is similar to that of the human presenilins with at least seven putative transmembrane domains (Kyte-Doolittle hydrophobicity analyses using a window of 15 and cut-off of 1.5). Evidence of at least one alternative splice form was detected in that clone pds13 contained an ORF of 541 amino acids, whereas clones pds7, pds14 and pds1 lacked nucleotides 1300–1341 inclusive. This alternative splicing would result in the alteration of Gly to Ala at residue 384 in the putative TM6→7 loop, and an in-frame fusion to the Glu residue at codon 399 of the longer ORF. The principal differences between the amino acid sequence of the *D. melanogaster* and human genes were in the N-terminal acid hydrophilic domain and in the acidic hydrophilic portion of the TM6→7 loop. The residues surrounding the TM6→7 loop are especially conserved (residues 220–313 and 451–524), suggesting that these are functionally important domains. Sixteen out of twenty residues identified to be mutated in human PS1 or PS2 and giving rise to human FAD are conserved in the *D. melanogaster* homologue.

The DNA sequence of the DmPS gene as cloned has been incorporated into a Bluescript plasmid. This stable vector was deposited with the ATCC, Rockville, Md., under ATCC Accession Number 97428 on Jan. 26, 1996.

5. Characterization of the Human Presenilin Genes

A. hPS1 Transcripts and Gene Structure

Figure 2:
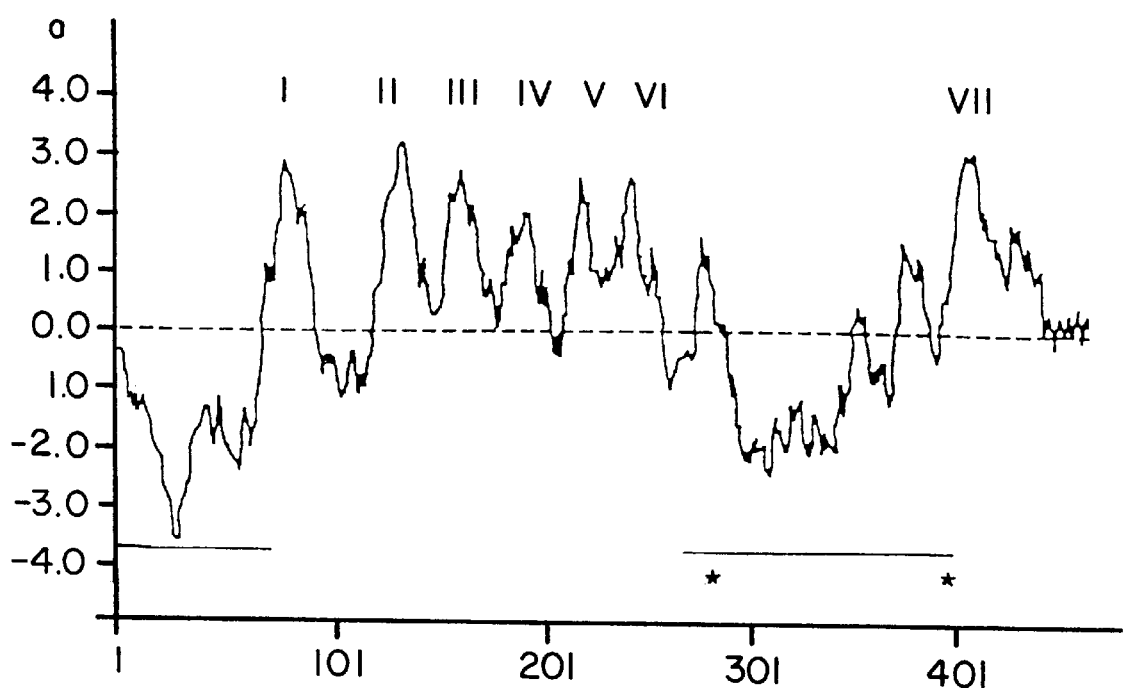
FIG. 2: This figure is a representation of a hydropathy plot of the putative PS1 protein. The plot was calculated according to the method of Kyte and Doolittle (1982) *J. Mol. Biol.* 157:105.

Hybridization of the PS1 (S182) clone to northern blots identified a transcript expressed widely in many areas of brain and peripheral tissues as a major ~2.8 kb transcript and a minor transcript of ~7.5 kb (see, e.g., FIG. 2 in Sherrington et al., 1995). PS1 is expressed fairly uniformly in most regions of the brain and in most peripheral tissues except liver, where transcription is low. Although the identity of the ~7.5 kb transcript is unclear, two observations suggest that the ~2.8 kb transcript represents an active product of the gene. Hybridization of the PS1 clone to northern blots containing mRNA from a variety of murine tissues, including brain, identifies only a single transcript identical in size to the ~2.8 kb human transcript. All of the longer cDNA clones recovered to date (2.6–2.8 kb), which include both 5' and 3' UTRs and which account for the ~2.8 kb band on the northern blot, have mapped exclusively to the same physical region of chromosome 14.

From these experiments the ~7.5 kb transcript could represent either a rare alternatively spliced or polyadenylated isoform of the ~2.8 kb transcript, or could represent another gene with homology to PS1. A cDNA library from the CaCo2 cell line which expresses high levels of both PS1 and PS2 was screened for long transcripts. Two different clones were obtained, GL40 and B53. Sequencing revealed that both clones contained a similar 5' UTR and an ORF which was identical to that of the shorter 2.8 kb transcripts in brain.

Both clones contained an unusually long 3' UTR. This long 3' UTR represents the use of an alternate polyadenylation site approximately 3 kb further downstream. This long 3' UTR contains a number of nucleotide sequence motifs which result in palindromes or stem-loop structures. These structures are associated with mRNA stability and also translational efficiency. The utility of this observation is that it may be possible to create recombinant expression constructs and/or transgenes in which the upstream polyadenylation site is ablated, thereby forcing the use of the downstream polyadenylation site and the longer 3' UTR. In certain instances, this may promote the stability of selected mRNA species, with preferential translation that could be utilized to alter the balance of mutant versus wild-type transcripts in targeted cell lines, or even in vivo in the brain, either by germ line therapy or by the use of viral vectors such as modified herpes simplex virus vectors as a form of gene therapy.

The hPS1 gene spans a genomic interval of at least 60 kb within a 200 kb PAC1 clone RPCI-1 54D12 from the Roswell Park PAC library and three overlapping cosmid clones 57-H10, 1-G9, and 24-D5 from the Los Alamos Chromosome 14 cosmid library. Transcripts of the PS1 gene contain RNA from 13 exons which were identified by reiterative hybridization of oligonucleotide and partial cDNA probes to subcloned restriction fragments of the PAC and cosmid clones, and by direct nucleotide sequencing of these subclones. The 5' UTR is contained within Exons 1–4, with Exons 1 and 2 representing alternate 5' ends of the transcript. The ORF is contained in Exons 4 to 13, with alternative splicing events resulting in the absence of part of Exon 4 or all of Exon 9. Exon 13 also includes the 3' UTR.

Unless stated otherwise, in the interests of clarity and brevity, all references to nucleotide positions in hPS1 derived nucleotide sequences will employ the base numbering of SEQ ID NO:1 (L42 110), an hPS1 cDNA sequence starting with Exon 1. In this cDNA, Exon 1 is spliced directly to Exon 3, which is spliced to Exons 4–13. In SEQ ID NO:1, Exon 1 spans nucleotide positions 1 to 113, Exon 3 spans positions 114 to 195, Exon 4 spans positions 196 to 335, Exon 5 spans positions 336 to 586, Exon 6 spans positions 587 to 728, Exon 7 spans positions 729 to 796, Exon 8 spans positions 797 to 1017, Exon 9 spans positions 1018 to 1116, Exon 10 spans positions 1117 to 1203, Exon 11 spans positions 1204 to 1377, Exon 12 spans positions 1378 to 1496, Exon 13 spans positions 1497 to 2765. Similarly, unless stated otherwise, all references to amino acid residue positions in hPS1 derived protein sequences will employ the residue numbering of SEQ ID NO:2, the translation product of SEQ ID NO:1.

Flanking genomic sequences have been obtained for Exons 1–12, and are presented in SEQ ID NOs: 5–14

(Accession numbers: L76518–L76527). Genomic sequence 5' from Exon 13 has also been determined and is presented in SEQ ID NO:15 (Accession number: L76528). SEQ ID NOs: 5–14 also include the complete Exon sequences. SEQ ID NO: 15, however, does not include the 3' end of Exon 13. The genomic sequences corresponding to Exons 1 and 2 are located approximately 240 bp apart on a 2.6 kb BamHI-HindIII fragment, SEQ ID NO:5. Exons 3 and 4 (which contains the ATG start codon) are located on a separate 3 kb BamHI fragment. The complete sequence of Intron 2 between the BamHI site ~850 bp downstream of Exon 2 and the BamHI site ~600 bp upstream of Exon 3 has not yet been identified, and was not immediately recovered by extended PCR using primers from the flanking BamHI sites, implying that Intron 2 may be large.

Analysis of the nucleotide sequence surrounding Exons 1 and 2 (SEQ ID NO:5) revealed numerous CpG dinucleotides including a NotI restriction site in Intron 1. Consensus sequences for several putative transcriptional regulatory proteins including multiple clusters of Activator Protein-2 (AP-2), Signal Transducers and Activators of Transcription (STAT3) (Schindler and Darnell (1995) *Annu. Rev. Biochem.* 64:621–651), Gamma Activator Sequences (GAS or STAT1), Multiple start site Element Downstream (MED) (Ince and Scotto (1995) *J. Biol. Chem.* 270:30249–30252), and GC elements were present in both Intron 1 and in the sequence 5' from Exon 1 (see SEQ ID NO:5). Two putative TATA boxes exist upstream of Exon 1, at bp 925–933 and 978–987 of SEQ ID NO:5, and are followed by two putative transcription initiation (CAP or Chambon-Trifonov) consensus sequences at 1002–1007 bp and 1038–1043 bp 484 of SEQ ID NO:5. In contrast, the sequences immediately upstream of Exon 2 lack TATA boxes or CAP sites, but are enriched in clusters of CpG islands.

Figure 1B:
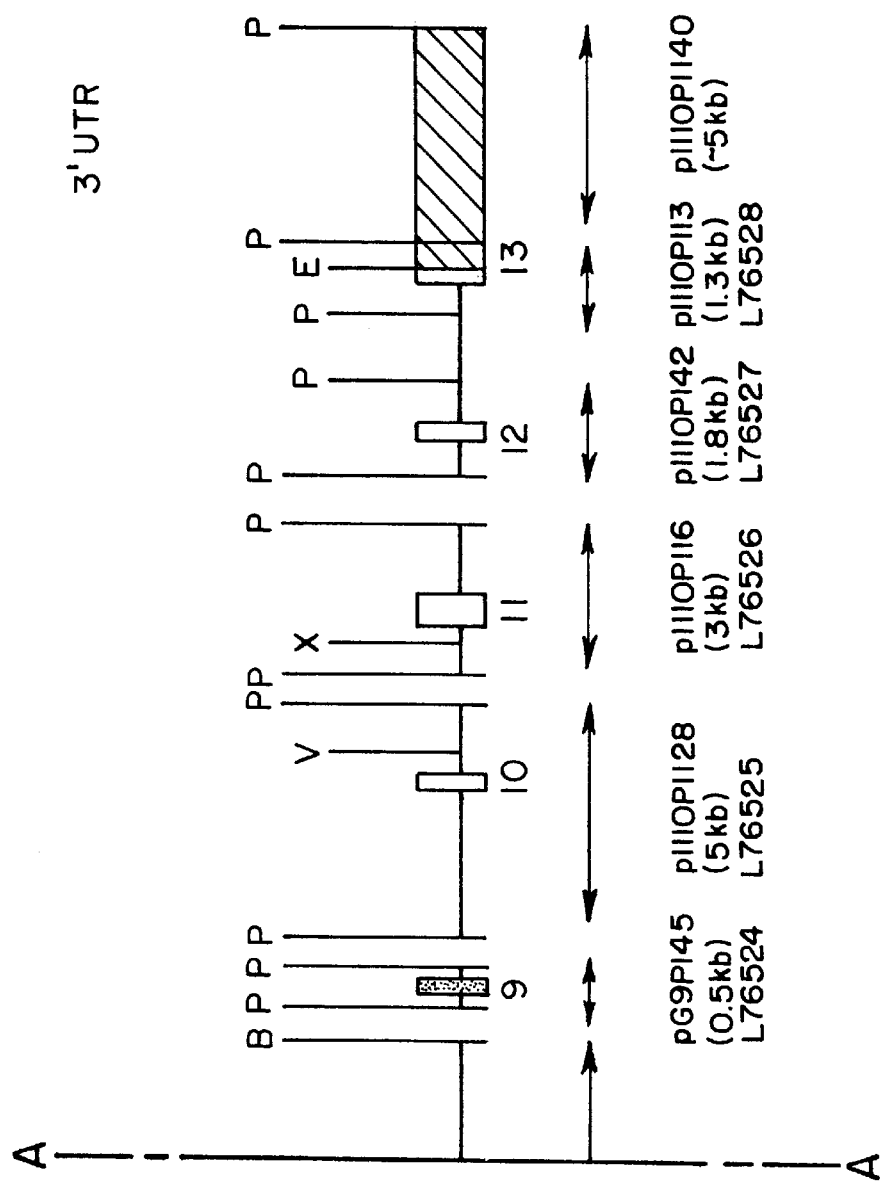

A schematic map of the structural organization of the hPS1 gene is presented as FIG. 1. Non-coding exons are depicted by solid shaded boxes. Coding exons are depicted by open boxes or hatched boxes for alternatively spliced sequences. Restriction sites are indicated as: B=BamHI; E=EcoRI; H=HindIII; N=NotI; P=PstI; V=PvuII; X=XbaI. Discontinuities in the horizontal line between restriction sites represent undefined genomic sequences. Cloned genomic fragments containing each exon are depicted by double-ended horizontal arrows. The size of the genomic subclones and Accession number for each genomic sequence are also provided.

Predictions of DNA secondary structure based upon the nucleotide sequence within 290 bp upstream of Exon 1 and within Intron 1 reveal several palindromes with stability greater than −16 kcal/mol. These secondary structure analyses also predict the presence of three stable stem-loop motifs (at bp 1119–1129/1214–1224; at bp 1387–1394/1462–1469; and at bp 1422–1429/1508–1515; all in SEQ ID NO:5) with a loop size sufficient to encircle a nucleosome (~76 bp). Such stem loop structures are a common feature of TATA containing genes (Kollmar and Farnham (1993) *Proc. Soc. Expt. Biol. Med.* 203:127–137).

A summary of the features in these 5' regions is presented in Table 1. All references to base positions are relative to SEQ ID NO:5.

The longest predicted open reading frame in SEQ ID NO:1 encodes a protein of 467 amino acids, SEQ ID NO:2. The start codon for this open reading frame is the first in-phase ATG located downstream of a TGA stop codon. There are no classical Kozak consensus sequences around the first two in phase ATG codons (Sherrington et al., 1995).

Like other genes lacking classical 'strong' start codons, the putative 5' UTR of the human transcripts is rich in GC.

B. Alternative Transcription and Splicing of the hPS1 5' UTR

Although the first three exons and part of the fourth exon contain non-translated sequences, analysis of multiple full length cDNA clones isolated from a human hippocampus cDNA library (Stratagene, La Jolla Calif.) and from a colon adenocarcinoma cell line (CaCo2 from J. Rommens) revealed that in the majority of clones the initial sequences were derived from Exon 1 and were directly spliced to Exon 3 (Accession number L421 10, SEQ ID NO:1). Less frequently (1 out of 9 clones), the initial transcribed sequences were derived from Exon 2 and were spliced onto Exon 3 (Accession number L76517, SEQ ID NO:3). Direct nucleotide sequencing of at least 40 independent RT-PCR transcripts isolated using a primer in Exon 1 failed to identify any clones containing both Exon 1 and Exon 2. Finally, inspection of the genomic sequence upstream of Exon 2 did not reveal a 3' splice site sequence. These observations argue that Exon 2 is a true initial exon rather than an alternative splice form of transcripts beginning in Exon 1 or an artifact of cDNA cloning. Furthermore, since a clone (cc44) containing Exon 2 was obtained from the same monoclonal CaCo2 cell lines, it is likely that both Exon-1-containing transcripts and Exon-2-containing transcripts exist in the same cells.

To test the predictions about transcription initiation sites based upon the nucleotide sequence of the 5' upstream region near Exon 1, we examined the 5' end sequence of three independent "full-length" cDNA clones containing Exon 1 (cc33, cc58 and cc48) and three sequences recovered by primer extension using an antisense primer located in Exon 3. The farthest 5' extension was seen in the cDNA G40L, which mapped the most proximal transcription start site to position 1214 bp in the genomic sequence containing Exon 1 SEQ ID NO:5 (L76518), and which therefore corresponds to position −10 of SEQ ID NO:11. Two additional clones (cDNA cc48 and 5' RACE product #5) shared a common start site at position 1259 bp in the genomic sequence, SEQ ID NO:5, which corresponds to position 34 in SEQ ID NO: 1. The two remaining cDNAs, as well as the remaining 5' RACE clones, began at more distal positions within Exon 1. A 5' RACE clone #8 began at 1224 bp, equal to position 1 of SEQ ID NO: 1. None of these clones therefore extended to the predicted CAP site upstream of Exon 1. Due to the low prevalence of transcripts containing initial sequences from Exon 2, similar studies of their start sites were not performed.

C. Alternative Splicing of the hPS1 ORF

In addition to transcripts with different initial sequences, the analysis of multiple cDNA clones recovered from a variety of libraries also revealed two variations in PS1 transcripts which affect the ORF.

The first of these is the absence of 12 nucleotides from the 3' end of Exon 4, nucleotides 324 to 335 of SEQ ID NO: 1. This would result from splicing of Exon 4 after nucleotide 323 instead of after nucleotide 335. Transcripts resulting from this alternative splicing of Exon 4 do not encode amino acid residues Val26-Arg27-Ser28-Gln29 of SEQ ID NO:2. Transcripts resulting from these two alternative splicing events for Exon 4 were detected with approximately equal frequencies in all tissues surveyed. It is of note in the clones examined to date that the murine PS1 transcripts do contain only the cDNA sequence for Ile26-Arg27-Ser28-Gln29, and that the sequence for the Val-Arg-Ser-Gln motif is only partially conserved in human PS2 as Arg48-Ser49-Gln50 (Rogaev et al., 1995). Each of these observations suggests that these differences are not critical to proper PS1 functioning.

The second splicing variation affecting the ORF results in the absence of Exon 9, nucleotides 1018 to 1116 in SEQ ID NO: 1. Analysis of RT-PCR products derived from mRNA of a variety of tissues showed that brain (including neocortical areas typically affected by AD) and several other tissues (muscle, heart, lung, colon) predominantly expressed a single transcript bearing Exon 9. Leukocytes (but not lymphoblasts) on the other hand, also expressed a shorter form lacking Exon 9. Alternative splicing of Exon 9 is predicted to change an aspartate residue at position 257 in SEQ ID NO:2 to alanine, eliminate the next 33 residues, and result in an in-frame fusion to the rest of the protein beginning at the threonine at position 291 encoded in Exon 10.

D. hPS2 Transcripts

The genomic DNA including the human PS2 gene has not yet been fully characterized. Nonetheless, many similarities between the PS1 and PS2 genes are apparent. The intron/exon boundaries of both genes, however, appear to be very similar or identical except in the region of the TM6→7 loop.

Hybridization of the PS2 cDNA clones to Northern Blots detected a ~2.3 kb mRNA band in many tissues, including regions of the brain, as well as a ~2.6 kb mRNA band in muscle, cardiac muscle and pancreas. PS2 is expressed at low levels in most regions of the brain except the corpus callosum, where transcription is high. In skeletal muscle, cardiac muscle and pancreas, the PS2 gene is expressed at relatively higher levels than in brain and as two different transcripts of 2.3 kb and ~2.6 kb. Both of the transcripts have sizes clearly distinguishable from that of the 2.7 kb PS1 transcript, and did not cross-hybridize with PS1 probes at high stringency. The cDNA sequence of one hPS2 allele is identified as SEQ ID NO: 18 (Accession No. L44577).

The longest ORF within this PS2 cDNA consensus nucleotide sequence predicts a polypeptide containing 448 amino acids (SEQ ID NO: 19) numbering from the first in-phase ATG codon, at positions 366–368 in SEQ ID NO: 18, which was surrounded by a Kozak consensus sequence. The stop codon is at positions 1710–1712.

As for PS1, analysis of PS2 RT-PCR products from several tissues, including brain and muscle, RNA revealed two alternative splice variants in which a relatively large segment may be spliced out. Thus, at a relatively low frequency, transcripts are produced in which nucleotides 1152–1250 of the PS2 transcript, SEQ ID NO:18, (encoding residues 263–295, SEQ ID NO:19) are alternatively spliced. As discussed below, this splicing event corresponds closely to the alternative splicing of Exon 9 of PS1 (Rogaev et al., 1995).

An additional splice variant of the PS2 cDNA sequence lacking the GAA triplet at nucleotide positions 1338–1340 in SEQ ID NO: 18 has also been found in all tissues examined. This alternative splice results in the omission of a Glu residue at amino acid position 325.

6. Structure of the Presenilin Proteins

A. The Presenilin Protein Family

The presenilins are now disclosed to be a novel family of highly conserved integral membrane proteins with a common structural motif, common alternative splicing patterns, and common mutational regions hot spots which correlate with putative structural domains which are present in many invertebrate and vertebrate animal cells. Analysis of the predicted amino acid sequences of the human presenilin genes using the Hopp and Woods algorithm suggests that the proteins are multispanning integral membrane proteins such as receptors, channel proteins, or structural membrane proteins. A Kyte-Doolittle hydropathy plot of the putative hPS1 protein is depicted in FIG. 2. The hydropathy plot and structural analysis suggest that these proteins possess approximately seven hydrophobic transmembrane domains (designated TM1 through TM7) separated by hydrophilic "loops." Other models can be predicted to have as few as 5 and as many as 10 transmembrane domains depending upon the parameters used in the prediction algorithm. The presence of seven membrane spanning domains, however, is characteristic of several classes of G-coupled receptor proteins, but is also observed with other proteins (e.g., channel proteins). The absence of a recognizable signal peptide and the paucity of glycosylation sites are noteworthy.

The amino acid sequences of the hPS1 and mPS1 proteins are compared in FIG. 3, and the sequences of the hPS1 and hPS2 proteins are compared in FIG. 4. In each figure, identical amino acid residues are indicated by vertical bars. The seven putative transmembrane domains are indicated by horizontal lines above or below the sequences.

The major differences between members of this family reside in the amino acid sequences of the hydrophilic, acidic loop domains at the N-terminus and between the putative TM6 and TM7 domains of the presenilin proteins (the TM6→7 loop). Most of the residues encoded by hPS1 Exon 9, which is alternatively spliced in some non-neural tissues, form part of the putative TM6→7 loop. In addition, the corresponding alternative splice variant identified in hPS2 appears to encode part of the TM6→7 loop. The variable splicing of this hydrophilic loop, and the fact that the amino acid sequence of the loop differs between members of the gene family, suggest that this loop is an important functional domain of the protein and may confer some specificity to the physiologic and pathogenic interactions of the individual presenilin proteins. Because the N-terminal hydrophilic domain shares the same acidic charge as the TM6→7 hydrophilic acid loop, and in a seven transmembrane domain model is likely to have the same orientation with respect to the membrane, and is also variable amongst the presenilins, it is very likely that these two domains share functionality either in a coordinated or independent fashion (e.g. the same or different ligands or functional properties). Thus, it is likely that the N-terminus is also an important functional domain of the protein and may confer some specificity to the physiologic and pathogenic interactions of the individual presenilin proteins.

Figure 5:
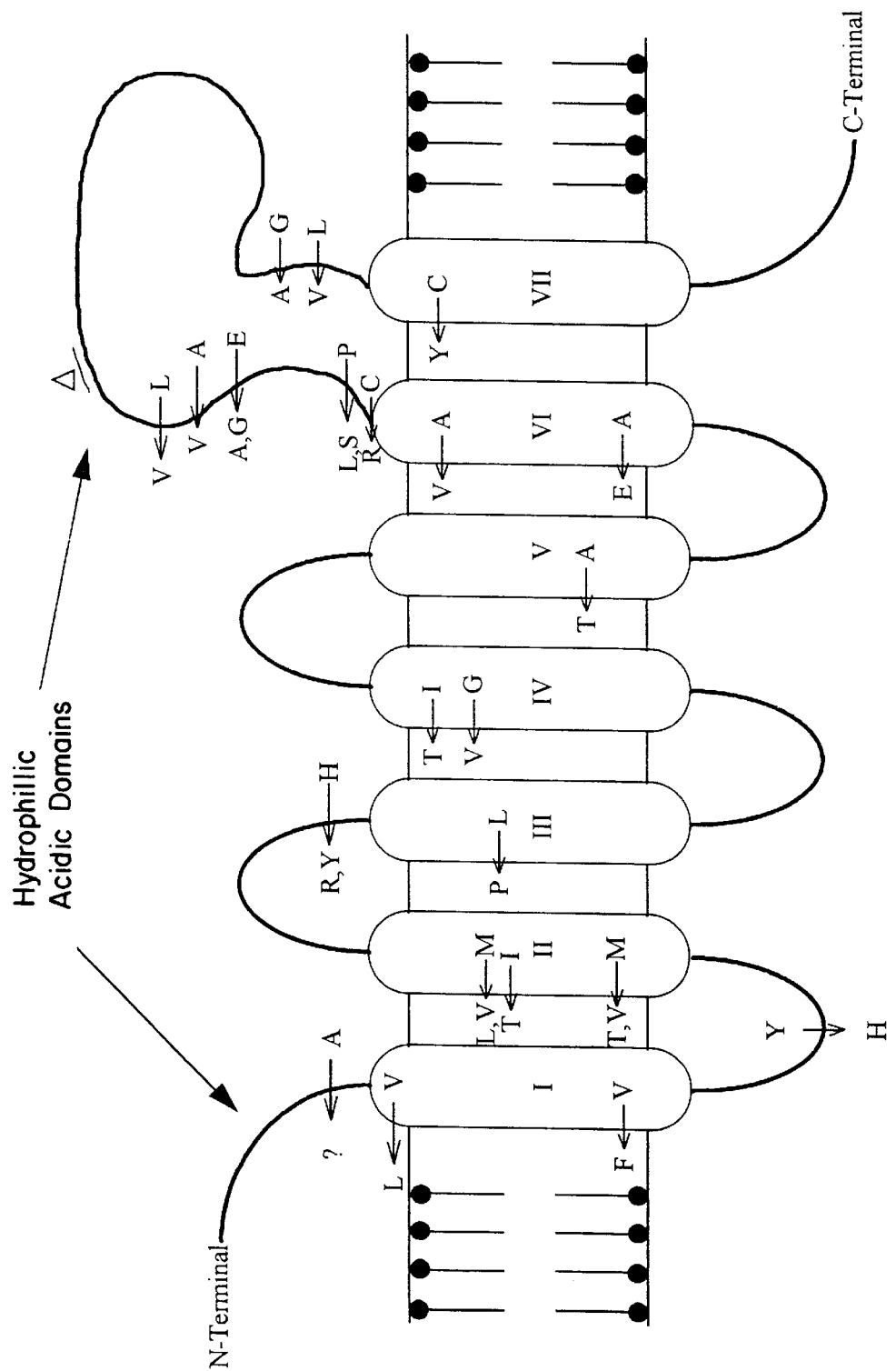
FIG. 5: This figure is a schematic drawing of the predicted structure of the PS1 protein. Roman numerals depict the transmembrane domains. Putative glycosylation sites are indicated as asterisks and most of the phosphorylation sites are located on the same membrane face as the two acidic hydrophilic loops. The MAP kinase site is present at residue 115 and the PKC site at residue 114. FAD mutation sites are indicated by horizontal arrows.
Figure 6:
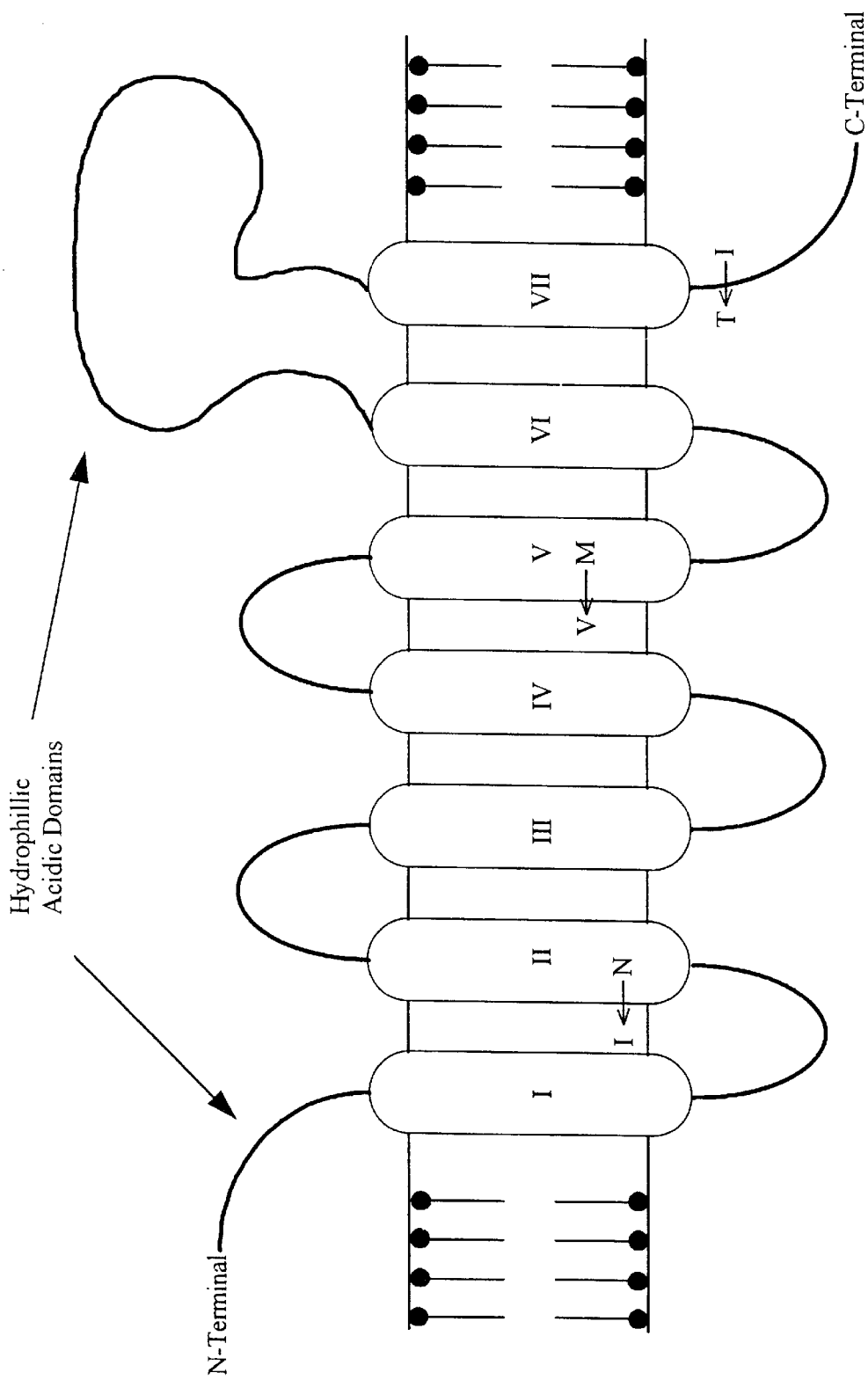
FIG. 6: This figure is a schematic drawing of the predicted structure of the PS2 protein. Roman numerals depict the transmembrane domains. Putative glycosylation sites are indicated as asterisks and most of the phosphorylation sites are located on the same membrane face as the two acidic hydrophilic loops. FAD mutation sites are indicated by horizontal arrows.

As detailed below, the pathogenic mutations in PS1 and PS2 cluster around the TM1→2 loop and TM6→7 loop domains, further suggesting that these domains are the functional domains of these proteins. FIGS. 5 and 6 depict schematic drawings of predicted structures of the PS1 and PS2 proteins, respectively, with the known mutational sites indicated on the figures. As shown in the figures, the TM112 linking sequence is predicted to reside on the opposite side of the membrane to that of the N-terminus and TM6→7 loop, and may be important in transmembrane communication. This is supported by the PS1 Y15H mutation which was observed in a pedigree with early onset familial AD (30–40 years) and by additional mutations in the TM 1→2 helices which might be expected to destabilize the loop. The TM 1→2 loop is relatively short (PS1: residues 101–132; PS2: residues 107–134) making these sequence more amenable to conventional peptide synthesis. Seven PS1 mutations cluster in the region between about codon 82 and codon 146, which comprises the putative first transmembrane domain (TM1), the TM1→2 loop, and the TM2 domain in PS1. Similarly, a mutation at codon 141 of PS2 is also located in the TM2 domain. These mutations probably destabilize the TM1→2 loop domain and its anchor points in TM1 and TM2. At least twelve different PS1 mutations result in the alteration of amino acids between about codons 246 and 410, which are involved in the TM6, TM6→7 loop, and TM7 domains. These mutations may modify the structure or stability of the TM6→7 loop (either directly or by modifying the conformation of TM6 or TM7).

Further evidence for an important functional role residing in the TM6→7 loop is the sequence divergence in the central part of the TM6→7 loop (approximately amino acids 300 to 371) among different members of the presenilin protein family. Similarly, because the N-terminus sequences of members of the presenilin protein family are also divergent, it is likely that the slightly divergent sequences play a role in conferring specificity to the function of each of the different presenilin proteins while the conserved sequences confer the common biologic activities. These regions may represent ligand binding sites. If this is so, mutations in the TM6→7 region are likely to modify ligand binding activity. The TM1→2 loop, which is conserved amongst different members of the presenilin protein family, probably represents an effector domain on the opposing membrane face. With the exception of the Exon 10 splicing mutation, most of the other (missense) mutations align on the same surfaces of putative transmembrane helices, which suggests that they may affect ligand binding or channel functions. Thus, these domains (e.g., TM6→7 and TM1→2 loops) can be used as sites to develop specific binding agents to inhibit the effects of the mutations and/or restore the normal function of the presenilin protein in subjects with Alzheimer's Disease.

The similarity between the putative products of the *C. elegans* SPE-4 and the PS1 genes implies that they may have similar activities. The SPE-4 protein appears to be involved in the formation and stabilization of the fibrous body-membrane organelle (FBMO) complex during spermatogenesis. The FBMO is a specialized Golgi-derived organelle, consisting of a membrane bound vesicle attached to and partly surrounding a complex of parallel protein fibers and may be involved in the transport and storage of soluble and membrane-bound polypeptides. Mutations in SPE-4 disrupt the FBMO complexes and arrest spermatogenesis. Therefore the physiologic function of SPE-4 may be either to stabilize interactions between integral membrane budding and fusion events, or to stabilize interactions between the membrane and fibrillary proteins during the intracellular transport of the FBMO complex during spermatogenesis. Comparable functions could be envisaged for the presenilins. For example, PS1 could be involved either in the docking of other membrane-bound proteins such as βAPP, or the axonal transport and fusion budding of membrane-bound vesicles during protein transport, such as in the Golgi apparatus or endosome-lysosome system. If these hypotheses are correct, then mutations might be expected to result in aberrant transport and processing of βAPP and/or abnormal interactions with cytoskeletal proteins such as the microtubule-associated protein Tau. Abnormalities in the intracellular and in the extracellular disposition of both βAPP and Tau are in fact an integral part of the neuropathologic features of Alzheimer's Disease. Although the location of the PS1 and PS2 mutations in highly conserved residues within conserved domains of the putative proteins suggests that they are pathogenic, at least three of these mutations are themselves conservative, which is commensurate with the onset of disease in adult life. Because none of the mutations observed so far are deletions or nonsense mutations that would be expected to cause a complete loss of expression or function, we cannot predict whether these mutations will have a dominant gain-of-function effect, thus promoting aberrant processing of βAPP or a dominant loss-of-function effect causing arrest of normal βAPP processing. The Exon 10 splicing mutation causes an in-frame fusion of Exon 9 to Exon 10, and may have a structural effect on the PS1 protein which could alter intracellular targeting or ligand binding, or may otherwise affect PS1 function.

An alternative possibility is that the PS1 gene product may represent a receptor or channel protein. Mutations of such proteins have been causally related to several other dominant neurological disorders in both vertebrate (e.g., malignant hyperthermia, hyperkalemic periodic paralysis in humans) and in invertebrate organisms (deg-1(d)mutants in *C. elegans*). Although the pathology of these other disorders does not resemble that of Alzheimer's Disease, there is evidence for functional abnormalities in ion channels in Alzheimer's Disease. For example, anomalies have been reported in the tetra-ethylammonium-sensitive 113pS potassium channel and in calcium homeostasis. Perturbations in transmembrane calcium fluxes might be especially relevant in view of the weak homology between PS1 and the α-ID subunit of voltage-dependent calcium channels and the observation that increases in intracellular calcium in cultured cells can replicate some of the biochemical features of Alzheimer's Disease, such as alteration in the phosphorylation of Tau-microtubule-associated protein and increased production of Aβ peptides.

B. hPS1 Structure

As shown in SEQ ID NO:2, the largest known form of the human PS1 protein comprises 467 amino acids and has a predicted molecular mass of approximately 51.37 kDa. A variant with the above-described alternative splicing of Exon 4 (in which the residues corresponding to positions 26–29 of SEQ ID NO:2 are deleted) would include 4 fewer amino acids and have a mass of approximately 50.93 kDa. Similarly, a variant with the above-described alternative splicing of Exon 9 (in which the residues corresponding to positions 258–290 of SEQ ID NO:2 are deleted) would include 33 fewer amino acids and would have a molecular mass of approximately 47.74 kDa.

The positions of the putative domains are presented in Table 2. Note again that the numbering of the residue positions is with respect to SEQ ID NO:2 and is approximate (i.e. ±2 residues).

A schematic drawing of the putative PS1 structure is shown in FIG. 5. The N-terminus is a highly hydrophilic, negatively charged domain with several potential phosphorylation domains, followed sequentially by a hydrophobic membrane spanning domain of approximately 19 residues (TM1), a charged hydrophilic loop of approximately 32 residues (TM1→2), five additional hydrophobic membrane spanning domains (TM2 through TM6) interspersed with short (1–15 residue) hydrophilic domains (TM2→3 through TM5→6), an additional larger, acidic hydrophilic charged loop (TM6→7) and at least one (TM7), and possibly two, other hydrophobic potentially membrane-spanning domains, culminating in a polar domain at the C-terminus.

The protein also contains a number of potential phosphorylation sites, one of which is a MAP kinase consensus site which is also involved in the hyperphosphorylation of Tau during the conversion of normal Tau to neurofibrillary tangles. This consensus sequence may provide a putative element linking this protein's activity to other biochemical aspects of Alzheimer's Disease, and would represent a likely therapeutic target. Review of the protein structure reveals two sequences YTPF (residues 115–118, SEQ ID NO:2) and STPE (residues 353–356, SEQ ID NO:2) which represent the 5/T-P motif which is the MAP kinase consensus sequence. Several other phosphorylation sites exist with consensus sequences for Protein Kinase C (PKC) activity. Because PKC activity is associated with differences in the metabolism of APP which are relevant to Alzheimer's Disease, these sites on the PS1 protein and its homologues are also sites for targeting therapeutics. Preliminary evidence indicates that, at least in transfected cells, the PS1 protein is phosphorylated only to a minor degree while the PS2 protein is significantly phosphorylated. For PS2 at least, it appears that this phosphorylation occurs on serine residues in the N-terminal domain by a mechanism which does not involve PKC (Capell et al., 1996).

Note that the alternative splicing at the end of Exon 4 removes four amino-acids from the hydrophilic N-terminal domain, and would be expected to remove a phosphorylation consensus sequence. In addition, the alternative splicing of Exon 9 results in a truncated isoform of the PS1 protein wherein the C-terminal five hydrophobic residues of TM6 and part of the hydrophilic negatively-charged TM6→7 loop immediately C-terminal to TM6 is absent. This alternatively spliced isoform is characterized by preservation of the sequence from the N-terminus up to and including the tyrosine at position 256 of SEQ ID NO:2, changing of the aspartate at position 257 to alanine, and splicing to the C-terminal part of the protein from and including tyrosine 291. Such splicing differences are often associated with important functional domains of the proteins. This argues that this hydrophilic loop (and consequently the N-terminal hydrophilic loop with similar amino acid charge) is/are active functional domains of the PS1 product and thus sites for therapeutic targeting.

C. hPS2 Structure

The human PS1 and PS2 proteins show 63% over-all amino acid identity and several domains display virtually complete identity. As would be expected, therefore, hydrophobicity analyses suggest that both proteins also share a similar structural organization. Thus, both proteins are predicted to possess seven hydrophobic putative transmembrane domains, and both proteins bear large acidic hydrophilic domains at the N-terminus and between TM6 and TM7. A further similarity was apparent from the above-described analysis of RT-PCR products from brain and muscle RNA, which revealed that nucleotides 1153–1250 of the PS2 transcript are alternatively spliced. These nucleotides encode amino acids 263–296, which are located within the TM6→7 loop domain of the putative PS2 protein and which share 94% sequence identity with the alternatively spliced amino acids 257–290 in PS1.

The positions of the putative functional domains of the hPS2 protein are described in Table 3. Note that residue positions refer to the residue positions of SEQ ID NO:19, and that the positions are approximate (i.e., ±2 residues).

A schematic drawing of the putative PS2 structure is shown in FIG. 6. The similarity between hPS1 and hPS2 is greatest in several domains of the protein corresponding to the intervals between TM1 and TM6, and from TM7 to the C-terminus of the PS1 protein. The major differences between PS1 and PS2 are in the size and amino acid sequences of the negatively-charged hydrophilic TM6→7 loops, and in the sequences of the N-terminal hydrophilic domains.

The most noticeable differences between the two predicted amino acid sequences occur in the amino acid sequence in the central portion of the TM6→7 hydrophilic loop (residues 304–374 of hPS1; 310–355 of hPS2), and in the N-terminal hydrophilic domain. By analogy, this domain is also less highly conserved between the murine and human PS1 genes (identity=47/60 residues), and shows no similarity to the equivalent region of SPE-4.

7. Presenilin Mutants

A. PS1 Mutants

Several mutations in the PS1 gene have been identified which cause a severe type of familial Alzheimer's Disease. One or a combination of these mutations may be responsible for this form of Alzheimer's Disease as well as several other neurological disorders. The mutations may be any form of nucleotide sequence substitution, insertion or deletion that leads to a change in predicted amino acid sequence or that leads to aberrant transcript processing, level or stability. Specific disease causing mutations in the form of nucleotide and/or amino acid deletions or substitutions are described below but it is anticipated that additional mutations will be found in other families. Indeed, after the initial discovery of five different missense mutations amongst eight different pedigrees (Sherrington et al. 1995), it was expected from experience with other inherited disease (e.g., Amyotrophic lateral sclerosis associated with mutations in the $Ca^{2+}$ superoxide dismutase gene) that additional mutations would be identified. This expectation has been fulfilled by our subsequent discovery of additional mutations in the presenilins (Rogaev et al., 1995) and by similar observations by others (e.g., Cruts et al. (1995) *Hum. Molec. Genet.,* 4:2363–2371; Campion et al., (1995) *Hum. Molec. Genet.* 4:2373–2377). Thus, as used herein with respect to PS1 genes and proteins, the term "mutant" is not restricted to these particular mutations but, rather, is to be construed as defined above.

Direct sequencing of overlapping RT-PCR products spanning the 2.8 kb S182 transcript isolated from affected members of the six large pedigrees linked to chromosome 14 led initially to the discovery of five missense mutations in each of the six pedigrees. Each of these mutations co-segregated with the disease in the respective pedigrees, and were absent from upwards of 142 unrelated neurologically normal subjects drawn from the same ethnic origins as the FAD pedigrees (284 unrelated chromosomes). The location of the gene within the physical interval segregating with AD3 trait, the presence of eight different missense mutations which co-segregate with the disease trait in six pedigrees definitively linked to chromosome 14, and the absence of these mutations in 284 independent normal chromosomes cumulatively confirmed that the PS1 gene is the AD3 locus. Further biological support for this hypothesis arises from the facts that the residues mutated in FAD kindreds are conserved in evolution (e.g., hPS1 v. mPS1), that the mutations are located in domains of the protein which are also highly conserved in other vertebrate and invertebrate homologues, and that the PS1 gene product is expressed at high levels in most regions of the brain, including those most severely affected by AD.

Since the original discovery of the PS1 gene, many additional mutations associated with the development of AD have been catalogued. Table 4 characterizes a number of these. Each of the observed nucleotide deletions or substitutions occurred within the putative ORF of the PS1 transcript, and would be predicted to change the encoded amino acid at the positions shown. The mutations are listed with reference to their nucleotide locations in SEQ ID NO: 1 and with reference to their amino acid positions in SEQ ID NO:2. An entry of "NA" indicates that the data was not available. As discussed in the next section, a number of PS2 mutations have also been found. A comparison of the hPS1 and hPS2 sequences is shown in FIG. 4 and reveals that these pathogenic mutations are in regions of the PS2 protein which are conserved in the PS1 protein. Therefore, corresponding mutations in the PS1 protein may also be expected to be pathogenic and are included in the PS1 mutants provided and enabled herein. Furthermore, any pathogenic mutation identified in any conserved region of a presenilin gene may be presumed to represent a mutant of the other presenilins which share that conserved region.

Interestingly, mutations A260V, C263R, P264L, P267S, E280A, E280G, A285V, L286V, A291-319, G384A, L392V, and C410Y all occur in or near the acidic hydrophilic loop between the putative transmembrane domains TM6 and TM7. Eight of these mutations (A260V, C263R, P264L, P267S, E280A, E280G, A285V, L286V) are also located in the alternative splice domain (residues 257–290 of SEQ ID NO:2).

All of these mutations can be assayed by a variety of strategies (direct nucleotide sequencing, allele specific oligonucleotides, ligation polymerase chain reaction, SSCP, RFLPs, new "DNA chip" technologies, etc.) using RT-PCR products representing the mature mRNA/cDNA sequence or genomic DNA.

B. PS2 Mutants

The strong similarity between PS1 and the PS2 gene product raised the possibility that the PS2 gene might be the site of disease-causing mutations in some of a small number of early onset AD pedigrees in which genetic linkage studies have excluded chromosomes 14, 19 and 21. RT-PCR was used to isolate cDNAs corresponding to the PS2 transcript from lymphoblasts, fibroblasts or postmortem brain tissue of affected members of eight pedigrees with early onset FAD in which mutations in the βAPP and PS1 genes had previously been excluded by direct sequencing studies.

Examination of these RT-PCR products detected a heterozygous A→G substitution at nucleotide 1080 in all four affected members of an extended pedigree of Italian origin (Flo10) with early onset, pathologically confirmed FAD (onset 50–70 yrs). This mutation would be predicted to cause a Met-Val missense mutation at codon 239 in TM5.

A second mutation (A→T at nucleotide 787) causing a Asn-Ile substitution at codon 141 in TM2 was found in affected members of a group of related pedigrees of Volga German ancestry (represented by cell lines AG09369, AG09907, AG09952, and AG09905, Coriell Institute, Camden N.J.). Significantly, one subject (AG09907) was homozygous for this mutation, an observation compatible with the inbred nature of these pedigrees. Significantly, this subject did not have a significantly different clinical picture from those subjects heterozygous for the N141I mutation. Neither of the PS2 gene mutations were found in 284 normal Caucasian controls nor were they present in affected members of pedigrees with the AD3 type of AD.

Both of these PS2 mutations would be predicted to cause substitution of residues which are highly conserved within the PS1/PS2 gene family.

An additional PS2 mutation is caused by a T→C substitution at base pair 1624 causing an Ile to Thr substitution at codon 420 of the C-terminus. This mutation was found in an additional case of early onset (45 yrs) familial AD.

These hPS2 mutations are listed in Table 5 with reference to their nucleotide locations in SEQ ID NO:18 and with reference to their amino acid positions in SEQ ID NO:19. An entry of "NA" in the table indicates that the data was not available. As discussed in the previous section, a number of PS1 mutations have also been found. A comparison of the hPS1 and hPS2 sequences is shown in FIG. 4 and reveals that these pathogenic mutations are in regions of the PS1 protein which are largely conserved in the PS2 protein. Therefore, corresponding mutations in the PS2 protein may also be expected to be pathogenic and are included in the PS2 mutants provided and enabled herein. Furthermore, any pathogenic mutation identified in any conserved region of a presenilin gene may be presumed to represent a mutant of the other presenilins which share that conserved region.

The finding of a gene whose product is predicted to share substantial amino acid and structural similarities with the PS1 gene product suggests that these proteins may be functionally related as independent proteins with overlapping functions but perhaps with slightly different specific activities, as physically associated subunits of a multimeric polypeptide or as independent proteins performing consecutive functions in the same pathway.

The observation of three different missense mutations in conserved domains of the PS2 protein in subjects with a familial form of AD argues that these mutations are, like those in the PS1 gene, causal to AD. This conclusion is significant because, while the disease phenotype associated with mutations in the PS1 gene (onset 30–50 yrs, duration 10 yrs) is subtly different from that associated with mutations in the PS2 gene (onset 40–70 yrs; duration up to 20 yrs), the general similarities clearly argue that the biochemical pathway subsumed by members of this gene family is central to the genesis of at least early onset AD. The subtle differences in disease phenotype may reflect a lower level of expression of the PS2 transcript in the CNS, or may reflect a different role for the PS2 gene product.

By analogy to the effects of PS1 mutations, PS2 when mutated may cause aberrant processing of APP (Amyloid Precursor Protein) into AP peptide, hyperphosphorylation of Tau microtubule associated protein and abnormalities of intracellular calcium homeostasis. Interference with these anomalous interactions provides for therapeutic intervention in AD.

Finally, at least one nucleotide polymorphism has been found in one normal individual whose PS2 cDNA had a T→C change at bp 626 of SEQ ID NO:18, without any change in the encoded amino acid sequence.

8. Presenilin Processing and Interactions

Employing the antibodies and protein-binding assays disclosed herein, the processing and protein-protein interactions of both normal and mutant presenilins were investigated. It was found that mutations in the presenilins lead to dramatic changes in both their intracellular processing (e.g., endoproteolytic cleavage, ubiquitination, and clearance) and their intracellular interactions with other proteins expressed in human brain. As described below, knowledge of presenilin processing and interactions, and particularly changes in mutant presenilin processing and interactions, provides for new diagnostic and therapeutic targets for Alzheimer's Disease and related disorders.

Western blot analysis suggests that the normal presenilins undergo proteolytic cleavage to yield characteristic N- and C-terminal fragments. As noted above, the normal presenilin proteins have an expected molecular mass of 47–51 kDa depending, in part, upon mRNA splice variations. Analysis of Western blots suggests, however, that the normal presenilin proteins undergo proteolytic cleavage to yield an approximately 35 kDa N-terminal fragment and an approximately 18 kDa C-terminal fragment. In particular, Western blots bearing lysates from wild-type native human fibroblasts, human neocortical brain tissue from control subjects, and neocortical brain tissue from non-transgenic and PS1 transgenic mice using antibodies ("14.2") recognizing PS1-specific residues 1–25 at the N-terminus reveal the presence of a strong immunoreactive band of approximately 35 kDa and, after longer exposures, a weaker band of approximately 45 kDa which presumably represents the full-length PS1 protein. Antibodies ("520") directed at residues 304–318 at the apex of the TM6→7 loop of PS1, and antibodies ("4627") directed at residues 457–467 in the C-terminus of PS1, both recognize the same strong band of approximately 18 kDa. Antibodies 520 also recognize a weak band of 45 kDa coincident with the PS1 band detected by 14.2. These observations suggest that an endoproteolytic cleavage event occurs near the junction of exons 9 and 10 of PS1. Sequencing of the major C-terminal fragment from PS1-transfected human embryonic kidney cells (HEK 293) showed that the principal endoproteolytic cleavage occurs near M298 in the proximal portion of the TM6→7 loop. Full length PS1 in these cells is quickly turned over ($t_{1/2}$<60 min.).

To determine whether mutations in the presenilin proteins result in alterations of their proteolytic cleavage, Western blots containing lysates of fibroblast and neocortical brain homogenates from normal subjects and subjects carrying PS1 mutations were compared. In fibroblasts, there were no obvious differences in the relative intensities of the protein bands when lysates from heterozygous carriers of the PS1 mutations were compared with normal homozygotes. In contrast, a dramatic difference between carriers and normals was detected in homogenates of temporal neocortex from AD affected heterozygous carriers of either the PS1 A246E or C410Y mutations (which are located in TM6 and TM7 respectively). In heterozygotes, a strongly immunoreactive band of approximately 45 kDa was detected which initially appeared to correspond to the full-length PS1 protein. Fragments with different apparent molecular weights were observed is contemplated to reflect either alternate cleavage sites such as that arising from activation of Caspase-3 by apoptosis, or they might arise from partial ubiquitination of conventional fragments and failed proteasomal degradation. The implication is that the biochemical processes leading to the genesis of these bands (and/or the bands themselves) might be diagnostically useful and indicate a failure of normal processing of PS1, and thus represent a potential therapeutic target.

In order to identify proteins which bind to or otherwise interact with the presenilins, a yeast two-hybrid system was used as described below (Example 15). In particular, because mutations in the TM6→7 loop domains are known to be causative of AD, a yeast two-hybrid system was used to identify cellular proteins which interact with the normal presenilin TM6→7 loop domains. In brief, cDNA sequences encoding the TM6→7 loop (i.e., residues 266 to 409 of PS1) were ligated in-frame to the GAL4 DNA-binding domain in the pAS2-1 yeast expression plasmid vector (Clontech). This plasmid was then co-transformed into *S. cerevisiae* strain Y190 together with a library of human brain cDNAs ligated into the pACT2 yeast expression vector bearing the GAL4 activation domain (Clontech). After appropriate selection, a number of clones were recovered and sequenced bearing human brain cDNAs encoding peptides which interact with the normal presenilin TM6→7 domain. To determine whether presenilin interactions would be modified by AD related mutations within the TM6→7 loop, the yeast two-hybrid system was again used with TM6→7 loop peptides containing the L286V, the L392V, and the exon 10 splicing mutants. When these mutant constructs were used as "bait" to re-screen the brain cDNA: GAL4 activation domain library, some but not all of the brain cDNA sequences which interacted with the normal presenilin were recovered. In addition, several new clones were identified which interacted with the mutant but not the normal presenilins. The clones corresponding to the presenilin-interacting proteins with the highest presenilin affinity are described in Example 15 and below.

Two overlapping clones have been identified as representing a portion of the human protein alternatively known as Antisecretory Factor ("ASF") or the Multiubiquitin chain-binding S5a subunit of the 26S proteasome ("S5a"). These clones, which together include residues 70–377 of S5a, were shown to interact with the normal presenilin TM6→7 loop domain but only weakly with two TM6→7 loop domain mutants tested (L286V, L392V). The PS1:S5a interaction was confirmed by co-immunoprecipitation studies, and immunocytochemical studies showed S5a and PS1 are expressed in contiguous intracellular domains (e.g., Golgi and ER).

The interaction between PS1 and the proteasome could be relevant to the pathogenesis of Alzheimer's Disease (AD) through several possible mechanisms. First, most mammalian cells seem to maintain very low levels of the PS1 holoprotein. A notable exception to this are cells expressing the PS1 Δ290–319 splicing mutation, which results in a mutant PS1 holoprotein which is not endoproteolytically cleaved and which is, therefore, readily detectable. In the case of the Δ290–319 splicing mutation at least, the accumulation of the mutant PS1 holoprotein, or the failure to produce the 35 kDa N-terminal and 18 kDa C-terminal fragments, appears sufficient to cause AD. It is possible, therefore, that even very subtle changes in the turnover of the mutant PS1 holoprotein might have significant pathophysiological effects. Thus, mutations in either the presenilins or S5a which perturb the PS1:S5a interaction in the mammalian CNS may cause the presenilin holoprotein to be aberrantly processed and cause AD. Therefore, modulation of presenilin proteolytic pathways might be applied therapeutically to enhance removal of mutant holoprotein.

To assess a potential in vivo relationship between PS1 and the S5a subunit of the 26S proteasome, we investigated the effects of proteasome inhibitors on PS1 metabolism. Short term organotypic cultures of neonatal rat hippocampus and carcinoma of colon (CaCo2) cells (which express high levels of both PS1 and PS2) were administered either the specific, reversible proteasome inhibitor N-acetyl-leucinyl-leucinyl-norleucinyl-H (LLnL) (Rock et al. (1994) *Cell* 78:761–771), or the specific irreversible proteasome inhibitor lactacystin (Fenteany et al., 1995). Both agents caused an increase in the steady state levels of PS1 holoprotein. Both agents also prolonged the half-life of the PS1 holoprotein in pulse chase experiments in hippocampal slices from 15 minutes to 35 minutes. As noted above, the PS1 holoprotein appears to be rapidly turned over in normal cells. However, even after four hours of metabolic labeling, neither of the proteasome inhibitors affected the level of the 35 kDa N-terminal PS1 fragment, or resulted in the appearance of novel species. These studies imply that the majority of the PS1 holoprotein is catabolized directly via a rapid, proteasome dependent pathway in a manner similar to several other integral membrane proteins (e.g. Sec61 and CFTR). On the other hand, because the ~35 kDa and ~18 kDa terminal fragments are still produced in the presence of proteasome inhibitors, this endoproteolytic cleavage of PS1 is probably not mediated by the proteasome pathway. Therefore, it appears that at least two proteolytic pathways act upon the PS1 holoprotein.

That PS1 and S5a interact within mammalian cells is strongly supported by coimmunoprecipitation studies in HEK293 cells transiently transfected with wild type human PS1 and/or S5a tagged with a c-myc epitope. These experiments confirm that myc-S5a could be specifically co-immunoprecipitated with PS1 only from double transfected cells. While this interaction was stabilized by the use of the membrane soluble cross-linking agent DSP, it was also weakly detectable in its absence, and could be reproduced with several independent anti-PS1 antibodies. Immunocytochemical studies add further proof to the notion that this interaction may occur under physiologic circumstances. Thus, PS1 and S5a proteins are both presented within neurons in the mouse cerebellum, neocortex and hippocampus (Lee, et al. (1996) *J. Neurosci.* 16, 7513–7525. Furthermore, these proteins are expressed in contiguous intracellular compartments in native fibroblasts. S5a is predominantly localized within the perinuclear cytoplasm where it overlaps with the Golgi marker p58 and to a lesser extent with markers of the ER (not shown). PS1 is also expressed in the ER, Golgi and cytoplasmic vesicles (Walter, et al, (1996) *Molec. Medicine* 2, 673–691. Cumulatively, these studies strongly support the existence of a physiologic interaction between PS1 and S5a.

To determine whether FAD-linked mutations within the $PS1_{260-409}$ loop might modify this interaction, we used the yeast-two-hybrid interaction assay to compare the affinity between S5a (expressed as a GAL4-DNA-Activation Domain fusion construct) and mutant or wild type $PS1_{260-409}$ loop proteins (expressed as GAL4-DNA-Binding Domain (GBD) fusion constructs). The interaction of S5a with the Leu286Val and Leu392Val mutant $PS1_{260-409}$ loops was significantly diminished compared to the wild type $PS1_{260-409}$ loop (p<0.05). These differences were not attributable to instability of the mutant $PS1_{260-409}$-GBD mRNAs or fusion proteins because equivalent quantities of wild-type or mutant $PS1_{260-409}$/GBD fusion proteins were present in the transformed yeast cells. The disruption of the PS1:S5a interaction by clinically relevant single hydrophobic residue substitutions inn the $PS1_{260-409}$ loop is analogous to the disruption of the S5a:ubiquitin interaction caused by comparable mutations in ubiquitin (e.g. Leu8Ala, I13rrAla, or Val70Ala)(Beal, Deveraux, Xia, Rechsteiner & Pickart (1966) *Proc. Natl. Acad. Sci. USA* 93, 861–866). Our studies do not address whether or how mutations in other domains might affect the PS1:S5a interaction. However, it is conceivable that they could alter the conformation of PS1 or affect other biochemical events upstream or downstream of the PS1:S5a interaction.

The PS1:S5a interaction might simply reflect the known involvement of the proteasome in the degradation of PS1 holoprotein (Fraser, et al (1997) *Neurobiol. Aging* in the press). However, two observations suggest that this is unlikely to be the sole explanation. First, ubiquitinated-PS1 was not detectable in the anti-PS1 immunoprecipitates which also contain S5a (data not shown). Consequently, it is unlikely that the interaction simply reflects binding of S5a to ubiquitinated-PS1 targeted for proteasomal degradation. Second, no other proteasome subunits were identified in the yeast-two-hybrid assay. An alternate explanation for the PS1: S5a interaction is that it may allow PS1 to modify the activity of S5a. Not all of the activities of S5a are known (Johansson, Lonnroth, Lange, Jonson & Jennishe (1995) *J. Biol. Chem.* 270, 20615–20620). However, there is strong evidence that S5a and its evolutionary homologues in *S. cerevisiae* (McbI) and Arabiodopsis (MbpI) are involved in regulated protein processing. Thus, deletion mutants of McbI reveal that McbI and S5a play a role only in regulating proteasome degradation of selected proteins (van Nocker et al. (1996) *Molec. Cell Biol.* 16, 6020–6028). In addition, an appreciable proportion of cellular S5a/MbpI exists free of the proteasome, and excess free MbpI inhibits proteasome function in vitro (Deveraux, van Nocker, Mahaffey, Vierstra & Rechsteiner (1995) *J. Biol. Chem.* 270, 29660–29663). The reduction in the PS1: S5a interaction caused by some PS1 mutations might therefore lead to dysregulation of the proteasome and mis-processing of selected proteasome substrates.

Indirect evidence for defective proteasome-mediated degradation in AD emerges from: 1) the widespread accumulation of ubiquitinated proteins in AD brain (Kudo, Iqbal, Ravid, Swaab & Grundke-Iqbal (1994) *Brain Research* 639, 1–7)(Morishima-Kawashima & Ihara (Springer-Verlag, Berlin, 1995) in *Alzheimer's Disease: lessons from cell biology.* (eds. Kosik, Christen, Y. & Selkoe, D. J.); 2) from the discovery of proteasome subunits as immunoreactive components of AD neuropathology (Fergusson, et al. (1996) *Neurosci. Letts.* 219, 167–170).; and 3) from in vitro experiments suggesting that the proteasome may partially degrade βAPP but not AB (Gregori, Bhasin, & Goldgaber (1994) *Biochem. Biophys. Res. Comm.* 203, 1731–1738)(Goldgaber & Gregori (1996) *Neurobiol. Aging* 17, A763 pg S189) (Klafki, Abramowski, Swoboda, Paganetti & Stafenbiel (1996) *Biol. Chem.* 271, 28655–28659)(Marambaud, Wilk & Checler (1996) *J. Neurochem.* 67, 2616–2619). To investigate a potential link between the PS1:S5a interaction and βAPP processing we examined the effects of the proteasome inhibitors on βAPP processing in HEK293 cell lines stably transfected with wild type human $\Delta APP_{695}$. These agents did not alter βAPP transcription or cellular viability (data not shown). However, significant changes in βAPP processing were detected in cells treated with either LLnL or lactacystin (not shown). Thus proteasome inhibitors caused significant accumulation of intracellular 10 kDa C-terminal βAPP secretase fragment and N-glycosylated immature βAPP, but caused only a much smaller increase in mature N-/O-glycosylated βAPP. Both LLnL and lactcystin also caused significant increases in secreted soluble βAPP-a, AB and p3. To explore both the speciation of AB and the effects of PS1 mutations, LLnL was administered to HEK293 cells stably transfected with wild-type human $APP_{695}$ and either wild-type or L392V mutant human PS1 cDNAs. Both cell types responded to LLnL by dramatically increasing secreted $A\beta_{42}$ but not $A\beta_{40}$. However, cells with mutant PS1 showed a minimally larger increase in $A\beta_{42}$ ($A\beta_{x-42}$: 421±13.01%; of baseline; $A\beta_{1-42}$: 413±11.5% of baseline) relative to wild type cells ($A\beta_{x-42}$: 360±19.8%; $A\beta_{1-42}$: 364±52.49%) (p=n.s.).

These experiments lead to two conclusions. First, some PS1 mutations can modulate the interaction between PS1 and a regulatory subunit of the proteasome. Second, inhibition of the proteasome causes the accumulation of immature βAPP in the ER, which is subsequently catabolized through a variety of pathways to render greatly increased quantities of $A\beta_{42}$. This is congruent with recent observations that mutations in PS1 are associated with increased production of $A\beta_{42}^{6-9}$; that $A\beta_{42}$ is present in the ER lumen of neuronal cells (Harmann et al. submitted, 1997); that there are different intracellular locations for $A\beta_{40}$ and $A\beta_{42}$ production (Tienari et al. (1997) *Proc. Natl. Acad Sci USA* 94, 4125–4130); that blockade of ER to Golgi trafficking with Brefeldin A or thermal block causes increased intracellular $A\beta_{42}$ production (Harmann, et al. (1997) *Nature Med* submitted)(Wild, et al. (1997) *J. Biol. Chem* in the press); and that N-glycosylated immature (ER) forms of βAPP can be co-immunoprecipitated with PS2 and perhaps PS1 (Tienari et al. (1997) *Proc. Natl. Acad Sci USA* 94, 4125–4130). In the context of these results, our data suggest that the PS1:proteasome interaction in the ER-Golgimay subserve a proof-reading/trafficking function for a limited number of protein substrates including βAPP. Mutations in PS1 may alter this function, resulting in aberrant ER/Golgi processing of βAPP and overproduction of $A\beta_{42}$. Finally, activation of ubiquitin-dependent proteasome mediated proteolysis is necessary for long term potentiation (LTP) (Cook, et al. (1997) *Keystonia Symposia*). The interaction between PS1 and regulatory subunit of the proteasome may therefore also provide an explanation for abnormalities in LTP which have been observed in transgenic mice overexpressing mutant human PS1 but not normal PS1 (Agopyan et al. submitted).

Thus, the presenilin-proteasome interaction appears significant in several respects. First, the facts that the normal presenilin TM6→7 loop domain interacts with the S5a protein, that the mutant presenilin TM6→7 loop domains fail to interact (or interact very weakly) with the S5a protein, that presenilins bearing mutations in the TM6→7 loop domain appear to be differently cleaved and multiubiquitinated, that proteasomes are known to be involved in the cleavage and clearance of a variety of proteins (particularly multiubiquitinated proteins), that inhibition of proteasome activity inhibits cleavage of the presenilin holoproteins, and that SSa processing is altered in AD brains, all suggest that either (1) the S5a subunit and the 26S proteasome are involved in the normal processing of the presenilins and that mutations which disrupt this normal interaction may be responsible for the abnormal processing observed in TM6→7 loop domain mutants, or (2) that the presenilin-proteasome interaction may modulate the activity of one or both proteins without involving proteasome-mediated presenilin processing. In support of these hypotheses, it should be noted that failure to clear hyperubiquitinated phosphorylated Tau and other microtubule associated proteins is a prominent feature of Alzheimer's Disease (Kosik and Greenberg (1994) *Alzheimer Disease*. New York, Raven Press. 335–344), suggesting a possible link between TM6→7 loop domain mutants, presenilin-proteasome interactions, Tau-proteasome interactions, and the neurofibrillary tangles of Tau protein in AD brains. Finally, proteasomes are known to be capable of degrading APP and of binding the Aβ peptides which are associated with Alzheimer's Disease, suggesting a possible link between TM6→7 loop domain mutants, presenilin-proteasome interactions, APP-proteasome interactions, and the amyloid plaques characteristic of AD brains.

Therefore, presenilin processing and the presenilin-proteasome interaction are clear targets for the diagnosis as well as therapeutic intervention in AD. Thus, as described below, assays may now be provided for drugs which affect the proteasome-mediated cleavage of the presenilins, which affect the alternative endoproteolytic cleavage and ubiquitination of the mutant presenilins, or which otherwise affect the processing and trafficking of the presenilins or the S5a subunit of the proteasome. In addition, as mutations in the 26S proteasome which disrupt the normal processing of the presenilins are likely to be causative of Alzheimer's Disease, additional diagnostic assays are provided for detecting mutations in the S5a or other subunits of the proteasome. Finally, additional transformed cell lines and transgenic models may now be provided which have been altered by the introduction of a normal or mutant sequence encoding at least a functional domain of the proteasome.

Another presenilin-interacting protein, designated GT24, was identified from several overlapping clones obtained using the yeast two-hybrid system and a human adult brain cDNA library. Six longer GT24 clones of ~3.8 kb in size were subsequently obtained by screening of conventional cDNA libraries. The open reading frame within the longest GT24 clone obtained to date (Accession number U81004) suggests that GT24 is a protein of at least 1040 amino acids with a unique N-terminus, and considerable homology to several armadillo (arm) repeat proteins at its C-terminus. Thus, for example, residues 440–862 of GT24 (numbering from Accession number U81004) have 32–56% identity ($p=1.2e^{-133}$) to residues 440–854 of murine p120 protein (Accession number Z17804), and residues 367–815 of GT24 have 26–42% identity (p=0.0017) to residues 245–465 of the *D. melanogaster* armadillo segment polarity protein (Accession number P18824). The GT24 gene maps to chromosome 5p15 near the anonymous microsatellite marker D5S748 and the Cri-du-Chat syndrome locus.

Hybridization of unique 5' sequences of GT24 to Northern blots reveals that the GT24 gene is expressed as a range of transcripts varying in size between ~3.9 and 5.0 kb in several regions of human brain, and in several non-neurologic tissues such as heart. In addition, in situ hybridization studies using a 289 bp single copy fragment from the 5' end of GT24 in four month old murine brain reveal GT24 transcription closely parallels that of PS1, with robust expression in dentate and hippocampal neurons, in scattered neocortical neurons, and in cerebellar Purkinje cells. In day E13 murine embryos, GT24 is widely expressed at low levels, but is expressed at somewhat higher levels in somites and in the neural tube. A physiological in vivo interaction between GT24 and PS1 is supported by co-immunoprecipitation studies in HBEK293 cells transiently transfected with a wild type human PS1 cDNA, a c-mac-tagged cDNA encoding residues 484–1040 of GT24 (including the C-terminal arm repeats), or both cDNAs. Cell lysates were immunoprecipitated with anti-PS1 antibodies and then investigated for the presence of the myc-GT24 protein by immuno-blotting. In PS1/myc-GT24 double transfected cells, the immunoprecipitates contained a robust anti-mc reactive band of Mr ~60 kDa, which co-migrated with a mc-GT24 control. In cells transfected with mcGT24 only, a very weak band was detected after long exposures, presumably reflecting interaction of the myc-GT24 with low levels of endogenous PS1. No myc-reactive bands were detected in cells transfected with PS1 alone, or in any of the transfected cells immunoprecipitated with pre-immune serum. Taken together, these observations strongly suggest that the observed PS1:GT24 interaction is physiologically relevant.

To explore whether mutations in the TM6–TM7 loop of PS1 might influence the PS1:GT24 interaction, we employed quantitative liquid β-galactosidase assays to directly compare the yeast-two-hybrid interaction of the C-terminal residues 499–1040 of GT24 with wildtype and mutant $PS1_{266-409}$. These studies revealed that the interaction of $GT24_{499-1040}$ with a L286V mutant PS1 domain was not significantly different from the interaction with the corresponding wild type PS1 domain. In contrast, there was a significant reduction in the $GT24_{499-1040}$ interaction with the L392V mutant PS1 construct. The absence of an effect of the L286V mutation, and the presence of an effect with the L392V mutation, may suggest that some mutations may effect PS1:GT24 binding, while others may modulate the PS1 response to GT24 binding.

The PS1:GT24 interaction could support several functions. The arm repeat motif of GT24 has been detected in several proteins with diverse functions including β-catenin and its invertebrate homologue armadillo, plakoglobin, p120, the adenomatous polyposis coli (APC) gene, suppressor of RNA polymerase 1 in yeast (SRP1), and smGDS. For example, β-catenin, p120 and plakoglobin play an essential role in intercellular adhesion. β-catenin/armadillo is involved in transduction of wingless/Wnt signals during cell fate specification, and β-catenin and p120 may play a role in other receptor mediated signal transduction events including responses to trophic factors such as PDGF, EGF, CSF-1 and NGF.

If the PS1:GT24 interaction is part of intercellular signaling pathways for trophic factors, or is involved in cell-cell adherence, disruption of the interaction may be involved in the neurodegenerative processes in PS-linked FAD brains, and in the increased sensitivity of PS1 or PS2 transfected cells to apoptosis (Wolozin et al. (1996) *Science* 274:1710–1713). It is of note that at least one arm protein, smGDS, stimulates GDP/GTP exchange on intracellular G-proteins (Kikuchi et al. (1992) *Oncogene* 7:289–293; Borguski et al. (1993) *Nature* 366:643–654), and that mutant forms of both βAPP and PS2 are thought to activate programmed cell death pathways through mechanisms involving heterotrimeric GTP/GDP proteins (Wolozin et al., 1996; Okamoto, et al. (1995) *J. Biol. Chem.* 270:4205–4208; Yamatsuji et al. (1996) *Science* 272:1349–1352).

The interaction between PS1 and GT24 may also be involved in some of the developmental phenotypes associated with homozygous PS1 knockouts in mice such as failed somitogenesis of the caudal embryo, short tail, and fatal cerebral hemorrhage at around day E13.5 (Wong et al. (1996) *Neuroscience* 22:728). The resemblance of these skeletal phenotypes to those associated with null mutations in PAXI and Notch, and the apparent suppressor effect of mutations in se112 on Notch/lin12 mediated signaling in *C. elegans* suggest that the PS proteins function in the Notch signaling pathway. In addition, mice homozygous for a knockout of the Wnt-3a gene (Takada et al. (1994) *Genes & Dev.* 8: 174–189), and murine homozygotes for a spontaneous mutation, "vestigial tail" or vt, in the Wnt-3a gene (Greco et al. (1996) *Genes & Dev.* 10:313–324), have skeletal phenotypes of defective caudal somite and tail bud formation. The Wnt-3a knockouts are embryonic lethal by day 12.5. These phenotypes are similar to those of homozygous knockouts of the murine PS1 gene (Wong et al., 1996). The observation that GT24 binds to PS1, is expressed in embryonic somites, and contains the armadillo repeat motif of other proteins used in the downstream signaling in the Wingless/Wnt pathway suggests that PS1 is a downstream element in the GT24-Wingless/Wnt pathway. This can be exploited to create a bioassay for drugs affecting the GT24-PS1 interaction directly, or affecting upstream or downstream elements of that interaction, and can therefore be used to monitor the effects of presenilin mutations. For example, cells transfected with normal or mutant presenilins may be exposed to soluble Wnt-3a protein (or other Wnt proteins such as Wnt-1) and assayed for changes which are specific to the Wingless/Wnt signaling pathway, or for any of the other changes described herein for cell assays (e.g., intracellular ion levels, Aβ processing, apoptosis, etc.).

In addition, we have observed that GT24 also interacts with PS2. Transfection of GT24 causes significant morphological changes in several different cell types. These changes, including dendritic arborizations of the cytoplasm and the apparent aggregation of GT24 near regions of cell:cell contact, suggest that the PS2/PS2:GT24 interaction may be involved in both cytoskeletal organization, in anchoring of cellular membranes to the cytoskeleton and in intercellular signal transduction. These multiple functions are analogous to the multiple functions of armadillo proteins and beta-catenin. This suggests a role in differentiation and argues that, like other armadillo proteins such as beta-catenin and APC, GT24 (and its interaction with PS1 and PS2) may play a role in regeneration and repair after injury, and in oncogenesis. Thus, PS1, PS2 and GT24 may also be useful in tissue regeneration and repair and cancer models.

Thus, the GT24 protein also presents new targets for diagnosis as well as therapeutic intervention in AD. For example, as mutations in the GT24 protein may also be causative of Alzheimer's Disease, additional diagnostic assays are provided for detecting mutations in these sequences. Similarly, additional transformed cell lines and transgenic models may now be provided which have been altered by introduction of a normal or mutant nucleic acid encoding at least a functional domain of the GT24 protein, and particularly the functional domains (e.g., residues 70–377) which interact with the presenilins. Such transformed cells and transgenics will have utility in assays for compounds which modulate the presenilin-GT24 interactions.

Another independent clone isolated in the initial screening with the wild type $PS1_{266-409}$ "bait" also encodes a peptide with C-terminal arm repeats (clone Y2H25, Accession number U81005). A longer cDNA sequence corresponding to the Y2H25 clone has been deposited with GenBank as human protein p0071 (Accession number X81889). Comparison of the predicted sequence of the Y2H25/p0071 ORF with that of GT24 confirms that they are related proteins with 47% overall amino acid sequence identity, and with 70% identity between residues 346–862 of GT24 and residues 509–1022 of Y2H25. This suggests that PS1 interacts with a novel class of arm repeat containing proteins. The broad ~4.5 kb hybridization signal obtained on Northern blots with the unique 5' end of GT24 could reflect either alternative splicing/polyadenylation of GT24 or, less likely, the existence of additional members of this family with higher degrees of N-terminal homology to GT24 than Y2H25. Cells transformed with these sequences, or transgenic animals including these sequences, will have additional utility as animal models of AD and for use in screening for compounds which modulate the action of normal and mutant presenilins.

The yeast two-hybrid system also identified a clone which shows sequence identity to the human p40 subunit (Mov34) of the 26S proteasome. Interestingly, this clone was identified by interaction with a mutant PS1 TM6→7 loop domain but not with the wild type TM6→7 domain. For all of the reasons stated above with respect to the S5a subunit of the 26S proteasome, the interaction between the presenilins and the p40 subunit is a clear target for the diagnosis as well as therapeutic intervention in AD. Thus, as described below, assays may now be provided for drugs which affect the proteasome-mediated cleavage and clearance of the presenilins, which affect the alternative endoproteolytic cleavage and ubiquitination of the mutant presenilins, or which otherwise affect the processing and trafficking of the presenilins. In addition, as mutations in the p40 subunit which disrupt the normal processing of the presenilins may be causative of Alzheimer's Disease, additional diagnostic assays are provided for detecting mutations in the p40 subunit of the proteasome. Finally, additional transformed cell lines and transgenic models may now be provided which have been altered by the introduction of a normal or mutant sequence encoding at least a functional domain of this proteasome subunit.

A number of other presenilin-interacting proteins have been identified according to the methods of the present invention. These are described in Example 15. Each of these proteins, and particularly those which interact selectively with either the normal or mutant presenilins, provide new targets for the identification of useful pharmaceuticals, new targets for diagnostic tools in the identification of individuals at risk, new sequences for the production of transformed cell lines and transgenic animal models, and new bases for therapeutic intervention in Alzheimer's Disease.

The onset of AD may therefore be associated with aberrant interactions between mutant presenilin proteins and proteins such as those identified using the methods described herein. However, similar aberrant interactions could result from normal presenilins binding to mutant forms of proteins which do not normally interact with the presenilins. Aberrant interactions involving normal presenilin proteins may be associated with a number of AD cases where no mutations are found in the presenilin genes. The mutant interacting proteins can be isolated and identified using methods known in the art. For example, protein extracts are made from tissue samples derived from Alzheimer patients with no mutations in their presenilin genes. These protein extracts are then exposed to normal presenilin protein bound to a matrix, and interacting proteins are specifically retained on the matrix. These proteins are then isolated and characterized. The genes encoding these proteins can then be cloned and the specific mutations responsible for the aberrant interactions can be identified. It is expected that some of these proteins will be mutant forms of wild type proteins which were found to interact specifically with mutant presenilins. These mutant proteins which interact with normal presenilins may also be identified using genetic approaches such as the yeast two-hybrid system described in Example 15. These results can be used to develop therapeutic and diagnostic methods as described herein.

III. Preferred Embodiments

Based, in part, upon the discoveries disclosed and described herein, the following preferred embodiments of the present invention are provided.

1. Isolated Nucleic Acids

In one series of embodiments, the present invention provides isolated nucleic acids corresponding to, or relating to, the presenilin nucleic acid sequences disclosed herein. As described more fully below, these sequences include normal PS1 and PS2 sequences from humans and other mammalian species, mutant PS1 and PS2 sequences from humans and other mammalian species, homologous sequences from non-mammalian species such as Drosophila and C. elegans subsets of these sequences useful as probes and PCR primers, subsets of these sequences encoding fragments of the presenilin proteins or corresponding to particular structural domains or polymorphic regions, complementary or antisense sequences corresponding to fragments of the presenilin genes, sequences in which the presenilin coding regions have been operably joined to exogenous regulatory regions, and sequences encoding fusion proteins of the portions of the presenilin proteins fused to other proteins useful as markers of expression, as "tags" for purification, or in screens and assays for proteins interacting with the presenilins.

Thus, in a first series of embodiments, isolated nucleic acid sequences are provided which encode normal or mutant versions of the PS1 and PS2 proteins. Examples of such nucleic acid sequences are disclosed herein. These nucleic acids may be genomic sequences (e.g., SEQ ID NOs: 5–15) or may be cDNA sequences (e.g., SEQ ID NOs: 1, 3, 16, and 18). In addition, the nucleic acids may be recombinant genes or "minigenes" in which all or some of the introns have been removed, or in which various combinations of the introns and exons and local cis acting regulatory elements have been engineered in propagation or expression constructs or vectors. Thus, for example, the invention provides nucleic acid sequences in which the alternative splicing variations described herein are incorporated at the DNA level, thus enabling cells including these sequences to express only one of the alternative splice variants at each splice position. As an example, a recombinant gene may be produced in which the 3' end of Exon 1 of the PS1 gene (bp 1337 of SEQ ID NO:5) has been joined directly to the 5' end of Exon 3 (bp 588 of SEQ ID NO:6) so that only transcripts corresponding to the predominant transcript are produced. Obviously, one also may create a recombinant gene "forcing" the alternative splice of Exon 2 and Exon 3. Similarly, a recombinant gene may be produced in which one of the Exon 4 or Exon 9 splice variants of PS1 (or the corresponding TM6→7 splice variant of PS2) is incorporated into DNA such that cells including this recombinant gene can express only one of these variants. For purposes of reducing the size of a recombinant presenilin gene, a cDNA gene may be employed or various combinations of the introns and untranslated exons may be removed from a DNA construct. Finally, recombinant genes may be produced in which the 5' UTR is altered such that transcription proceeds necessarily from one or the other of the two transcription initiation sites. Such constructs may be particularly useful, as described below, in identifying compounds which can induce or repress the expression of the presenilins. Many variations on these embodiments are now enabled by the detailed description of the presenilin genes provided herein.

In addition to the disclosed presenilin sequences, one of ordinary skill in the art is now enabled to identify and isolate nucleic acids representing presenilin genes or cDNAs which are allelic to the disclosed sequences or which are heterospecific homologues. Thus, the present invention provides isolated nucleic acids corresponding to these alleles and homologues, as well as the various above-described recombinant constructs derived from these sequences, by means which are well known in the art. Briefly, one of ordinary skill in the art may now screen preparations of genomic or cDNA, including samples prepared from individual organisms (e.g., human AD patients or their family members) as well as bacterial, viral, yeast or other libraries of genomic or cDNA, using probes or PCR primers to identify allelic or homologous sequences. Because it is desirable to identify additional presenilin gene mutations which may contribute to the development of AD or other disorders, because it is desirable to identify additional presenilin polymorphisms which are not pathogenic, and because it is also desired to create a variety of animal models which may be used to study AD and screen for potential therapeutics, it is particularly contemplated that additional presenilin sequences will be isolated from other preparations or libraries of human nucleic acids and from preparations or libraries from animals including rats, mice, hamsters, guinea pigs, rabbits, dogs, cats, goats, sheep, pigs, and non-human primates. Furthermore, presenilin homologues from yeast or invertebrate species, including *C. elegans* and other nematodes, as well as Drosophila and other insects, may have particular utility for drug screening. For example, invertebrates bearing mutant presenilin homologues (or mammalian presenilin transgenes) which cause a rapidly occurring and easily scored phenotype (e.g., abnormal vulva or eye development after several days) can be used as screens for drugs which block the effect of the mutant gene. Such invertebrates may prove far more rapid and efficient for mass screenings than larger vertebrate animals. Once lead compounds are found through such screens, they may be tested in higher animals.

Standard hybridization screening or PCR techniques may be employed (as used, for example, in the identification of the mPS1 gene) to identify and/or isolate such allelic and homologous sequences using relatively short presenilin gene sequences. The sequences may include 8 or fewer nucleotides depending upon the nature of the target sequences, the method employed, and the specificity required. Future technological developments may allow the advantageous use of even shorter sequences. With current technology, sequences of 9–50 nucleotides, and preferably about 18–24 are preferred. These sequences may be chosen from those disclosed herein, or may be derived from other allelic or heterospecific homologues enabled herein. When probing mRNA or screening cDNA libraries, probes and primers from coding sequences (rather than introns) are preferably employed, and sequences which are omitted in alternative splice variants typically are avoided unless it is specifically desired to identify those variants. Allelic variants of the presenilin genes may be expected to hybridize to the disclosed sequences under stringent hybridization conditions, as defined herein, whereas lower stringency may be employed to identify heterospecific homologues.

In another series of embodiments, the present invention provides for isolated nucleic acids which include subsets of the presenilin sequences or their complements. As noted above, such sequences will have utility as probes and PCR primers in the identification and isolation of allelic and homologous variants of the presenilin genes. Subsequences corresponding to the polymorphic regions of the presenilins, as described above, will also have particular utility in screening and/or genotyping individuals for diagnostic purposes, as described below. In addition, and also as described below, such subsets will have utility for encoding (1) fragments of the presenilin proteins for inclusion in fusion proteins, (2) fragments which comprise functional domains of the presenilin proteins for use in binding studies, (3) fragments of the presenilin proteins which may be used as immunogens to raise antibodies against the presenilin proteins, and (4) fragments of the presenilins which may act as competitive inhibitors or as mimetics of the presenilins to inhibit or mimic their physiological functions. Finally, such subsets may encode or represent complementary or antisense sequences which can hybridize to the presenilin genes or presenilin mRNA transcripts under physiological conditions to inhibit the transcription or translation of those sequences. Therefore, depending upon the intended use, the present invention provides nucleic acid subsequences of the presenilin genes which may have lengths varying from 8–10 nucleotides (e.g., for use as PCR primers) to nearly the full size of the presenilin genomic or cDNAs. Thus, the present invention provides isolated nucleic acids comprising sequences corresponding to at least 8–10, preferably 15, and more preferably at least 20 consecutive nucleotides of the presenilin genes, as disclosed or otherwise enabled herein, or to their complements. As noted above, however, shorter sequences may be useful with different technologies.

In another series of embodiments, the present invention provides nucleic acids in which the presenilin coding sequences, with or without introns or recombinantly engineered as described above, are operably joined to endogenous or exogenous 5' and/or 3' regulatory regions. The endogenous regulatory regions of the hPS1 gene are described and disclosed in detail herein. Using the present disclosure and standard genetic techniques (e.g., PCR extensions, targeting gene walking), one of ordinary skill in the art is also now enabled to clone the corresponding hPS2 5' and/or 3' endogenous regulatory regions. Similarly, allelic variants of the hPS1 and hPS2 endogenous regulatory regions, as wells as endogenous regulatory regions from other mammalian homologues, are similarly enabled without undue experimentation. Alternatively, exogenous regulatory regions (i.e., regulatory regions from a different conspecific gene or a heterospecific regulatory region) may be operably joined to the presenilin coding sequences in order to drive expression. Appropriate 5' regulatory regions will include promoter elements and may also include additional elements such as operator or enhancer sequences, ribosome binding sequences, RNA capping sequences, and the like. The regulatory region may be selected from sequences that control the expression of genes of prokaryotic or eukaryotic cells, their viruses, and combinations thereof. Such regulatory regions include, but are not limited to, the lac system, the trp system, the tac system and the trc system; major operator and promoter regions of phage $\lambda$; the control region of the fd coat protein; early and late promoters of SV40; promoters derived from polyoma, adenovirus, retrovirus, baculovirus, and simian virus; 3-phosphoglycerate kinase promoter; yeast acid phosphatase promoters; yeast alpha-mating factors; promoter elements of other eukaryotic genes expressed in neurons or other cell types; and combinations thereof. In particular, regulatory elements may be chosen which are inducible or repressible (e.g., the $\beta$-galactosidase promoter) to allow for controlled and/or manipulable expression of the presenilin genes in cells transformed with these nucleic acids. Alternatively, the presenilin coding regions may be operably joined with regulatory elements which provide for tissue specific expression in multicellular organisms. Such constructs are particularly useful for the production of transgenic organisms to cause expression of the presenilin genes only in appropriate tissues. The choice of appropriate regulatory regions is within the ability and discretion of one of ordinary skill in the art and the recombinant use of many such regulatory regions is now established in the art.

In another series of embodiments, the present invention provides for isolated nucleic acids encoding all or a portion of the presenilin proteins in the form of a fusion protein. In these embodiments, a nucleic acid regulatory region (endogenous or exogenous) is operably joined to a first coding region which is covalently joined in-frame to a second coding region. The second coding region optionally may be covalently joined to one or more additional coding regions and the last coding region is joined to a termination codon and, optionally, appropriate 3' regulatory regions (e.g., polyadenylation signals). The presenilin sequences of the fusion protein may represent the first, second, or any additional coding regions. The presenilin sequences may be conserved or nonconserved domains and can be placed in any coding region of the fusion. The non-presenilin sequences of the fusion may be chosen according to the needs and discretion of the practitioner and are not limited by the present invention. Useful non-presenilin sequences include, however, short sequence "tags" such as antigenic determinants or poly-His tags which may be used to aid in the identification or purification of the resultant fusion protein. Alternatively, the non-presenilin coding region may encode a large protein or protein fragment, such as an enzyme or binding protein which also may assist in the identification and purification of the protein, or which may be useful in an assay such as those described below. Particularly contemplated presenilin fusion proteins include poly-His and GST (glutathione S-transferase) fusions which are useful in isolating and purifying the presenilins, and the yeast two hybrid fusions, described below, which are useful in assays to identify other proteins which bind to or interact with the presenilins.

In another series of embodiments, the present invention provides isolated nucleic acids in the form of recombinant DNA constructs in which a marker or reporter gene (e.g., β-galactosidase, luciferase) is operably joined to the 5' regulatory region of a presenilin gene such that expression of the marker gene is under the control of the presenilin regulatory sequences. Using the presenilin regulatory regions disclosed or otherwise enabled herein, including regulatory regions from PS1 and PS2 genes from human and other mammalian species, one of ordinary skill in the art is now enabled to produce such constructs. As discussed more fully below, such isolated nucleic acids may be used to produce cells, cell lines or transgenic animals which are useful in the identification of compounds which can, directly or indirectly, differentially affect the expression of the presenilins.

In addition to the presenilin sequences disclosed and enabled herein, the present invention also provides for nucleic acid sequences encoding peptides or proteins which interact with the presenilins in vivo. Thus, as described above with respect to presenilin processing and interactions, and as detailed below in Example 15, a number of brain proteins which interact with the presenilins have been identified by using a yeast two-hybrid system to screen a human brain cDNA library. Employing other methods of identifying presenilin-interacting or "PS-interacting" proteins, as disclosed below and known in the art, or employing cDNA libraries from other tissues or species, one is now enabled to identify and isolate a variety of nucleic acids encoding PS-interacting proteins. Once identified, these sequences may be used to clone larger cDNAs or genomic fragments (including entire genes which include PS-interacting functional domains) or may be used to identify smaller, minimally active fragments which retain PS-interacting activity (e.g., by iteratively deleting residues from the ends of PS-interacting peptides and testing for retention of activity). In addition, as shown below, PS-interacting peptides or proteins may be identified which interact with specific functional domains of the presenilins (e.g., TM6→7 loop domain, TM1→2 loop domain, N-terminus, C-terminus), which interact with specific presenilins (e.g., hPS1, hPS2, mPS1, DmPS), or which interact specifically with mutant or normal forms (e.g., C410Y mutants, M146L mutants).

The nucleic acids encoding the PS-interacting peptides or proteins of the present invention may be employed in essentially all of the embodiments described above with respect to the presenilins. Thus, nucleic acids encoding PS-interacting peptides are provided which include genomic or cDNA sequences; minigenes with some or all introns removed; subsequences with utility for encoding (1) fragments of the PS-interacting proteins for inclusion in fusion proteins, (2) fragments which comprise functional domains of the PS-interacting proteins for use in binding studies, (3) fragments of the PS-interacting proteins which may be used as immunogens to raise antibodies against the PS-interacting proteins, and (4) fragments of the PS-interacting proteins which may act as competitive inhibitors or as mimetics of their physiological interaction with the presenilins; sequences operably joined to endogenous or exogenous regulatory elements; sequences joined inframe with other coding sequences to encode a fusion protein (e.g., as in the yeast two-hybrid system); etc.

Finally, the isolated nucleic acids of the present invention include any of the above described sequences when included in vectors. Appropriate vectors include cloning vectors and expression vectors of all types, including plasmids, phagemids, cosmids, episomes, and the like, as well as integration vectors. The vectors may also include various marker genes (e.g., antibiotic resistance or susceptibility genes) which are useful in identifying cells successfully transformed therewith. In addition, the vectors may include regulatory sequences to which the nucleic acids of the invention are operably joined, and/or may also include coding regions such that the nucleic acids of the invention, when appropriately ligated into the vector, are expressed as fusion proteins. Such vectors may also include vectors for use in yeast "two hybrid," baculovirus, and phage-display systems. The vectors may be chosen to be useful for prokaryotic, eukaryotic or viral expression, as needed or desired for the particular application. For example, vaccinia virus vectors or simian virus vectors with the SV40 promoter (e.g., pSV2), or Herpes simplex virus or adeno-associated virus may be useful for transfection of mammalian cells including neurons in culture or in vivo, and the baculovirus vectors may be used in transfecting insect cells (e.g., butterfly cells). A great variety of different vectors are now commercially available and otherwise known in the art, and the choice of an appropriate vector is within the ability and discretion of one of ordinary skill in the art.

2. Substantially Pure Proteins

The present invention provides for substantially pure preparations of the presenilin proteins, fragments of the presenilin proteins, and fusion proteins including the presenilins or fragments thereof. The proteins, fragments and fusions have utility, as described herein, in the generation of antibodies to normal and mutant presenilins, in the identification of presenilin binding proteins, and in diagnostic and therapeutic methods. Therefore, depending upon the intended use, the present invention provides substantially pure proteins or peptides comprising amino acid sequences which are subsequences of the complete presenilin proteins and which may have lengths varying from 4–10 amino acids (e.g., for use as immunogens), or 10–100 amino acids (e.g., for use in binding assays), to the complete presenilin proteins. Thus, the present invention provides substantially pure proteins or peptides comprising sequences corresponding to at least 4–5, preferably 6–10, and more preferably at least 50 or 100 consecutive amino acids of the presenilin proteins, as disclosed or otherwise enabled herein.

The proteins or peptides of the invention may be isolated and purified by any of a variety of methods selected on the basis of the properties revealed by their protein sequences. Because the presenilins possess properties of integral or membrane-spanning proteins, a membrane fraction of cells in which the presenilin is normally highly expressed (e.g., neurons, oligodendroglia, muscle, pancreas) may be isolated and the proteins extracted by, for example, detergent solubilization. Alternatively the presenilin protein, fusion protein, or fragment thereof, may be purified from cells transformed or transfected with expression vectors (e.g., baculovirus systems such as the pPbac and pMbac vectors (Stratagene, La Jolla, Calif.); yeast expression systems such as the pYESHIS Xpress vectors (Invitrogen, San Diego, Calif.); eukaryotic expression systems such as pcDNA3 (Invitrogen, San Diego, Calif.) which has constant constitutive expression, or LacSwitch (Stratagene, La Jolla, Calif.) which is inducible; or prokaryotic expression vectors such as pKK233-3 (Clontech, Palo Alto, Calif.). In the event that the protein or fragment integrates into the endoplasmic reticulum or plasma membrane of the recombinant cells (e.g., immortalized human cell lines or other eukaryotic cells), the protein may be purified from the membrane fraction. Alternatively, if the protein is not properly localized or aggregates in inclusion bodies within the recombinant cells (e.g., prokaryotic cells), the protein may be purified from whole lysed cells or from solubilized inclusion bodies.

Purification can be achieved using standard protein purification procedures including, but not limited to, gel-filtration chromatography, ion-exchange chromatography, high-performance liquid chromatography (RP-HPLC, ion-exchange HPLC, size-exclusion HPLC, high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties and hydrophobicity.

A presenilin protein, or a fragment thereof, may also be conveniently purified by creating a fusion protein including the desired presenilin sequence fused to another peptide such as an antigenic determinant or poly-His tag (e.g., QIAexpress vectors, QIAGEN Corp., Chatsworth, Calif.), or a larger protein (e.g., GST using the pGEX-27 vector (Amrad, USA) or green fluorescent protein using the Green Lantern vector (GIBCO/BRL. Gaithersburg, Md.). The fusion protein may be expressed and recovered from prokaryotic or eukaryotic cells and purified by any standard method based upon the fusion vector sequence. For example, the fusion protein may be purified by immunoaffinity or immunoprecipitation with an antibody to the non-presenilin portion of the fusion or, in the case of a poly-His tag, by affinity binding to a nickel column. The desired presenilin protein or fragment can then be further purified from the fusion protein by enzymatic cleavage of the fusion protein. Methods for preparing and using such fusion constructs for the purification of proteins are well known in the art and several kits are now commercially available for this purpose. In light of the present disclosure, one is now enabled to employ such fusion constructs with the presenilins.

3. Antibodies to the Presenilins

The present invention also provides antibodies, and methods of making antibodies, which selectively bind to the presenilin proteins or fragments thereof. Of particular importance, by identifying the functional domains of the presenilins and the polymorphic regions associated with AD, the present invention provides antibodies, and methods of making antibodies, which will selectively bind to and, thereby, identify and/or distinguish normal and mutant (i.e., pathogenic) forms of the presenilin proteins. The antibodies of the invention have utility as laboratory reagents for, inter alia immunoaffinity purification of the presenilins, Western blotting to identify cells or tissues expressing the presenilins, and immunocytochemistry or immunofluorescence techniques to establish the subcellular location of the protein. In addition, as described below, the antibodies of the invention may be used as diagnostics tools to identify carriers of AD-related presenilin alleles, or as therapeutic tools to selectively bind and inhibit pathogenic forms of the presenilin proteins in vivo.

The antibodies of the invention may be generated using the entire presenilin proteins of the invention or using any presenilin epitope which is characteristic of that protein and which substantially distinguishes it from other host proteins. Such epitopes may be identified by comparing sequences of, for example, 4–10 amino acid residues from a presenilin sequence to computer databases of protein sequences from the relevant host. Preferably, the epitopes are chosen from the N- and C-termini, or from the loop domains which connect the transmembrane domains of the proteins. In particular, antibodies to the polymorphic N-terminal region, TM1→2 loop, or TM6→7 loop are expected to have the greatest utility both diagnostically and therapeutically. On the other hand, antibodies against highly conserved domains are expected to have the greatest utility for purification or identification of presenilins.

Using the IBI Pustell program, amino acid residue positions were identified as potential antigenic sites in the hPS1 protein and may be useful in generating the antibodies of the invention. These positions, corresponding to positions in SEQ ID NO:2, are listed in Table 6.

Other methods of choosing antigenic determinants may, of course, are known in the art and be employed. In addition, larger fragments (e.g., 8–20 or, preferably, 9–15 residues) including some of these epitopes may also be employed. For example, a fragment including the 109–112 epitope may comprise residues 107–114, or 105–116. Even larger fragments, including for example entire functional domains or multiple function domains (e.g., TM1, TM1→2, and TM2 or TM6, TM6→7, and TM7) may also be preferred. For other presenilin proteins (e.g., for mPS1 or other non-human homologues, or for PS2), homologous sites may be chosen.

Using the same IBI Pustell program, amino acid residue positions were identified as potential antigenic sites in the hPS2 protein and may be useful in generating the antibodies of the invention. These positions, corresponding to positions in SEQ ID NO: 19, are listed in Table 7.

As for PS1, other methods of choosing antigenic determinants may, of course, are known in the art and be employed. In addition, larger fragments (e.g., 8–20 or, preferably, 9–15 residues) including some of these epitopes may also be employed. For example, a fragment including the 310–314 epitope may comprise residues 308–316, or 307–317. Even larger fragments, including for example entire functional domains or multiple function domains (e.g., TM1, TM1→2, and TM2 or TM6, TM6→7, and TM7) may also be preferred. For other presenilin proteins (e.g., for mPS2 or other non-human homologues, or for PS1), homologous sites may be chosen.

Presenilin immunogen preparations may be produced from crude extracts (e.g., membrane fractions of cells highly expressing the proteins), from proteins or peptides substantially purified from cells which naturally or recombinantly express them or, for short immunogens, by chemical peptide synthesis. The presenilin immunogens may also be in the form of a fusion protein in which the nonpresenilin region is chosen for its adjuvant properties. As used herein, a presenilin immunogen shall be defined as a preparation including a peptide comprising at least 4–8, and preferably at least 9–15 consecutive amino acid residues of the presenilin proteins, as disclosed or otherwise enabled herein. Sequences of fewer residues may, of course, also have utility depending upon the intended use and fixture technological developments. Therefore, any presenilin derived sequences which are employed to generate antibodies to the presenilins should be regarded as presenilin immunogens.

The antibodies of the invention may be polyclonal or monoclonal, or may be antibody fragments, including Fab fragments, $F(ab')_2$, and single chain antibody fragments. In addition, after identifying useful antibodies by the method of the invention, recombinant antibodies may be generated, including any of the antibody fragments listed above, as well as humanized antibodies based upon non-human antibodies to the presenilin proteins. In light of the present disclosures of presenilin proteins, as well as the characterization of other presenilins enabled herein, one of ordinary skill in the art may produce the above-described antibodies by any of a variety of standard means well known in the art. For an overview of antibody techniques, see *Antibody Engineering: A Practical Guide*, Borrebaek, ed., W.H. Freeman & Company, NY (1992), or *Antibody Engineering*, 2nd Ed., Borrebaek, ed., Oxford University Press, Oxford (1995).

As a general matter, polyclonal antibodies may be generated by first immunizing a mouse, rabbit, goat or other suitable animal with the presenilin immunogen in a suitable carrier. To increase the immunogenicity of the preparation, the immunogen may be coupled to a carrier protein or mixed with an adjuvant (e.g., Freund's adjuvant). Booster injections, although not necessary are recommended. After an appropriate period to allow for the development of a humoral response, preferably several weeks, the animals may be bled and the sera may be purified to isolate the immunoglobulin component.

Similarly, as a general matter, monoclonal anti-presenilin antibodies may be produced by first injecting a mouse, rabbit, goat or other suitable animal with a presenilin immunogen in a suitable carrier. As above, carrier proteins or adjuvants may be utilized and booster injections (e.g., bi- or tri-weekly over 8–10 weeks) are recommended. After allowing for development of a humoral response, the animals are sacrificed and their spleens are removed and resuspended in, for example, phosphate buffered saline (PBS). The spleen cells serve as a source of lymphocytes, some of which are producing antibody of the appropriate specificity. These cells are then fused with an immortalized cell line (e.g., myeloma), and the products of the fusion are plated into a number of tissue culture wells in the presence of a selective agent such as HAT. The wells are serially screened and replated, each time selecting cells making useful antibody. Typically, several screening and replating procedures are carried out until over 90% of the wells contain single clones which are positive for antibody production. Monoclonal antibodies produced by such clones may be purified by standard methods such as affinity chromatography using Protein A Sepharose, by ion-exchange chromatography, or by variations and combinations of these techniques.

The antibodies of the invention may be labelled or conjugated with other compounds or materials for diagnostic and/or therapeutic uses. For example, they may be coupled to radionuclides, fluorescent compounds, or enzymes for imaging or therapy, or to liposomes for the targeting of compounds contained in the liposomes to a specific tissue location.

4. Transformed Cell Lines

The present invention also provides for cells or cell lines, both prokaryotic and eukaryotic, which have been transformed or transfected with the nucleic acids of the present invention so as to cause clonal propagation of those nucleic acids and/or expression of the proteins or peptides encoded thereby. Such cells or cell lines will have utility both in the propagation and production of the nucleic acids and proteins of the present invention but also, as further described herein, as model systems for diagnostic and therapeutic assays. As used herein, the term "transformed cell" is intended to embrace any cell, or the descendant of any cell, into which has been introduced any of the nucleic acids of the invention, whether by transformation, transfection, infection, or other means. Methods of producing appropriate vectors, transforming cells with those vectors, and identifying transformants are well known in the art and are only briefly reviewed here (see, for example, Sambrook et al. (1989) *Molecular Cloning: A Laboratory Manual,* 2nd ed., Cold Spring Harbor Laboratory Press, Cold Spring Harbor, New York).

Prokaryotic cells useful for producing the transformed cells of the invention include members of the bacterial genera Escherichia (e.g., *E. coli*), Pseudomonas (e.g., *P. aeruginosa*), and Bacillus (e.g., *B. subtillus, B. stearothermophilus*), as well as many others well known and frequently used in the art. Prokaryotic cells are particularly useful for the production of large quantities of the proteins or peptides of the invention (e.g., normal or mutant presenilins, fragments of the presenilins, fusion proteins of the presenilins). Bacterial cells (e.g., *E. coli*) may be used with a variety of expression vector systems including, for example, plasmids with the T7 RNA polymerase/promoter system, bacteriophage λ regulatory sequences, or M13 Phage mGPI-2. Bacterial hosts may also be transformed with fusion protein vectors which create, for example, lacZ, trpE, maltose-binding protein, poly-His tags, or glutathione-S-transferase fision proteins. All of these, as well as many other prokaryotic expression systems, are well known in the art and widely available commercially (e.g., pGEX-27 (Amrad, USA) for GST fusions).

Eukaryotic cells and cell lines useful for producing the transformed cells of the invention include mammalian cells and cell lines (e.g., PC12, COS, CHO, fibroblasts, myelomas, neuroblastomas, hybridomas, human embryonic kidney 293, oocytes, embryonic stem cells), insect cells lines (e.g., using baculovirus vectors such as pPbac or pMbac (Stratagene, La Jolla, Calif.)), yeast (e.g., using yeast expression vectors such as pYESHIS (Invitrogen, Calif.)), and fungi. Eukaryotic cells are particularly useful for embodiments in which it is necessary that the presenilin proteins, or functional fragments or variants thereof, or muteins thereof, perform the functions and/or undergo the intracellular interactions associated with either the normal or mutant proteins. Thus, for example, transformed eukaryotic cells are preferred for use as models of presenilin function or interaction, and assays for screening candidate therapeutics preferably employ transformed eukaryotic cells.

To accomplish expression in eukaryotic cells, a wide variety of vectors have been developed and are commercially available which allow inducible (e.g., LacSwitch expression vectors, Stratagene, La Jolla, Calif.) or cognate (e.g., pcDNA3 vectors, Invitrogen, Chatsworth, Calif.) expression of presenilin nucleotide sequences under the regulation of an artificial promoter element. Such promoter elements are often derived from CMV or SV40 viral genes, although other strong promoter elements which are active in eukaryotic cells can also be employed to induce transcription of presenilin nucleotide sequences. Typically, these vectors also contain an artificial polyadenylation sequence and 3' UTR which can also be derived from exogenous viral gene sequences or from other eukaryotic genes. Furthermore, in some constructs, artificial, non-coding, spliceable introns and exons are included in the vector to enhance expression of the nucleotide sequence of interest (in this case, presenilin sequences). These expression systems are commonly available from commercial sources and are typified by vectors such as pcDNA3 and pZeoSV (Invitrogen, San Diego, Calif.). Both of the latter vectors have been successfully used to cause expression of presenilin proteins in transfected COS, CHO, and PC12 cells (Levesque et al. 1996). Innumerable commercially-available as well as custom-designed expression vectors are available from commercial sources to allow expression of any desired presenilin transcript in more or less any desired cell type, either constitutively or after exposure to a certain exogenous stimulus (e.g., withdrawal of tetracycline or exposure to IPTG).

Vectors may be introduced into the recipient or "host" cells by various methods well known in the art including, but not limited to, calcium phosphate transfection, strontium phosphate transfection, DEAE dextran transfection, electroporation, lipofection (e.g., Dosper Liposomal transfection reagent, Boehringer Mannheim, Germany), microinjection, ballistic insertion on microbeads, protoplast fusion or, for viral or phage vectors, by infection with the recombinant virus or phage.

5. Transgenic Animal Models

The present invention also provides for the production of transgenic non-human animal models in which mutant or wild type presenilin sequences are expressed, or in which the presenilin genes have been inactivated (e.g., "knock-out" deletions), for the study of Alzheimer's Disease, for the screening of candidate pharmaceutical compounds, for the creation of explanted mammalian CNS cell cultures (e.g., neuronal, glial, organotypic or mixed cell cultures), and for the evaluation of potential therapeutic interventions. In addition, the present invention provides for animal models in which mutant or wild type sequences encoding proteins which interact with the presenilins (e.g., S5a) are expressed, or in which these genes have been inactivated (e.g., "knockout" deletions). Prior to the present invention, a partial animal model for Alzheimer's Disease existed via the insertion and over-expression of a mutant form of the human amyloid precursor protein gene as a minigene under the regulation of the platelet-derived growth factor β receptor promoter element (Games et al. (1995) *Nature* 373:523–527). This mutant ($\beta APP_{717}$ Val→Ile) causes the appearance of synaptic pathology and amyloid β peptide deposition in the brain of transgenic animals bearing this transgene in high copy number. These changes in the brain of the transgenic animal are very similar to that seen in human AD (Games et al., 1995). It is, however, as yet unclear whether these animals become demented, but there is general consensus that it is now possible to recreate at least some aspects of AD in mice.

Animal species suitable for use in the animal models of the present invention include, but are not limited to, rats, mice, hamsters, guinea pigs, rabbits, dogs, cats, goats, sheep, pigs, and nonhuman primates (e.g., Rhesus monkeys, chimpanzees). For initial studies, transgenic rodents (e.g., mice) are preferred due to their relative ease of maintenance and shorter life spans. Indeed, as noted above, transgenic yeast or invertebrates (e.g., nematodes, insects) may be preferred for some studies because they will allow for even more rapid and inexpensive screening. Transgenic non-human primates, however, may be preferred for longer term studies due to their greater similarity to humans and their higher cognitive abilities.

Using the nucleic acids disclosed and otherwise enabled herein, there are now several available approaches for the creation of a transgenic animal model for Alzheimer's Disease. Thus, the enabled animal models include: (1) Animals in which sequences encoding at least a functional domain of a normal human presenilin gene have been recombinantly introduced into the genome of the animal as an additional gene, under the regulation of either an exogenous or an endogenous promoter element, and as either a minigene or a large genomic fragment; in which sequences encoding at least a functional domain of a normal human presenilin gene have been recombinantly substituted for one or both copies of the animal's homologous presenilin gene by homologous recombination or gene targeting; and/or in which one or both copies of one of the animal's homologous presenilin genes have been recombinantly "humanized" by the partial substitution of sequences encoding the human homologue by homologous recombination or gene targeting. These animals are useful for evaluating the effects of the transgenic procedures, and the effects of the introduction or substitution of a human, or humanized presenilin gene. (2) Animals in which sequences encoding at least a functional domain of a mutant (i.e., pathogenic) human presenilin gene have been recombinantly introduced into the genome of the animal as an additional gene, under the regulation of either an exogenous or an endogenous promoter element, and as either a minigene or a large genomic fragment; in which sequences encoding at least a functional domain of a mutant human presenilin gene have been recombinantly substituted for one or both copies of the animal's homologous presenilin gene by homologous recombination or gene targeting; and/ or in which one or both copies of one of the animal's homologous presenilin genes have been recombinantly "humanized" by the partial substitution of sequences encoding a mutant human homologue by homologous recombination or gene targeting. These animals are useful as models which will display some or all of the characteristics, whether at the biochemical, physiological and/or behavioral level, of humans carrying one or more alleles which are pathogenic of Alzheimer's Disease or other diseases associated with mutations in the presenilin genes. (3) Animals in which sequences encoding at least a functional domain of a mutant version of one of that animal's presenilin genes (bearing, for example, a specific mutation corresponding to, or similar to, one of the pathogenic mutations of the human presenilins) have been recombinantly introduced into the genome of the animal as an additional gene, under the regulation of either an exogenous or an endogenous promoter element, and as either a minigene or a large genomic fragment; and/or in which sequences encoding at least a functional domain of a mutant version of one of that animal's presenilin genes (bearing, for example, a specific mutation corresponding to, or similar to, one of the pathogenic mutations of the human presenilins) have been recombinantly substituted for one or both copies of the animal's homologous presenilin gene by homologous recombination or gene targeting. These animals are also useful as models which will display some or all of the characteristics, whether at the biochemical, physiological and/or behavioral level, of humans carrying one or more alleles which are pathogenic of Alzheimer's Disease. (4) "Knock-out" animals in which one or both copies of one of the animal's presenilin genes have been partially or completely deleted by homologous recombination or gene targeting, or have been inactivated by the insertion or substitution by homologous recombination or gene targeting of exogenous sequences (e.g., stop codons, lox p sites). Such animals are useful models to study the effects which loss of presenilin gene expression may have, to evaluate whether loss of function is preferable to continued expression of mutant forms, and to examine whether other genes can be recruited to replace a mutant presenilin (e.g., substitute PS1 with PS2) or to intervene with the effects of other genes (e.g., APP or ApoE) causing AD as a treatment for AD or other disorders. For example, a normal presenilin gene may be necessary for the action of mutant APP genes to actually be expressed as AD and, therefore, transgenic presenilin animal models may be of use in elucidating such multigenic interactions.

In addition to transgenic animal models in which the expression of one or more of the presenilins is altered, the present invention also provides for the production of transgenic animal models in which the expression of one or more of the proteins which interact with the presenilins is altered. Thus, as detailed below, the present invention provides for a variety of methods of identifying proteins which interact with the normal and/or mutant presenilins (e.g., affinity chromatography, co-immunoprecipitation, biomolecular interaction assays, yeast two-hybrid systems). The nucleic acids encoding these "PS-interacting proteins," or encoding the interacting domains of these proteins, may then be isolated and transgenics may be produced which bear normal or mutant sequences for these proteins in addition to, or instead of, any corresponding endogenous sequences. Indeed, because animal models may differ from humans not only in their presenilin sequences but also in the sequences of these PS-interacting proteins, it is particularly contemplated that transgenics may be produced which bear normal or mutant human sequences for at least one PS-interacting protein in addition to a presenilin. Such co-transformed animal models would possess more elements of the human molecular biology and, therefore, are expected to be better models of human disorders. Thus, in accordance with the present invention, transgenic animal models may first be produced bearing normal or mutant sequences for one or more PS-interacting proteins, or interacting domains of these proteins. These animals will have utility in that they can be crossed with animals bearing a variety of normal or mutant presenilin sequences to produce co-transformed animal models. Furthermore, as detailed below, it is expected that mutations in the PS-interacting genes, like mutations in the presenilins themselves, may be causative of Alzheimer's Disease and/or other disorders as well (e.g., other cognitive, intellectual, neurological or psychological disorders such as cerebral hemorrhage, schizophrenia, depression, mental retardation and epilepsy). Therefore, transgenic animal models bearing normal or mutant sequences corresponding to the PS-interacting proteins, absent transformation with any presenilin sequences, will have utility of their own in the study of such disorders.

As detailed below, preferred choices for transgenic animal models transformed with PS-interacting proteins, or domains of PS-interacting proteins, include those transformed with normal or mutant sequences corresponding to the clones identified and described in Example 15 and disclosed in SEQ ID NOs: 26–41. These clones, which interact with normal or mutant PS1 TM6→7 loop domains, were identified according to the methods of the present invention employing a yeast two-hybrid system. These clones, longer nucleic acid sequences comprising these clones, and other clones identified according to this and other methods of the invention (e.g., clones encoding proteins which interact with other domains of the presenilins, which interact specifically with PS1 or PS2, or which interact specifically with normal or mutant forms of the presenilins) may all be employed in accordance with the present invention to produce animal models which, with or without co-transformation with presenilin sequences, will have utility in the study of Alzheimer's Disease and/or other cognitive, intellectual, neurological or psychological disorders.

Thus, using the nucleic acids disclosed and otherwise enabled herein, one of ordinary skill in the art may now produce any of the following types of transgenic animal models with altered PS-interacting protein expression: (1) Animals in which sequences encoding at least a functional domain of a normal human PS-interacting protein gene have been recombinantly introduced into the genome of the animal as an additional gene, under the regulation of either an exogenous or an endogenous promoter element, and as either a minigene or a large genomic fragment; in which sequences encoding at least a functional domain of a normal human PS-interacting protein gene have been recombinantly substituted for one or both copies of the animal's homologous PS-interacting protein gene by homologous recombination or gene targeting; and/or in which one or both copies of one of the animal's homologous PS-interacting protein genes have been recombinantly "humanized" by the partial substitution of sequences encoding the human homologue by homologous recombination or gene targeting. These animals are useful for providing better transgenic models which express human PS-interacting proteins as well as human presenilin proteins. They are also useful in evaluating the effects of the transgenic procedures, and the effects of the introduction or substitution of a human or humanized PS-interacting protein gene. (2) Animals in which sequences encoding at least a functional domain of a mutant (i.e., pathogenic) human PS-interacting protein gene have been recombinantly introduced into the genome of the animal as an additional gene, under the regulation of either an exogenous or an endogenous promoter element, and as either a minigene or a large genomic fragment; in which sequences encoding at least a functional domain of a mutant human PS-interacting protein gene have been recombinantly substituted for one or both copies of the animal's homologous PS-interacting protein gene by homologous recombination or gene targeting; and/or in which one or both copies of one of the animal's homologous PS-interacting protein genes have been recombinantly "humanized" by the partial substitution of sequences encoding a mutant human homologue by homologous recombination or gene targeting. These animals are useful as models which will display some or all of the characteristics, whether at the biochemical, physiological and/or behavioral level, of humans carrying one or more alleles which are pathogenic of Alzheimer's Disease or other diseases associated with mutations in these PS-interacting genes. (3) Animals in which sequences encoding at least a functional domain of a mutant version of one of that animal's PS-interacting protein genes (bearing, for example, a specific mutation corresponding to, or similar to, one of the pathogenic mutations of the human PS-interacting proteins) have been recombinantly introduced into the genome of the animal as an additional gene, under the regulation of either an exogenous or an endogenous promoter element, and as either a minigene or a large genomic fragment; and/or in which sequences encoding at least a functional domain of a mutant version of one of that animal's PS-interacting protein genes (bearing, for example, a specific mutation corresponding to, or similar to, one of the pathogenic mutations of the humans PS-interacting proteins) have been recombinantly substituted for one or both copies of the animal's homologous PS-interacting protein gene by homologous recombination or gene targeting. These animals are also useful as models which will display some or all of the characteristics, whether at the biochemical, physiological and/or behavioral level, of humans carrying one or more alleles which are pathogenic of Alzheimer's Disease. (4) "Knock-out" animals in which one or both copies of one of the animal's PS-interacting protein genes have been partially or completely deleted by homologous recombination or gene targeting, or have been inactivated by the insertion or substitution by homologous recombination or gene targeting of exogenous sequences (e.g., stop codons, lox p sites). Such animals are useful models to study the effects which loss of PS-interacting protein gene expression may have, to evaluate whether loss of function is preferable to continued expression, and to examine whether other genes can be recruited to replace a mutant PS-interacting protein or to intervene with the effects of other genes (e.g., APP or ApoE) causing AD as a treatment for AD or other disorders. For example, a normal PS-interacting protein may be necessary for the action of mutant PS1, PS2 or APP genes to actually be expressed as AD and, therefore, transgenic PS-interacting protein animal models may be of use in elucidating such multigenic interactions.

To create an animal model (e.g., a transgenic mouse), a normal or mutant presenilin gene (e.g., normal or mutant hPS1, mPS1, hPS2, mPS2, etc.), a normal or mutant version of a recombinant nucleic acid encoding at least a functional domain of a presenilin (e.g., a recombinant construct comprising an mPS1 sequence into which has been substituted a nucleotide sequence corresponding to a human mutant sequence), a normal or mutant PS-interacting protein gene (e.g., 26S proteasome S5a or p40 subunit, Rab11), or a normal or mutant version of a recombinant nucleic; acid encoding at least a functional domain of a PS-interacting protein (e.g., yeast two-hybrid clones Y2H24, Y2H29, Y2H31, Y2HEx10-6), can be inserted into a germ line or stem cell using standard techniques of oocyte microinjection, or transfection or microinjection into embryonic stem cells. Animals produced by these or similar processes are referred to as transgenic. Similarly, if it is desired to inactivate or replace an endogenous presenilin or PS-interacting protein gene, homologous recombination using embryonic stem cells may be employed. Animals produced by these or similar processes are referred to as "knock-out" (inactivation) or "knock-in" (replacement) models.

For oocyte injection, one or more copies of the recombinant DNA constructs of the present invention may be inserted into the pronucleus of a just-fertilized oocyte. This oocyte is then reimplanted into a pseudo-pregnant foster mother. The liveborn animals are screened for integrants using analysis of DNA (e.g., from the tail veins of offspring mice) for the presence of the inserted recombinant transgene sequences. The transgene may be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the recombinant DNA constructs of the invention. In this method, the transgene (e.g., a normal or mutant hPS1 or PS2 sequence) is inserted into a retroviral vector which is used to infect embryos (e.g., mouse or non-human primate embryos) directly during the early stages of development to generate chimeras, some of which will lead to germline transmission.

Homologous recombination using stem cells allows for the screening of gene transfer cells to identify the rare homologous recombination events. Once identified, these can be used to generate chimeras by injection of blastocysts, and a proportion of the resulting animals will show germline transmission from the recombinant line. This methodology is especially useful if inactivation of a gene is desired. For example, inactivation of the mPS1 gene in mice may be accomplished by designing a DNA fragment which contains sequences from an mPS1 exon flanking a selectable marker. Homologous recombination leads to the insertion of the marker sequences in the middle of an exon, causing inactivation of the mPS1 gene and/or deletion of internal sequences. DNA analysis of individual clones can then be used to recognize the homologous recombination events.

The techniques of generating transgenic animals, as well as the techniques for homologous recombination or gene targeting, are now widely accepted and practiced. A laboratory manual on the manipulation of the mouse embryo, for example, is available detailing standard laboratory techniques for the production of transgenic mice (Hogan et al. (1986) *Manipulating the Mouse Embryo,* Cold Spring Harbor Laboratory Press, Cold Spring Harbor, N.Y.). To create a transgene, the target sequence of interest (e.g., normal or mutant presenilin sequences, normal or mutant PS-interacting protein sequences) are typically ligated into a cloning site located downstream of some promoter element which will regulate the expression of RNA from the sequence. Downstream of the coding sequence, there is typically an artificial polyadenylation sequence. In the transgenic models that have been used to successfully create animals which mimic aspects of inherited human neurodegenerative diseases, the most successful promoter elements have been the platelet-derived growth factor receptor $\beta$ gene subunit promoter and the hamster prion protein gene promoter, although other promoter elements which direct expression in central nervous system cells would also be useful. An alternate approach to creating a transgene is to use an endogenous presenilin or PS-interacting protein gene promoter and regulatory sequences to drive expression of the transgene. Finally, it is possible to create transgenes using large genomic DNA fragments such as YACs which contain the entire desired gene as well as its appropriate regulatory sequences. Such constructs have been successfully used to drive human APP expression in transgenic mice (Lamb et al. (1993) *Nature Genetics* 5:22–29).

Animal models can also be created by targeting the endogenous presenilin or PS-interacting protein gene in order to alter the endogenous sequence by homologous recombination. These targeting events can have the effect of removing endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish this and appropriate sources of genomic DNA for mouse and other animal genomes to be targeted are commercially available from companies such as GenomeSystems Inc. (St. Louis, Mo., USA). The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out. Again, innumerable model systems have been created, particularly for targeted knockouts of genes including those relevant to neurodegenerative diseases (e.g., targeted deletions of the murine APP gene by Zheng et al. (1995) *Cell* 81:525–531; targeted deletion of the murine prion gene associated with adult onset human CNS degeneration by Bueler et al. (1996) *Nature* 356:577–582).

Finally, equivalents of transgenic animals, including animals with mutated or inactivated presenilin genes, or mutated or inactivated PS-interacting protein genes, may be produced using chemical or x-ray mutagenesis of gametes, followed by fertilization. Using the isolated nucleic acids disclosed or otherwise enabled herein, one of ordinary skill may more rapidly screen the resulting offspring by, for example, direct sequencing RFLP, PCR, or hybridization analysis to detect mutants, or Southern blotting to demonstrate loss of one allele by dosage.

6. Assays for Drugs Which Affect Presenilin Expression

In another series of embodiments, the present invention provides assays for identifying small molecules or other compounds which are capable of inducing or inhibiting the expression of the presenilin genes and proteins (e.g., PS1 or PS2). The assays may be performed in vitro using nontransformed cells, immortalized cell lines, or recombinant cell lines, or in vivo using the transgenic animal models enabled herein.

In particular, the assays may detect the presence of increased or decreased expression of PS1, PS2 or other presenilin-related genes or proteins on the basis of increased or decreased mRNA expression (using, e.g., the nucleic acid probes disclosed and enabled herein), increased or decreased levels of PS1, PS2 or other presenilin-related protein products (using, e.g., the anti-presenilin antibodies disclosed and enabled herein), or increased or decreased levels of expression of a marker gene (e.g., β-galactosidase or luciferase) operably joined to a presenilin 5' regulatory region in a recombinant construct.

Thus, for example, one may culture cells known to express a particular presenilin and add to the culture medium one or more test compounds. After allowing a sufficient period of time (e.g., 0–72 hours) for the compound to induce or inhibit the expression of the presenilin, any change in levels of expression from an established baseline may be detected using any of the techniques described above and well known in the art. In particularly preferred embodiments, the cells are from an immortalized cell line such as a human neuroblastoma, glioblastoma or a hybridoma cell line. Using the nucleic acid probes and/or antibodies disclosed and enabled herein, detection of changes in the expression of a presenilin, and thus identification of the compound as an inducer or repressor of presenilin expression, requires only routine experimentation.

In particularly preferred embodiments, a recombinant assay is employed in which a reporter gene such a β-galactosidase, green fluorescent protein, alkaline phosphatase, or luciferase is operably joined to the 5' regulatory regions of a presenilin gene. Preferred vectors include the Green Lantern 1 vector (GIBCO/BRL, Gaithersburg, Md. and the Great EScAPe pSEAP vector (Clontech, Palo Alto). The hPS1 regulatory regions disclosed herein, or other presenilin regulatory regions, may be easily isolated and cloned by one of ordinary skill in the art in light of the present disclosure of the coding regions of these genes. The reporter gene and regulatory regions are joined in-frame (or in each of the three possible reading frames) so that transcription and translation of the reporter gene may proceed under the control of the presenilin regulatory elements. The recombinant construct may then be introduced into any appropriate cell type although mammalian cells are preferred, and human cells are most preferred. The transformed cells may be grown in culture and, after establishing the baseline level of expression of the reporter gene, test compounds may be added to the medium. The ease of detection of the expression of the reporter gene provides for a rapid, high through-put assay for the identification of inducers and repressors of the presenilin gene.

Compounds identified by this method will have potential utility in modifying the expression of the PS1, PS2 or other presenilin-related genes in vivo. These compounds may be further tested in the animal models disclosed and enabled herein to identify those compounds having the most potent in vivo effects. In addition, as described herein with respect to small molecules having presenilin-binding activity, these molecules may serve as "lead compounds" for the further development of pharmaceuticals by, for example, subjecting the compounds to sequential modifications, molecular modeling, and other routine procedures employed in rational drug design.

7. Identification of Compounds with Presenilin Binding Capacity

In light of the present disclosure, one of ordinary skill in the art is enabled to practice new screening methodologies which will be useful in the identification of proteins and other compounds which bind to, or otherwise directly interact with, the presenilins. The proteins and compounds will include endogenous cellular components which interact with the presenilins in vivo and which, therefore, provide new targets for pharmaceutical and therapeutic interventions, as well as recombinant, synthetic and otherwise exogenous compounds which may have presenilin binding capacity and, therefore, may be candidates for pharmaceutical agents. Thus, in one series of embodiments, cell lysates or tissue homogenates (e.g., human brain homogenates, lymphocyte lysates) may be screened for proteins or other compounds which bind to one of the normal or mutant presenilins. Alternatively, any of a variety of exogenous compounds, both naturally occurring and/or synthetic (e.g., libraries of small molecules or peptides), may be screened for presenilin binding capacity. Small molecules are particularly preferred in this context because they are more readily absorbed after oral administration, have fewer potential antigenic determinants, and/or are more likely to cross the blood brain barrier than larger molecules such as nucleic acids or proteins. The methods of the present invention are particularly useful in that they may be used to identify molecules which selectively or preferentially bind to a mutant form of a presenilin protein (rather than a normal form) and, therefore, may have particular utility in treating the heterozygous victims of this dominant autosomal disease.

Because the normal physiological roles of PS1 and PS2 are still unknown, compounds which bind to normal, mutant or both forms of these presenilins may have utility in treatments and diagnostics. Compounds which bind only to a normal presenilin may, for example, act as enhancers of its normal activity and thereby at least partially compensate for the lost or abnormal activity of mutant forms of the presenilin in Alzheimer's Disease victims. Compounds which bind to both normal and mutant forms of a presenilin may have utility if they differentially affect the activities of the two forms so as to alleviate the overall departure from normal function. Alternatively, blocking the activity of both normal and mutant forms of either PS1 or PS2 may have less severe physiological and clinical consequences than the normal progress of the disease and, therefore, compounds which bind to and inhibit the activity of both normal and mutant forms of a presenilin may be therapeutically useful. Preferably, however, compounds are identified which have a higher affinity of binding to mutant presenilin than to normal presenilin (e.g., at least 2–10 fold higher $K_a$) and which selectively or preferentially inhibit the activity of the mutant form. Such compounds may be identified by using any of the techniques described herein and by then comparing the binding affinities of the candidate compound(s) for the normal and mutant forms of PS1 or PS2.

The effect of agents which bind to the presenilins (normal or mutant forms) can be monitored either by the direct monitoring of this binding using instruments (e.g., BIAcore, LKB Pharmacia, Sweden) to detect this binding by, for example, a change in fluorescence, molecular weight, or concentration of either the binding agent or presenilin component, either in a soluble phase or in a substrate-bound phase.

Once identified by the methods described above, the candidate compounds may then be produced in quantities sufficient for pharmaceutical administration or testing (e.g., $\mu$g or mg or greater quantities), and formulated in a pharmaceutically acceptable carrier (see, e.g., *Remington's Pharmaceutical Sciences*, Gennaro, A., ed., Mack Pub., 1990). These candidate compounds may then be administered to the transformed cells of the invention, to the transgenic animal models of the invention, to cell lines derived from the animal models or from human patients, or to Alzheimer's patients. The animal models described and enabled herein are of particular utility in further testing candidate compounds which bind to normal or mutant presenilin for their therapeutic efficacy.

In addition, once identified by the methods described above, the candidate compounds may also serve as "lead compounds" in the design and development of new pharmaceuticals. For example, as in well known in the art, sequential modification of small molecules (e.g., amino acid residue replacement with peptides; functional group replacement with peptide or non-peptide compounds) is a standard approach in the pharmaceutical industry for the development of new pharmaceuticals. Such development generally proceeds from a "lead compound" which is shown to have at least some of the activity (e.g., PS1 binding or blocking ability) of the desired pharmaceutical.. In particular, when one or more compounds having at least some activity of interest (e.g., modulation of presenilin activity) are identified, structural comparison of the molecules can greatly inform the skilled practitioner by suggesting portions of the lead compounds which should be conserved and portions which may be varied in the design of new candidate compounds. Thus, the present invention also provides a means of identifying lead compounds which may be sequentially modified to produce new candidate compounds for use in the treatment of Alzheimer's Disease. These new compounds then may be tested both for presenilin-binding or blocking (e.g., in the binding assays described above) and for therapeutic efficacy (e.g., in the animal models described herein). This procedure may be iterated until compounds having the desired therapeutic activity and/or efficacy are identified.

In each of the present series of embodiments, an assay is conducted to detect binding between a "presenilin component" and some other moiety. Of particular utility will be sequential assays in which compounds are tested for the ability to bind to only the normal or only the mutant forms of the presenilin functional domains using mutant and normal presenilin components in the binding assays. Such compounds are expected to have the greatest therapeutic utilities, as described more fully below. The "presenilin component" in these assays may be a complete normal or mutant form of a presenilin protein (e.g., an hPS1 or hPS2 variant) but need not be. Rather, particular functional domains of the presenilins, as described above, may be employed either as separate molecules or as part of a fusion protein. For example, to isolate proteins or compounds that interact with these functional domains, screening may be carried out using fusion constructs and/or synthetic; peptides corresponding to these regions. Thus, for PS2, GST-fusion peptides may be made including sequences corresponding approximately to amino acids 1 to 87 (N-terminus), or 269–387 (TM6→7 loop), or to any other conserved domain of interest. For shorter functional domains, a synthetic peptide may be produced corresponding, for example, approximately to amino acids 107 to 134 (TM1→2 loop). Similarly, for PS1, GST- or other fusion peptides may be produced including sequences corresponding approximately to amino acids 1 to 81 (N-terminus) or 266 to 410 (TM6→7 loop) or a synthetic peptide may be produced corresponding approximately to amino acids 101 to 131 (TM1→2 loop). Obviously, various combinations of fusion proteins and presenilin functional domains are possible and these are merely examples. In addition, the functional domains may be altered so as to aid in the assay by, for example, introducing into the functional domain a reactive group or amino acid residue (e.g., cysteine) which will facilitate immobilization of the domain on a substrate (e.g., using sulfhydryl reactions). Thus, for example, the PS1 TM1→2 loop fragment (31-mer) has been synthesized containing an additional C-terminal cysteine residue. This peptide will be used to create an affinity substrate for affinity chromatography (Sulfo-link; Pierce) to isolate binding proteins for microsequencing. Similarly, other functional domain or antigenic fragments may be created with modified residues (see, e.g., Example 10).

The proteins or other compounds identified by these methods may be purified and characterized by any of the standard methods known in the art. Proteins may, for example, be purified and separated using electrophoretic (e.g., SDS-PAGE, 2D PAGE) or chromatographic (e.g., HPLC) techniques and may then be microsequenced. For proteins with a blocked N-terminus, cleavage (e.g., by CNBr and/or trypsin) of the particular binding protein is used to release peptide fragments. Further purification/characterization by HPLC and microsequencing and/or mass spectrometry by conventional methods provides internal sequence data on such blocked proteins. For non-protein compounds, standard organic chemical analysis techniques (e.g., IR, NMR and mass spectrometry; functional group analysis; X-ray crystallography) may be employed to determine their structure and identity.

Methods for screening cellular lysates, tissue homogenates, or small molecule libraries for candidate presenilin-binding molecules are well known in the art and, in light of the present disclosure, may now be employed to identify compounds which bind to normal or mutant presenilin components or which modulate presenilin activity as defined by non-specific measures (e.g., changes, in intracellular $Ca^{2+}$, GTP/GDP ratio) or by specific measures (e.g., changes in A$\beta$ peptide production or changes in the expression of other downstream genes which can be monitored by differential display, 2D gel electrophoresis, differential hybridization, or SAGE methods). The preferred methods involve variations on the following techniques: (1) direct extraction by affinity chromatography; (2) co-isolation of presenilin components and bound proteins or other compounds by immunoprecipitation; (3) the Biomolecular Interaction Assay (BIAcore); and (4) the yeast two-hybrid systems. These and others are discussed separately below.

A. Affinity Chromatography

In light of the present disclosure, a variety of affinity binding techniques well known in the art may be employed to isolate proteins or other compounds which bind to the presenilins disclosed or otherwise enabled herein. In general, a presenilin component may be immobilized on a substrate (e.g., a column or filter) and a solution including the test compound(s) is contacted with the presenilin protein, fusion or fragment under conditions which are permissive for binding. The substrate is then washed with a solution to remove unbound or weakly bound molecules. A second wash may then elute those compounds which strongly bound to the immobilized normal or mutant presenilin component. Alternatively, the test compounds may be immobilized and a solution containing one or more presenilin components may be contacted with the column, filter or other substrate. The ability of the presenilin component to bind to the test compounds may be determined as above or a labeled form of the presenilin component (e.g., a radiolabeled or chemiluminescent functional domain) may be used to more rapidly assess binding to the substrate-immobilized compound(s). In addition, as both PS1 and PS2 are believed to be membrane associated proteins, it may be preferred that the presenilin proteins, fusion or fragments be incorporated into lipid bilayers (e.g., liposomes) to promote their proper folding. This is particularly true when a presenilin component including at least one transmembrane domain is employed. Such presenilin-liposomes may be immobilized on substrates (either directly or by means of another element in the liposome membrane), passed over substrates with immobilized test compounds, or used in any of a variety of other well known binding assays for membrane proteins. Alternatively, the presenilin component may be isolated in a membrane fraction from cells producing the component, and this membrane fraction may be used in the binding assay.

B. Co-Immunoprecipitation

Another well characterized technique for the isolation of the presenilin components and their associated proteins or other compounds is direct immunoprecipitation with antibodies. This procedure has been successfully used, for example, to isolate many of the synaptic vesicle associated proteins (Phizicky and Fields (1994) *Microbiol. Reviews* 59:94–123). Thus, either normal or mutant, free or membrane-bound presenilin components may be mixed in a solution with the candidate compound(s) under conditions which are permissive for binding, and the presenilin component may be immunoprecipitated. Proteins or other compounds which co-immunoprecipitate with the presenilin component may then be identified by standard techniques as described above. General techniques for immunoprecipitation may be found in, for example, Harlow and Lane, (1988) *Antibodies: A Laboratory Manual,* Cold Spring Harbor Press, Cold Spring Harbor, N.Y.

The antibodies employed in this assay, as described and enabled herein, may be polyclonal or monoclonal, and include the various antibody fragments (e.g., Fab, F(ab')$_2$,) as well as single chain antibodies, and the like.

C. The Biomolecular Interaction Assay

Another useful method for the detection and isolation of binding proteins is the Biomolecular Interaction Assay or "BIAcore" system developed by Pharmacia Biosensor and described in the manufacturer's protocol (LKB Pharmacia, Sweden). In light of the present disclosure, one of ordinary skill in the art is now enabled to employ this system, or a substantial equivalent, to identify proteins or other compounds having presenilin binding capacity. The BIAcore system uses an affinity purified anti-GST antibody to immobilize GST-fusion proteins onto a sensor chip. Obviously, other fusion proteins and corresponding antibodies may be substituted. The sensor utilizes surface plasmon resonance which is an optical phenomenon that detects changes in refractive indices. A homogenate of a tissue of interest is passed over the immobilized fusion protein and protein-protein interactions are registered as changes in the refractive index. This system can be used to determine the kinetics of binding and to assess whether any observed binding is of physiological relevance.

D. The Yeast Two-Hybrid System

The yeast "two-hybrid" system takes advantage of transcriptional factors that are composed of two physically separable, functional domains (Phizicky and Fields, 1994). The most commonly used is the yeast GAL4 transcriptional activator consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and, if interactions occur, activation of a reporter gene (e.g., lacZ) produces a detectable phenotype. For example, the Clontech Matchmaker System-2 may be used with the Clontech brain cDNA GAL4 activation domain fusion library with presenilin-GAL4 binding domain fusion clones (Clontech, Palo Alto, Calif.). In light of the disclosures herein, one of ordinary skill in the art is now enabled to produce a variety of presenilin fusions, including fusions including either normal or mutant functional domains of the presenilin proteins, and to screen such fusion libraries in order to identify presenilin binding proteins.

E. Other Methods

The nucleotide sequences and protein products, including both mutant and normal forms of these nucleic acids and their corresponding proteins, can be used with the above techniques to isolate other interacting proteins, and to identify other genes whose expression is altered by the over-expression of normal presenilin sequences, by the under-expression of normal presenilins sequences, or by the expression of mutant presenilin sequences. Identification of these interacting proteins, as well as the identification of other genes whose expression levels are altered in the face of mutant presenilin sequences (for instance) will identify other gene targets which have direct relevance to the pathogenesis of this disease in its clinical or pathological forms. Specifically, other genes will be identified which may themselves be the site of other mutations causing Alzheimer's Disease, or which can themselves be targeted therapeutically (e.g., to reduce their expression levels to normal or to pharmacologically block the effects of their over-expression) as a potential treatment for this disease. Specifically, these techniques rely on PCR-based and/or hybridization-based methods to identify genes which are differentially expressed between two conditions (a cell line expressing normal presenilins compared to the same cell type expressing a mutant presenilin sequence). These techniques include differential display, serial analysis of gene expression (SAGE), and mass-spectrometry of protein 2D-gels and subtractive hybridization (reviewed in Nowak (1995) *Science* 270:368–371 and Kahn (1995) *Science* 270:369–370).

As will be obvious to one of ordinary skill in the art, there are numerous other methods of screening individual proteins or other compounds, as well as large libraries of proteins or other compounds (e.g., phage display libraries and cloning systems from Stratagene, La Jolla, Calif.) to identify molecules which bind to normal or mutant presenilin components. All of these methods comprise the step of mixing a normal or mutant presenilin protein, fusion, or fragment with test compounds, allowing for binding (if any), and assaying for bound complexes. All such methods are now enabled by the present disclosure of substantially pure presenilins, substantially pure presenilin functional domain fragments, presenilin fusion proteins, presenilin antibodies, and methods of making and using the same.

8. Disrupting presenilin interactions

The ability to disrupt specific presenilin interactions with other proteins is potentially of great therapeutic value, and will be important in understanding the etiology of AD and in identifying additional targets for therapy. The methods used to identify compounds which disrupt presenilin interactions may be applied equally well to interactions involving either normal or mutant presenilins and either normal or mutant interacting proteins.

Assays for compounds which can disrupt presenilin interactions may be performed by any of a variety of methods well known in the art. In essence, such assays will parallel those assays for identifying presenilin-interacting proteins and compounds. Thus, once a presenilin-interacting protein is identified by any method, that method or an equivalent method may be performed in the presence of candidate compounds to identify compounds which disrupt the interaction. Thus, for example, the assay may employ methods including (1) affinity chromatography; (2) immunoprecipitation; (3) the Biomolecular Interaction Assay (BIAcore); or (4) the yeast two-hybrid systems. Such assays can be developed using either normal or mutant purified presenilin proteins, and/or either normal or mutant and purified presenilin-interacting proteins.

For affinity methods, either the presenilin or the presenilin-interacting protein may be affixed to a matrix, for example in a column, and the counterpart protein (the interacting protein if presenilin is affixed to the matrix, or the presenilin protein if the interacting protein is affixed to the matrix) is then exposed to the affixed protein either before or after adding the candidate compound(s). In the absence of a disruptive effect by the candidate compound(s), the interaction between the presenilin and presenilin-interacting protein will cause the counterpart protein to bind to the affixed protein. Any compound which disrupts the interaction will cause release of the counterpart protein from the matrix. Release of the counterpart protein from the matrix can be measured using methods known in the art.

For presenilin interactions which are detectable by yeast two-hybrid systems, these assays may also be employed to identify compounds which disrupt the interaction. Briefly, the presenilin and presenilin-interacting proteins (or appropriate structural domains of each) are employed in the fusion proteins of the system and the cells may be exposed to candidate compounds to determine their effect upon the expression of the reporter gene. By appropriate choice of a reporter gene, such a system can be readily adapted for high through-put screening of large libraries of compounds by, for example, using a reporter gene which confers resistance to an antibiotic which is present in the medium, or which rescues an auxotrophic strain grown in minimal medium.

These assays may be used to screen many different types of compounds for their disruptive effect on the interactions of the presenilins. For example, the compounds may belong to a library of synthetic molecules, or be specifically designed to disrupt the interaction. The compounds may also be peptides corresponding to the interacting domain of either protein. This type of assay can be used to identify compounds that disrupt a specific interaction between a given presenilin variant and a given interacting protein. In addition, compounds that disrupt all interactions with presenilins may be identified. For example, a compound that specifically disrupts the folding of presenilin proteins would be expected to disrupt all interactions between presenilins and other proteins. Alternatively, this type of disruption assay can be used to identify compounds which disrupt only a range of different presenilin interactions, or only a single presenilin interaction.

9. Methods of Identifying Compounds Modulating Presenilin Activity

In another series of embodiments, the present invention provides for methods of identifying compounds with the ability to modulate the activity of normal and mutant presenilins. As used with respect to this series of embodiments, the term "activity" broadly includes gene and protein expression, presenilin protein post-translation processing, trafficking and localization, and any functional activity (e.g., enzymatic, receptor-effector, binding, channel), as well as downstream affects of any of these. The presenilins appear to be integral membrane proteins normally associated with the endoplasmic reticulum and/or Golgi apparatus and may have functions involved in the transport or trafficking of APP and/or the regulation of intracellular calcium levels. In addition, it is known that presenilin mutations are associated with the increased production of $A\beta$ peptides, the appearance of amyloid plaques and neurofibrillary tangles, decreases in cognitive function, and apoptotic cell death. Therefore, using the transformed cells and transgenic animal models of the present invention, cells obtained from subjects bearing a mutant presenilin gene, or animals or human subjects bearing naturally occurring presenilin mutations, it is now possible to screen candidate pharmaceuticals and treatments for their therapeutic effects by detecting changes in one or more of these functional characteristics or phenotypic manifestations of normal or mutant presenilin expression.

Thus, the present invention provides methods for screening or assaying for proteins, small molecules or other compounds which modulate presenilin activity by contacting a cell in vivo or in vitro with a candidate compound and assaying for a change in a marker associated with normal or mutant presenilin activity. The marker associated with presenilin activity may be any measurable biochemical, physiological, histological and/or behavioral characteristic associated with presenilin expression. In particular, useful markers will include any measurable biochemical, physiological, histological and/or behavioral characteristic which distinguishes cells, tissues, animals or individuals bearing at least one mutant presenilin gene from their normal counterparts. In addition, the marker may be any specific or non-specific measure of presenilin activity. Presenilin specific measures include measures of presenilin expression (e.g., presenilin mRNA or protein levels) which may employ the nucleic acid probes or antibodies of the present invention. Non-specific measures include changes in cell physiology such as pH, intracellular calcium, cyclic AMP levels, GTP/GDP ratios, phosphatidylinositol activity, protein phosphorylation, etc., which can be monitored on devices such as the cytosensor microphysiometer (Molecular Devices Inc., United States). The activation or inhibition of presenilin activity in its mutant or normal form can also be monitored by examining changes in the expression of other genes which are specific to the presenilin pathway leading to Alzheimer's Disease. These can be assayed by such techniques as differential display, differential hybridization, and SAGE (sequential analysis of gene expression), as well as by two dimensional gel electrophoresis of cellular lysates. In each case, the differentially-expressed genes can be ascertained by inspection of identical studies before and after application of the candidate compound. Furthermore, as noted elsewhere, the particular genes whose expression is modulated by the administration of the candidate compound can be ascertained by cloning, nucleotide sequencing, amino acid sequencing, or mass spectrometry (reviewed in Nowak, 1995).

In general, a cell may be contacted with a candidate compound and, after an appropriate period (e.g., 0–72 hours for most biochemical measures of cultured cells), the marker of presenilin activity may be assayed and compared to a baseline measurement. The baseline measurement may be made prior to contacting the cell with the candidate compound or may be an external baseline established by other experiments or known in the art. The cell may be a transformed cell of the present invention or an explant from an animal or individual. In particular, the cell may be an explant from a carrier of a presenilin mutation (e.g., a human subject with Alzheimer's Disease) or an animal model of the invention (e.g., a transgenic nematode or mouse bearing a mutant presenilin gene). To augment the effect of presenilin mutations on the AD pathway, transgenic cells or animals may be employed which have increased Aβ production. Preferred cells include those from neurological tissues such as neuronal, glial or mixed cell cultures; and cultured fibroblasts, liver, kidney, spleen, or bone marrow. The cells may be contacted with the candidate compounds in a culture in vitro or may be administered in vivo to a live animal or human subject. For live animals or human subjects, the test compound may be administered orally or by any parenteral route suitable to the compound. For clinical trials of human subjects, measurements may be conducted periodically (e.g., daily, weekly or monthly) for several months or years.

Because most carriers of presenilin mutations will be heterozygous (i.e., bearing one normal and one mutant presenilin allele), compounds may be tested for their ability to modulate normal as well as mutant presenilin activity. Thus, for example, compounds which enhance the function of normal presenilins may have utility in treating presenilin associated disorders such as Alzheimer's Disease. Alternatively, because suppression of the activity of both normal and mutant presenilins in a heterozygous individual may have less severe clinical consequences than progression of the associated disease, it may be desired to identify compounds which inactivate or suppress all forms of the presenilins. Preferably, however, compounds are identified which selectively or specifically inactivate or suppress the activity of a mutant presenilin without disrupting the function of a normal presenilin gene or protein.

In light of the identification, characterization, and disclosure herein of the presenilin genes and proteins, the presenilin nucleic acid probes and antibodies, and the presenilin transformed cells and transgenic animals of the invention, one of ordinary skill in the art is now enabled by perform a great variety of assays which will detect the modulation of presenilin activity by candidate compounds. Particularly preferred and contemplated embodiments are discussed in some detail below.

A. Presenilin Expression

In one series of embodiments, specific measures of presenilin expression are employed to screen candidate compounds for their ability to affect presenilin activity. Thus, using the presenilin nucleic acids and antibodies disclosed and otherwise enabled herein, one may use mRNA levels or protein levels as a marker for the ability of a candidate compound to modulate presenilin activity. The use of such probes and antibodies to measure gene and protein expression is well known in the art and discussed elsewhere herein. Of particular interest may be the identification of compounds which can alter the relative levels of different splice variants of the presenilins. Many of the presenilin mutations associated with Alzheimer's Disease, for example, are located in the region of the putative TM6→7 loop which is subject to alternative splicing in some peripheral tissues (e.g., white blood cells). Compounds which can increase the relative frequency of this splicing event may, therefore, be effective in preventing the expression of mutations in this region.

B. Intracellular Localization

In another series of embodiments, compounds may be screened for their ability to modulate the activity of the presenilins based upon their effects on the trafficking and intracellular localization of the presenilins. The presenilins have been seen immunocytochemically to be localized in membrane structures associated with the endoplasmic reticulum and Golgi apparatus, and one presenilin mutant (H163R), but not others, has been visualized in small cytoplasmic vesicles of unknown function. Differences in localization of mutant and normal presenilins may, therefore, contribute to the etiology of presenilin-related diseases. Compounds which can affect the localization of the presenilins may, therefore, be identified as potential therapeutics. Standard techniques known in the art may be employed to detect the localization of the presenilins. Generally, these techniques will employ the antibodies of the present invention, and in particular antibodies which selectively bind to one or more mutant presenilins but not to normal presenilins. As is well known in the art, such antibodies may be labeled by any of a variety of techniques (e.g., fluorescent or radioactive tags, labeled secondary antibodies, avidin-biotin, etc.) to aid in visualizing the intracellular location of the presenilins. The presenilins may be co-localized to particular structures, as in known in the art, using antibodies to markers of those structures (e.g., TGN38 for the Golgi, transferrin receptor for post-Golgi transport vesicles, LANP2 for lysosomes). Western blots of purified fractions from cell lysates enriched for different intracellular membrane bound organelles (e.g., lysosomes, synaptosomes, Golgi) may also be employed. In addition, the relative orientation of different domains of the presenilins across cellular domains may be assayed using, for example, electron microscopy and antibodies raised to those domains.

C. Ion Regulation/Metabolism

In another series of embodiments, compounds may be screened for their ability to modulate the activity of the presenilins based upon measures in intracellular $Ca^{2+}$, $Na^+$ or K⁺ levels or metabolism. As noted above, the presenilins are membrane associated proteins which may serve as, or interact with, ion receptors or ion channels. Thus, compounds may be screened for their ability to modulate presenilin-related calcium or other ion metabolism either in vivo or in vitro by measurements of ion channel fluxes and/or transmembrane voltage or current fluxes using patch clamp, voltage clamp and fluorescent dyes sensitive to intracellular calcium or transmembrane voltage. Ion channel or receptor function can also be assayed by measurements of activation of second messengers such as cyclic AMP, cGMP tyrosine kinases, phosphates, increases in intracellular $Ca^{2+}$ levels, etc. Recombinantly made proteins may also be reconstructed in artificial membrane systems to study ion channel conductance and, therefore, the "cell" employed in such assays may comprise an artificial membrane or cell. Assays for changes in ion regulation or metabolism can be performed on cultured cells expressing endogenous normal or mutant presenilins. Such studies also can be performed on cells transfected with vectors capable of expressing one of the presenilins, or functional domains of one of the presenilins, in normal or mutant form. In addition, the enhance the signal measured in such assays, cells may be co-transfected with genes encoding ion channel proteins. For example, Xenopus oocytes or rat kidney (HEK293) cells may be co-transfected with normal or mutant presenilin sequences and sequences encoding rat brain $Na^+\beta 1$ subunits, rabbit skeletal muscle $Ca^{2+}\beta 1$ subunits, or rat heart $K^+\beta 1$ subunits. Changes in presenilin-related or presenilin-mediated ion channel activity can be measured by two-microelectrode voltage-clamp recordings in oocytes or by whole-cell patch-clamp recordings in HEK293 cells.

D. Apoptosis or Cell Death

In another series of embodiments, compounds may be screened for their ability to modulate the activity of the presenilins based upon their effects on presenilin-related or presenilin-mediated apoptosis or cell death. Thus, for example, baseline rates of apoptosis or cell death may be established for cells in culture, or the baseline degree of neuronal loss at a particular age may be established post-mortem for animal models or human subjects, and the ability of a candidate compound to suppress or inhibit apoptosis or cell death may be measured. Cell death may be measured by standard microscopic techniques (e.g., light microscopy) or apoptosis may be measured more specifically by characteristic nuclear morphologies or DNA fragmentation patterns which create nucleosomal ladders (see, e.g., Gavrieli et al. (1992) *J. Cell Biol.* 119:493–501; Jacobson et al. (1993) *Nature* 361:365; Vito et al. (1996) *Science* 271:521–525). TUNEL may also be employed to evaluate cell death in brain (see, e.g., Lassmann et al., 1995). In preferred embodiments, compounds are screened for their ability to suppress or inhibit neuronal loss in the transgenic animal models of the invention. Transgenic mice bearing, for example, a mutant human, mutant mouse, or humanized mutant presenilin gene may be employed to identify or evaluate compounds which may delay or arrest the neurodegeneration associated with Alzheimer's Disease. A similar transgenic mouse model, bearing a mutant APP gene, has recently been reported by Games et al. (1995).

E. Aβ Peptide Production

In another series of embodiments, compounds may be screened for their ability to modulate presenilin-related or presenilin-mediated changes in APP processing. The Aβ peptide is produced in several isoforms resulting from differences in APP processing. The Aβ peptide is a 39 to 43 amino acid derivative of βAPP which is progressively deposited in diffuse and senile plaques and in blood vessels of subjects with AD. In human brain, Aβ peptides are heterogeneous at both the N- and C-termini. Several observations, however, suggest that both the full length and N-terminal truncated forms of the long-tailed Aβ peptides ending at residue 42 or 43 (i.e., Aβ1-42/43 and Aβx-42/43) have a more important role in AD than do peptides ending at residue 40. Thus, Aβ1-42/43 and Aβx-42/43 are an early and prominent feature of both senile plaques and diffuse plaques, while peptides ending at residue 40 (i.e., Aβ1-40 and Aβx-40) are predominantly associated with a subset of mature plaques and with amyloidotic blood vessels (see, e.g., Iwatsubo et al. (1995) *Ann. Neurol.* 37:294–299; Gravina et al. (1995) *J. Biol. Chem.* 270:7013–7016; Tamaoka et al. (1995) *Brain Res.* 679:151–156; Podlisny et al. (1995) *J. Biol. Chem.* 270:9564–9570). Furthermore, the long-tailed isoforms have a greater propensity to fibril formation, and are thought to be more neurotoxic than Aβ1-40 peptides (Pike et al., 1993; Hilbich et al. (1991) *J. Mol. Biol.* 218:149–163). Finally, missense mutations at codon 717 of the βAPP gene associated with early onset FAD result in overproduction of long-tailed Aβ in the brain of affected mutation carriers, in peripheral cells and plasma of both affected and presymptomatic carriers, and in cell lines transfected with $\beta APP_{717}$ mutant cDNAs (Tamaoka et al. (1994) *J. Biol. Chem.* 269:32721–32724; Suzuki et al. (1994) *Science* 264:1336–1340) As described in Example 18 below, we now disclose that increased production of the long-forms of the Aβ peptide are also associated with mutations in the presenilin genes.

Thus, in one series of embodiments, the present invention provides methods for screening candidate compounds for their ability to block or inhibit the increased production of long isoforms of the Aβ peptides in cells or transgenic animals expressing a mutant presenilin gene. In particular, the present invention provides such methods in which cultured mammalian cells, such as brain cells or fibroblasts, have been transformed according to the methods disclosed herein, or in which transgenic animals, such as rodents or non-human primates, have been produced by the methods disclosed herein, to express relatively high levels of a mutant presenilin. Optionally, such cells or transgenic animals may also be transformed so as to express a normal form of the βAPP protein at relatively high levels.

In this series of embodiments, the candidate compound is administered to the cell line or transgenic animals (e.g., by addition to the media of cells in culture; or by oral or parenteral administration to an animal) and, after an appropriate period (e.g., 0–72 hours for cells in culture, days or months for animal models), a biological sample is collected (e.g., cell culture supernatant or cell lysate from cells in culture; tissue homogenate or plasma from an animal) and tested for the level of the long isoforms of the Aβ peptides. The levels of the peptides may be determined in an absolute sense (e.g., nMol/ml) or in a relative sense (e.g., ratio of long to short Aβ isoforms). The Aβ isoforms may be detected by any means known in the art (e.g., electrophoretic separation and sequencing) but, preferably, antibodies which are specific to the long isoform are employed to determine the absolute or relative levels of the Aβ1-42/43 or Aβx-42/43 peptides. Candidate pharmaceuticals or therapies which reduce the absolute or relative levels of these long Aβ isoforms, particularly in the transgenic animal models of the invention, are likely to have therapeutic utility in the treatment of Alzheimer's Disease, or other disorders caused by presenilin mutations or aberration in APP metabolism.

F. Phosphorylation of Microtubule Associated Proteins

In another series of embodiments, candidate compounds may be screened for their ability to modulate presenilin activity by assessing the effect of the compound on levels of phosphorylation of microtubule associated proteins (MAPs) such as Tau. The abnormal phosphorylation of Tau and other MAPs in the brains of victims of Alzheimer's Disease is well known in the art. Thus, compounds which prevent or inhibit the abnormal phosphorylation of MAPs may have utility in treating presenilin associated diseases such as AD. As above, cells from normal or mutant animals or subjects, or the transformed cell lines and animal models of the invention may be employed. Preferred assays will employ cell lines or animal models transformed with a mutant human or humanized mutant presenilin gene. The baseline phosphorylation state of MAPs in these cells may be established and then candidate compounds may be tested for their ability to prevent, inhibit or counteract the hyperphosphorylation associated with mutants. The phosphorylation state of the MAPs may be determined by any standard method known in the art but, preferably, antibodies which bind selectively to phosphorylated or unphosphorylated epitopes are employed. Such antibodies to phosphorylation epitopes of the Tau protein are known in the art (e.g., ALZ50).

10. Screening and Diagnostics for Alzheimer's Disease

A. General Diagnostic Methods

The presenilin genes and gene products, as well as the presenilin-derived probes, primers and antibodies, disclosed or otherwise enabled herein, are useful in the screening for carriers of alleles associated with Alzheimer's Disease, for diagnosis of victims of Alzheimer's Disease, and for the screening and diagnosis of related presenile and senile dementias, psychiatric diseases such as schizophrenia and depression, and neurologic diseases such as stroke and cerebral hemorrhage, all of which are seen to a greater or lesser extent in symptomatic human subjects bearing mutations in the PS1 or PS2 genes or in the APP gene. Individuals at risk for Alzheimer's Disease, such as those with AD present in the family pedigree, or individuals not previously known to be at risk, may be routinely screened using probes to detect the presence of a mutant presenilin gene or protein by a variety of techniques. Diagnosis of inherited cases of these diseases can be accomplished by methods based upon the nucleic acids (including genomic and mRNA/cDNA sequences), proteins, and/or antibodies disclosed and enabled herein, including functional assays designed to detect failure or augmentation of the normal presenilin activity and/or the presence of specific new activities conferred by the mutant presenilins. Preferably, the methods and products are based upon the human PS1 or PS2 nucleic acids, proteins or antibodies, as disclosed or otherwise enabled herein. As will be obvious to one of ordinary skill in the art, however, the significant evolutionary conservation of large portions of the PS1 and PS2 nucleotide and amino acid sequences, even in species as diverse as humans, mice, *C. elegans,* and Drosophila, allow the skilled artisan to make use of such non-human presenilin-homologue nucleic acids, proteins and antibodies, even for applications directed toward human or other animal subjects. Thus, for brevity of exposition, but without limiting the scope of the invention the following description will focus upon uses of the human homologues of PS1 and PS2. It will be understood, however, that homologous sequences from other species, including those disclosed herein, will be equivalent for many purposes.

As will be appreciated by one of ordinary skill in the art, the choice of diagnostic methods of the present invention will be influenced by the nature of the available biological samples to be tested and the nature of the information required. PS1, for example, is highly expressed in brain tissue but brain biopsies are invasive and expensive procedures, particularly for routine screening. Other tissues which express PS1 at significant levels, however, may demonstrate alternative splicing (e.g., lymphocytes) and, therefore, PS1 mRNA or protein from such cells may be less informative. Thus, an assay based upon a subject's genomic PS1 DNA may be the preferred because no information will be dependent upon alternative splicing and because essentially any nucleate cells may provide a usable sample. Diagnostics based upon other presenilins (e.g., hPS2, mPS1) are subject to similar considerations: availability of tissues, levels of expression in various tissues, and alternative mRNA and protein products resulting from alternative splicing.

B. Protein Based Screens and Diagnostics

When a diagnostic assay is to be based upon presenilin proteins, a variety of approaches are possible. For example, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In preferred embodiments, protein-based diagnostics will employ differences in the ability of antibodies to bind to normal and mutant presenilin proteins (especially hPS1 or hPS2). Such diagnostic tests may employ antibodies which bind to the normal proteins but not to mutant protein, or vice versa. In particular, an assay in which a plurality of monoclonal antibodies, each capable of binding to a mutant epitope, may be employed. The levels of anti-mutant antibody binding in a sample obtained from a test subject (visualized by, for example, radiolabelling, ELISA or chemiluminescence) may be compared to the levels of binding to a control sample. Alternatively, antibodies which bind to normal but not mutant presenilins may be employed, and decreases in the level of antibody binding may be used to distinguish homozygous normal individuals from mutant heterozygotes or homozygotes. Such antibody diagnostics may be used for in situ immunohistochemistry using biopsy samples of CNS tissues obtained antemortem or postmortem, including neuropathological structures associated with these diseases such as neurofibrillary tangles and amyloid plaques, or may be used with fluid samples such a cerebrospinal fluid or with peripheral tissues such as white blood cells.

C. Nucleic Acid Based Screens and Diagnostics

When the diagnostic assay is to be based upon nucleic acids from a sample, the assay may be based upon mRNA, cDNA or genomic DNA. When mRNA is used from a sample, many of the same considerations apply with respect to source tissues and the possibility of alternative splicing. That is, there may be little or no expression of transcripts unless appropriate tissue sources are chosen or available, and alternative splicing may result in the loss of some information or difficulty in interpretation. However, we have already shown (Sherrington et al., 1995; Rogaev et al., 1995) that mutations in the 5' UTR, 3' UTR, open reading frame and splice sites of both PS1 and PS2 can reliably be identified in mRNA/cDNA isolated from white blood cells and/or skin fibroblasts. Whether mRNA, cDNA or genomic DNA is assayed, standard methods well known in the art may be used to detect the presence of a particular sequence either in situ or in vitro (see, e.g., Sambrook et al., (1989) *Molecular Cloning: A Laboratory Manual*, 2nd ed., Cold Spring Harbor Press, Cold Spring Harbor, N.Y.). As a general matter, however, any tissue with nucleated cells may be examined Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, direct nucleotide sequencing, hybridization using specific oligonucleotides, restriction enzyme digest and mapping, PCR mapping, RNase protection, chemical mismatch cleavage, ligase-mediated detection, and various other methods may be employed. Oligonucleotides specific to particular sequences can be chemically synthesized and labeled radioactively or non-radioactively (e.g., biotin tags, ethidium bromide), and hybridized to individual samples immobilized on membranes or other solid-supports (e.g., by dot-blot or transfer from gels after electrophoresis), or in solution. The presence or absence of the target sequences may then be visualized using methods such as autoradiography, fluorometry, or colorimetry. These procedures can be automated using redundant, short oligonucleotides of known sequence fixed in high density to silicon chips.

(1) Appropriate Probes and Primers

Whether for hybridization, RNase protection, ligase-mediated detection, PCR amplification or any other standards methods described herein and well known in the art, a variety of subsequences of the presenilin sequences disclosed or otherwise enabled herein will be useful as probes and/or primers. These sequences or subsequences will include both normal presenilin sequences and deleterious mutant sequences. In general, useful sequences will include at least 8–9, more preferably 10–50, and most preferably 18–24 consecutive nucleotides from the presenilin introns, exons or intron/exon boundaries. Depending upon the target sequence, the specificity required, and future technological developments, shorter sequences may also have utility. Therefore, any presenilin derived sequence which is employed to isolate, clone, amplify, identify or otherwise manipulate a presenilin sequence may be regarded as an appropriate probe or primer. Particularly contemplated as useful will be sequences including nucleotide positions from the presenilin genes in which disease-causing mutations are known to be present, or sequences which flank these positions.

(a) PS1 Probes and Primers

As discussed above, a variety of disease-causing mutations have now been identified in the human PS1 gene. Detection of these and other PS1 mutations is now enabled using isolated nucleic acid probes or primers derived from normal or mutant PS1 genes. Particularly contemplated as useful are probes or primers derived from sequences encoding the N-terminus, the TM1–TM2 region, and the TM6–TM7 region. As disclosed above, however, mutations have already been detected which affect other regions of the PS1 protein and, using the methods disclosed herein, more will undoubtedly be detected. Therefore, the present invention provides isolated nucleic acid probes and primers corresponding to normal and mutant sequences from any portion of the PS1 gene, including introns and 5' and 3' UTRs, which may be shown to be associated with the development of Alzheimer's Disease.

Merely as an example, and without limiting the invention, probes and primers derived from the hPS1 DNA segment immediately surrounding the C410Y mutation may be employed in screening and diagnostic methods. This mutation arises, at least in some individuals, from the substitution of an A for a G at position 1477 of SEQ ID NO:1. Thus, genomic DNA, mRNA or cDNA acquired from peripheral blood samples from an individual can be screened using oligonucleotide probes or primers including this potentially mutant site. For hybridization probes for this mutation, probes of 8–50, and more preferably 18–24 bases spanning the mutation site (e.g., bp 1467–1487 of SEQ ID NO: 1) may be employed. If the probe is to be used with mRNA, it should of course be complementary to the mRNA (and, therefore, correspond to the non-coding strand of the PS1 gene. For probes to be used with genomic DNA or cDNA, the probe may be complementary to either strand. To detect sequences including this mutation by PCR methods, appropriate primers would include sequences of 8–50, and preferably 18–24, nucleotides in length derived from the regions flanking the mutation on either side, and which correspond to positions anywhere from 1 to 1000 bp, but preferably 1–200 bp, removed from the site of the mutation. PCR primers which are 5' to the mutation site (on the coding strand) should correspond in sequence to the coding strand of the PS1 gene whereas PCR primers which are 3' to the mutation site (on the coding strand) should correspond to the non-coding or antisense strand (e.g., a 5' primer corresponding to bp 1451–1468 of SEQ ID NO:1 and a 3' primer corresponding to the complement of 719–699 of SEQ ID NO:14).

Similar primers may be chosen for other PS1 mutations or for the mutational "hot spots" in general. For example, a 5' PCR primer for the M146L mutation (A→C at bp 684) may comprise a sequence corresponding to approximately bp 601–620 of SEQ ID NO:1 and a 3' primer may correspond to the complement of approximately bp 1328–1309 of SEQ ID NO:8. Note that this example employs primers from both intronic and exonic sequences. As another example, an appropriate 5' primer for the A246E mutation (C→A at bp 985) may comprise a sequence corresponding to approximately bp 907–925 of SEQ ID NO:1 or a 3' primer corresponding to the complement of approximately bp 1010–990 of SEQ ID NO:1. As another example, a 5' primer for the H163R mutation (A→G at bp 736 of SEQ ID NO:1 or bp 419 of SEQ ID NO:9) comprising a sequence corresponding to approximately bp 354–375 of SEQ ID NO:9 with a 3' primer corresponding to the complement of approximately bp 581–559 of SEQ ID NO:9. Similarly, intronic or exonic sequences may be employed, for example, to produce a 5' primer for the L286V mutation (C→G at bp 1104 of SEQ ID NO:1 or bp 398 of SEQ ID NO:11) comprising a sequence corresponding to approximately bp 249–268 of SEQ ID NO:11 or bp 1020–1039 of SEQ ID NO:1, and a 3' primer corresponding to the complement of approximately bp 510–491 of SEQ ID NO: 11.

It should also be noted that the probes and primers may include specific mutated nucleotides. Thus, for example, a hybridization probe or 5' primer may be produced for the C410Y mutation comprising a sequence corresponding to approximately bp 1468–1486 of SEQ ID NO:1 to screen for or amplify normal alleles, or corresponding to the same sequence but with the bp corresponding to bp 1477 altered (G→T) to screen for or amplify mutant alleles.

(b) PS2 Probes and Primers

The same general considerations described above with respect to probes and primers for PS1, apply equally to probes and primers for PS2. In particular, the probes or primers may correspond to intron, exon or intron/exon boundary sequences, may correspond to sequences from the coding or non-coding (antisense) strands, and may correspond to normal or mutant sequences.

Merely as examples, the PS1 N141I mutation (A→T at bp 787) may be screened for by PCR amplification of the surrounding DNA fragment using a 5' primer corresponding to approximately bp 733–751 of SEQ ID NO:18 and a 3' primer corresponding to the complement of approximately bp 846–829 of SEQ ID NO:18. Similarly, a 5' primer for the M239V mutation (A→G at bp 1080) may comprise a sequence corresponding to approximately bp 1009–1026 and a 3' primer may correspond to the complement of approximately bp 1118–1101 of SEQ ID NO:18. As another example, the sequence encoding the region surrounding the 1420T mutation (T→C at bp 1624) may be screened for by PCR amplification of genomic DNA using a 5' primer corresponding to approximately bp 1576–1593 of SEQ ID NO: 18 and a 3' primer corresponding to the complement of approximately bp 1721–1701 of SEQ ID NO:18 to generate a 146 base pair product. This product may, for example, then be probed with allele specific oligonucleotides for the wild-type (e.g., bp 1616–1632 of SEQ ID NO:18) and/or mutant (e.g., bp 1616–1632 of SEQ ID NO:18 with T→C at bp 1624) sequences.

(2) Hybridization Screening

For in situ detection of a normal or mutant PS1, PS2 or other presenilin-related nucleic acid sequence, a sample of tissue may be prepared by standard techniques and then contacted with one or more of the above-described probes, preferably one which is labeled to facilitate detection, and an assay for nucleic acid hybridization is conducted under stringent conditions which permit hybridization only between the probe and highly or perfectly complementary sequences. Because most of the PS1 and PS2 mutations detected to date consist of a single nucleotide substitution, high stringency hybridization conditions will be required to distinguish normal sequences from most mutant sequences. When the presenilin genotypes of the subject's parents are known, probes may be chosen accordingly. Alternatively, probes to a variety of mutants may be employed sequentially or in combination. Because most individuals carrying presenilin mutants will be heterozygous, probes to normal sequences also may be employed and homozygous normal individuals may be distinguished from mutant heterozygotes by the amount of binding (e.g., by intensity of radioactive signal). In another variation, competitive binding assays may be employed in which both normal and mutant probes are used but only one is labeled.

(3) Restriction Mapping

Sequence alterations may also create or destroy fortuitous restriction enzyme recognition sites which are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Such restriction fragment length polymorphism analysis (RFLP), or restriction mapping, may be employed with genomic DNA, mRNA or cDNA. The presenilin sequences may be amplified by PCR using the above-described primers prior to restriction, in which case the lengths of the PCR products may indicate the presence or absence of particular restriction sites, and/or may be subjected to restriction after amplification. The presenilin fragments may be visualized by any convenient means (e.g., under UV light in the presence of ethidium bromide).

Merely as examples, it is noted that the PS1 M146L mutation (A→C at bp 684 of SEQ ID NO:1) destroys a PsphI site; the H163R mutation (A→G at bp 736) destroys an NlaIII site; the A246E mutation (C→A at bp 985) creates a DdeI site; and the L286V mutation (C→G at bp 1104) creates a PvuIII site. One of ordinary skill in the art may easily choose from the many commercially available restriction enzymes and, based upon the normal and mutant sequences disclosed and otherwise enabled herein, perform a restriction mapping analysis which will detect virtually any presenilin mutation.

(4) PCR Mapping

In another series of embodiments, a single base substitution mutation may be detected based on differential PCR product length or production in PCR. Thus, primers which span mutant sites or which, preferably, have 3' termini at mutation sites, may be employed to amplify a sample of genomic DNA, mRNA or cDNA from a subject. A mismatch at a mutational site may be expected to alter the ability of the normal or mutant primers to promote the polymerase reaction and, thereby, result in product profiles which differ between normal subjects and heterozygous and/or homozygous presenilin mutants. The PCR products of the normal and mutant gene may be differentially separated and detected by standard techniques, such as polyacrylamide or agarose gel electrophoresis and visualization with labeled probes, ethidium bromide or the like. Because of possible non-specific priming or readthrough of mutation sites, as well as the fact that most carriers of mutant alleles will be heterozygous, the power of this technique may be low.

(5) Electrophoretic Mobility

Genetic testing based on DNA sequence differences also may be achieved by detection of alterations in electrophoretic mobility of DNA, mRNA or cDNA fragments in gels. Small sequence deletions and insertions, for example, can be visualized by high resolution gel electrophoresis of single or double stranded DNA, or as changes in the migration pattern of DNA heteroduplexes in non-denaturing gel electrophoresis. Presenilin mutations or polymorphisms may also be detected by methods which exploit mobility shifts due to single-stranded conformational polymorphisms (SSCP) associated with mRNA or single-stranded DNA secondary structures.

(6) Chemical Cleavage of Mismatches

Mutations in the presenilins may also be detected by employing the chemical cleavage of mismatch (CCM) method (see, e.g., Saleeba and Cotton, 1993, and references therein). In this technique, probes (up to ~1 kb) may be mixed with a sample of genomic DNA, cDNA or mRNA obtained from a subject. The sample and probes are mixed and subjected to conditions which allow for heteroduplex formation (if any). Preferably, both the probe and sample nucleic acids are double-stranded, or the probe and sample may be PCR amplified together, to ensure creation of all possible mismatch heteroduplexes. Mismatched T residues are reactive to osmium tetroxide and mismatched C residues are reactive to hydroxylamine. Because each mismatched A will be accompanied by a mismatched T, and each mismatched G will be accompanied by a mismatched C, any nucleotide differences between the probe and sample (including small insertions or deletions) will lead to the formation of at least one reactive heteroduplex. After treatment with osmium tetroxide and/or hydroxylamine to modify any mismatch sites, the mixture is subjected to chemical cleavage at any modified mismatch sites by, for example, reaction with piperidine. The mixture may then be analyzed by standard techniques such as gel electrophoresis to detect cleavage products which would indicate mismatches between the probe and sample.

(7) Other Methods

Various other methods of detecting presenilin mutations, based upon the presenilin sequences disclosed and otherwise enabled herein, will be apparent to those of ordinary skill in the art. Any of these may be employed in accordance with the present invention. These include, but are not limited to, nuclease protection assays (SI or ligase-mediated), ligated PCR, denaturing gradient gel electrophoresis (DGGE; see, e.g., Fischer and Lerman (1983) *Proc. Natl. Acad. Sci. (USA)* 80:1579–1583), restriction endonuclease fingerprinting combined with SSCP (REF-SSCP; see, e.g., Liu and Sommer, 1995), and the like.

D. Other Screens and Diagnostics

In inherited cases, as the primary event, and in non-inherited cases as a secondary event due to the disease state, abnormal processing of PS1, PS2, APP, or proteins reacting with PS1, PS2, or APP may occur. This can be detected as abnormal phosphorylation, glycosylation, glycation amidation or proteolytic cleavage products in body tissues or fluids (e.g., CSF or blood).

Diagnosis also can be made by observation of alterations in presenilin transcription, translation, and post-translational modification and processing as well as alterations in the intracellular and extracellular trafficking of presenilin gene products in the brain and peripheral cells. Such changes will include alterations in the amount of presenilin messenger RNA and/or protein, alteration in phosphorylation state, abnormal intracellular location/distribution, abnormal extracellular distribution, etc. Such assays will include: Northern Blots (with presenilin-specific and non-specific nucleotide probes), Western blots and enzyme-linked immunosorbent assays (ELISA) (with antibodies raised specifically to a presenilin or presenilin functional domain, including various post-translational modification states including glycosylated and phosphorylated isoforms). These assays can be performed on peripheral tissues (e.g., blood cells, plasma, cultured or other fibroblast tissues, etc.) as well as on biopsies of CNS tissues obtained antemortem or postmortem, and upon cerebrospinal fluid. Such assays might also include in situ hybridization and immunohistochemistry (to localize messenger RNA and protein to specific subcellular compartments and/or within neuropathological structures associated with these diseases such as neurofibrillary tangles and amyloid plaques).

E. Screening and Diagnostic Kits

In accordance with the present invention, diagnostic kits are also provided which will include the reagents necessary for the above-described diagnostic screens. For example, kits may be provided which include antibodies or sets of antibodies which are specific to one or more mutant epitopes. These antibodies may, in particular, be labeled by any of the standard means which facilitate visualization of binding. Alternatively, kits may be provided in which oligonucleotide probes or PCR primers, as described above, are present for the detection and/or amplification of mutant PS1, PS2 or other presenilin-related nucleotide sequences. Again, such probes may be labeled for easier detection of specific hybridization. As appropriate to the various diagnostic embodiments described above, the oligonucleotide probes or antibodies in such kits may be immobilized to substrates and appropriate controls may be provided.

11. Methods of Treatment

The present invention now provides a basis for therapeutic intervention in diseases which are caused, or which may be caused, by mutations in the presenilins. As detailed above, mutations in the hPS1 and hPS2 genes have been associated with the development of early onset forms of Alzheimer's Disease and, therefore, the present invention is particularly directed to the treatment of subjects diagnosed with, or at risk of developing, Alzheimer's Disease. In view of the expression of the PS1 and PS2 genes in a variety of tissues, however, it is quite likely that the effects of mutations at these loci are not restricted to the brain and, therefore, may be causative of disorders in addition to Alzheimer's Disease. Therefore, the present invention is also directed at diseases manifest in other tissues which may arise from mutations, mis-expression, mis-metabolism or other inherited or acquired alterations in the presenilin genes and gene products. In addition, although Alzheimer's Disease manifests as a neurological disorder, this manifestation may be caused by mutations in the presenilins which first affect other organ tissues (e.g., liver), which then release factors which affect brain activity, and ultimately cause Alzheimer's Disease. Hence, in considering the various therapies described below, it is understood that such therapies may be targeted at tissue other than the brain, such as heart, placenta, lung, liver, skeletal muscle, kidney and pancreas, where PS1 and/or PS2 are also expressed.

Without being bound to any particular theory of the invention, the effect of the Alzheimer's Disease related mutations in the presenilins appears to be a gain of a novel function, or an acceleration of a normal function, which directly or indirectly causes aberrant processing of the Amyloid Precursor Protein (APP) into Aβ peptide, abnormal phosphorylation homeostasis, and/or abnormal apoptosis in the brain. Such a gain of function or acceleration of function model would be consistent with the adult onset of the symptoms and the dominant inheritance of Alzheimer's Disease. Nonetheless, the mechanism by which mutations in the presenilins may cause these effects remains unknown.

It is known that APP may be metabolized through either of two pathways. In the first, APP is metabolized by passage through the Golgi network and then to secretory pathways via clathrin-coated vesicles. Mature APP is then passaged to the plasma membrane where it is cleaved by α-secretase to produce a soluble fraction (Protease Nexin II) plus a non-amyloidogenic C-terminal peptide (Selkoe et al. (1995); Gandy et al. (1993)). Alternatively, mature APP can be directed to the endosome-lysosome pathway where it undergoes β and γ-secretase cleavage to produce the Aβ peptides. The Aβ peptide derivatives of APP are neurotoxic (Selkoe et al. (1994)). The phosphorylation state of the cell determines the relative balance between the α-secretase (nonamyloidogenic) or Aβ pathways (amyloidogenic pathway) (Gandy et al. 1993), and can be modified pharmacologically by phorbol esters, muscarinic agonists and other agents. The phosphorylation state of the cell appears to be mediated by cytosolic factors (especially protein kinase C) acting upon one or more integral membrane proteins in the Golgi network.

Without being bound to any particular theory of the invention, the presenilins, in particular hPS1 or hPS2 (which carry several phosphorylation consensus sequences for protein kinase C), may be the integral membrane proteins whose phosphorylation state determines the relative balance between the α-secretase and Aβ pathways. Thus, mutations in the PS1 or PS2 genes may cause alterations in the structure and function of their products leading to defective interactions with regulatory elements (e.g., protein kinase C) or with APP, thereby promoting APP to be directed to the amyloidogenic endosome-lysosome pathway. Environmental factors (e.g., viruses, toxins, or aging) may also have similar effects on PS1 or PS2.

Again without being bound to any particular theory of the invention, it is also noted that both the PS1 and PS2 proteins have substantial amino acid sequence homology to human ion channel proteins and receptors. For instance, the PS2 protein shows substantial homology to the human sodium channel α-subunit (E=0.18, P=0.16, identities= 22–27% over two regions of at least 35 amino acid residues)

using the BLASTP paradigm of Altschul et al. (1990). Other diseases (such as malignant hyperthermia and hyperkalemic periodic paralysis in humans, and the degeneration of mechanosensory neurons in *C. elegans*) arise through mutations in ion channels or receptor proteins. Mutation of the PS1 or PS2 gene could, therefore, affect similar functions and lead to Alzheimer's Disease and/or other psychiatric and neurological diseases.

Therapies to treat presenilin-associated diseases such as AD may be based upon (1) administration of normal PS1 or PS2 proteins, (2) gene therapy with normal PS1 or PS2 genes to compensate for or replace the mutant genes, (3) gene therapy based upon antisense sequences to mutant PS1 or PS2 genes or which "knock-out" the mutant genes, (4) gene therapy based upon sequences which encode a protein which blocks or corrects the deleterious effects of PS1 or PS2 mutants, (5) immunotherapy based upon antibodies to normal and/or mutant PS1 or PS2 proteins, or (6) small molecules (drugs) which alter PS1 or PS2 expression, block abnormal interactions between mutant forms of PS1 or PS2 and other proteins or ligands, or which otherwise block the aberrant function of mutant PS1 or PS2 proteins by altering the structure of the mutant proteins, by enhancing their metabolic clearance, or by inhibiting their function.

A. Protein Therapy

Treatment of presenilin-related Alzheimer's Disease, or other disorders resulting from presenilin mutations, may be performed by replacing the mutant protein with normal protein, by modulating the function of the mutant protein, or by providing an excess of normal protein to reduce the effect of any aberrant function of the mutant proteins.

To accomplish this, it is necessary to obtain, as described and enabled herein, large amounts of substantially pure PS1 protein or PS2 protein from cultured cell systems which can express the protein. Delivery of the protein to the affected brain areas or other tissues can then be accomplished using appropriate packaging or administrating systems including, for example, liposome mediated protein delivery to the target cells.

B. Gene Therapy

In one series of embodiments, gene therapy is may be employed in which normal copies of the PS1 gene or the PS2 gene are introduced into patients to code successfully for normal protein in one or more different affected cell types. The gene must be delivered to those cells in a form in which it can be taken up and code for sufficient protein to provide effective function. Thus, it is preferred that the recombinant gene be operably joined to a strong promote so as to provide a high level of expression which will compensate for, or out-compete, the mutant proteins. As noted above, the recombinant construct may contain endogenous or exogenous regulatory elements, inducible or repressible regulatory elements, or tissue-specific regulatory elements.

In another series of embodiments, gene therapy may be employed to replace the mutant gene by homologous recombination with a recombinant construct. The recombinant construct may contain a normal copy of the targeted presenilin gene, in which case the defect is corrected in situ, or may contain a "knock-out" construct which introduces a stop codon, antisense mutation, or deletion which abolished function of the mutant gene. It should be noted in this respect that such a construct may knock-out both the normal and mutant copies of the targeted presenilin gene in a heterozygous individual, but the total loss of presenilin gene function may be less deleterious to the individual than continued progression of the disease state.

In another series of embodiments, antisense gene therapy may be employed. The antisense therapy is based on the fact that sequence-specific suppression of gene expression can be achieved by intracellular hybridization between mRNA or DNA and a complementary antisense species. The formation of a hybrid duplex may then interfere with the transcription of the gene and/or the processing, transport, translation and/or stability of the target presenilin mRNA. Antisense strategies may use a variety of approaches including the administration of antisense oligonucleotides or antisense oligonucleotide analogs (e.g., analogs with phosphorothioate backbones) or transfection with antisense RNA expression vectors. Again, such vectors may include exogenous or endogenous regulatory regions, inducible or repressible regulatory elements, or tissue-specific regulatory elements.

In another series of embodiments, gene therapy may be used to introduce a recombinant construct encoding a protein or peptide which blocks or otherwise corrects the aberrant function caused by a mutant presenilin gene. In one embodiment, the recombinant gene may encode a peptide which corresponds to a mutant domain of a presenilin which has been found to abnormally interact with another cell protein or other cell ligand. Thus, for example, if a mutant TM6→7 domain is found to interact with a particular cell protein but the corresponding normal TM6→7 domain does not undergo this interaction, gene therapy may be employed to provide an excess of the mutant TM6→7 domain which may compete with the mutant protein and inhibit or block the aberrant interaction. Alternatively, the portion of a protein which interacts with a mutant, but not a normal, presenilin may be encoded and expressed by a recombinant construct in order to compete with, and thereby inhibit or block, the aberrant interaction. Finally, in another embodiment, the same effect might be gained by inserting a second mutant protein by gene therapy in an approach similar to the correction of the "Deg 1(d)" and "Mec 4(d)" mutations in *C. elegans* by insertion of mutant transgenes.

Retroviral vectors can be used for somatic cell gene therapy especially because of their high efficiency of infection and stable integration and expression. The targeted cells however must be able to divide and the expression of the levels of normal protein should be high because the disease is a dominant one. The full length PS1 or PS2 genes, subsequences encoding functional domains of the presenilins, or any of the other therapeutic peptides described above, can be cloned into a retroviral vector and driven from its endogenous promoter, from the retroviral long terminal repeat, or from a promoter specific for the target cell type of interest (e.g., neurons). Other viral vectors which can be used include adeno-associated virus, vaccinia virus, bovine papilloma virus, or a herpes virus such as Epstein-Barr virus.

C. Immunotherapy

Immunotherapy is also possible for Alzheimer's Disease. Antibodies are raised to a mutant PS1 or PS2 protein (or a portion thereof) and are administered to the patient to bind or block the mutant protein and prevent its deleterious effects. Simultaneously, expression of the normal protein product could be encouraged. Alternatively, antibodies are raised to specific complexes between mutant or wild-type PS1 or PS2 and their interaction partners.

A further approach is to stimulate endogenous antibody production to the desired antigen. Administration could be in the form of a one time immunogenic preparation or vaccine immunization. An immunogenic composition may be prepared as injectables, as liquid solutions or emulsions. The PS1 or PS2 protein or other antigen may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

D. Small Molecule Therapeutics

As described and enabled herein, the present invention provides for a number of methods of identifying small molecules or other compounds which may be useful in the treatment of Alzheimer's Disease or other disorders caused by mutations in the presenilins. Thus, for example, the present invention provides for methods of identifying presenilin binding proteins and, in particular, methods for identifying proteins or other cell components which bind to or otherwise interact with mutant presenilins but not with the normal presenilins. The invention also provides for methods of identifying small molecules which can be used to disrupt aberrant interactions between mutant presenilins and such proteins or other cell components.

Such interactions, involving mutant but not normal presenilins, not only provide information useful in understanding the biochemical pathways disturbed by mutations in the presenilins, and causative of Alzheimer's Disease, but also provide immediate therapeutic targets for intervention in the etiology of the disease. By identifying these proteins and analyzing these interactions, it is possible to screen for or design compounds which counteract or prevent the interaction, thus providing possible treatment for abnormal interactions. These treatments would alter the interaction of the presenilins with these partners, alter the function of the interacting protein, alter the amount or tissue distribution or expression of the interaction partners, or alter similar properties of the presenilins themselves.

Therapies can be designed to modulate these interactions and thus to modulate Alzheimer's Disease and the other conditions associated with acquired or inherited abnormalities of the PS1 or PS2 genes or their gene products. The potential efficacy of these therapies can be tested by analyzing the affinity and function of these interactions after exposure to the therapeutic agent by standard pharmacokinetic measurements of affinity (Kd and Vmax etc.) using synthetic peptides or recombinant proteins corresponding to functional domains of the PS1 gene, the PS2 gene or other presenilin homologues. Another method for assaying the effect of any interactions involving functional domains such as the hydrophilic loop is to monitor changes in the intracellular trafficking and post-translational modification of the relevant genes by in situ hybridization, immunohistochemistry, Western blotting and metabolic pulse-chase labeling studies in the presence of, and in the absence of, the therapeutic agents. A further method is to monitor the effects of "downstream" events including (i) changes in the intracellular metabolism, trafficking and targeting of APP and its products; (ii) changes in second messenger events, e.g., cAMP intracellular $Ca^{2+}$, protein kinase activities, etc.

As noted above, the presenilins may be involved in APP metabolism and the phosphorylation state of the presenilins may be critical to the balance between the α-secretase and Aβ pathways of APP processing. Using the transformed cells and animal models of the present invention, one is enabled to better understand these pathways and the aberrant events which occur in presenilin mutants. Using this knowledge, one may then design therapeutic strategies to counteract the deleterious affects of presenilin mutants.

To treat Alzheimer's Disease, for example, the phosphorylation state of PS1 and/or can be altered by chemical and biochemical agents (e.g. drugs, peptides and other compounds) which alter the activity of protein kinase C and other protein kinases, or which alter the activity of protein phosphatases, or which modify the availability of PS1 to be post-translationally modified. The interactions of kinases and phosphatases with the presenilin proteins, and the interactions of the presenilin proteins with other proteins involved in the trafficking of APP within the Golgi network, can be modulated to decrease trafficking of Golgi vesicles to the endosome-lysosome pathway, thereby inhibiting Aβ peptide production. Such compounds will include peptide analogues of APP, PS1, PS2, and other presenilin homologues, as well as other interacting proteins, lipids, sugars, and agents which promote differential glycosylation of PS1, PS2 and/or their homologues; agents which alter the biologic half-life of presenilin mRNA or proteins, including antibodies and antisense oligonucleotides; and agents which act upon PS1 and/or PS2 transcription.

The effect of these agents in cell lines and whole animals can be monitored by monitoring transcription, translation, and post-translational modification of PS1 and/or PS2 (e.g. phosphorylation or glycosylation), as well as intracellular trafficking of PS1 and/or PS2 through various intracellular and extracellular compartments. Methods for these studies include Western and Northern blots, immunoprecipitation after metabolic labeling (pulse-chase) with radio-labelled methionine and ATP, and immunohistochemistry. The effect of these agents can also be monitored using studies which examine the relative binding affinities and relative amounts of PS1 and/or PS2 proteins involved in interactions with protein kinase C and/or APP, using either standard binding affinity assays or coprecipitation and Western blots using antibodies to protein kinase C, APP, PS1, PS2, or other presenilin homologues. The effect of these agents can also be monitored by assessing the production of Aβ peptides by ELISA before and after exposure to the putative therapeutic agent (see, e.g., Huang et al., 1993). The effect can also be monitored by assessing the viability of cell lines after exposure to aluminum salts and/or the Aβ peptides which are thought to be neurotoxic in Alzheimer's Disease. Finally, the effect of these agents can be monitored by assessing the cognitive function of animals bearing normal genotypes at APP and/or their presenilin homologues, bearing human APP transgenes (with or without mutations), bearing human presenilin transgenes (with or without mutations), or bearing any combination of these.

Similarly, as noted above, the presenilins may be involved in the regulation of $Ca^{2+}$ as receptors or ion channels. This role of the presenilins also may be explored using the transformed cell lines and animal models of the invention. Based upon these results, a test for Alzheimer's Disease can be produced to detect an abnormal receptor or an abnormal ion channel function related to abnormalities that are acquired or inherited in the presenilin genes and their products, or in one of the homologous genes and their products. This test can be accomplished either in vivo or in vitro by measurements of ion channel fluxes and/or transmembrane voltage or current fluxes using patch clamp, voltage clamp and fluorescent dyes sensitive to intracellular calcium or transmembrane voltage. Defective ion channel or receptor function can also be assayed by measurements of activation of second messengers such as cyclic AMP, cGMP tyrosine kinases, phosphates, increases in intracellular Ca$^{2+}$ levels, etc. Recombinantly made proteins may also be reconstructed in artificial membrane systems to study ion channel conductance. Therapies which affect Alzheimer's Disease (due to acquired/inherited defects in the PS1 gene or PS2 gene; due to defects in other pathways leading to this disease such as mutations in APP; and due to environmental agents) can be tested by analysis of their ability to modify an abnormal ion channel or receptor function induced by mutation in a presenilin gene. Therapies could also be tested by their ability to modify the normal function of an ion channel or receptor capacity of the presenilin proteins. Such assays can be performed on cultured cells expressing endogenous normal or mutant PS1 genes/gene products or PS2 genes/gene products. Such studies also can be performed on cells transfected with vectors capable of expressing one of the presenilins, or functional domains of one of the presenilins, in normal or mutant form. Therapies for Alzheimer's Disease can be devised to modify an abnormal ion channel or receptor function of the PS1 gene or PS2 gene. Such therapies can be conventional drugs, peptides, sugars, or lipids, as well as antibodies or other ligands which affect the properties of the PS1 or PS2 gene product. Such therapies can also be performed by direct replacement of the PS1 gene and/or PS2 gene by gene therapy. In the case of an ion channel, the gene therapy could be performed using either mini-genes (cDNA plus a promoter) or genomic constructs bearing genomic DNA sequences for parts or all of a presenilin gene. Mutant presenilins or homologous gene sequences might also be used to counter the effect of the inherited or acquired abnormalities of the presenilin genes as has recently been done for replacement of the Mec 4 and Deg 1 in *C. elegans* (Huang and Chalfie (1994)). The therapy might also be directed at augmenting the receptor or ion channel function of one homologue, such as the PS2 gene, in order that it may potentially take over the functions of a mutant form of another homologue (e.g., a PS1 gene rendered defective by acquired or inherited defects). Therapy using antisense oligonucleotides to block the expression of the mutant PS1 gene or the mutant PS2 gene, co-ordinated with gene replacement with normal PS1 or PS2 gene can also be applied using standard techniques of either gene therapy or protein replacement therapy.

EXAMPLES

Example 1
Development of the genetic physical "contig" and transcriptional map of the minimal co-segregating region.

The CEPH MegaYAC and the RPCI PAC human total genomic DNA libraries were searched for clones containing genomic DNA fragments from the AD3 region of chromosome 14q24.3 using oligonucleotide probes for each of the 12 SSR marker loci used in the genetic linkage studies as well as additional markers (Albertsen et al. (1990) *Proc. Natl. Acad. Sci.* (*USA*) 87:4256–4260; Chumakov et al. (1992) *Nature* 359:380–387; Ioannu et al. (1994) *Nature Genetics* 6:84–89). The genetic map distances between each marker are depicted above the contig, and are derived from published data (NIH/CEPH Collaborative Mapping Group (1992) *Science* 258:67–86; Wang (1992) *Genomics* 13: 532–536; Weissenbach et al., 1992; Gyapay et al., 1994. Clones recovered for each of the initial marker loci were arranged into an ordered series of partially overlapping clones ("contig") using four independent methods. First, sequences representing the ends of the YAC insert were isolated by inverse PCR (Riley et al. (1990) *Nucl. Acid Res.* 18:2887–2890), and hybridized to Southern blot panels containing restriction digests of DNA from all of the YAC clones recovered for all of the initial loci in order to identify other YAC clones bearing overlapping sequences. Second, inter-Alu PCR was performed on each YAC, and the resultant band patterns were compared across the pool of recovered YAC clones in order to identify other clones bearing overlapping sequences (Bellamne-Chartelot et al. (1992) *Cell* 70:1059–1068; Chumakov et al., 1992. Third, to improve the specificity of the Alu-PCR fingerprinting, the YAC DNA was restricted with HaeIII or RsaI, the restriction products were amplified with both Alu and L1H consensus primers, and the products were resolved by polyacrylamide gel electrophoresis. Finally, as additional STSs were generated during the search for transcribed sequences, these STSs were also used to identify overlaps. The resultant contig was complete except for a single discontinuity between YAC932C7 bearing D14S53 and YAC746B4 containing D14S61. The physical map order of the STSs within the contig was largely in accordance with the genetic linkage map for this region (NIH/CEPH Collaborative Mapping Group, 1992; Wang and Weber, 1992; Weissenbach et al., 1992; Gyapay et al., 1994). However, as with the genetic maps, it was not possible to resolve unambiguously the relative order of the loci within the D14S43/D14S71 cluster and the D14S76/D14S273 cluster. PAC1 clones suggested that D14S277 is telomeric to D14S268, whereas genetic maps have suggested the reverse order. Furthermore, a few STS probes failed to detect hybridization patterns in at least one YAC clone which, on the basis of the most parsimonious consensus physical map and from the genetic map, would have been predicted to contain that STS. For instance, the D14S268 (AFM265) and RSCAT7 STSs are absent from YAC788H12. Because these results were reproducible, and occurred with several different STS markers, these results most likely reflect the presence of small interstitial deletions within one of the YAC clones.

Example 2
Cumulative two-point lod scores for chromosome 14q24.3 markers.

Genotypes at each polymorphic microsatellite marker locus were determined by PCR from 100 ng of genomic DNA of all available affected and unaffected pedigree members as previously described (St. George-Hyslop et al., 1992) using primer sequences specific for each microsatellite locus (Weissenbach et al., 1992; Gyapay et al., 1994). The normal population frequency of each allele was determined using spouses and other neurologically normal subjects from the same ethnic groups, but did not differ significantly from those established for mixed Caucasian populations (Weissenbach et al., 1992; Gyapay et al., 1994). The maximum likelihood calculations assumed an age of onset correction, marker allele frequencies derived from published series of mixed Caucasian subjects, and an estimated allele frequency for the AD3 mutation of 1:1000 as previously described (St. George-Hyslop et al., 1992). The analyses were repeated using equal marker allele frequencies, and using phenotype information only from affected pedigree members as previously described to ensure that inaccuracies in the estimated parameters used in the maximum likelihood calculations did not misdirect the analyses (St. George-Hyslop et al., 1992). These supplemental analyses did not significantly alter either the evidence supporting linkage, or the discovery of recombination events.

Example 3
Haplotypes between flanking markers segregate with AD3 in FAD.

Extended haplotypes between the centromeric and telomeric flanking markers on the parental copy of chromosome 14 segregating with AD3 in fourteen early onset FAD pedigrees (pedigrees NIH2, MGH1, Tor1.1, FAD4, FAD1, MEX1, and FAD2) show pedigree specific lod scores>+3.00 with at least one marker between D14S258 and D14S53. Identical partial haplotypes are observed in two regions of the disease bearing chromosome segregating in several pedigrees of similar ethnic origin. In region A, shared alleles are seen at D14S268 ("B": allele size=126 bp, allele frequency in normal Caucasians=0.04; "C": size=124 bp, frequency=0.38); D14S277 ("B": size=156 bp, frequency=0.19; "C": size=154 bp, frequency=0.33); and RSCAT6 ("D": size=111 bp, frequency 0.25; "E": size=109 bp, frequency=0.20; "F": size=107 bp, frequency=0.47). In regionB, alleles of identical size are observed at D14S43 ("A": size=193 bp, frequency=0.01; "D": size=187 bp, frequency=0.12; "E": size=185 bp, frequency=0.26; "I": size=160 bp, frequency =0.38); D14S273 ("3": size=193 bp, frequency=0.38; "4" size=191 bp, frequency=0.16; "5": size=189 bp, frequency=0.34; "6": size=187 bp, frequency=0.02) and D14S76 ("1": size=bp, frequency=0.01; "5": size= bp, frequency=0.38; "6": size=bp, frequency=0.07; "9": size=bp, frequency=0.38). See Sherrington et al. (1995) for details.

Example 4
Recovery of transcribed sequences from the AD3 interval.

Putative transcribed sequences encoded in the AD3 interval were recovered using a direct hybridization method in which short cDNA fragments generated from human brain mRNA were hybridized to immobilized cloned genomic DNA fragments (Rommens et al., 1993). The resultant short putatively transcribed sequences were used as probes to recover longer transcripts from human brain cDNA libraries (Stratagene, La Jolla). The physical locations of the original short clone and of the subsequently acquired longer cDNA clones were established by analysis of the hybridization pattern generated by hybridizing the probe to Southern blots containing a panel of EcoRI digested total DNA samples isolated from individual YAC clones within the contig. The nucleotide sequence of each of the longer cDNA clones was determined by automated cycle sequencing (Applied Biosystems Inc., CA), and compared to other sequences in nucleotide and protein databases using the blast algorithm (Altschul et al., 1990). Accession numbers for the transcribed sequences are: L40391, L40392, L40393, L40394, L40395, L40396, L40397, L40398, L40399, L40400, L40401, L40402, and L40403.

Example 5
Locating mutations in the PS1 gene using restriction enzymes.

The presence of the A246E mutation, which creates a DdeI restriction site, was assayed in genomic DNA by PCR using an end labeled primer corresponding essentially to bp 907–925 of SEQ ID NO:1 and an unlabelled primer corresponding to the complement of bp 1010–990 of SEQ ID NO: 1, to amplify an 84 bp genomic exon fragment using 100 ng of genomic DNA template, 2 mM $MgCl_2$, 10 pMoles of each primer, 0.5 U Taq polymerase, 250 uM dNTPs for 30 cycles of 95° C.×20 seconds, 60° C.×20 seconds, 72° C.×5 seconds. The products were incubated with an excess of DdeI for 2 hours according to the manufacturer's protocol, and the resulting restriction fragments were resolved on a 6% non-denaturing polyacrylamide gel and visualized by autoradiography. The presence of the mutation was inferred from the cleavage of the 84 bp fragment to due to the presence of a DdeI restriction site. All affected members of the FAD1 pedigree and several at-risk members carried the DdeI site. None of the obligate escapees (those individuals who do not get the disease, age>70 years), and none of the normal controls carried the DdeI mutation.

Example 6
Locating mutations in the PS1 gene using allele specific oligonucleotides.

The presence of the C410Y mutation was assayed using allele specific oligonucleotides. 100 ng of genomic DNA was amplified with an exonic sequence primer corresponding to bp 1451–1468 of SEQ ID NO:1 and an opposing intronic sequence primer complementary to bp 719–699 of SEQ ID NO:14 using the above reaction conditions except 2.5 mM $MgCl_2$, and cycle conditions of 94° C.×20 seconds, 58° C.×20 seconds, and 72° C. for 10 seconds). The resultant 216 bp genomic fragment was denatured by 10-fold dilution in 0.4M NaOH, 25 mM EDTA, and was vacuum slot-blotted to duplicate nylon membranes. An end-labeled "wild type" primer (corresponding to bp 1468–1486 of SEQ ID NO:1) and an end-labeled "mutant" primer (corresponding to the same sequence but with a G→A substitution at position 1477) were hybridized to separate copies of the slot-blot filters in 5×SSC, 5×Denhardt's, 0.5% SDS for 1 hour at 48° C., and then washed successively in 2×SSC at 23° C. and 2×SSC, 0.1% SDS at 50° C. and then exposed to X-ray film. All testable affected members as well as some at-risk members of the AD3 and NIH2 pedigrees possessed the C410Y mutation. Attempts to detect the C410Y mutation by SSCP revealed that a common intronic sequence polymorphism migrated with the same SSCP pattern.

Example 7
Northern hybridization demonstrating the expression of PS1 protein mRNA in a variety of tissues.

Total cytoplasmic RNA was isolated from various tissue samples (including heart, brain and different regions of placenta, lung, liver, skeletal muscle, kidney and pancreas) obtained from surgical pathology using standard procedures such as CsCl purification. The RNA was then electrophoresed on a formaldehyde gel to permit size fractionation. The nitrocellulose membrane was prepared and the RNA was then transferred onto the membrane. $^{32}$P-labeled cDNA probes were prepared and added to the membrane in order for hybridization between the probe the RNA to occur. After washing, the membrane was wrapped in plastic film and placed into imaging cassettes containing X-ray film. The autoradiographs were then allowed to develop for one to several days. Sizing was established by comparison to standard RNA markers. Analysis of the autoradiographs revealed a prominent band at 3.0 kb in size (see FIG. 2 of Sherrington et al., 1995). These northern blots demonstrated that the PS1 gene is expressed in all of the tissues examined.

Example 8
Eukaryotic and prokaryotic expression vector systems.

Constructs suitable for use in eukaryotic and prokaryotic expression systems have been generated using three different classes of PS 1 nucleotide cDNA sequence inserts. In the first class, termed full-length constructs, the entire PS1 cDNA sequence is inserted into the expression plasmid in the correct orientation, and includes both the natural 5' UTR and 3' UTR sequences as well as the entire open reading frame. The open reading frames bear a nucleotide sequence cassette which allows either the wild type open reading frame to be included in the expression system or alternatively, single or a combination of double mutations can be inserted into the open reading frame. This was accomplished by removing a restriction fragment from the wild type open reading frame using the enzymes NarI and PflmI and replacing it with a similar fragment generated by reverse transcriptase PCR and bearing the nucleotide sequence encoding either the M146L mutation or the H163R mutation. A second restriction fragment was removed from the wild type normal nucleotide sequence for the open reading frame by cleavage with the enzymes PflmI and NcoI and replaced with a restriction fragment bearing the nucleotide sequence encoding the A246E mutation, the A260V mutation, the A285V mutation, the L286V mutation, the L392V mutation or the C410Y mutation. A third variant, bearing a combination of either the M146L or H163R mutation in tandem with one of the remaining mutations, was made by linking a NarI-PflmI fragment bearing one of the former mutations and a PflmI-NcoI fragment bearing one of the latter mutations.

The second class of cDNA inserts, termed truncated constructs, was constructed by removing the 5' UTR and part of the 3' UTR sequences from full length wild type or mutant cDNA sequences. The 5' UTR sequence was replaced with a synthetic oligonucleotide containing a KpnI restriction site (GGTAC/C) and a small sequence (GCCACC) to create a Kozak initiation site around the ATG at the beginning of the PS1 ORF (bp 249–267 of SEQ ID NO:1). The 3' UTR was replaced with an oligonucleotide corresponding to the complement of bp 2568–2586 of SEQ ID NO:1 with an artificial EcoRI site at the 5' end. Mutant variants of this construct were then made by inserting the mutant sequences described above at the NarI-Pflml and PsImI-NcoI sites as described above.

The third class of constructs included sequences derived from clone cc44 in which an alternative splice of Exon 4 results in the elimination of four residues in the N-terminus (SEQ ID NO:3).

For eukaryotic expression, these various cDNA constructs bearing wild type and mutant sequences, as described above, were cloned into the expression vector pZeoSV in which the SV60 promoter cassette had been removed by restriction digestion and replaced with the CMV promoter element of pcDNA3 (Invitrogen). For prokaryotic expression, constructs have been made using the glutathione S-transferase (GST) fusion vector pGEX-kg. The inserts which have been attached to the GST fusion nucleotide sequence are the same nucleotide sequences described above bearing either the normal open reading frame nucleotide sequence, or bearing a combination of single and double mutations as described above. These GST fusion constructs allow expression of the partial or full-length protein in prokaryotic cell systems as mutant or wild type GST fusion proteins, thus allowing purification of the full-length protein followed by removal of the GST fusion product by thrombin digestion. A further cDNA construct was made with the GST fusion vector, to allow the production of the amino acid sequence corresponding to the hydrophilic acidic loop domain between TM6 and TM7 of the full-length protein, either as a wild type nucleotide sequence or as a mutant sequence bearing either the A285V mutation, the L286V mutation or the L392V mutation. This was accomplished by recovering wild type or mutant sequence from appropriate sources of RNA using a 5' oligonucleotide primer corresponding to bp 1044–1061 of SEQ ID NO:1 with a 5 BamHI restriction site (G/GATCC), and a 3' primer corresponding to the complement of bp 1476–1458 oh SEQ ID NO:1 with a 5 EcoRI restriction site (G/AATTC). This allowed cloning of the appropriate mutant or wild type nucleotide sequence corresponding to the hydrophilic acidic loop domain at the BamHI and the EcoRI sites within the pGEX-KG vector.

Example 9

Locating additional mutations in the PS1 gene.

Mutations in the PS1 gene can be assayed by a variety of strategies (direct nucleotide sequencing, allele specific oligos, ligation polymerase chain reaction, SSCP, RFLPs) using RT-PCR products representing the mature mRNA/cDNA sequence or genomic DNA. For the A260V and the A285V mutations, genomic DNA carrying the exon can be amplified using the same PCR primers and methods as for the L286V mutation.

PCR products were then denatured and slot blotted to duplicate nylon membranes using the slot blot protocol described for the C410Y mutation.

The A260V mutation was scored on these blots by using hybridization with end-labeled allele-specific oligonucleotides corresponding to the wild type sequence (bp 1017–1036 of SEQ ID NO:1) or the mutant sequence (bp 1017–1036 of SEQ ID NO:1 with C→T at bp 1027) by hybridization at 48° C. followed by a wash at 52° C. in 3×SSC buffer containing 0.1% SDS. The A285V mutation was scored on these slot blots as described above but using instead the allele-specific oligonucleotides for the wild type sequence (bp 1093–1111 of SEQ ID NO:1) or the mutant primer (bp 1093–1111 of SEQ ID NO:1 with C→T at bp 1102) at 48° C. followed by washing at 52° C. as above except that the wash solution was 2×SSC.

The L392V mutation was scored by amplification of the exon from genomic DNA using primers (5' corresponding to bp 439–456 of SEQ ID NO:14 and 3' complementary to 719–699 of SEQ ID NO:14) using standard PCR buffer conditions except that the magnesium concentration was 2 mM and cycle conditions were 94° C.×10 seconds, 56° C.×20 seconds, and 72° C.×10 seconds. The resulting 200 base pair genomic fragment was denatured as described for the C410Y mutation and slot-blotted in duplicate to nylon membranes. The presence or absence of the mutation was then scored by differential hybridization to either a wild type end-labeled oligonucleotide (bp 1413–1431 of SEQ ID NO:1) or with an end-labeled mutant primer (bp 1413–1431 of SEQ ID NO:1 with C→G at bp 1422) by hybridization at 45° C. and then successive washing in 2×SSC at 23° C. and then at 68° C.

Example 10

Antibody production.

Peptide antigens corresponding to portions of the PS1 protein were synthesized by solid-phase techniques and purified by reverse phase high pressure liquid chromatography. Peptides were covalently linked to keyhole limpet hemocyanin (KLH) via disulfide linkages that were made possible by the addition of a cysteine residue at the peptide C-terminus of the presenilin fragment. This additional residue does not appear normally in the protein sequence and was included only to facilitate linkage to the KLH molecule. The specific presenilin sequences to which antibodies were raised are as follows:

| Polyclonal antibody # | hPS1 antigen (SEQ ID NO:2) |
| --- | --- |
| 1142 | 30–44 |
| 519 | 109–123 |
| 520 | 304–318 |
| 1143 | 346–360 |

These sequences are contained within specific domains of the PS1 protein. For example, residues 30–44 are within the N-terminus, residues 109–123 are within the TM1→2 loop, and residues 304–318 and 346–360 are within the large TM6→7 loop. Each of these domains is exposed to the aqueous media and may be involved in binding to other proteins critical for the development of the disease phenotype. The choice of peptides was based on analysis of the protein sequence using the IBI Pustell antigenicity prediction algorithm.

A total of three New Zealand white rabbits were immunized with peptide-KLH complexes for each peptide antigen in combination with Freund's adjuvant and were subsequently given booster injections at seven day intervals. Antisera were collected for each peptide and pooled and IgG precipitated with ammonium sulfate. Antibodies were then affinity purified with Sulfo-link agarose (Pierce) coupled with the appropriate peptide. This final purification is required to remove nonspecific interactions of other antibodies present in either the pre- or post-immune serum.

The specificity of each antibody was confirmed by three tests. First, each detected single predominant bands of the approximate size predicted for presenilin-1 on Western blots of brain homogenate. Second, each cross-reacted with recombinant fusion proteins bearing the appropriate sequence. Third each could be specifically blocked by pre-absorption with recombinant PS1 or the immunizing peptide.

In addition, two different PS1 peptide glutathione S-transferase (GST) fusion proteins have been used to generate PS1 antibodies. The first fusion protein included amino acids 1–81 (N terminus) of PS1 fused to GST. The second fusion protein included amino acids 266–410 (the TM6→7 loop domain) of PS1 fused to GST. Constructs encoding these fusion proteins were generated by inserting the appropriate nucleotide sequences into pGEX-2T expression plasmid (Amrad). The resulting constructs included sequences encoding GST and a site for thrombin sensitive cleavage between GST and the PS1 peptide. The expression constructs were transfected into DH5a *E. coli* and expression of the fusion proteins was induced using IPTG. The bacterial pellets were lysed and the soluble GST-fusion proteins were purified by single step affinity chromatography on glutathione sepharose beads (Boehringer-Mannheim, Montreal). The GST-fusion proteins were used to immunize mice to generate monoclonal antibodies using standard procedures. Clones obtained from these mice were screened with purified presenilin fragments.

In addition, the GST-fusion proteins were cleaved with thrombin to release PS1 peptide. The released peptides were purified by size exclusion HPLC and used to immunize rabbits for the generation of polyclonal antisera.

By similar methods, GST fusion proteins were made using constructs including nucleotide sequences for amino acids 1 to 87 (N terminus) or 272 to 390 (TM6→TM7 loop) of presenilin-2 and employed to generate monoclonal antibodies to that protein. The PS2-GST fusion proteins were also cleaved with thrombin and the released, purified peptides used to immunize rabbits to prepare polyclonal antisera.

Example 11
Identification of mutations in PS2 gene.

RT-PCR products corresponding to the PS2 ORF were generated from RNA of lymphoblasts or frozen post-mortem brain tissue using a first oligonucleotide primer pair with the 5' primer corresponding to bp 478–496 of SEQ ID NO:18, and the 3' primer complementary to bp 1366–1348 of SEQ ID NO:18, for a 888 bp product, and a second primer pair with the 5' primer corresponding to bp 1083–1102 of SEQ ID NO:18, and the 3' primer complementary to bp 1909–1892 of SEQ ID NO:18, for a 826 bp product. PCR was performed using 250 mMol dNTPs, 2.5 mM $MgCl_2$, 10 pMol oligonucleotides in 10 ml cycled for 40 cycles of 94° C.×20 seconds, 58° C.×20 seconds, 72° C.×45 seconds. The PCR products were sequenced by automated cycle sequencing (ABI, Foster City, Calif.) and the fluorescent chromatograms were scanned for heterozygous nucleotide substitutions by direct inspection and by the Factura (ver 1.2.0) and Sequence Navigator (ver 1.0.1b15) software packages (data not shown).

Detection of the N141I mutation: The A→T substitution at nucleotide 787 creates a BclI restriction site. The exon bearing this mutation was amplified from 100 ng of genomic DNA using 10 pMol each of oligonucleotides corresponding to bp 733–751 of SEQ ID NO:18 (end-labeled) and the complement of bp 846–829 of SEQ ID NO:18 (unlabelled), and PCR reaction conditions similar to those described below for the M239V mutation. 2 ml of the PCR product was restricted with BclI (NEBL, Beverly, Mass.) in 10 ml reaction volume according to the manufacturers' protocol, and the products were resolved by non-denaturing polyacrylamide gel electrophoresis. In subjects with wild type sequences, the 114 bp PCR product is cleaved into 68 bp and 46 bp fragments. Mutant sequences cause the product to be cleaved into 53 bp, 46 bp and 15 bp.

Detection of the M239V mutation: The A→G substitution at nucleotide 1080 deletes a NlaIII restriction site, allowing the presence of the M239V mutation to be detected by amplification from 100 ng of genomic DNA using 10 pMol each of oligonucleotides corresponding to bp 1009–1026 of SEQ ID NO:18 and the complement of bp 1118–1101 of SEQ ID NO:18. PCR conditions were: 0.5 U Taq polymerase, 250 mM dNTPS, 1 mCi $\alpha^{32}$P-dCTP, 1.5 mM $MgCl_2$, 10 ml volume; 30 cycles of 94° C.×30 seconds, 58° C.×20 seconds, 72° C.×20 seconds, to generate a 110 bp product. 2 ml of the PCR reaction were diluted to 10 ml and restricted with 3 U of NlaII (NEBL, Beverly, Mass.) for 3 hours. The restriction products were resolved by non-denaturing polyacrylamide gel electrophoresis and visualized by autoradiography. Normal subjects show cleavage products of 55, 35, 15 and 6 bp, whereas the mutant sequence gives fragments of 55, 50 and 6 bp.

Detection of the I420T mutation: Similarly to the procedures above, the I420T mutation may be screened for by PCR amplification of genomic DNA using primers corresponding to bp 1576–1593 of SEQ ID NO:18 and the complement of bp 1721–1701 of SEQ ID NO:18 to generate a 146 base pair product. This product may then be probed with allele specific oligonucleotides for the wild-type (e.g., bp 1616–1632 of SEQ ID NO:18) and mutant (e.g., bp 1616–1632 of SEQ ID NO:18 with a T→C substitution at bp 1624) sequences.

Example 12
Transgenic mice.

A series of wild type and mutant PS1 and PS2 genes were constructed for use in the preparation of transgenic mice. Mutant versions of PS1 and PS2 were generated by site-directed mutagenesis of the cloned cDNAs cc33 (PS1) and cc32 (PS2) using standard techniques.

cDNAs cc33 and cc32 and their mutant versions were used to prepare two classes of mutant and wild type PS1 and PS2 cDNAs, as described in Example 8. The first class, referred to as "full-length" cDNAs, were prepared by removing approximately 200 bp of the 3' untranslated region immediately before the polyA site by digestion with EcoRI (PS1) or PvuIII (PS2). The second class, referred to as "truncated" cDNAs, were prepared by replacing the 5' untranslated region with a ribosome binding site (Kozak consensus sequence) placed immediately 5' of the A→G start codon.

Various full length and truncated wild type and mutant PS1 and PS2 cDNAs, prepared as described above, were introduced into one or more of the following vectors and the resulting constructs were used as a source of gene for the production of transgenic mice.

The cos.TET expression vector: This vector was derived from a cosmid clone containing the Syrian hamster PrP gene. It has been described in detail by Scott et al. (1992) *Protein Sci.* 1:986–997 and Hsiao et al. (1995) *Neuron.* (in press). PS1 and PS2 cDNAs (full length or truncated) were inserted into this vector at its SalI site. The final constructs contain 20 kb of 5' sequence flanking the inserted cDNA. This 5' flanking sequence includes the PrP gene promoter, 50 bp of a PrP gene 5' untranslated region exon, a splice donor site, a 1 kb intron, and a splice acceptor site located immediately adjacent to the SalI site into which the PS1 or PS2 cDNA was inserted. The 3' sequence flanking the inserted cDNA includes an approximately 8 kb segment of PrP 3' untranslated region including a polyadenylation signal. Digestion of this construct with NotI (PS1) or FseI (PS2) released a fragment containing a mutant or wild type PS gene under the control of the PrP promoter. The released fragment was gel purified and injected into the pronuclei of fertilized mouse eggs using the method of Hsiao et al. (1995).

Platelet-derived growth factor receptor β-subunit constructs: PS cDNAs were also introduced between the SalI (full length PS1 cDNAs) or HindIII (truncated PS1 cDNAs, full length PS2 cDNAs, and truncated PS2 cDNAs) at the 3' end of the human platelet derived growth factor receptor β-subunit promoter and the EcoRI site at the 5' end of the SV40 polyA sequence and the entire cassette was cloned into the pZeoSV vector (Invitrogen, San Diego, Calif.). Fragments released by ScaI/BamHI digestion were gel purified and injected into the pronuclei of fertilized mouse eggs using the method of Hsiao et al. (1995).

Human β-actin constructs: PS1 and PS2 cDNAs were inserted into the SalI site of pBAcGH. The construct produced by this insertion includes 3.4 kb of the human β actin 5' flanking sequence (the human β actin promoter, a spliced 78 bp human β actin 5' untranslated exon and intron) and the PS1 or PS2 insert followed by 2.2 kb of human growth hormone genomic sequence containing several introns and exons as well as a polyadenylation signal. SfiI was used to release a PS-containing fragment which was gel purified and injected into the pronuclei of fertilized mouse eggs using the method of Hsiao et al. (1995).

Phosphoalycerate kinase constructs: PS1 and PS2 cDNAs were introduced into the pkJ90 vector. The cDNAs were inserted between the KpnI site downstream of the human phosphoglycerate kinase promoter and the XbaI site upstream of the 3' untranslated region of the human phosphoglycerate kinase gene. PvuI/HindIII (PS1 cDNAs) or PvuII (PS2 cDNAs) digestion was used to release a PS-containing fragment which was then gel purified and injected into the pronuclei of fertilized mouse eggs as described above.

Analysis of Aβ in transgenic murine hippocampus: To analyze the effect of a mutant human PS1 transgene in mice, a PS1 mutation observed in conjunction with a particularly severe form of early-onset PS1-linked Alzheimer's disease was used, namely the M146L missense mutation (Sherrington et al., 1995). The animals, which were heterozygous for the PS1 mutant transgene on a mixed FVB-C57BL/6 strain background, were cross-bred with similar mice bearing the human wild-type βAPP695 cDNA under the same Syrian hamster PrP promoter similar to those animals recently described by Hsiao et al., 1995. These cross breedings were done because it is thought that human Aβ is more susceptible to the formation of aggregates than are murine Aβ peptides.

The progeny of these $PS1_{M146L} \times \beta APP_{WT}$ cross-breedings were then genotyped to identify animals that contained both the human wild-type $\beta APP_{695}$ transgene and also the mutant human $PS1_{M146L}$ transgene. These mice were aged until two to three months of age and then sacrificed, with the hippocampus and neocortex being dissected rapidly from the brain and frozen. Litter mates of these mice, which contained only the wild-type human $\beta APP_{695}$ transgene were also sacrificed, and their hippocampi and neocortices were dissected and rapidly frozen as well.

The concentration of both total Aβ peptides ($A\beta_{X-40}$ and $A\beta_{X-42(43)}$) as well as the subset of Aβ peptides ending on residues 42 or 43 (long-tailed $A\beta_{42}$ peptides) were then measured using a two-sandwich ELISA as described previously (Tamaoka et al., 1994; Suzuki et al., 1994). These results convincingly showed a small increase in total Aβ peptides in the double transgenic animals bearing wild-type human $\beta APP_{695}$ and mutant human $PS1_{M146L}$ transgenes compared to the wild-type human $\beta APP_{695}$ controls. More impressively, these measurements also showed that there was an increase in the amount of long-tailed Aβ peptides ending on residues 42 or 43 ($A\beta_{42}$). In contrast, litter mates bearing only the wild-type human $\beta APP_{695}$ transgene had $A\beta_{42}$ long-tailed peptide values which were below the limit of quantitation ("BLQ"). The results are presented below:

| PS1 GENOTYPE AND THE Aβ PEPTIDE CONTENT OF HIPPOCAMPUS | | | |
| --- | --- | --- | --- |
| GENOTYPE | ANIMAL ID | Aβ42 | Aβ |
| Wild Type | 4 | BLQ | 36.21 |
| Wild Type | 5 | BLQ | 34.31 |
| Wild Type | 6 | BLQ | 41.29 |
| Wild Type | 8 | BLQ | 39.07 |
| Wild Type | 10 | BLQ | 44.66 |
| Wild Type | 13 | BLQ | 44.31 |
| Wild Type | 14 | BLQ | 37.47 |
| Wild Type | 16 | BLQ | 36.74 |
| M146L PS1 | 1 | 8.14 | 52.17 |
| M146L PS1 | 2 | 6.39 | 60.01 |
| M146L PS1 | 3 | 8.94 | 65.82 |
| M146L PS1 | 7 | 6.81 | 56.51 |
| M146L PS1 | 9 | 5.71 | 51.32 |
| M146L PS1 | 11 | 6.87 | 53.37 |
| M146L PS1 | 12 | 5.34 | 52.18 |
| M146L PS1 | 15 | 7.11 | 55.99 |

These observations therefore confirm that the construction of transgenic animals can recapitulate some of the biochemical features of human Alzheimer's disease (namely the overproduction of Aβ peptide and, in particular, overproduction of long-tailed isoforms of Aβ peptide). These observations thus prove that the transgenic models are in fact useful in exploring therapeutic targets relevant to the treatment and prevention of Alzheimer's disease.

Analysis of hippocampus dependent memory functions in PS1 transgenic mice: Fourteen transgenic C57BL/6×FVB mice bearing the human $PS1_{M146V}$ mutant transgene under the PrP promoter (as described) above and 12 wild type litter mates aged 2.5–3 months of age (both groups were balanced for age, weight, and sex) were investigated for behavioral differences attributable to the mutant transgene. Also the qualitative observation of murine behavior in their home cages did not indicate bimodal distribution of behaviors in the sample of animals.

Experiment 1. To test for subtle differences in exploratory behavior (e.g. locomotion, scanning of the environment through rearing, and patterns of investigation of unfamiliar environment), both $PS1_{M146V}$ and wild type litter mates were tested in the open-field (Janus et al. (1995). *Neurobiology of Learning and Memory*, 64:58–67). The results of the test revealed no significant differences between transgenics and controls in exploration of a new environment measured by mice locomotor behaviors (walking, pausing, wall leaning, rearing, grooming), (F(1,24) =0.98, NS). Thus, differences any in behavior on the Morris water maze test (see below) cannot be attributed to differences in locomotor abilities, etc.

Experiment 2. One week after the open-field test, the $PS1_{M146V}$ mutant transgenic mice and their litter mates were trained in the Morris water maze. In this test, a mouse has to swim in a pool in order to find a submerged escape platform. The animal solves that test through learning the location of the platform using the available extra-maze spatial cues (Morris (1990) *Cold Spring Harbor Symposia on Quantitative Biology*, 55:161–173). This test was chosen because there is strong evidence that the hippocampal formation is involved in this form of learning. The hippocampus is also a major site of AD neuropathology in humans and defects in spatial learning (geographic disorientation, losing objects, wandering, etc.) are prominent early features of human AD. As a result the test is likely to detect early changes equivalent to those seen in human AD. The Morris test is conducted in three phases. In the first phase (the learning acquisition phase), the mouse has to learn the spatial position of the platform. In the second phase (the probe trial), the platform is removed from the pool and the mouse's search for the platform is recorded. In the final phase (the learning transfer phase), the platform is replaced in a new position in the pool, and the mouse has to learn that new spatial position of the platform.

Transgenic and wild type mice did not differ in their latencies to find the platform during learning acquisition (F(1,24)=0.81, NS), and both groups showed rapid learning across trials (F(10,15)=11.57, p<0.001). During the probe trial phase, mice from both groups searched the quadrant of the pool which originally contained the platform significantly longer than other areas of the pool which had not contained the platform (F(3,22)=28.9, p<0.001). However, the wild type controls showed a trend which was not quite statistically significant (t(24)=1.21, p=0.24) for an increased number of crossings of the exact previous position of the platform. In the learning transfer test, both groups showed the same latency of finding the new position of the platform in the initial block of trials (t(24)=1.11, NS). Such long latency to find the new spatial position is expected because the mice spent most of their time searching for the platform in the old spatial position. However, in later trials in the learning transfer phase, the wild type mice showed shorter swim latencies to the new position of the platform compared to the $PS1_{M146V}$ mutant transgenics (F(1,24) 2.36, p=0.14). The results indicate that $PS1_{M146V}$ mutant transgenic mice were less flexible in transferring learned information to a new situation and tended to persevere in their search for the platform in the old location.

In conclusion, no differences were found in the spontaneous exploration of a new environment and in the acquisition of new spatial information between the wild type and the $PS1_{M146V}$ mutant transgenic mice. However the $PS1_{M146V}$ mutant transgenic mice were impaired in switching and/or adapting this knowledge in later situations.

Electrophysiological Recordings in the hippocampus of mutant transgenic mice: Five to six months old litter mate control and human $PS1_{M146V}$ mutant transgenic mice on the same C57BL/6 ×FVB strain backgrounds as above were used to study long term potentiation (LTP) as an electrophysiologic correlate of learning and memory in the hippocampus. Recordings were carried out on 400 µm thick hippocampal slices according to conventional techniques. Briefly, brains were removed and transverse sections containing hippocampi were obtained within 1 min. after mice were decapitated under halothane anesthesia. Slices were kept at room temperature in oxygenated artificial cerebrospinal fluid for one hour prior to recording. One slice at a time was transferred to the recording chamber, where they were maintained at 32° C. in an interface between oxygenated artificial cerebrospinal fluid and humidified air. Slices were then allowed to equilibrate in the recording chamber for another hour.

Extracellular field recordings were carried out in the CA1 subfield of the hippocampus at the Schaeffer collateral-pyramidal cell synapse. Synaptic responses were induced by the stimulation of Schaeffer collaterals at a frequency of 0.03 Hz and an intensity of 30–50% of maximal response. Tetani to evoke long-term potentiation consisted of 5 trains of 100 Hz stimulation lasting for 200 ms at an intertrain interval of 10 seconds. Field potentials were recorded using an Axopatch 200B amplifier (Axon Instrument). Glass pipettes were fabricated from borosilicate glass with an outer diameter of 1.5 mm, and pulled with a two step Narishige puller. Data were acquired on a 486-IBM compatible computer using PCLAMP6 software (Axon Instrument).

To test for any abnormality in presynaptic function, we investigated the differences in paired-pulse facilitation, which is an example of use-dependent increase in synaptic efficacy and is considered to be presynaptic in origin. In hippocampus, when two stimuli are delivered to the Schaeffer collaterals in rapid succession, paired-pulse facilitation manifests itself as an enhanced dendritic response to the second stimulus as the interstimulus interval gets shorter. In three pairs of wild-type/transgenic mice, we did not observe any difference in the paired-pulse facilitation over an interstimulus interval range of 20 ms to 1 sec. These data suggest that in $PS1_{M146V}$ mutant transgenic mice, the excitability of Schaeffer collateral fibers and neurotransmitter release are likely to be normal.

Tetanic stimulation induced a long-lasting increase in the synaptic strength in both control (n=3) and $PS1_{M146V}$ mutant transgenic mice (n=2). In slices obtained from the $PS1_{M146V}$ mutant transgenic mice, long-lasting increase in the synaptic strength was 30% more than that obtained from control mice.

Example 13

Expression of recombinant PS1 and PS2 in eukaryotic cells.

Recombinant PS1 and PS2 have been expressed in a variety of cell types (e.g. PC12, neuroblastoma, Chinese hamster ovary, and human embryonic kidney 293 cells)

using the pcDNA3 vector (Invitrogen, San Diego, Calif.). The PS1 and PS2 cDNAs inserted into this vector were the same full length and truncated cDNAs described in Example 8.

These cDNAs were inserted between the CMV promoter and the bovine growth hormone polyadenylation site of pcDNA3. The transgenes were expressed at high levels.

In addition, PS1 and PS2 have been expressed in COS cells using the pCMX vector. To facilitate tagging and tracing of the intracellular localization of the presenilin proteins, oligonucleotides encoding a sequence of 11 amino acids derived from the human c-myc antigen (see, e.g., Evan et al. (1985) Mol. Cell Biol. 5:3610–3616) and recognized by the monoclonal anti-myc antibody MYC 1-9E10.2 (Product CRL 1729, ATCC, Rockville, Md.) were ligated in-frame either immediately in front of or immediately behind the open reading frame of PS1 and PS2 cDNAs. Untagged pCMX constructs were also prepared. The c-myc-tagged constructs were also introduced into pcDNA3 for transfection into CHO cells.

Transient and stable transfection of these constructs has been achieved using Lipofectarnine (Gibco/BRL) according to the manufacturer's protocols. Cultures were assayed for transient expression after 48 hours. Stably transfected lines were selected using 0.5 mg/ml Geneticin (Gibco/BRL).

Expression of transfected PS proteins was assayed by Western blot using the antipresenilin antibodies 1142, 519 and 520 described above. Briefly, cultured transfected cells were solubilized (2% SDS, 5 mM EDTA, 1 mg/ml leupeptin and aprotinin), and the protein concentration was determined by Lowry. Proteins were separated on SDS-PAGE gradient gels (4–20% Novex) and transferred to PVDF (10 mM CAPS) for 2 hr at a constant voltage (SOV). Non-specific binding was blocked with skim milk (5%) for 1 hr. The proteins were then probed with the two rabbit polyclonal antibodies (~1 mg/ml in TBS, pH 7.4) for 12 hrs. Presenilin cross-reactive species were identified using biotinylated goat-anti rabbit secondary antibody which was visualized using horseradish peroxidase-conjugated strepavadin tertiary, 4-chloro-napthol, and hydrogen peroxide. The c-myc-tagged presenilin peptides were assayed by Western blotting using both the anti-presenilin antibodies described above (to detect the presenilin peptide antigen), and culture supernatant from the hybridoma MYC 1-9E10.2 diluted 1:10 for Western blots and 1:3 for immunocytochemistry (to detect the myc-epitope). A major band of immunoreactivity of 50–60 kDa was identified by each of the various presenilin antibodies, and by the myc-epitope antibodies (for cell lines transfected with myc-containing plasmids). Minor bands at ~10–19 kDa and at ~70 kDa were detected by some presenilin antibodies.

For immunocytochemistry, transfected cells were fixed with 4% formaldehyde in Tris buffered saline (TBS), washed extensively with TBS plus 0.1% Triton and non-specific binding blocked with 3% BSA. Fixed cells were probed with the presenilin antibodies (e.g., antibodies 520 and 1142, above; typically 5–10 mg/ml), washed and visualized with FITC- or rhodamine-conjugated goat-anti rabbit secondary antibody. For c-myc-tagged presenilin constructs, the hybridoma MYC 19E10.2 supernatant diluted 1:3 was used with anti-mouse secondary antibody. Slides were mounted in 90% glycerol with 0.1% phenylenediamine (ICN) to preserve fluorescence. Anti-BIP (or anticalnexin) (StressGen, Victoria, B.C.) and wheat germ agglutinin (EY Labs, San Mateo, Calif.) were used as markers of endoplasmic reticulum and Golgi respectively. Double-immuno-labeling was also performed with anti-actin (Sigma, St. Louis, Mo.), anti-amyloid precursor protein (22C11, Boehringer Mannheim) and anti-neurofilament (NF-M specific, Sigma) in neuronal line NSC34. These immunofluorescence studies demonstrated that the transfection product is widely distributed within the cell, with a particularly intense perinuclear localization suggestive of the endoplasmic reticulum and the Golgi apparatus, which is similar to that observed in untransfected cells but is more intense, sometimes spilling over into the nuclear membrane. Co-immunolocalization of the c-myc and PS epitopes was observed in CHO and COS cells transiently transfected with the myc-tagged presenilin constructs.

Robust expression of the transfected presenilin gene in the transfected cells was thus proven by immunocytochemistry, Northern blot, Western blots (using antibodies to presenilins as above, and using the monoclonal antibody MYC1-9E10.2 to the myc tag in constructs with 3' or 5' c-myc tags).

Example 14

Isolation of presenilin binding proteins by affinity chromatography.

To identify the proteins which may be involved in the biochemical function of the presenilins, PS1 -binding proteins were isolated using affinity chromatography. A GST-fusion protein containing the PS1 TM6→7 loop, prepared as described in Example 8, was used to probe human brain extracts, prepared by homogenizing brain tissue by Polytron in physiological salt solution. Non-specific binding was eliminated by pre-clearing the brain homogenates of endogenous GST-binding components by incubation with glutathione-Sepharose beads. These GST-free homogenates were then incubated with the GST-PS fusion proteins to produce the desired complexes with functional binding proteins. These complexes were then recovered using the affinity glutathione-Sepharose beads. After extensive washing with phosphate buffered saline, the isolated collection of proteins was separated by SDS-polyacrylamide gel electrophoresis (SDS-PAGE; Tris-tricine gradient gel 4–20%). Two major bands were observed at ~14 and 20 kD in addition to several weaker bands ranging from 50 to 60 kD.

Pharmacologic modification of interaction between these proteins and the TM6→7 loop may be employed in the treatment of Alzheimer's Disease. In addition, these proteins which are likely to act within the presenilin biochemical pathway may be novel sites of mutations that cause Alzheimer's Disease.

Example 15

Isolation of PS-interacting proteins by two-hybrid yeast system.

To identify proteins interacting with the presenilin proteins, a commercially available yeast two-hybrid kit ("Matchmaker System 2" from Clontech, Palo Alto, Calif.) was employed to screen a brain cDNA library for clones which interact with functional domains of the presenilins. In view of the likelihood that the TM6→7 loop domains of the presenilins are important functional domains, partial cDNA sequences encoding either residues 266–409 of the normal PS1 protein or residues 272–390 of the normal PS2 protein were ligated in-frame into the EcoRI and BamHI sites of the pAS2-1 fusion-protein expression vector (Clontech). The resultant fusion proteins contain the GAL4 DNA binding domain coupled in-frame either to the TM6→7 loop of the PS1 protein or to the TM6→7 loop of the PS2 protein. These expression plasmids were co-transformed into S. cerevisiae strain Y190 together with a library of human brain cDNAs ligated into the pACT2 yeast fusion-protein expression vector (Clontech) bearing the GAL4 activation domain using modified lithium acetate protocols of the "Matchmaker System 2" yeast two-hybrid kit (Clontech, Palo Alto, Calif.). Yeast clones bearing human brain cDNAs which interact with the TM6→7 loop domain were selected for His- resistance by plating on SD minimal medium lacking histidine and for βgal+activation by color selection. The His+βgal+clones were then purged of the pAS2-1 "bait" construct by culture in 10 μg/ml cyclohexamide and the unknown "trapped" inserts of the human brain cDNAs encoding PS-interacting proteins were isolated by PCR and sequenced. Of 6 million initial transfornants, 200 positive clones were obtained after His- selection, and 42 after βgal+color selection, carried out in accordance with the manufacturer's protocol for selection of positive colonies. Of these 42 clones there were several independent clones representing the same genes.

To address the likelihood that mutations in the presenilins cause AD through the acquisition of a novel but toxic function (i.e., dominant gain of function mutation) which is mediated by a novel interaction between the mutant proteins and one or more other cellular proteins, the human brain cDNA library cloned into the pACT2 expression vector (Clontech) was re-screened using mutant TM6→7 loop domain sequences as described above and according to manufacturer's protocols. In particular, mutant presenilin sequences corresponding to residues 260–409 of PS1 TM6→7 loop domains bearing mutations L286V, L392V and A290–319 were ligated in-frame into the GAL4 DNA-binding domain of the pAS2-1 vector (Clontech) and used to screen the human brain cDNA:GAL4 activation domain library of pACT vectors (Clontech). Yeast were co-transformed, positive colonies were selected, and "trapped" sequences were recovered and sequenced as described above. In addition to some of the same sequences recovered with the normal TM6→7 loop domains, several new sequences were obtained which reflect aberrant interactions of the mutant presenilins with normal cellular proteins.

The recovered and sequenced clones corresponding to these PS-interacting proteins were compared to the public sequence databases using the BL:ASTN algorithm via the NCBI e-mail server. Descriptions of several of these clones follow:

Antisecretory Factor/Proteasome S5a Subunit. Two overlapping clones (Y2H29 and Y2H31) were identified which correspond to a C-terminal fragment of a protein alternatively identified as Antisecretory Factor ("ASF") or the Multiubiquitin chain binding S5a subunit of the 26S proteasome ("S5a") (Johansson et al. (1995) *J.Biol.Chem.* 270:20615–20620; Ferrell et al. (1996) *FEBS Lett.* 381:143–148). The complete nucleotide and amino acid sequences of the S5a subunit are available through the public databases under Accession number U51007 and are reproduced here as SEQ ID NO:26 and SEQ ID NO:27. The nucleotide sequences of the Y2H29 and Y2H31 clones include nucleotides 351–1330 of SEQ ID NO:26 and amino acid residues 70–377 of SEQ ID NO:27. Thus, residues 70–377 of the full S5a subunit include the PS-interacting domain of this protein. Residues 206–377 of S5a contain certain motifs that are important for protein-protein interactions (Ferrell et al., 1996).

The PS1-S5a subunit interaction was directly re-tested for both wild type and mutant PS1 TM6→7 loop (residues 260–409) by transforming Y187 yeast cells with the appropriate wild type or mutant (L286V, L392V or A290–319) cDNA ligated in-frame to the GAL4-DNA binding domain of pACT2. The Δ290–319 mutant fusion construct displayed autonomous βgal activation in the absence of any S5a "target sequence" and, therefore, could not be further analyzed. In contrast, both the L286V and L392V mutant constructs interacted specifically with the S5a construct. Quantitative assays, however, showed that these interactions were weaker than those involving the wild type $PS1_{260-409}$ sequence and that the degree of interaction was crudely correlated with the age of onset of FAD. The difference in βgal activation was not attributable to instability of the mutant $PS1_{260-409}$ construct mRNAs or fusion proteins because Western blots of lysates of transformed yeast showed equivalent quantities of mutant or wild-type fusion proteins.

Because one of the putative functions of S5a is to bind multi-ubiquitinated proteins, the PS1:S5a interaction observed in *S. cerevisiae* could arise either through yeast-dependent ubiquitination of the $PS1_{260-409}$ construct, or by direct interaction. The former would reflect a degradative pathway, a functional and perhaps reciprocal interaction between PS1 and S5a, or both. A direct interaction is favored by the fact that the PS1:S5a interaction is decreased rather than increased by the presence of the L286V and L392V mutations, and by the fact that neither of these mutations affect ubiquitin conjugation sites in the $PS1_{260-409}$ loop (i.e., K265, K311, K314 or K395). To further examine this possibility, we investigated the direct interaction of recombinant His-tagged fusion proteins corresponding to full length S5a and the $PS1_{260-409}$ loop. Partially purified recombinant His-tagged $PS1_{260-409}$ loop and His-tagged S5a proteins and appropriate controls were mixed in phosphate buffered saline. The mixture was then subjected to size exclusion chromatography, and eluates were examined by SDS-PAGE and Western blotting using anti-His-tag monoclonal antibodies (Quiagen). In the crude $PS1_{260-409}$ loop preparation alone, the $PS1_{260-409}$ loop eluted from the size exclusion column as a broad peak at 35 minutes. In the crude S5a preparation alone, S5a eluted at 25 minutes. However, when the crude $PS1_{260-409}$ loop and S5a preparations were mixed, there was a significant shift in the elution of $PS1_{260-409}$ toward a higher molecular weight complex. Co-elution of S5a and $PS1_{260-409}$ in the same fraction was confirmed by SDS-PAGE and Western blotting of fractions using the anti-His-tag antibody. These results are consistent with a ubiquitin-independent and, therefore, possibly functional interaction.

Rab11 gene. This clone (Y2H9), disclosed herein as SEQ ID NO:28, was identified as interacting with the normal PS1 TM6→7 loop domain and appears to correspond to a known gene, Rab11, available through Accession numbers X56740 and X53143. Rab11 is believed to be involved in protein/vesicle trafficking in the ER/Golgi. Note the possible relationship to processing of membrane proteins such as βAPP and Notch with resultant overproduction of toxic Aβ peptides (especially neurotoxic $Aβ_{1-42(43)}$ isoforms) (Scheuner et al. (1995) *Soc. Neurosci. Abstr.* 21:1500).

Retinoid X receptor-β gene. This clone (Y2H23b), disclosed herein as SEQ ID NO:29, was identified as interacting with the normal PS1 TM6→7 loop domain and appears to correspond to a known gene, known variously as the retinoid X receptor-β, nuclear receptor co-regulator or MHC Class I regulatory element, and available through Accession numbers M84820, X63522 and M81766. This gene is believed to be involved in intercellular signaling, suggesting a possible relationship to the intercellular signaling function mediated by *C. elegans* sel12 and Notch/lin-12 (transcription activator).

Unknown gene (Y2H35). This clone (Y2H35), disclosed herein as SEQ ID NO:30, was identified as interacting with the normal PS1 TM6→7 loop domain and appears to correspond to a known gene of unknown function, available through Accession number R12984, which shows conservation down through yeast.

Cytoplasmic chaperonin gene. This clone (Y2H27), disclosed herein as SEQ ID NO:31, was identified as interacting with the normal PS1 TM6→7 loop domain and appears to correspond to a known gene, a cytoplasmic chaperonin containing TCP-1, available through Accession numbers U17104 and X74801.

Unknown gene (Y2H171). This clone (Y2H171), disclosed herein as SEQ ID NO:32, was identified as interacting with the normal PS1 TM6→7 loop domain and appears to correspond to a known expressed repeat sequence available through Accession number D55326.

GT24 and related genes with homology to p120/plakoglobin family. Five over-lapping clones (Y2H6, Y2H10b, Y2H17h2, Y2H24, and Y2H25) were obtained which interact with the normal PS1 TM6→7 loop domain and which appear to represent at least one novel gene. The Y2H24 clone was also found to interact with the mutant PS1 TM6→7 loop domains. Note that it appears that more than one member of the gene family was isolated, suggesting a family of genes interacting differentially with different presenilins. The most complete available cDNA corresponding to these clones was designated GT24 and is disclosed herein as SEQ ID NO:33 and has been deposited with GenBank as Accession number U81004. The open reading frame suggests that GT24 is a protein of at least 1040 amino acids with a unique N-terminus, and considerable homology to several armadillo (arm) repeat proteins at its C-terminus. Thus, for example, residues 440–862 of GT24 (numbering from Accession number U81004) have 32–56% identity ($p=1.2e^{-133}$) to residues 440–854 of murine p120 protein (Accession number Z17804), and residues 367–815 of GT24 have 26–42% identity ($p=0.0017$) to residues 245–465 of the *D. melanogaster* armadillo segment polarity protein (Accession number P18824). The GT24 gene maps to chromosome 5p15 near the anonymous microsatellite marker D5S748 and the Cri-du-Chat syndrome locus. This sequence is also nearly identical to portions of two human ESTs of unknown function (i.e., nucleotides 2701–3018 of Accession number F08730 and nucleotides 2974–3348 of Accession number T18858). These clones also show lower degrees of homology with other partial cDNA and gDNA sequences (e.g., H17245, T06654, T77214, H24294, M62015, T87427 and G04019).

An additional His⁻, βgal⁺ clone isolated in the initial screening with wild type $PS1_{266-409}$ "bait" had a similar nucleotide sequence to GT24 (target clone Y2H25; Accession number U81005), and would also be predicted to encode a peptide with C-terminal arm repeats. A longer cDNA sequence closely corresponding to the Y2H25 clone has been deposited in GenBank as human protein p0071 (Accession number X81889). Comparison of the predicted sequence of the Y2H25/p0071 ORF with that of GT24 confirms that they are related proteins with 47% overall amino acid sequence identity, and with 70% identity between residues 346–862 of GT24, and residues 509–1022 of Y2H25/p0071 (which includes residues encoded by the Y2H25 cDNA). The latter result strongly suggests that PS1 interacts with a novel class of arm repeat containing proteins. The broad ~4 kb hybridization signal obtained on Northern blots with the unique 5' end of GT24 could reflect either alternate splicing/polyadenylation of GT24, or the existence of additional members of this family with higher degrees of N-terminal homology to GT24 than Y2H25/p0071.

Unknown gene (Y2H41). This clone (Y2H41) was identified which reacts strongly with the TM6→7 loop domains of both PS1 and PS2 as well as the mutant loop domains of PS1. The sequence, disclosed as SEQ ID NO:34, shows strong homology to an EST of unknown function (Accession number T64843).

Unknown gene (Y2H3-1). This clone (Y2H3-1) was identified which reacts with both the normal and mutant PS1 TM6→7 loop domains. The sequence is disclosed herein as SEQ ID NO:35.

Proteasome p40 Subunit (Mov34). This clone (Y2HEx 10-6) was identified by interaction with a mutant PS1 TM6→7 loop domain but not with the wild type TM6→7 domain. This clone shows sequence identity to the human p40 subunit (Mov34) of the 26S proteasome. The full sequence of this subunit is available through Accession number D50063. The sequence of clone Y2HEx10-6 is disclosed as SEQ ID NO:36.

Unknown gene (Y2HEx10-17-1). This clone (Y2HEx10-17-1) was identified by interaction with a mutant PS1 TM6→7 loop domain but not with the wild type TM6→7 domain. This clone shows no strong homologies to any known sequences. The sequence of this clone is disclosed as SEQ ID NO:37. Note that this is a reverse sequence from the 3' end.

Unknown gene (Ex10/17-1). This clone (Ex10/17-1) was identified by interaction with a mutant PS1 TM6→7 loop domain but not with the wild type TM6→7 domain. This clone shows no strong homologies to any known sequences. The sequence of this clone is disclosed as SEQ ID NO:38.

Unknown gene (Ex10/24-1). This clone (Ex10/24-1) was identified by interaction with a mutant PS1 TM6→7 loop domain but not with the wild type TM6→7 domain. This clone shows no strong homologies to any known sequences. The sequence of this clone is disclosed as SEQ ID NO:39. The disclosed sequence is the 3' end.

Unknown gene with homology to human Tubulin. This clone (Ex1/1-2) was identified by interaction with a mutant PS1 TM6→7 loop domain but not with the wild type TM6→7 domain. This clone has strong homology and identity with human Tubulin α chain. This sequence of this clone is disclosed as SEQ ID NO:40.

Unknown gene (mutTM1–TM2). This clone (mutTM1–TM2), disclosed herein as SEQ ID NO:41, was identified as interacting with mutant PS1 TM1→TM2 loop domain and appears to correspond to a known heat-shock serine protease gene.

Example 16

Transgenic *C. elegans*.

Transgenic *C. elegans* were obtained by microinjection of oocytes. The vectors pPD49.3 hsp 16–41 and pPD49.78 hsp 16-2 were chosen for this purpose. Using the first of these vectors, transgenic *C. elegans* were produced in which a normal hPS1 gene or a mutant (L392V) was introduced. Transformed animals were detected by assaying expression of human cDNA on northern blots or western blots using human cDNA probe cc32 and antibodies 519, 520 and 1142, described above. Vectors were also prepared and/or injected bearing a cis double mutant hPS1 gene (M146L and L392V), a normal hPS2 gene, and a mutant (N141I) hPS2 gene.

Example 17

Cloning of a Drosophila presenilin homologue, DmPS.

Redundant oligonucleotides 5' ctn ccn gar tgg acn gyc tgg (SEQ ID NO:22) and 5' rca ngc (agt)at ngt ngt rtt cca (SEQ ID NO:23) were designed from published nucleotide sequence data for highly conserved regions of the presenilin/ sel-12 proteins ending/beginning with Trp (e.g., at residues Trp247 and Trp404 in PS1; Trp253 and Trp385 in PS2). These primers were used for RTPCR (50 ml volume, 2 mM MgCl$_2$, 30 cycles of 94° C.×30", 57° C.×20", 72° C.×20") from mRNA from adult and embryonic *D. melanogaster*. The products were then reamplified using cycle conditions of 94° C.×1', 59° C.×0.5' and 72° C.×1' and internal conserved redundant primer 5'ttt ttt ctc gag acn gcn car gar aga aay ga (SEQ ID NO:24) and 5' ttt ttt gga tcc tar aa(agt) atr aar tcn cc (SEQ ID NO:25). The 600 bp product was cloned into the BamHI and XhoI sites of pBS. These products were sequenced and shown to contain an open reading frame with a putative amino acid sequence highly homologous to that of the human presenilins. This fragment was then used to screen a conventional *D. melanogaster* cDNA/Zap library (Stratagene, Calif.) to recover six independent cDNA clones of size ~2–2.5 kb (clones pds8, pds13, pds1, pds3, pds7 and pds14) which were sequenced. The longest ORF encodes a polypeptide of 541 amino acids with 52% identity to the human presenilins.

Example 18

Assays for long isoforms of the Aβ peptides.

Aβ peptides were extracted with 99% formic acid for 60 minutes (20° C.) from frozen cerebral cortex of histopathologically confirmed cases of FAD with PS1 or βAPP$_{717}$ mutations; sporadic AD with no known family history of the disease; other adult onset neurodegenerative disorders (HD= Huntington Disease; ALS=amyotrophic lateral sclerosis); Down's Syndrome (DS); and control subjects without neurologic symptoms. After centrifugation at 200,000×g for 20 minutes, the supernatant was separated from the pellet, diluted, neutralized and examined by ELISA. To quantitate different species of Aβ, four monoclonal antibodies were used. Antibody BNT-77 (which detects epitopes from the center of Aβ) and antibody BAN-50 (which detects N-terminal residues) were used first to bind all types of Aβ including heterologous forms with or without N-terminal truncation (BNT-77) or only without N-terminal truncation (BAN-50). Two additional monoclonal antibodies, which specifically detect either short-tailed Aβ ending at residue 40 (antibody BA-27) or long-tailed Aβ ending at residues 42/43 (antibody BC-05), were then used to distinguish the different C-terminal forms of Aβ. Two site ELISA was carried out as described previously (Tamaoka et al., 1994; Suzuki et al., 1994). Briefly, 100 µg of standard peptides or the supernatants from brain tissue were applied onto microplates coated with the BNT-77 antibody, incubated at 4° C. for 24 hours, washed with phosphate-buffered saline, and then incubated with HRP-labeled BA-27 and BC-05 antibodies at 4° C. for 24 hours. IRP activities were assayed by color development using the TNB microwell peroxidase system as previously described. Cortical Aβ levels were compared between diagnostic groups using paired Student-t tests. Joint evaluation of all the Aβ isoform data, using the Student-Newman-Keuls multiple comparison of means test, revealed that Aβ1-42 levels from βAPP$_{717}$ and sporadic AD subjects were distinct from those for PS1 mutation cases, but similar to controls. In contrast, three group were distinguishable when Aβx-42 levels were considered: high (PS1 and βAPP$_{717}$ AD), medium (sporadic AD) and low (control).

Specifically, measurement of the concentrations of the various Aβ isoforms in the cerebral cortex of 14 control subjects, including five subjects with other neurodegenerative diseases with onset in the fourth and fifth decades of life, revealed only low concentrations of both short-tailed Aβ (Aβ1-40: 0.06±0.02 nMol/gram wet tissue±SEM; Aβx-40: 0.17±0.40) and long-tailed Aβ (Aβ1-42/43: 0.35±0.17; Aβx-42/43: 1.17±0.80). In contrast, the long-tailed Aβ peptides were significantly elevated in the cerebral cortex of all four subjects with PS1 mutations (Aβ1-42/43: 6.54 ±2.0, p=0.05; Aβx-42/43: 23.91±4.00, p<0.01). Similar increases in the concentration of long-tailed Aβ peptides were detected in the cortex of both subjects with βAPP$_{717}$ mutations (Aβ1-42/43: 2.03±1.04; Aβx-42/43: 25.15±15.74), and subjects with sporadic AD (Aβ1-42/43: 1.21±10.40, p =0.008; Aβx-42/43: 14.45±2.81, p=0.001). In subjects with PS1 or βAPP$_{717}$ mutations, this increase in long-tailed isoforms of Aβ was accompanied by a small but non-significant increase in short-tailed Aβ isoforms (e.g., Aβx-40: 3.08±1.31 in PS1 mutants; 1.56±0.07 in βAPP$_{717}$ mutants). Thus, the ratio of long to short isoforms was also significantly increased. However, in the sporadic AD cases, the observed increase in long-tailed Aβ was accompanied typically by a much larger increase in short-tailed Aβ isoforms (Aβ-40: 3.92±1.42; Aβx-40: 16.60±5.88). This increase in short-tailed Aβ was statistically significant when compared to controls (p<0.03 for both Aβ1-40 and Aβx-40), but was of borderline statistical significance when compared to the PS1 and βAPP$_{717}$ cases (p>0.05). Analysis of cortical samples from an adult subject with Down's syndrome revealed a pattern similar to that observed in sporadic AD.

Although preferred embodiments of the invention have been described herein in detail, it will be understood by those skilled in the art that variations may be made thereto without departing from the spirit of the invention or the scope of the appended claims.

TABLE 1

| ELEMENT | POSITION | | ELEMENT | POSITION |
|---|---|---|---|---|
| STAT1 (GAS) | 38–46 | 611–619 | CAT box | 895–900 |
| | 278–286 | 631–639 | | 975–982 |
| | 431–439 | 1582–1590 | TATA box | 925–933 |
| | 443–451 | 1965–1973 | | 978–988 |
| | 495–503 | 2125–2133 | TFIID | 578–581 |
| | 533–541 | | | 982–985 |
| STAT3 | 36–43 | 737–744 | TRXN (CAP) start | 1002–1007 |
| | 124–131 | 811–898 | | 1038–1043 |
| | 429–436 | 1063–1070 | GC box (SP1) | 1453–1460 |
| | 496–503 | 1686–1693 | | 1454–1462 |
| | 533–540 | 1966–1973 | AP2, AP2-like | numerous occurrences |

TABLE 1-continued

| ELEMENT | POSITION | | ELEMENT | POSITION | |
|---|---|---|---|---|---|
| | 537–544 | 2104–2111 | | throughout sequence | |
| | 632–639 | 2407–2414 | NFIL6 | 611–620 | 1567–1576 |
| MED1, MED1-like | 1121–1126 | 1235–1240 | | 890–899 | 1945–1954 |
| | 1126–1131 | 1716–1721 | | 1062–1071 | |

TABLE 2

| PS1 Domain | Approximate Position |
|---|---|
| N-terminus | 1–81 |
| TM1 | 82–100 |
| TM1→2 | 101–132 |
| TM2 | 133–154 |
| TM2→3 | 155–163 |
| TM3 | 164–183 |
| TM3→4 | 184–194 |
| TM4 | 195–212 |
| TM4→5 | 213–220 |
| TM5 | 221–238 |
| TM5→6 | 239–243 |
| TM6 | 244–262 |
| TM6→7 | 263–407 |
| TM7 | 408–428 |
| C-terminus | 429–467 |

TABLE 3

| PS2 Domain | Approximate Position |
|---|---|
| N-terminus | 1–87 |
| TM1 | 88–106 |
| TM1→2 | 107–134 |
| TM2 | 135–160 |
| TM2→3 | 161–169 |
| TM3 | 170–189 |
| TM3→4 | 190–200 |
| TM4 | 201–218 |
| TM4→5 | 219–224 |
| TM5 | 225–244 |
| TM5→6 | 245–249 |
| TM6 | 250–268 |
| TM6→7 | 269–387 |
| TM7 | 388–409 |
| C-terminus | |

TABLE 4

| | Position in SEQ ID NO:1 | Nucleotide Change | Amino Acid Change | Functional Domain | Age of Onset of FAD |
|---|---|---|---|---|---|
| 1. | NA | NA | A79? | N-terminus | 64 |
| 2. | 492 | G→C | V82L | TM1 | 55 |
| 3. | NA | NA | V96F | TM1 | NA |
| 4. | 591 | T→C | Y115H | TM1→2 | 37 |
| 5. | 664 | T→C | M139T | TM2 | 49 |
| 6. | NA | NA | M139V | TM2 | 40 |
| 7. | 676 | T→C | I143T | TM2 | 35 |
| 8. | 684 | A→C | M146L | TM2 | 45 |
| 9. | NA | NA | M146V | TM2 | 38 |
| 10. | 736 | A→G | H163R | TM2→3 | 50 |
| 11. | NA | NA | H163Y | TM2→3 | 47 |
| 12. | NA | T→C | L171P | TM3 | 35 |
| 13. | NA | T→C | F177S | TM3 | NA |
| 14. | NA | NA | G209V | TM4 | NA |
| 15. | NA | NA | I211T | TM4 | NA |
| 16. | 939 | G→A | A231T | TM5 | 52 |
| 17. | 985 | C→A | A246E | TM6 | 55 |
| 18. | 1027 | C→T | A260V | TM6 | 40 |
| 19. | NA | NA | C263R | TM6→7 | 47 |
| 20. | 1039 | C→T | P264L | TM6→7 | 45 |
| 21. | NA | NA | P267S | TM6→7 | 35 |
| 22. | NA | NA | E280A | TM6→7 | 47 |
| 23. | NA | NA | E280G | TM6→7 | 42 |
| 24. | 1102 | C→T | A285V | TM6→7 | 50 |
| 25. | 1104 | C→G | L286V | TM6→7 | 50 |
| 26. | NA | deletion | Δ291–319 | TM6→7 | NA |
| 27. | 1399 | G→C | G384A | TM6→7 | 35 |
| 28. | 1422 | C→G | L392V | TM6→7 | 25–40 |
| 29. | 1477 | G→A | C410Y | TM7 | 48 |
| 30. | 1563 | A→G | 1439V | C-terminus | NA |

TABLE 5

| | Position in SEQ ID NO:18 | Nucleotide Change | Amino Acid Change | Functional Domain | Age of Onset of FAD |
|---|---|---|---|---|---|
| 1. | 787 | A→T | N141I | TM2 | 50–65 |
| 2. | 1080 | A→G | M239V | TM5 | 50–70 |
| 3. | 1624 | T→C | 1420T | C-terminus | 45 |

TABLE 6

| | |
|---|---|
| 28–61 | 302–310 |
| 65–71 | 311–325 |
| 109–112 | 332–342 |
| 120–122 | 346–359 |
| 218–221 | 372–382 |
| 241–243 | 400–410 |
| 267–269 | |

TABLE 7

| | |
|---|---|
| 25–45 | 282–290 |
| 50–63 | 310–314 |
| 70–75 | 321–338 |
| 114–120 | 345–352 |
| 127–132 | 380–390 |
| 162–167 | 430–435 |
| 221–226 | |

What is claimed is:

1. A method for identifying substances that affect the interaction of a presenilin-1-interacting protein with a mammalian presenilin-1 protein, or a fragment, variant or mutein of said mammalian presenilin-1 protein that binds to said presenilin-1-interacting protein, comprising:

(a) providing a preparation containing: a mammalian presenilin-1 protein, or a fragment, variant or mutein of said mammalian presenilin-1 protein that binds to said presenilin-1-interacting protein; a presenilin-1-interacting protein; and a candidate substance; and (b) detecting whether said candidate substance affects said interaction of said presenilin-1-interacting protein with said mammalian presenilin-1 protein, or a fragment, variant or mutein of said mammalian presenilin-1 protein that binds to said presenilin-1-interacting protein.

2. The method of claim 1, wherein said mammalian presenilin-1 protein is defined by an amino acid sequence set forth in SEQ ID NO:2 or SEQ ID NO:4.

3. The method of claim 1, wherein said preparation contains a mammalian presenilin-1 mutein.

4. The method of claim 3, wherein said preparation contains a mammalian presenilin-1 mutein of the protein defined in SEQ ID NO:2, and which has at least one amino acid substitution selected from the group consisting of I143T, M146L, L171P, F177S, A260V, C263R, P264L, P267S, E280A, E280G, A285V, L286V, L322V, L392V, C410Y and I439V.

5. The method of claim 1, wherein said presenilin-1-interacting protein is an S5a subunit of 26S proteasome.

6. The method of claim 1, wherein said presenilin-1-interacting protein is a GT24 protein.

7. The method of claim 1, wherein said presenilin-1-interacting protein encoded by a nucleotide sequence selected from the group consisting of SEQ ID NO:26, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 and SEQ ID NO:41.

* * * * *

UNITED STATES PATENT AND TRADEMARK OFFICE
CERTIFICATE OF CORRECTION

PATENT NO.   : 6,020,143
DATED        : Feb. 1, 2000
INVENTOR(S)  : Peter H. St. George-Hyslop et al.

It is certified that errors appear in the above-identified patent and that said Letters Patent is hereby corrected as shown below:

On the title page, item:

[73], Assignee, "RESEARCH AND DEVELOPMENT LIMITED PARTNERSHIP" should be --HSC RESEARCH AND DEVELOPMENT LIMITED PARTNERSHIP--.

Signed and Sealed this

Eighth Day of May, 2001

*Attest:*

NICHOLAS P. GODICI

*Attesting Officer*    *Acting Director of the United States Patent and Trademark Office*

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
      (A) LENGTH: 2765 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 249..1649

(ix) FEATURE:
      (A) NAME/KEY: misc_feature
      (B) LOCATION: 1..2675
      (D) OTHER INFORMATION: /note= "hPS1-1"

(xi) SEQUENCE DESCRIPTION: SEQ ID NO:1:

```
tgggacaggc agctccgggg tccgcggttt cacatcggaa acaaaacagc ggctggtctg    60
gaaggaacct gagctacgag ccgcggcggc agcggggcgg cggggaagcg tatacctaat   120
ctgggagcct gcaagtgaca acagcctttg cggtccttag acagcttggc ctggaggaga   180
acacatgaaa gaaagaacct caagaggctt tgttttctgt gaaacagtat ttctatacag   240 ttgctcca atg aca gag tta cct gca ccg ttg tcc tac ttc cag aat gca     290
         Met Thr Glu Leu Pro Ala Pro Leu Ser Tyr Phe Gln Asn Ala
           1               5                  10 cag atg tct gag gac aac cac ctg agc aat act gta cgt agc cag aat     338
Gln Met Ser Glu Asp Asn His Leu Ser Asn Thr Val Arg Ser Gln Asn
 15                  20                  25                  30 gac aat aga gaa cgg cag gag cac aac gac aga cgg agc ctt ggc cac     386
Asp Asn Arg Glu Arg Gln Glu His Asn Asp Arg Arg Ser Leu Gly His
                 35                  40                  45 cct gag cca tta tct aat gga cga ccc cag ggt aac tcc cgg cag gtg     434
Pro Glu Pro Leu Ser Asn Gly Arg Pro Gln Gly Asn Ser Arg Gln Val
             50                  55                  60 gtg gag caa gat gag gaa gaa gat gag gag ctg aca ttg aaa tat ggc     482
Val Glu Gln Asp Glu Glu Glu Asp Glu Glu Leu Thr Leu Lys Tyr Gly
         65                  70                  75 gcc aag cat gtg atc atg ctc ttt gtc cct gtg act ctc tgc atg gtg     530
Ala Lys His Val Ile Met Leu Phe Val Pro Val Thr Leu Cys Met Val
     80                  85                  90 gtg gtc gtg gct acc att aag tca gtc agc ttt tat acc cgg aag gat     578
Val Val Val Ala Thr Ile Lys Ser Val Ser Phe Tyr Thr Arg Lys Asp
 95                 100                 105                 110 ggg cag cta atc tat acc cca ttc aca gaa gat acc gag act gtg ggc     626
Gly Gln Leu Ile Tyr Thr Pro Phe Thr Glu Asp Thr Glu Thr Val Gly
                115                 120                 125 cag aga gcc ctg cac tca att ctg aat gct gcc atc atg atc agt gtc     674
Gln Arg Ala Leu His Ser Ile Leu Asn Ala Ala Ile Met Ile Ser Val
            130                 135                 140 att gtt gtc atg act atc ctc ctg gtg gtt ctg tat aaa tac agg tgc     722
Ile Val Val Met Thr Ile Leu Leu Val Val Leu Tyr Lys Tyr Arg Cys
        145                 150                 155 tat aag gtc atc cat gcc tgg ctt att ata tca tct cta ttg ctg         770
Tyr Lys Val Ile His Ala Trp Leu Ile Ile Ser Ser Leu Leu Leu Leu
    160                 165                 170 ttc ttt ttt tca ttc att tac ttg ggg gaa gtg ttt aaa acc tat aac     818
```

-continued

| | | | | | | | | | | | | | | | |
|---|---|---|---|---|---|---|---|---|---|---|---|---|---|---|---|
| Phe | Phe | Phe | Ser | Phe | Ile | Tyr | Leu | Gly | Glu | Val | Phe | Lys | Thr | Tyr | Asn |
| 175 | | | | 180 | | | | | 185 | | | | | 190 | |

```
gtt gct gtg gac tac att act gtt gca ctc ctg atc tgg aat ttt ggt      866
Val Ala Val Asp Tyr Ile Thr Val Ala Leu Leu Ile Trp Asn Phe Gly
            195                 200                 205 gtg gtg gga atg att tcc att cac tgg aaa ggt cca ctt cga ctc cag      914
Val Val Gly Met Ile Ser Ile His Trp Lys Gly Pro Leu Arg Leu Gln
            210                 215                 220 cag gca tat ctc att atg att agt gcc ctc atg gcc ctg gtg ttt atc      962
Gln Ala Tyr Leu Ile Met Ile Ser Ala Leu Met Ala Leu Val Phe Ile
            225                 230                 235 aag tac ctc cct gaa tgg act gcg tgg ctc atc ttg gct gtg att tca     1010
Lys Tyr Leu Pro Glu Trp Thr Ala Trp Leu Ile Leu Ala Val Ile Ser
            240                 245                 250 gta tat gat tta gtg gct gtt ttg tgt ccg aaa ggt cca ctt cgt atg     1058
Val Tyr Asp Leu Val Ala Val Leu Cys Pro Lys Gly Pro Leu Arg Met
255                 260                 265                 270 ctg gtt gaa aca gct cag gag aga aat gaa acg ctt ttt cca gct ctc     1106
Leu Val Glu Thr Ala Gln Glu Arg Asn Glu Thr Leu Phe Pro Ala Leu
                275                 280                 285 att tac tcc tca aca atg gtg tgg ttg gtg aat atg gca gaa gga gac     1154
Ile Tyr Ser Ser Thr Met Val Trp Leu Val Asn Met Ala Glu Gly Asp
            290                 295                 300 ccg gaa gct caa agg aga gta tcc aaa aat tcc aag tat aat gca gaa     1202
Pro Glu Ala Gln Arg Arg Val Ser Lys Asn Ser Lys Tyr Asn Ala Glu
            305                 310                 315 agc aca gaa agg gag tca caa gac act gtt gca gag aat gat gat ggc     1250
Ser Thr Glu Arg Glu Ser Gln Asp Thr Val Ala Glu Asn Asp Asp Gly
            320                 325                 330 ggg ttc agt gag gaa tgg gaa gcc cag agg gac agt cat cta ggg cct     1298
Gly Phe Ser Glu Glu Trp Glu Ala Gln Arg Asp Ser His Leu Gly Pro
335                 340                 345                 350 cat cgc tct aca cct gag tca cga gct gct gtc cag gaa ctt tcc agc     1346
His Arg Ser Thr Pro Glu Ser Arg Ala Ala Val Gln Glu Leu Ser Ser
                355                 360                 365 agt atc ctc gct ggt gaa gac cca gag gaa agg gga gta aaa ctt gga     1394
Ser Ile Leu Ala Gly Glu Asp Pro Glu Glu Arg Gly Val Lys Leu Gly
            370                 375                 380 ttg gga gat ttc att ttc tac agt gtt ctg gtt ggt aaa gcc tca gca     1442
Leu Gly Asp Phe Ile Phe Tyr Ser Val Leu Val Gly Lys Ala Ser Ala
            385                 390                 395 aca gcc agt gga gac tgg aac aca acc ata gcc tgt ttc gta gcc ata     1490
Thr Ala Ser Gly Asp Trp Asn Thr Thr Ile Ala Cys Phe Val Ala Ile
            400                 405                 410 tta att ggt ttg tgc ctt aca tta tta ctc ctt gcc att ttc aag aaa     1538
Leu Ile Gly Leu Cys Leu Thr Leu Leu Leu Ala Ile Phe Lys Lys
415                 420                 425                 430 gca ttg cca gct ctt cca atc tcc atc acc ttt ggg ctt gtt ttc tac     1586
Ala Leu Pro Ala Leu Pro Ile Ser Ile Thr Phe Gly Leu Val Phe Tyr
            435                 440                 445 ttt gcc aca gat tat ctt gta cag cct ttt atg gac caa tta gca ttc     1634
Phe Ala Thr Asp Tyr Leu Val Gln Pro Phe Met Asp Gln Leu Ala Phe
            450                 455                 460 cat caa ttt tat atc tagcatattt gcggttagaa tcccatggat gtttcttctt     1689
His Gln Phe Tyr Ile
            465 tgactataac caaatctggg gaggacaaag gtgattttcc tgtgtccaca tctaacaaag     1749 tcaagattcc cggctggact tttgcagctt ccttccaagt cttcctgacc accttgcact     1809 attggacttt ggaaggaggt gcctatagaa aacgattttg aacatacttc atcgcagtgg     1869
```

-continued

```
actgtgtccc tcggtgcaga aactaccaga tttgagggac gaggtcaagg agatatgata   1929
ggcccggaag ttgctgtgcc ccatcagcag cttgacgcgt ggtcacagga cgatttcact   1989
gacactgcga actctcagga ctaccggtta ccaagaggtt aggtgaagtg gtttaaacca   2049
aacggaactc ttcatcttaa actacacgtt gaaaatcaac ccaataattc tgtattaact   2109
gaattctgaa cttttcagga ggtactgtga ggaagagcag gcaccagcag cagaatgggg   2169
aatggagagg tgggcagggg ttccagcttc cctttgattt tttgctgcag actcatcctt   2229
tttaaatgag acttgttttc ccctctcttt gagtcaagtc aaatatgtag attgcctttg   2289
gcaattcttc ttctcaagca ctgacactca ttaccgtctg tgattgccat ttcttcccaa   2349
ggccagtctg aacctgaggt tgctttatcc taaaagtttt aacctcaggt tccaaattca   2409
gtaaattttg gaaacagtac agctatttct catcaattct ctatcatgtt gaagtcaaat   2469
ttggattttc caccaaattc tgaatttgta gacatacttg tacgctcact tgcccccaga   2529
tgcctcctct gtcctcattc ttctctccca cacaagcagt cttttctac agccagtaag    2589 gcagctctgt crtggtagca gatggtccca ttattctagg gtcttactct ttgtatgatg   2649
aaaagaatgt gttatgaatc ggtgctgtca gccctgctgt cagaccttct tccacagcaa   2709
atgagatgta tgcccaaagc ggtagaatta aagaagagta aatggctgt tgaagc        2765
```

(2) INFORMATION FOR SEQ ID NO:2:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Asp Glu Glu Leu Thr Leu Lys Tyr Gly Ala Lys
 65                 70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
```

```
                195                 200                 205
Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
    275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
                355                 360                 365

Leu Ala Gly Glu Asp Pro Glu Glu Arg Gly Val Lys Leu Gly Leu Gly
                370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
                435                 440                 445

Thr Asp Tyr Leu Val Gln Pro Phe Met Asp Gln Leu Ala Phe His Gln
    450                 455                 460

Phe Tyr Ile
465

(2) INFORMATION FOR SEQ ID NO:3:

(i) SEQUENCE CHARACTERISTICS:
        (A) LENGTH: 3086 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 557..1945

(ix) FEATURE:
        (A) NAME/KEY: misc_feature
        (B) LOCATION: 1..3086
        (D) OTHER INFORMATION: /note= "hPS1-2"

(xi) SEQUENCE DESCRIPTION: SEQ ID NO:3:

gaattcggca cgagggaaat gctgtttgct cgaagacgtc tcagggcgca ggtgccttgg      60
gccgggatta gtagccgtct gaactggagt ggagtaggag aaagaggaag cgtcttgggc    120
tgggtctgct tgagcaactg gtgaaactcc gcgcctcacg ccccgggtgt gtccttgtcc    180
aggggcgacg agcattctgg gcgaagtccg cacscctctt gttcgaggcg gaagacgggg    240
```

-continued

```
tctgatsctt tctccttggt cgggmctgtc tcgaggcatg catgtccagt gactcttgtg      300
tttgctgctg cttccctctc agattcttct caccgttgtg gtcagctctg ctttaggcat      360
attaatccat agtggaggct gggatgggtg agagaattga ggtgactttt ccataattca      420
gacctaatct gggagcctgc aagtgacaac agcctttgcg gtccttagac agcttggcct      480
ggaggagaac acatgaaaga agaacctcag agaggctttg ttttctgtga aacagtattt      540
ctatacagtt gctcca atg aca gag tta cct gca ccg ttg tcc tac ttc         589
               Met Thr Glu Leu Pro Ala Pro Leu Ser Tyr Phe
                 1               5                  10 cag aat gca cag atg tct gag gac aac cac ctg agc aat act aat gac        637
Gln Asn Ala Gln Met Ser Glu Asp Asn His Leu Ser Asn Thr Asn Asp
             15                  20                  25 aat aga gaa cgg cag gag cac aac gac aga cgg agc ctt ggc cac cct        685
Asn Arg Glu Arg Gln Glu His Asn Asp Arg Arg Ser Leu Gly His Pro
         30                  35                  40 gag cca tta tct aat gga cga ccc cag ggt aac tcc cgg cag gtg gtg        733
Glu Pro Leu Ser Asn Gly Arg Pro Gln Gly Asn Ser Arg Gln Val Val
     45                  50                  55 gag caa gat gag gaa gaa gat gag gag ctg aca ttg aaa tat ggc gcc        781
Glu Gln Asp Glu Glu Glu Asp Glu Glu Leu Thr Leu Lys Tyr Gly Ala
 60                  65                  70                  75 aag cat gtg atc atg ctc ttt gtc cct gtg act ctc tgc atg gtg gtg        829
Lys His Val Ile Met Leu Phe Val Pro Val Thr Leu Cys Met Val Val
                 80                  85                  90 gtc gtg gct acc att aag tca gtc agc ttt tat acc cgg aag gat ggg        877
Val Val Ala Thr Ile Lys Ser Val Ser Phe Tyr Thr Arg Lys Asp Gly
             95                  100                 105 cag cta atc tat acc cca ttc aca gaa gat acc gag act gtg ggc cag        925
Gln Leu Ile Tyr Thr Pro Phe Thr Glu Asp Thr Glu Thr Val Gly Gln
         110                 115                 120 aga gcc ctg cac tca att ctg aat gct gcc atc atg atc agt gtc att        973
Arg Ala Leu His Ser Ile Leu Asn Ala Ala Ile Met Ile Ser Val Ile
     125                 130                 135 gtt gtc atg act atc ctc ctg gtg gtt ctg tat aaa tac agg tgc tat       1021
Val Val Met Thr Ile Leu Leu Val Val Leu Tyr Lys Tyr Arg Cys Tyr
140                 145                 150                 155 aag gtc atc cat gcc tgg ctt att ata tca tct cta ttg ttg ctg ttc       1069
Lys Val Ile His Ala Trp Leu Ile Ile Ser Ser Leu Leu Leu Leu Phe
                 160                 165                 170 ttt ttt tca ttc att tac ttg ggg gaa gtg ttt aaa acc tat aac gtt       1117
Phe Phe Ser Phe Ile Tyr Leu Gly Glu Val Phe Lys Thr Tyr Asn Val
             175                 180                 185 gct gtg gac tac att act gtt gca ctg ctg atc tgg aat ttg ggt gtg       1165
Ala Val Asp Tyr Ile Thr Val Ala Leu Leu Ile Trp Asn Leu Gly Val
         190                 195                 200 gtg gga atg att tcc att cac tgg aaa ggt cca ctt cga ctc cag cag       1213
Val Gly Met Ile Ser Ile His Trp Lys Gly Pro Leu Arg Leu Gln Gln
     205                 210                 215 gca tat ctc att atg att agt gcc ctc atg gcc ctg gtg ttt atc aag       1261
Ala Tyr Leu Ile Met Ile Ser Ala Leu Met Ala Leu Val Phe Ile Lys
220                 225                 230                 235 tac ctc cct gaa tgg act gcg tgg ctc atc ttg gct gtg att tca gta       1309
Tyr Leu Pro Glu Trp Thr Ala Trp Leu Ile Leu Ala Val Ile Ser Val
                 240                 245                 250 tat gat tta gtg gct gtt ttg tgt ccg aaa ggt cca ctt cgt atg ctg       1357
Tyr Asp Leu Val Ala Val Leu Cys Pro Lys Gly Pro Leu Arg Met Leu
             255                 260                 265 gtt gaa aca gct cag gag aga aat gaa acg ctt ttt cca gct ctc att       1405
```

-continued

| | | | | | | | | | | | | | | |
|---|---|---|---|---|---|---|---|---|---|---|---|---|---|---|
| Val | Glu | Thr | Ala | Gln | Glu | Arg | Asn | Glu | Thr | Leu | Phe | Pro | Ala | Leu | Ile |
| | | 270 | | | | 275 | | | | | 280 | | | | |

```
tac tcc tca aca atg gtg tgg ttg gtg aat atg gca gaa gga gac ccg   1453
Tyr Ser Ser Thr Met Val Trp Leu Val Asn Met Ala Glu Gly Asp Pro
        285                 290                 295 gaa gct caa agg aga gta tcc aaa aat tcc aag tat aat gca gaa agc   1501
Glu Ala Gln Arg Arg Val Ser Lys Asn Ser Lys Tyr Asn Ala Glu Ser
300                 305                 310                 315 aca gaa agg gag tca caa gac act gtt gca gag aat gat gat ggc ggg   1549
Thr Glu Arg Glu Ser Gln Asp Thr Val Ala Glu Asn Asp Asp Gly Gly
                320                 325                 330 ttc agt gag gaa tgg gaa gcc cag agg gac agt cat cta ggg cct cat   1597
Phe Ser Glu Glu Trp Glu Ala Gln Arg Asp Ser His Leu Gly Pro His
            335                 340                 345 cgc tct aca cct gag tca cga gct gct gtc cag gaa ctt tcc agc agt   1645
Arg Ser Thr Pro Glu Ser Arg Ala Ala Val Gln Glu Leu Ser Ser Ser
        350                 355                 360 atc ctc gct ggt gaa gac cca gag gaa agg gga gta aaa ctt gga ttg   1693
Ile Leu Ala Gly Glu Asp Pro Glu Glu Arg Gly Val Lys Leu Gly Leu
365                 370                 375 gga gat ttc att ttc tac agt gtt ctg gtt ggt aaa gcc tca gca aca   1741
Gly Asp Phe Ile Phe Tyr Ser Val Leu Val Gly Lys Ala Ser Ala Thr
380                 385                 390                 395 gcc agt gga gac tgg aac aca acc ata gcc tgt ttc gta gcc ata tta   1789
Ala Ser Gly Asp Trp Asn Thr Thr Ile Ala Cys Phe Val Ala Ile Leu
                400                 405                 410 att ggt ttg tgc ctt aca tta tta ctc ctt gcc att ttc aag aaa gca   1837
Ile Gly Leu Cys Leu Thr Leu Leu Leu Ala Ile Phe Lys Lys Ala
            415                 420                 425 ttg cca gct ctt cca atc tcc atc acc ttt ggg ctt gtt ttc tac ttt   1885
Leu Pro Ala Leu Pro Ile Ser Ile Thr Phe Gly Leu Val Phe Tyr Phe
        430                 435                 440 gcc aca gat tat ctt gta cag cct ttt atg gac caa tta gca ttc cat   1933
Ala Thr Asp Tyr Leu Val Gln Pro Phe Met Asp Gln Leu Ala Phe His
445                 450                 455 caa ttt tat atc tagcatattt gcggttagaa tcccatggat gtttcttctt      1985
Gln Phe Tyr Ile
460 tgactataac caaatctggg gaggacaaag gtgattttcc tgtgtccaca tctaacaaag  2045 tcaagattcc cggctggact tttgcagctt ccttccaagt cttcctgacc accttgcact  2105 attggacttt ggaaggaggt gcctatagaa aacgattttg aacatacttc atcgcagtgg  2165 actgtgtcct cggtgcagaa actaccagat ttgagggacg aggtcaagga gatatgatag  2225 gcccggaagt tgctgtgccc catcagcagc ttgacgcgtg gtcacaggac gatttcactg  2285 acactgcgaa ctctcaggac taccggttac aagaggtta ggtgaagtgg tttaaaccaa  2345 acggaactct tcatcttaaa ctacacgttg aaaatcaacc caataattct gtattaactg  2405 aattctgaac ttttcaggag gtactgtgag gaagagcagg caccagcagc agaatgggga  2465 atggagaggt gggcagggt tccagcttcc ctttgatttt tgctgcaga ctcatcctt    2525 ttaaatgaga cttgttttcc cctctctttg agtcaagtca aatatgtaga tgcctttggc  2585 aattcttctt ctcaagcact gacactcatt accgtctgtg attgccattt cttcccaagg  2645 ccagtctgaa cctgaggttg ctttatccta aaagttttaa cctcaggttc caaattcagt  2705 aaattttgga aacagtacag ctatttctca tcaattctct atcatgttga agtcaaattt  2765 ggattttcca ccaaattctg aatttgtaga catacttgta cgctcacttg ccccagatgc  2825 ctcctctgtc ctcattcttc tctcccacac aagcagtctt tttctacagc cagtaaggca  2885
```

```
gctctgtcgt ggtagcagat ggtcccactt attctagggt cttactcttt gtatgatgaa     2945
aagaatgtgt tatgaatcgg tgctgtcagc cctgctgtca gaccttcttc cacagcaaat     3005
gagatgtatg cccaaagcgg tagaattaaa gaagagtaaa atggctgttg aagcaaaaaa     3065
aaaaaaaaaa aaaaaaaaaa a                                               3086
```

(2) INFORMATION FOR SEQ ID NO:4:

(i) SEQUENCE CHARACTERISTICS:
        (A) LENGTH: 463 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Glu Leu Pro Ala Pro Leu Ser Tyr Phe Gln Asn Ala Gln Met
 1               5                  10                  15

Ser Glu Asp Asn His Leu Ser Asn Thr Asn Asp Asn Arg Glu Arg Gln
                20                  25                  30

Glu His Asn Asp Arg Arg Ser Leu Gly His Pro Glu Pro Leu Ser Asn
            35                  40                  45

Gly Arg Pro Gln Gly Asn Ser Arg Gln Val Val Glu Gln Asp Glu Glu
        50                  55                  60

Glu Asp Glu Glu Leu Thr Leu Lys Tyr Gly Ala Lys His Val Ile Met
 65                  70                  75                  80

Leu Phe Val Pro Val Thr Leu Cys Met Val Val Val Ala Thr Ile
                85                  90                  95

Lys Ser Val Ser Phe Tyr Thr Arg Lys Asp Gly Gln Leu Ile Tyr Thr
                100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Met Thr Ile
        130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Phe Ser Phe Ile
                165                 170                 175

Tyr Leu Gly Glu Val Phe Lys Thr Tyr Asn Val Ala Val Asp Tyr Ile
            180                 185                 190

Thr Val Ala Leu Leu Ile Trp Asn Leu Gly Val Val Gly Met Ile Ser
        195                 200                 205

Ile His Trp Lys Gly Pro Leu Arg Leu Gln Gln Ala Tyr Leu Ile Met
        210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
                245                 250                 255

Val Leu Cys Pro Lys Gly Pro Leu Arg Met Leu Val Glu Thr Ala Gln
            260                 265                 270

Glu Arg Asn Glu Thr Leu Phe Pro Ala Leu Ile Tyr Ser Ser Thr Met
        275                 280                 285

Val Trp Leu Val Asn Met Ala Glu Gly Asp Pro Glu Ala Gln Arg Arg
    290                 295                 300

Val Ser Lys Asn Ser Lys Tyr Asn Ala Glu Ser Thr Glu Arg Glu Ser
305                 310                 315                 320
```

```
Gln Asp Thr Val Ala Glu Asn Asp Asp Gly Gly Phe Ser Glu Trp
                325                 330                 335

Glu Ala Gln Arg Asp Ser His Leu Gly Pro His Arg Ser Thr Pro Glu
            340                 345                 350

Ser Arg Ala Ala Val Gln Glu Leu Ser Ser Ser Ile Leu Ala Gly Glu
        355                 360                 365

Asp Pro Glu Glu Arg Gly Val Lys Leu Gly Leu Gly Asp Phe Ile Phe
    370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
                405                 410                 415

Thr Leu Leu Leu Leu Ala Ile Phe Lys Lys Ala Leu Pro Ala Leu Pro
                420                 425                 430

Ile Ser Ile Thr Phe Gly Leu Val Phe Tyr Phe Ala Thr Asp Tyr Leu
                435                 440                 445

Val Gln Pro Phe Met Asp Gln Leu Ala Phe His Gln Phe Tyr Ile
    450                 455                 460

(2) INFORMATION FOR SEQ ID NO:5:

(i) SEQUENCE CHARACTERISTICS:
        (A) LENGTH: 2494 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..2494
        (D) OTHER INFORMATION: /note= ""1Ex1n2""

(xi) SEQUENCE DESCRIPTION: SEQ ID NO:5:

aagcttttgt gtgtaaaaag tattagaatc tcatgttttt gaacaaggtt ggcagtgggt      60
tgggaggagg gattggagat tgatgcgata ggaatgtgaa gggatagctt ggggtggatt     120
ttatttttta attttaattt ttatttkttg agatggagtc ttgctctgtc tcccaggctg     180
gagtgcagtg gtgtgatctc agctcacggg ttcaagcgat tctcctgctg cagcctcccg     240
agtagctggg attacaggag cgcgccacca cacccggnta atttnnttgt attttagta      300 gagacgggt ttcaccatgt tgggttaggc tggtctagaa ctcccaacct catgatccgc      360
ctgcttcggc ctcccaaagt gccggaatta caggcgtgag cgactgcacc cggccgcttg     420
ggggtggatt tttaaagaaa ctttagaaga atgtaacttg sccagatacc atgtaccgtt     480
aatttcattt tcggttttk gaatacccat gtttgacatt tmtccgttca ccttgattaa     540
ataaggtagt attcattttt tagtttagc ttttggatat atgtgtaagt gtggtatgct     600
gtctaatgaa ttaagacaat tggtnctktc tttacccmam anctggacma agagcaggca     660
agatgcaaaa atcaagtgac ccagcaaacc agacacattt tctgctctca gctagcttgc     720
cacctagaaa gactggttgt caaagttgga gtccaagaat cgcggaggat gtttaaaatg     780
cagtttctca ggttctcncc acccaccaga agttttgatt cattgagtgg tgggagaggg     840
cagagatatt tgcgatttta acagcattct cttgattgtg atgcagctgg ttcscaaata     900
ggtaccctaa agaaatgaca ggtgttaaat ttaggatggc catcgcttgt atgccgggag     960
aagcacacgc tgggcccaat ttatataggg gctttcgtcc tcagctcgag carcctcaga    1020
accccgacaa ccyacgccag ckctctgggc ggattccrtc agktggggaa gsccaggtgg    1080
```

```
agctctggkt tctccccgca atcgtttctc caggccggag gccccgcccc cttcctcctg    1140
gctcctcccc tcctccgtgg gccgnccgcc aacgacgcca gagccggaaa tgacgacaac    1200
ggtgagggtt ctcgggcggg gcctgggaca ggcagctccg gggtccgcgg ttttcacatc    1260
ggaaacaaaa cagcggctgg tctggaagga acctgagcta cgacccgcgg cggcagcggg    1320
gcggcgggga agcgtatgtg cgtgatgggg agtccgggca agccaggaag gcaccgcgga    1380
catgggcggc cgcgggcagg gnccggncct ttgtggccgc ccggccgcg aagccggtgt     1440 cctaaaagat gaggggcggg gcgcggccgg ttggggctgg ggaacccgt gtgggaaacc     1500 aggaggggcg gcccgtttct cgggcttcgg gcgcggccgg gtggagagag attccgggga    1560
gccttggtcc ggaaatgctg tttgctcgaa gacgtctcag ggcgcaggtg ccttgggccg    1620
ggattagtag ccgtctgaac tggagtggag taggagaaag aggaagcgtc ttgggctggg    1680
tctgcttgag caactggtga aactccgcgc ctcacgcccc gggtgtgtcc ttgtccaggg    1740
gcgacgagca ttctgggcga agtccgcacg cctcttgttc gaggcggaag acgggtctt    1800 gatgctttct ccttggtcgg gactgtctcg aggcatgcat gtccagtgac tcttgtgttt    1860
gctgctgctt ccctctcaga ttcttctcac cgttgtggtc agctctgctt taggcatatt    1920
aatccatagt ggaggctggg atgggtgaga gaattgaggt gacttttcca taattcaggt    1980
gagatgtgat tagagtycgg atcctncggt ggtggcagag gcttaccaag aaacactaac    2040
gggacatggg aaccaattga ggatccaggg aataaagtgt gaagttgact aggaggtttt    2100
cagtttaaga acatggcaga gacattctca gaaataagga agttaggaag aaagacctgg    2160
tttagagagg agggcgagga agtggtttgg aagtgtcact ttggaagtgc cagcaggtga    2220
aaatgccctg tgaacaggac tggagctgaa acaggaatc aattccatag atttccagtt     2280
gatgttggag cagtggagaa gtctaancta aggaagggga agaggaggcc aagccaaaca    2340
cttaggaaca cttncnacga gggggtggaa gaagagcaag gagccagctg aggagaatga    2400
gtgtggttgg agaaccacca cagcncaggg tcgccaganc tgaggaaggg gagggaagct    2460
tatcgagkam sgwcracmkc gagttggcag ggat                                2494
```

(2) INFORMATION FOR SEQ ID NO:6:

(i) SEQUENCE CHARACTERISTICS:
        (A) LENGTH: 1117 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..1117
        (D) OTHER INFORMATION: /note= "1Ex3n4"

(xi) SEQUENCE DESCRIPTION: SEQ ID NO:6:

```
ggatccgccc gccttggcct cccaaagtgc tgggattaca ggcatgagcc accgctcctg      60
gctgagtctg cgatttcttg ccagctctac ccagttgtgt catcttaagc aagtcactga    120
acttctctgg attcccttct cctnnwgtaa aataagnatg ttatctgncc nncctgcctt    180
gggcattgtg ataaggataa gatgacatta tagaatntng caaaattaaa agcgctagac    240
aaatgatttt atgaaaatat aaagattagn ttgagtttgg gccagcatag aaaaaggaat    300
gttgagaaca ttccnttaag gattactcaa gcyccccttt tgstgknwaa tcaganngtc    360
atnnamntat cntntgtggg ytgaaaatgt ttggttgtct caggcggttc ctacttattg    420
ctaaagagtc ctaccttgag cttatagtaa atttgtcagt tagttgaaag tcgtgacaaa    480
```

-continued

```
ttaatacatt cctggtttac aaattggtct tataagtatt tgattggtnt aaatgnattt        540
actaggattt aactaacaat ggatgacctg gtgaaatcct atttcagacc taatctggga        600
gcctgcaagt gacaacagcc tttgcggtcc ttagacagct tggcctggag gagaacacat        660
gaaagaaagg tttgwntctg nttawtgtaa tctatgraag tgttttttwat macagtataa       720 ttgtmtgmac aaagttctgt ttttctttcc ctttncagaa cctcaagagg ctttgttttc        780
tgtgaaacag tatttctata cagttgctcc aatgacagag ttacctgcac cgttgtccta       840
cttccagaat gcacagatgt ctgaggacaa ccacctgagc aatactgtac gtagccaggt        900
acagcgtcag tytctnaaac tgcctyygnc agactggatt cacttatcat ctcccctcac       960
ctctgagaaa tgctgagggg gstaggnagg gctttctcta cttnaccaca tttnataatt      1020 attttttgggt gaccttcagc tgatcgctgg gagggacaca gggcttnttt aacacatagg      1080
gtgttggata cagncccctcc ctaattcaca tttcanc                              1117
```

(2) INFORMATION FOR SEQ ID NO:7:

(i) SEQUENCE CHARACTERISTICS:
      (A) LENGTH: 1727 base pairs
      (B) TYPE: nucleic acid
      (C) STRANDEDNESS: single
      (D) TOPOLOGY: linear (ix) FEATURE:
      (A) NAME/KEY: misc_feature
      (B) LOCATION: 1..1727
      (D) OTHER INFORMATION: /note= "1Ex5"

(xi) SEQUENCE DESCRIPTION: SEQ ID NO:7:

```
ggatccctcc ccttttaga ccatacaagg taacttccgg acgttgccat ggcatctgta         60
aactgtcatg gtgttggcgg ggagtgtctt ttagcatgct aatgtattat aattagcgta       120
tagtgagcag tgaggataac cagaggtcac tctcctcacc atcttggttt tggtgggttt       180
tggccagctt ctttattgca accagtttta tcagcaagat ctttatgagc tgtatcttgt       240
gctgacttcc tatctcatcc cgnaactaag agtacctaac ctcctgcaaa ttgmagncca       300
gnaggtcttg gncttatttn acccagcccc tattcaarat agagtngytc ttggnccaaa      360
cgccyctgac acaaggattt taaagtctta ttaattaagg taagatagkt ccttgsatat      420
gtggtctgaa atcacagaaa gctgaatttg gaaaaggtg cttggasctg cagccagtaa       480
acaagttttc atgcaggtgt cagtatttaa ggtacatctc aaaggataag tacaattgtg     540
tatgttggga tgaacagaga gaatggagca anccaagacc caggtaaaag agaggacctg      600
aatgccttca gtgaacaatg atagataatc tagacttta aactgcatac ttcctgtaca       660
ttgttttttc ttgcttcagg tttttagaac tcatagtgac gggtctgttg ttaatcccag      720
gtctaaccgt taccttgatt ctgctgagaa tctgatttac tgaaaatgtt tttcttgtgc     780
ttatagaatg acaatagaga acggcaggag cacaacgaca gacggagcct tggccaccct      840
gagccattat ctaatggacg accccagggt aactcccggc aggtggtgga gcaagatgag      900
gaagaagatg aggagctgac attgaaatat ggcgccaagc atgtgatcat gctctttgtc      960
cctgtgactc tctgcatggt ggtggtcgtg gctaccatta agtcagtcag cttttatacc     1020
cggaaggatg ggcagctgta cgtatgagtt tkgttttatt attctcaaas ccagtgtggc    1080
ttttctttac agcatgtcat catcaccttg aaggcctctn cattgaaggg gcatgactta    1140 gctgagagc ccatcctctg tgatggtcag gagcagttga gagancgagg ggttattact    1200
tcatgtttta agtggagaaa aggaacactg cagaagtatg tttcctgtat ggtattactg    1260
```

```
gatagggctg aagttatgct gaattgaaca cataaattct tttccacctc agggncattg      1320
ggcgcccatt gntcttctgc ctagaatatt ctttcctttn ctnacttkgg nggattaaat      1380
tcctgtcatc cccctcctct tggtgttata tataaagtnt tggtgccgca aaagaagtag      1440
cactcgaata taaaatttc cttttaattc tcagcaaggn aagttacttc tatatagaag       1500
ggtgcacccn tacagatgga acaatggcaa gcgcacattt gggacaaggg aggggaaagg      1560
gttcttatcc ctgacacacg tggtcccngc tgntgtgtnc tnccccact gantagggtt       1620 agactggaca ggcttaaact aattccaatt ggntaattta aagagaatna tggggtgaat      1680
gctttgggag gagtcaagga agagnaggta gnaggtaact tgaatga                    1727

(2) INFORMATION FOR SEQ ID NO:8:

(i) SEQUENCE CHARACTERISTICS:
        (A) LENGTH: 1883 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..1883
        (D) OTHER INFORMATION: /note= "1Ex6"

(xi) SEQUENCE DESCRIPTION: SEQ ID NO:8:

cncgtataaa agaccaacat tgccancnac aaccacaggc aagatcttct cctaccttcc        60
cccnnggtgt aataccaagt attcnccaat ttgtgataaa ctttcattgg aaagtgacca       120
ccctccttgg ttaatacatt gtctgtgcct gctttcacac tacagtagca cagttgagtg      180
tttgccctgg agaccatatg acccatagag cttaaaatat tcagtctggc tttttacaga      240
gatgtttctg actttgttaa tagaaaatca acccaactgg tttaaataat gcacatactt      300
tctctctcat agagtagtgc agaggtagnc agtccagatt agtasggtgg cttcacgttc      360
atccaaggac tcaatctcct tctttcttct ttagcttcta acctctagct tacttcaggg      420
tccaggctgg agccctascc ttcatttctg acagtaggaa ggagtagggg agaaaagaac      480
ataggacatg tcagcagaat tctctcctta gaagttccat acacaacaca tctccctaga      540
agtcattgcc cttacttgtt ctcatagcca tcctaaatat aagggagtca gaagtaaagt      600
ctkkntggct gggaatattg gcacctggaa taaaaatgtt tttctgtgaa tgagaaacaa      660
ggggaagatg gatatgtgac attatcttaa gacaactcca gttgcaatta ctctgcagat      720
gagaggcact aattataagc catattacct ttcttctgac aaccacttgt cagcccncgt      780
ggtttctgtg gcagaatctg gttcyatamc aagttcctaa taanctgtas ccnaaaaaat      840
ttgatgaggt attataatta tttcaatata aagcacccac tagatggagc cagtgtctgc      900
ttcacatgtt aagtccttct ttccatatgt tagacatttt ctttgaagca attttagagt      960
gtagctgttt ttctcaggtt aaaaattctt agctaggatt ggtgagttgg ggaaaagtga     1020
cttataagat ncgaattgaa ttaagaaaaa gaaaattctg tgttggaggt ggtaatgtgg     1080
ktggtgatct ycattaacac tganctaggg ctttkgkgtt tgktttattg tagaatctat     1140
accccattca cagaagatac cgagactgtg ggccagagag ccctgcactc aattctgaat     1200
gctgccatca tgatcagtgt cattgttgtc atgactatcc tcctggtggt tctgtataaa     1260
tacaggtgct ataaggtgag catgagacac agatctttgn tttccaccct gttcttctta     1320
tggttgggta ttccttgtcac agtaacttaa ctgatctagg aaagaaaaaa tgttttgtct    1380
tctagagata agttaatttt tagttttctt cctcctcact gtggaacatt caaaaaatac     1440
```

```
aaaaaggaag ccaggtgcat gtgtaatgcc aggctcagag gctgaggcag gaggatcgct    1500
tgggcccagg agttcacaag cagcttgggc aacgtagcaa gaccctgcct ctattaaaga    1560
aaacaaaaaa caaatattgg aagtatttta tatgcatgga atctatatgt catgaaaaaa    1620
ttagtgtaaa atatatatat tatgattagn tatcaagatt tagtgataat ttatgttatt    1680
ttgggatttc aatgccttt taggccattg tctcaamaaa taaaagcaga aaacaaaaaa     1740
agttgtaact gaaaataaa catttccata taatagcaca atctaagtgg gttttgntt     1800 gtttgtttgn ttgttgaagc agggccttgc cctnycaccc aggntggagt gaagtgcagt    1860
ggcacgattt tggctcactg cag                                            1883

(2) INFORMATION FOR SEQ ID NO:9:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..823
        (D) OTHER INFORMATION: /note= "1Ex7"

(xi) SEQUENCE DESCRIPTION: SEQ ID NO:9:

caggagtgga ctaggtaaat gnaagntgtt ttaaagagag atgnggncng ggacatagtg     60
gtacacanct gtaatgctca ncactkatgg ggagtactga aggnggnsgg atcacttgng    120
ggtcnggaat ntgagancag cctgggcaan atggcgaaac cctgtctcta ctaaaaatag    180
ccanaawnwa gcctagcgtg gtggcgcrca cgcgtggttc cacctactca ggaggcntaa    240
gcacgagnan tncttgaacc caggaggcag aggntgtggt garctgagat cgtgccactg    300
cactccagtc tgggcgacma agtgagaccc tgtctccnnn aagaaaaaaa aaatctgtac    360
tttttaaggg ttgtgggacc tgttaattat attgaaatgc ttctyttcta ggtcatccat    420
gcctggctta ttatatcatc tctattgttg ctgttcttt tttcattcat ttacttgggg    480
taagttgtga aatttggggt ctgtctttca gaattaacta cctnngtgct gtgtagctat    540
catttaaagc catgtacttt gntgatgaat tactctgaag ttttaattgt ntccacatat    600
aggtcatact tggtatataa aagactagnc agtattacta attgagacat tcttctgtng    660
ctcctngctt ataataagta gaactgaaag naacttaaga ctacagttaa ttctaagcct    720
ttggggaagg attatatagc cttctagtag gaagtcttgt gcnatcagaa tgtttntaaa    780
gaaagggtnt caaggaatng tataaanacc aaaaataatt gat                     823

(2) INFORMATION FOR SEQ ID NO:10:

(i) SEQUENCE CHARACTERISTICS:
        (A) LENGTH: 945 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..945
        (D) OTHER INFORMATION: /note= "1Ex8"

(xi) SEQUENCE DESCRIPTION: SEQ ID NO:10:

gttntccnaa ccaacttagg agnttggacc tgggraagac cnacntgatc tccgggaggn     60
aaagactnca gttgagccgt gattgcaccc actttactcc aagcctgggc aaccaaaatg    120
```

| | |
|---|---|
| agacactggc tccaaacaca aaaacaaaaa caaaaaaaga gtaaattaat ttanagggaa | 180 |
| gnattaaata aataatagca cagttgatat aggttatggt aaaattataa aggtgggana | 240 |
| ttaatatcta atgtttggga gccatcacat tattctaaat aatgttttgg tggaaattat | 300 |
| tgtacatctt ttaaaatctg tgtaattttt tttcagggaa gtgtttaaaa cctataacgt | 360 |
| tgctgtggac tacattactg ttgcactcct gatctggaat tttggtgtgg tgggaatgat | 420 |
| ttccattcac tggaaaggtc cacttcgact ccagcaggca tatctcatta tgattagtgc | 480 |
| cctcatggcc ctggtgttta tcaagtacct ccctgaatgg actgcgtggc tcatcttggc | 540 |
| tgtgatttca gtatatggta aaacccaaga ctgataattt gtttgtcaca ggaatgcccc | 600 |
| actggagtgt tttctttcct catctcttta tcttgattta gagaaaatgg taacgtgtac | 660 |
| atcccataac tcttcagtaa atcattaatt agctatagta actttttcat ttgaagattt | 720 |
| cggctgggca tggtagctca tgcctgtaat cttagcactt tgggaggctg aggcgggcag | 780 |
| atcacctaag cccagagttc aagaccagcc tgggcaacat ggcaaaacct cgtatctaca | 840 |
| gaaaatacaa aaattagccg ggcatggtgg tgcacacctg tagttccagc tacttaggag | 900 |
| gctgaggtgg gaggatcgat tgatcccagg aggtcaagnc tgcag | 945 |

(2) INFORMATION FOR SEQ ID NO:11:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..540
        (D) OTHER INFORMATION: /note= "1Ex9"

(xi) SEQUENCE DESCRIPTION: SEQ ID NO:11:

| | |
|---|---|
| ctgcagcttt cctttaaact aggaagactt gttcctatac cccagtaacg atacactgta | 60 |
| cactaagcaa atagcagtca aacccaaatg aaatttntac agatgttctg tgtcatttta | 120 |
| tnttgtttat gttgtctccc ccaccccccac cagttcacct gccatttatt tcatattcat | 180 |
| tcaacgtctn nntgtgtaaa aagagacaaa aaacattaaa cttttttcct tcgttaattc | 240 |
| ctccctacca cccatttaca agtttagccc atacatttta ttagatgtct tttatgtttt | 300 |
| tcttttncta gatttagtgg ctgttttgtg tccgaaaggt ccacttcgta tgctggttga | 360 |
| aacagctcag gagagaaatg aaacgctttt tccagctctc atttactcct gtaagtattt | 420 |
| ggagaatgat attgaattag taatcagngt agaatttatc gggaacttga aganatgtna | 480 |
| ctatggcaat ttcanggnac ttgtctcatc ttaaatgana gnatccctgg actcctgnag | 540 |

(2) INFORMATION FOR SEQ ID NO:12:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..509
        (D) OTHER INFORMATION: /note= "1Ex10"

(xi) SEQUENCE DESCRIPTION: SEQ ID NO:12:

| | |
|---|---|
| ccccgtcnat gcatactttg tgtgtccagt gcttacctgg aatccngtct ttcccaacag | 60 |

```
caacaatggt gtggttggtg aatatggcag aaggagaccc ggaagctcaa aggagagtat      120
ccaaaaattc caagtataat gcagaaagta ggtaactyyy nttagatamn atcttgattt      180
tncagggtca ctgttataag ctaacagtat agnaatgttt ttatcgtctt tctnkggnca      240
tagactcctn kgagaatctc ttgagaacta tgataatgcc cagtaaatac ncagataagt      300
atttaaggag tncagatact caaancccaa caatacngtc aaagcatcct aggttaagac      360
amcncccatt aaatacagaa taccagcatg gaaaggttca ggctgaggtt atgattgggt      420
ttgggttttg ggnnngtttt ttataagtca tgattttaaa aagaaaaaat aaactctctc      480
caaacatgta aaagtaagaa tctcctaaa                                        509
```

(2) INFORMATION FOR SEQ ID NO:13:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..1092
        (D) OTHER INFORMATION: /note= "1Ex11"

(xi) SEQUENCE DESCRIPTION: SEQ ID NO:13:

```
gtctagataa gncaacattc agggtagaa ggggactgtt tattttttcc tttagtctct       60
cttaaagagt gagaaaaatt ttcccaggaa tcccggtgga ctttgcttca ccactcatag      120
gttcatacca agttacaacc ccacaacctt agagcttttg ttaggaagag gcttggtggg      180
attaccgtgc ttggcttggc ttggtcagga ttcaccacca gagtcatgtg ggagggggtg     240
ggaacccaaa caattcagga ttctgccctc aggaaataaa ggagaaaata gctgttggat      300
aaactaccag caggcactgc tacagcccat gctttgtggt ttaagggcca gctagttaca     360
atgacagcta gttactgttt ccatgtaatt ttcttaaagg tattaaattt ttctaaatat      420
tagagctgta acttccactt tctcttgaag gcacagaaag ggagtcacaa gacactgttg     480
cagagaatga tgatggcggg ttcagtgagg aatgggaagc ccagagggac agtcatctag      540
ggcctcatcg ctctacacct gagtcacgag ctgctgtcca ggaactttcc agcagtatcc     600
tcgctggtga agacccagag gaaagtatgt tcanttctcc atntttcaaa gtcatggatt     660
cctttaggta gctacattat caaccttttt gagaataaaa tgaattgaga gtgttacagt     720
ctaattctat atcacatgta acttttattt ggatatatca gtaatagtgc tttttynttt      780 ttttttttt tttttttttt ttttnggnga nagagtctcg ctctgtcgcc aggttggagt      840
gcaatggtgc gatcttggct cactgaaagc tccaccnccc gggttcaagt gattctcctg     900
cctcagccnc ccaagtagnt gggactacag ggtgcgcca ccacgcctgg gataattttg       960 ggnttttag tagagatggc gtttcaccan cttggngcag gctggtcttg gaactcctga     1020
natcatgatc tgcctgcctt agcctcccca aagtgctggg attncagggg tgagccactg    1080
ttcctgggcc tc                                                        1092
```

(2) INFORMATION FOR SEQ ID NO:14:

(i) SEQUENCE CHARACTERISTICS:
        (A) LENGTH: 1003 base pairs
        (B) TYPE: nucleic acid
        (C) STRANDEDNESS: single
        (D) TOPOLOGY: linear (ix) FEATURE:

(A) NAME/KEY: misc_feature
            (B) LOCATION: 1..1003
            (D) OTHER INFORMATION: /note= "1Ex12"

(xi) SEQUENCE DESCRIPTION: SEQ ID NO:14:

ctgcagtgag ccgagatcat gctgctgtac tccagcctgg gccacagagc caaactccat      60
ctcccaaaaa aaaaaaatat taattaatat gatnaaatga tgcctatctc agaattcttg     120
taaggatttc ttagkacaag tgctgggtat aaactatana ttcratagat gncgattatt     180
acttaytatt gttattgata aataacagca gcatctacag ttaagactcc agagtcagtc     240
acatagaatc tggnactcct attgtagnaa accccnmmag aaagaaaaca cagctgaagc     300
ctaattttgt atatcattta ctgacttctc tcattcattg tggggttgag tagggcagtg     360 atattttga attgtgaaat catancaaag agtgaccaac tttttaatat ttgtaaccttt    420 tccttttag ggggagtaaa acttggattg ggagatttca ttttctacag tgttctggtt     480
ggtaaagcct cagcaacagc cagtggagac tggaacacaa ccatagcctg tttcgtagcc     540
atattaattg tmmstataca ctaataagaa tgtgtcagag ctcttaatgt cmaaactttg     600
attacacagt ccctttaagg cagttctgtt ttaaccccag gtgggttaaa tattccagct     660
atctgaggag cttttngata attggacctc accttagtag ttctctaccc tggccacaca     720
ttagaatcac ttgggagctt ttaaaactgt aagctctgcc ctgagatatt cttactcaat     780
ttaattgtgt agttttttaaa attccccagg aaattctggt atttctgttt aggaaccgct    840
gcctcaagcc tagcagcaca gatatgtagg aaattagctc tgtaaggttg gtcttacagg     900
gataaacaga tccttcctta gtccctggac ttaatcactg agagtttggg tggtggtttt     960
ggatttaatg acacaacctg tagcatgcag tgttacttaa gac                     1003

(2) INFORMATION FOR SEQ ID NO:15:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..736
        (D) OTHER INFORMATION: /note= "1Ex13"

(xi) SEQUENCE DESCRIPTION: SEQ ID NO:15:

gtctttccca tcttctccac agggtttgtg ccttacatta ttactccttg ccattttcaa      60
gaaagcattg ccagctcttc caatctccat caccttggg cttgtttttct actttgccac     120 agattatctt gtacagcctt ttatggacca attagcattc catcaattt atatctagca      180 tatttgcggt tagaatccca tggatgtttc ttctttgact ataacaaaat ctggggagga     240
caaaggtgat ttcctgtgtc cacatctaac aaatcaagat ccccggctgg acttttggag     300
gttccttcca agtcttcctg accaccttgc actattggac tttggaagga ggtgcctata     360
gaaaacgatt ttgaacatac ttcatcgcag tggactgtgt cctcggtgca gaaactacca     420
gatttgaggg acgaggtcaa ggagatatga taggcccgga agttgctgtg ccccatcagc     480
agcttgacgc gtggtcacag gacgattttc actgacactg cgaactctca ggactaccgt     540
taccaagagg ttaggtgaag tggtttaaac caaacggaac tcttcatctt aaactacacg     600
ttgaaaatca acccaataat tctgtattaa ctgaattctg aacttttcag gaggtactgt     660
gaggaagagc aggcaccacc agcagaatgg ggaatggaga ggtgggcagg ggttccagct     720

-continued

```
tcccttttgat tttttg                                              736
```

(2) INFORMATION FOR SEQ ID NO:16:

(i) SEQUENCE CHARACTERISTICS:
        (A) LENGTH: 1964 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 188..1588

(ix) FEATURE:
        (A) NAME/KEY: misc_feature
        (B) LOCATION: 1..1964
        (D) OTHER INFORMATION: /note= "mPS1"

(xi) SEQUENCE DESCRIPTION: SEQ ID NO:16:

```
accanacanc ggcagctgag gcggaaacct aggctgcgag ccggccgccc gggcgcggag    60
agagaaggaa ccaacacaag acagcagccc ttcgaggtct ttaggcagct tggaggagaa   120
cacatgagag aaagaatccc aagaggtttt gttttctttg agaaggtatt tctgtccagc   180 tgctcca atg aca gag ata cct gca cct ttg tcc tac ttc cag aat gcc    229
        Met Thr Glu Ile Pro Ala Pro Leu Ser Tyr Phe Gln Asn Ala
          1               5                  10 cag atg tct gag gac agc cac tcc agc agc gcc atc cgg agc cag aat    277
Gln Met Ser Glu Asp Ser His Ser Ser Ser Ala Ile Arg Ser Gln Asn
 15                  20                  25                  30 gac agc caa gaa cgg cag cag cag cat gac agg cag aga ctt gac aac    325
Asp Ser Gln Glu Arg Gln Gln Gln His Asp Arg Gln Arg Leu Asp Asn
                 35                  40                  45 cct gag cca ata tct aat ggg cgg ccc cag agt aac tca aga cag gtg    373
Pro Glu Pro Ile Ser Asn Gly Arg Pro Gln Ser Asn Ser Arg Gln Val
             50                  55                  60 gtg gaa caa gat gag gag gaa gac gaa gag ctg aca ttg aaa tat gga    421
Val Glu Gln Asp Glu Glu Glu Asp Glu Glu Leu Thr Leu Lys Tyr Gly
 65                  70                  75 gcc aag cat gtc atc atg ctc ttt gtc ccc gtg acc ctc tgc atg gtc    469
Ala Lys His Val Ile Met Leu Phe Val Pro Val Thr Leu Cys Met Val
         80                  85                  90 gtc gtc gtg gcc acc atc aaa tca gtc agc ttc tat acc cgg aag gac    517
Val Val Val Ala Thr Ile Lys Ser Val Ser Phe Tyr Thr Arg Lys Asp
 95                 100                 105                 110 ggt cag cta atc tac acc cca ttc aca gaa gac act gag act gta ggc    565
Gly Gln Leu Ile Tyr Thr Pro Phe Thr Glu Asp Thr Glu Thr Val Gly
                115                 120                 125 caa aga gcc ctg cac tcg atc ctg aat gcg gcc atc atg atc agt gtc    613
Gln Arg Ala Leu His Ser Ile Leu Asn Ala Ala Ile Met Ile Ser Val
            130                 135                 140 att gtc att atg acc atc ctc ctg gtg gtc ctg tat aaa tac agg tgc    661
Ile Val Ile Met Thr Ile Leu Leu Val Val Leu Tyr Lys Tyr Arg Cys
145                 150                 155 tac aag gtc atc cac gcc tgg ctt att att tca tct ctg ttg ctg         709
Tyr Lys Val Ile His Ala Trp Leu Ile Ile Ser Ser Leu Leu Leu
    160                 165                 170 ttc ttt ttt tcg ttc att tac tta ggg gaa gta ttt aag acc tac aat   757
Phe Phe Phe Ser Phe Ile Tyr Leu Gly Glu Val Phe Lys Thr Tyr Asn
175                 180                 185                 190 gtc gcc gtg gac tac gtt aca gta gca ctc cta atc tgg aat ttt ggt   805
Val Ala Val Asp Tyr Val Thr Val Ala Leu Leu Ile Trp Asn Phe Gly
                195                 200                 205
```

-continued

| | |
|---|---|
| gtg gtc ggg atg att gcc atc cac tgg aaa ggc ccc ctt cga ctg cag<br>Val Val Gly Met Ile Ala Ile His Trp Lys Gly Pro Leu Arg Leu Gln<br>210                        215                          220 | 853 |
| cag gcg tat ctc att atg atc agt gcc ctc atg gcc ctg gta ttt atc<br>Gln Ala Tyr Leu Ile Met Ile Ser Ala Leu Met Ala Leu Val Phe Ile<br>225                        230                         235 | 901 |
| aag tac ctc ccc gaa tgg acc gca tgg ctc atc ttg gct gtg att tca<br>Lys Tyr Leu Pro Glu Trp Thr Ala Trp Leu Ile Leu Ala Val Ile Ser<br>240                        245                        250 | 949 |
| gta tat gat ttg gtg gct gtt tta tgt ccc aaa ggc cca ctt cgt atg<br>Val Tyr Asp Leu Val Ala Val Leu Cys Pro Lys Gly Pro Leu Arg Met<br>255                       260                     265                 270 | 997 |
| ctg gtt gaa aca gct cag gaa aga aat gag act ctc ttt cca gct ctt<br>Leu Val Glu Thr Ala Gln Glu Arg Asn Glu Thr Leu Phe Pro Ala Leu<br>                  275                     280                     285 | 1045 |
| atc tat tcc tca aca atg gtg tgg ttg gtg aat atg gct gaa gga gac<br>Ile Tyr Ser Ser Thr Met Val Trp Leu Val Asn Met Ala Glu Gly Asp<br>          290                     295                     300 | 1093 |
| cca gaa gcc caa agg agg gta ccc aag aac ccc aag tat aac aca caa<br>Pro Glu Ala Gln Arg Arg Val Pro Lys Asn Pro Lys Tyr Asn Thr Gln<br>                 305                     310                     315 | 1141 |
| aga gcg gag aga gag aca cag gac agt ggt tct ggg aac gat gat ggt<br>Arg Ala Glu Arg Glu Thr Gln Asp Ser Gly Ser Gly Asn Asp Asp Gly<br>320                        325                        330 | 1189 |
| ggc ttc agt gag gag tgg gag gcc caa aga gac agt cac ctg ggg cct<br>Gly Phe Ser Glu Glu Trp Glu Ala Gln Arg Asp Ser His Leu Gly Pro<br>335                        340                     345                 350 | 1237 |
| cat cgc tcc act ccc gag tca aga gct gct gtc cag gaa ctt tct ggg<br>His Arg Ser Thr Pro Glu Ser Arg Ala Ala Val Gln Glu Leu Ser Gly<br>                  355                     360                     365 | 1285 |
| agc att cta acg agt gaa gac ccg gag gaa aga gga gta aaa ctt gga<br>Ser Ile Leu Thr Ser Glu Asp Pro Glu Glu Arg Gly Val Lys Leu Gly<br>               370                     375                     380 | 1333 |
| ctg gga gat ttc att ttc tac agt gtt ctg gtt ggt aag gcc tca gca<br>Leu Gly Asp Phe Ile Phe Tyr Ser Val Leu Val Gly Lys Ala Ser Ala<br>         385                     390                     395 | 1381 |
| acc gcc agt gga gac tgg aac aca acc ata gcc tgc ttt gta gcc ata<br>Thr Ala Ser Gly Asp Trp Asn Thr Thr Ile Ala Cys Phe Val Ala Ile<br>400                        405                        410 | 1429 |
| ctg atc ggc ctg tgc ctt aca tta ctc ctg ctc gcc att ttc aag aaa<br>Leu Ile Gly Leu Cys Leu Thr Leu Leu Leu Leu Ala Ile Phe Lys Lys<br>415                        420                     425                 430 | 1477 |
| gcg ttg cca gcc ctc ccc atc tcc atc acc ttc ggg ctc gtg ttc tac<br>Ala Leu Pro Ala Leu Pro Ile Ser Ile Thr Phe Gly Leu Val Phe Tyr<br>                  435                     440                     445 | 1525 |
| ttc gcc acg gat tac ctt gtg cag ccc ttc atg gac caa ctt gca ttc<br>Phe Ala Thr Asp Tyr Leu Val Gln Pro Phe Met Asp Gln Leu Ala Phe<br>               450                     455                     460 | 1573 |
| cat cag ttt tat atc tagcctttct gcagttagaa catggatgtt tcttctttga<br>His Gln Phe Tyr Ile<br>         465 | 1628 |
| ttatcaaaaa cacaaaaaca gagagcaagc ccgaggagga gactggtgac tttcctgtgt | 1688 |
| cctcagctaa caaaggcagg actccagctg gacttctgca gcttccttcc gagtctccct | 1748 |
| agccacccgc actactggac tgtggaagga agcgtctaca gaggaacggt ttccaacatc | 1808 |
| catcgctgca gcagacggtg tccctcagtg acttgagaga caaggacaag gaaatgtgct | 1868 |
| gggccaagga gctgccgtgc tctgctagct tgaccgtgg gcatggagat ttacccgcac | 1928 |
| tgtgaactct ctaaggtaaa caaagtgagg tgaacc | 1964 |

(2) INFORMATION FOR SEQ ID NO:17:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:17:

```
Met Thr Glu Ile Pro Ala Pro Leu Ser Tyr Phe Gln Asn Ala Gln Met
 1               5                  10                  15

Ser Glu Asp Ser His Ser Ser Ala Ile Arg Ser Gln Asn Asp Ser
            20                  25                  30

Gln Glu Arg Gln Gln His Asp Arg Gln Arg Leu Asp Asn Pro Glu
        35                  40                  45

Pro Ile Ser Asn Gly Arg Pro Gln Ser Asn Ser Arg Gln Val Val Glu
 50                  55                  60

Gln Asp Glu Glu Asp Glu Glu Leu Thr Leu Lys Tyr Gly Ala Lys
 65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Val Thr Val Ala Leu Leu Ile Trp Asn Phe Gly Val Val
            195                 200                 205

Gly Met Ile Ala Ile His Trp Lys Gly Pro Leu Arg Leu Gln Gln Ala
210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
290                 295                 300

Ala Gln Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Gly Ser Ile
            355                 360                 365
```

-continued

```
Leu Thr Ser Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
        450                 455                 460

Phe Tyr Ile
465
```

(2) INFORMATION FOR SEQ ID NO:18:

(i) SEQUENCE CHARACTERISTICS:
        (A) LENGTH: 2229 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 366..1712

(ix) FEATURE:
        (A) NAME/KEY: misc_feature
        (B) LOCATION: 1..2226
        (D) OTHER INFORMATION: /note= "hPS2"

(xi) SEQUENCE DESCRIPTION: SEQ ID NO:18:

```
gaattcggca cgagggcatt tccagcagtg aggagacagc cagaagcaag ctttt ggagc      60 tgaaggaacc tgagacagaa gctagtcccc cctctgaatt ttactgatga agaaactgag     120
gccacagagc taaagtgact tttcccaagg tcgcccagcg aggacgtggg acttctcaga     180
cgtcaggaga gtgatgtgag ggagctgtgt gaccatagaa agtgacgtgt taaaaaccag     240
cgctgccctc tttgaaagcc agggagcatc attcatttag cctgctgaga agaagaaacc     300
aagtgtccgg gattcaagac ctctctgcgg ccccaagtgt tcgtggtgct tccagaggca     360 gggct atg ctc aca ttc atg gcc tct gac agc gag gaa gaa gtg tgt         407
      Met Leu Thr Phe Met Ala Ser Asp Ser Glu Glu Glu Val Cys
        1               5                  10 gat gag cgg acg tcc cta atg tcg gcc gag agc ccc acg ccg cgc tcc       455
Asp Glu Arg Thr Ser Leu Met Ser Ala Glu Ser Pro Thr Pro Arg Ser
 15                  20                  25                  30 tgc cag gag ggc agg cag ggc cca gag gat gga gag aat act gcc cag       503
Cys Gln Glu Gly Arg Gln Gly Pro Glu Asp Gly Glu Asn Thr Ala Gln
                 35                  40                  45 tgg aga agc cag gag aac gag gag gac ggt gag gag gac cct gac cgc       551
Trp Arg Ser Gln Glu Asn Glu Glu Asp Gly Glu Glu Asp Pro Asp Arg
             50                  55                  60 tat gtc tgt agt ggg gtt ccc ggg cgg ccg cca ggc ctg gag gaa gag       599
Tyr Val Cys Ser Gly Val Pro Gly Arg Pro Pro Gly Leu Glu Glu Glu
         65                  70                  75 ctg acc ctc aaa tac gga gcg aag cat gtg atc atg ctg ttt gtg cct       647
Leu Thr Leu Lys Tyr Gly Ala Lys His Val Ile Met Leu Phe Val Pro
     80                  85                  90 gtc act ctg tgc atg atc gtg gtg gta gcc acc atc aag tct gtg cgc       695
Val Thr Leu Cys Met Ile Val Val Val Ala Thr Ile Lys Ser Val Arg
```

-continued

| | | | | |
|---|---|---|---|---|
| 95 | | 100 | 105 | 110 |

| | |
|---|---|
| ttc tac aca gag aag aat gga cag ctc atc tac acg cca ttc act gag<br>Phe Tyr Thr Glu Lys Asn Gly Gln Leu Ile Tyr Thr Pro Phe Thr Glu<br>                   115                   120                   125 | 743 |
| gac aca ccc tcg gtg ggc cag cgc ctc ctc aac tcc gtg ctg aac acc<br>Asp Thr Pro Ser Val Gly Gln Arg Leu Leu Asn Ser Val Leu Asn Thr<br>            130                135                  140 | 791 |
| ctc atc atg atc agc gtc atc gtg gtt atg acc atc ttc ttg gtg gtg<br>Leu Ile Met Ile Ser Val Ile Val Val Met Thr Ile Phe Leu Val Val<br>          145                  150                 155 | 839 |
| ctc tac aag tac cgc tgc tac aag ttc atc cat ggc tgg ttg atc atg<br>Leu Tyr Lys Tyr Arg Cys Tyr Lys Phe Ile His Gly Trp Leu Ile Met<br>       160                  165                 170 | 887 |
| tct tca ctg atg ctg ctg ttc ctc ttc acc tat atc tac ctt ggg gaa<br>Ser Ser Leu Met Leu Leu Phe Leu Phe Thr Tyr Ile Tyr Leu Gly Glu<br>175                 180                  185              190 | 935 |
| gtg ctc aag acc tac aat gtg gcc atg gac tac ccc acc ctc ttg ctg<br>Val Leu Lys Thr Tyr Asn Val Ala Met Asp Tyr Pro Thr Leu Leu Leu<br>                 195                 200               205 | 983 |
| act gtc tgg aac ttc ggg gca gtg ggc atg gtg tgc atc cac tgg aag<br>Thr Val Trp Asn Phe Gly Ala Val Gly Met Val Cys Ile His Trp Lys<br>            210                215                  220 | 1031 |
| ggc cct ctg gtg ctg cag cag gcc tac ctc atc atg atc agt gcg ctc<br>Gly Pro Leu Val Leu Gln Gln Ala Tyr Leu Ile Met Ile Ser Ala Leu<br>         225                  230                 235 | 1079 |
| atg gcc cta gtg ttc atc aag tac ctc cca gag tgg tcc gcg tgg gtc<br>Met Ala Leu Val Phe Ile Lys Tyr Leu Pro Glu Trp Ser Ala Trp Val<br>      240                 245                 250 | 1127 |
| atc ctg ggc gcc atc tct gtg tat gat ctc gtg gct gtg ctg tgt ccc<br>Ile Leu Gly Ala Ile Ser Val Tyr Asp Leu Val Ala Val Leu Cys Pro<br>255                 260                  265              270 | 1175 |
| aaa ggg cct ctg aga atg ctg gta gaa act gcc cag gag aga aat gag<br>Lys Gly Pro Leu Arg Met Leu Val Glu Thr Ala Gln Glu Arg Asn Glu<br>                 275                 280               285 | 1223 |
| ccc ata ttc cct gcc ctg ata tac tca tct gcc atg gtg tgg acg gtt<br>Pro Ile Phe Pro Ala Leu Ile Tyr Ser Ser Ala Met Val Trp Thr Val<br>            290                295                  300 | 1271 |
| ggc atg gcg aag ctg gac ccc tcc tct cag ggt gcc ctc cag ctc ccc<br>Gly Met Ala Lys Leu Asp Pro Ser Ser Gln Gly Ala Leu Gln Leu Pro<br>         305                  310                 315 | 1319 |
| tac gac ccg gag atg gaa gaa gac tcc tat gac agt ttt ggg gag cct<br>Tyr Asp Pro Glu Met Glu Glu Asp Ser Tyr Asp Ser Phe Gly Glu Pro<br>      320                 325                 330 | 1367 |
| tca tac ccc gaa gtc ttt gag cct ccc ttg act ggc tac cca ggg gag<br>Ser Tyr Pro Glu Val Phe Glu Pro Pro Leu Thr Gly Tyr Pro Gly Glu<br>335                 340                  345              350 | 1415 |
| gag ctg gag gaa gag gag gaa agg ggc gtg aag ctt ggc ctc ggg gac<br>Glu Leu Glu Glu Glu Glu Glu Arg Gly Val Lys Leu Gly Leu Gly Asp<br>                 355                 360               365 | 1463 |
| ttc atc ttc tac agt gtg ctg gtg ggc aag gcg gct gcc acg ggc agc<br>Phe Ile Phe Tyr Ser Val Leu Val Gly Lys Ala Ala Ala Thr Gly Ser<br>            370                375                 380 | 1511 |
| ggg gac tgg aat acc acg ctg gcc tgc ttc gtg gcc atc ctc att ggc<br>Gly Asp Trp Asn Thr Thr Leu Ala Cys Phe Val Ala Ile Leu Ile Gly<br>         385                  390                 395 | 1559 |
| ttg tgt ctg acc ctc ctg ctt gct gtg ttc aag aag gcg ctg ccc<br>Leu Cys Leu Thr Leu Leu Leu Ala Val Phe Lys Lys Ala Leu Pro<br>         400                  405                 410 | 1607 |
| gcc ctc ccc atc tcc atc acg ttc ggg ctc atc ttt tac ttc tcc acg<br>Ala Leu Pro Ile Ser Ile Thr Phe Gly Leu Ile Phe Tyr Phe Ser Thr | 1655 |

```
               415                 420                 425                 430
gac aac ctg gtg cgg ccg ttc atg gac acc ctg gcc tcc cat cag ctc          1703
Asp Asn Leu Val Arg Pro Phe Met Asp Thr Leu Ala Ser His Gln Leu
                435                 440                 445 tac atc tga gggacatggt gtgccacagg ctgcaagctg cagggaattt                  1752
Tyr Ile * tcattggatg cagttgtata gttttacact ctagtgccat atatttttaa gacttttctt        1812
tccttaaaaa ataaagtacg tgtttacttg gtgaggagga ggcagaacca gctctttggt        1872
gccagctgtt tcatcaccag actttggctc ccgctttggg gagcgcctcg cttcacggac        1932
aggaagcaca gcaggtttat ccagatgaac tgagaaggtc agattagggt ggggagaaga        1992
gcatccggca tgagggctga gatgcccaaa gagtgtgctc gggagtggcc cctggcacct        2052
gggtgctctg gctggagagg aaaagccagt tccctacgag gagtgttccc aatgctttgt        2112
ccatgatgtc cttgttattt tattnccytt anaaactgan tcctnttntt nttdcggcag        2172
tcacmctnct gggragtggc ttaatagtaa natcaataaa nagntgagtc ctnttag           2229
```

(2) INFORMATION FOR SEQ ID NO:19:

(i) SEQUENCE CHARACTERISTICS:
        (A) LENGTH: 448 amino acids
        (B) TYPE: amino acid
        (D) TOPOLOGY: linear (ii) MOLECULE TYPE: protein (xi) SEQUENCE DESCRIPTION: SEQ ID NO:19:

```
Met Leu Thr Phe Met Ala Ser Asp Ser Glu Glu Val Cys Asp Glu
 1               5                  10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
                100                 105                 110

Thr Glu Lys Asn Gly Gln Leu Ile Tyr Thr Pro Phe Thr Glu Asp Thr
            115                 120                 125

Pro Ser Val Gly Gln Arg Leu Leu Asn Ser Val Leu Asn Thr Leu Ile
        130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
```

```
                    225                 230                 235                 240
Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445

(2) INFORMATION FOR SEQ ID NO:20:

(i) SEQUENCE CHARACTERISTICS:
        (A) LENGTH: 1895 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 140..1762

(ix) FEATURE:
        (A) NAME/KEY: misc_feature
        (B) LOCATION: 1..1895
        (D) OTHER INFORMATION: /note= "DmPS"

(xi) SEQUENCE DESCRIPTION: SEQ ID NO:20:

tatatgagtc gctttaaaac aaaagaaagt ttttaccagc tacattcctt tggtttcctt      60
aactaaatcc catcacacaa ctacggcttc gcaggggag gcgtccagcg ctacggaggc      120
gaacgaacgc acaccactg atg gct gct gtc aat ctc cag gct tcg tgc tcc     172
                     Met Ala Ala Val Asn Leu Gln Ala Ser Cys Ser
                      1               5                  10 tcc ggg ctc gcc tct gag gat gac gcc aat gtg ggc agc cag ata ggc      220
Ser Gly Leu Ala Ser Glu Asp Asp Ala Asn Val Gly Ser Gln Ile Gly
             15                  20                  25 gcg gcg gag cgt ttg gaa cga cct cca agg cgg caa cag cag cgg aac      268
Ala Ala Glu Arg Leu Glu Arg Pro Pro Arg Arg Gln Gln Gln Arg Asn
         30                  35                  40 aac tac ggc tcc agc aat cag gat caa ccg gat gct gcc ata ctt gct      316
Asn Tyr Gly Ser Ser Asn Gln Asp Gln Pro Asp Ala Ala Ile Leu Ala
     45                  50                  55
```

-continued

| | |
|---|---|
| gtg ccc aat gtg gtg atg cgt gaa cct tgt ggc tcg cgc cct tca aga<br>Val Pro Asn Val Val Met Arg Glu Pro Cys Gly Ser Arg Pro Ser Arg<br>60                            65                     70                 75 | 364 |
| ctg acc ggt gga gga ggc ggc agt ggt ggt ccg ccc aca aat gaa atg<br>Leu Thr Gly Gly Gly Gly Ser Gly Gly Pro Pro Thr Asn Glu Met<br>80                          85                        90 | 412 |
| gag gaa gag cag ggc ctg aaa tac ggg gcc cag cat gtg atc aag tta<br>Glu Glu Glu Gln Gly Leu Lys Tyr Gly Ala Gln His Val Ile Lys Leu<br>95                     100                  105 | 460 |
| ttc gtc ccc gtc tcc ctt tgc atg ctg gta gtg gtg gct acc atc aac<br>Phe Val Pro Val Ser Leu Cys Met Leu Val Val Val Ala Thr Ile Asn<br>110                   115                 120 | 508 |
| tcc atc agc ttc tac aac agc acg gat gtc tat ctc ctc tac aca cct<br>Ser Ile Ser Phe Tyr Asn Ser Thr Asp Val Tyr Leu Leu Tyr Thr Pro<br>125                   130                 135 | 556 |
| ttc cat gaa caa tcg ccc gag cct agt gtt aag ttc tgg agt gcc ttg<br>Phe His Glu Gln Ser Pro Glu Pro Ser Val Lys Phe Trp Ser Ala Leu<br>140                   145                 150                 155 | 604 |
| gcg aac tcc ctg atc ctg atg agc gtg gtg gtg gtg atg acc ttt ttg<br>Ala Asn Ser Leu Ile Leu Met Ser Val Val Val Val Met Thr Phe Leu<br>160                   165                 170 | 652 |
| ctg att gtt ttg tac aag aag cgt tgc tat cgc atc att cac ggc tgg<br>Leu Ile Val Leu Tyr Lys Lys Arg Cys Tyr Arg Ile Ile His Gly Trp<br>175                   180                 185 | 700 |
| ctg att ctc tcc tcc ttc atg ttg ttg ttc att ttt acg tac tta tat<br>Leu Ile Leu Ser Ser Phe Met Leu Leu Phe Ile Phe Thr Tyr Leu Tyr<br>190                   195                 200 | 748 |
| ttg gaa gag ctt ctt cgc gcc tat aac ata ccg atg gac tac cct act<br>Leu Glu Glu Leu Leu Arg Ala Tyr Asn Ile Pro Met Asp Tyr Pro Thr<br>205                   210                 215 | 796 |
| gca cta ctg att atg tgg aac ttt gga gtg gtc gga atg atg tcc atc<br>Ala Leu Leu Ile Met Trp Asn Phe Gly Val Val Gly Met Met Ser Ile<br>220                   225                 230                 235 | 844 |
| cat tgg cag gga cct ctg cgg ttg cag caa gga tat ctc att ttc gtg<br>His Trp Gln Gly Pro Leu Arg Leu Gln Gln Gly Tyr Leu Ile Phe Val<br>240                   245                 250 | 892 |
| gca gcc ttg atg gcc ttg gtg ttc att aaa tac ctg cct gaa tgg act<br>Ala Ala Leu Met Ala Leu Val Phe Ile Lys Tyr Leu Pro Glu Trp Thr<br>255                   260                 265 | 940 |
| gcc tgg gct gta ttg gct gcc att tct att tgg gat ctt att gct gtc<br>Ala Trp Ala Val Leu Ala Ala Ile Ser Ile Trp Asp Leu Ile Ala Val<br>270                   275                 280 | 988 |
| ctt tcg cca aga gga ccc ctc cgc att ctg gtg gaa acg gct cag gag<br>Leu Ser Pro Arg Gly Pro Leu Arg Ile Leu Val Glu Thr Ala Gln Glu<br>285                   290                 295 | 1036 |
| cga aat gag caa atc ttc ccc gct ctg att tat tca tcc act gtc gtt<br>Arg Asn Glu Gln Ile Phe Pro Ala Leu Ile Tyr Ser Ser Thr Val Val<br>300                   305                 310                 315 | 1084 |
| tac gca ctt gta aac act gtt acg ccg cag caa tcg cag gcc aca gct<br>Tyr Ala Leu Val Asn Thr Val Thr Pro Gln Gln Ser Gln Ala Thr Ala<br>320                   325                 330 | 1132 |
| tcc tcc tcg ccg tcg tcc agc aac tcc acc aca acc acg agg gcc acg<br>Ser Ser Ser Pro Ser Ser Ser Asn Ser Thr Thr Thr Thr Arg Ala Thr<br>335                   340                 345 | 1180 |
| cag aac tcg ctg gct tcg cca gag gca gca gcg gct agt ggc caa cgc<br>Gln Asn Ser Leu Ala Ser Pro Glu Ala Ala Ala Ala Ser Gly Gln Arg<br>350                   355                 360 | 1228 |
| aca ggt aac tcc cat cct cga cag aat cag cgg gat gac ggc agt gta<br>Thr Gly Asn Ser His Pro Arg Gln Asn Gln Arg Asp Asp Gly Ser Val<br>365                   370                 375 | 1276 |

```
ctg gca act gaa ggt atg cca ctt gtg act ttt aaa agc aat ttg cgc   1324
Leu Ala Thr Glu Gly Met Pro Leu Val Thr Phe Lys Ser Asn Leu Arg
380                 385                 390                 395 gga aac gct gag gct gcg ggt ttc acg caa gag tgg tca gct aac ttg   1372
Gly Asn Ala Glu Ala Ala Gly Phe Thr Gln Glu Trp Ser Ala Asn Leu
                400                 405                 410 agc gaa cgt gtg gct cgt cgc cag att gaa gtt caa agt act cag agt   1420
Ser Glu Arg Val Ala Arg Arg Gln Ile Glu Val Gln Ser Thr Gln Ser
        415                 420                 425 gga aac gct cag cgc tcc aac gag tat agg aca gta aca gct ccg gat   1468
Gly Asn Ala Gln Arg Ser Asn Glu Tyr Arg Thr Val Thr Ala Pro Asp
            430                 435                 440 cag aat cat ccg gat ggg caa gaa gaa cgt ggc ata aag ctt ggc ctc   1516
Gln Asn His Pro Asp Gly Gln Glu Glu Arg Gly Ile Lys Leu Gly Leu
        445                 450                 455 ggc gac ttc atc ttc tac tcg gta tta gtg ggc aag gcc tcc agc tac   1564
Gly Asp Phe Ile Phe Tyr Ser Val Leu Val Gly Lys Ala Ser Ser Tyr
460                 465                 470                 475 ggc gac tgg acg acc aca atc gct tgc ttt gtg gcc atc ctc att gga   1612
Gly Asp Trp Thr Thr Thr Ile Ala Cys Phe Val Ala Ile Leu Ile Gly
                480                 485                 490 ctc tgc ctc act ctt ctg ctt ctg gcc att tgg cgc aag gcg cta ccc   1660
Leu Cys Leu Thr Leu Leu Leu Leu Ala Ile Trp Arg Lys Ala Leu Pro
        495                 500                 505 gcc ctg ccc atc tca ata acg ttc gga ttg ata ttt tgc ttc gcc act   1708
Ala Leu Pro Ile Ser Ile Thr Phe Gly Leu Ile Phe Cys Phe Ala Thr
            510                 515                 520 agt gcg gtg gtc aag ccg ttc atg gag gat cta tcg gcc aag cag gtg   1756
Ser Ala Val Val Lys Pro Phe Met Glu Asp Leu Ser Ala Lys Gln Val
        525                 530                 535 ttt ata taaacttgaa aagacaagga cacatcaagt gtcttacagt atcatagtct    1812
Phe Ile
540 aacaaagctt tttgtaatcc aattctttat ttaaccaaat gcatagtaac aacctcgact  1872 aaaaaaaaaa aaaaaaaaaa aaa                                          1895

(2) INFORMATION FOR SEQ ID NO:21:

(i) SEQUENCE CHARACTERISTICS:
        (A) LENGTH: 541 amino acids
        (B) TYPE: amino acid
        (D) TOPOLOGY: linear (ii) MOLECULE TYPE: protein (xi) SEQUENCE DESCRIPTION: SEQ ID NO:21:

Met Ala Ala Val Asn Leu Gln Ala Ser Cys Ser Ser Gly Leu Ala Ser
1               5                   10                  15

Glu Asp Asp Ala Asn Val Gly Ser Gln Ile Gly Ala Ala Glu Arg Leu
            20                  25                  30

Glu Arg Pro Pro Arg Arg Gln Gln Gln Arg Asn Asn Tyr Gly Ser Ser
        35                  40                  45

Asn Gln Asp Gln Pro Asp Ala Ala Ile Leu Ala Val Pro Asn Val Val
    50                  55                  60

Met Arg Glu Pro Cys Gly Ser Arg Pro Ser Arg Leu Thr Gly Gly Gly
65                  70                  75                  80

Gly Gly Ser Gly Gly Pro Pro Thr Asn Glu Met Glu Glu Glu Gln Gly
                85                  90                  95

Leu Lys Tyr Gly Ala Gln His Val Ile Lys Leu Phe Val Pro Val Ser
```

-continued

```
                    100                 105                 110
Leu Cys Met Leu Val Val Ala Thr Ile Asn Ser Ile Ser Phe Tyr
            115                 120                 125
Asn Ser Thr Asp Val Tyr Leu Leu Tyr Thr Pro Phe His Glu Gln Ser
130                 135                 140
Pro Glu Pro Ser Val Lys Phe Trp Ser Ala Leu Ala Asn Ser Leu Ile
145                 150                 155                 160
Leu Met Ser Val Val Val Met Thr Phe Leu Leu Ile Val Leu Tyr
            165                 170                 175
Lys Lys Arg Cys Tyr Arg Ile Ile His Gly Trp Leu Ile Leu Ser Ser
            180                 185                 190
Phe Met Leu Leu Phe Ile Phe Thr Tyr Leu Tyr Leu Glu Glu Leu Leu
            195                 200                 205
Arg Ala Tyr Asn Ile Pro Met Asp Tyr Pro Thr Ala Leu Leu Ile Met
    210                 215                 220
Trp Asn Phe Gly Val Val Gly Met Met Ser Ile His Trp Gln Gly Pro
225                 230                 235                 240
Leu Arg Leu Gln Gln Gly Tyr Leu Ile Phe Val Ala Ala Leu Met Ala
                    245                 250                 255
Leu Val Phe Ile Lys Tyr Leu Pro Glu Trp Thr Ala Trp Ala Val Leu
                    260                 265                 270
Ala Ala Ile Ser Ile Trp Asp Leu Ile Ala Val Leu Ser Pro Arg Gly
            275                 280                 285
Pro Leu Arg Ile Leu Val Glu Thr Ala Gln Glu Arg Asn Glu Gln Ile
            290                 295                 300
Phe Pro Ala Leu Ile Tyr Ser Ser Thr Val Val Tyr Ala Leu Val Asn
305                 310                 315                 320
Thr Val Thr Pro Gln Gln Ser Gln Ala Thr Ala Ser Ser Ser Pro Ser
                    325                 330                 335
Ser Ser Asn Ser Thr Thr Thr Arg Ala Thr Gln Asn Ser Leu Ala
            340                 345                 350
Ser Pro Glu Ala Ala Ala Ser Gly Gln Arg Thr Gly Asn Ser His
            355                 360                 365
Pro Arg Gln Asn Gln Arg Asp Asp Gly Ser Val Leu Ala Thr Glu Gly
370                 375                 380
Met Pro Leu Val Thr Phe Lys Ser Asn Leu Arg Gly Asn Ala Glu Ala
385                 390                 395                 400
Ala Gly Phe Thr Gln Glu Trp Ser Ala Asn Leu Ser Glu Arg Val Ala
                    405                 410                 415
Arg Arg Gln Ile Glu Val Gln Ser Thr Gln Ser Gly Asn Ala Gln Arg
                    420                 425                 430
Ser Asn Glu Tyr Arg Thr Val Thr Ala Pro Asp Gln Asn His Pro Asp
            435                 440                 445
Gly Gln Glu Glu Arg Gly Ile Lys Leu Gly Leu Gly Asp Phe Ile Phe
450                 455                 460
Tyr Ser Val Leu Val Gly Lys Ala Ser Tyr Gly Asp Trp Thr Thr
465                 470                 475                 480
Thr Ile Ala Cys Phe Val Ala Ile Leu Ile Gly Leu Cys Leu Thr Leu
                    485                 490                 495
Leu Leu Leu Ala Ile Trp Arg Lys Ala Leu Pro Ala Leu Pro Ile Ser
            500                 505                 510
Ile Thr Phe Gly Leu Ile Phe Cys Phe Ala Thr Ser Ala Val Val Lys
            515                 520                 525
```

```
Pro Phe Met Glu Asp Leu Ser Ala Lys Gln Val Phe Ile
    530                 535                 540
```

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:22:

```
ctnccngart ggacngyctg g                                           21
```

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

```
rcangcdatn gtngtrttcc a                                           21
```

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:24:

```
tttttctcg agacngcnca rgaragaaay ga                                32
```

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:25:

```
tttttggat cctaraadat raartcncc                                    29
```

(2) INFORMATION FOR SEQ ID NO:26:

(i) SEQUENCE CHARACTERISTICS:
        (A) LENGTH: 1330 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 145..1275
        (D) OTHER INFORMATION: /product= "S5a"

(xi) SEQUENCE DESCRIPTION: SEQ ID NO:26:

```
aattcccaaa tgaccttta tttcatacag agatacaaag gcaactatgt gcagcaacaa    60
tctgatgggc agtccaaact cttgggagga agtaaattca tggtaaatgt catgatggcg  120
gtcgggaggg aggaaggtgg caag atg gtg ttg gaa agc act atg gtg tgt    171
                          Met Val Leu Glu Ser Thr Met Val Cys
                           1               5 gtg gac aac agt gag tat atg cgg aat gga gac ttc tta ccc acc agg   219
```

-continued

| | | |
|---|---|---|
| Val Asp Asn Ser Glu Tyr Met Arg Asn Gly Asp Phe Leu Pro Thr Arg<br>10                        15                     20                   25 | | |
| ctg cag gcc cag cag gat gct gtc aac ata gtt tgt cat tca aag acc<br>Leu Gln Ala Gln Gln Asp Ala Val Asn Ile Val Cys His Ser Lys Thr<br>                    30                         35                     40 | 267 | |
| cgc agc aac cct gag aac aac gtg ggc ctt atc aca ctg gct aat gac<br>Arg Ser Asn Pro Glu Asn Asn Val Gly Leu Ile Thr Leu Ala Asn Asp<br>                          45                     50                       55 | 315 | |
| tgt gaa gtg ctg acc aca ctc acc cca gac act ggc cgt atc ctg tcc<br>Cys Glu Val Leu Thr Thr Leu Thr Pro Asp Thr Gly Arg Ile Leu Ser<br>       60                        65                      70 | 363 | |
| aag cta cat act gtc caa ccc aag ggc aag atc acc ttc tgc acg ggc<br>Lys Leu His Thr Val Gln Pro Lys Gly Lys Ile Thr Phe Cys Thr Gly<br>75                        80                     85 | 411 | |
| atc cgc gtg gcc cat ctg gct ctg aag cac cga caa ggc aag aat cac<br>Ile Arg Val Ala His Leu Ala Leu Lys His Arg Gln Gly Lys Asn His<br>90                        95                     100                   105 | 459 | |
| aag atg cgc atc att gcc ttt gtg gga agc cca gtg gag gac aat gag<br>Lys Met Arg Ile Ile Ala Phe Val Gly Ser Pro Val Glu Asp Asn Glu<br>                          110                   115                   120 | 507 | |
| aag gat ctg gtg aaa ctg gct aaa cgc ctc aag aag gag aaa gta aat<br>Lys Asp Leu Val Lys Leu Ala Lys Arg Leu Lys Lys Glu Lys Val Asn<br>                125                     130                   135 | 555 | |
| gtt gac att atc aat ttt ggg gaa gag gag gtg aac aca gaa aag ctg<br>Val Asp Ile Ile Asn Phe Gly Glu Glu Glu Val Asn Thr Glu Lys Leu<br>          140                     145                   150 | 603 | |
| aca gcc ttt gta aac acg ttg aat ggc aaa gat gga acc ggt tct cat<br>Thr Ala Phe Val Asn Thr Leu Asn Gly Lys Asp Gly Thr Gly Ser His<br>                155                     160                  165 | 651 | |
| ctg gtg aca gtg cct cct ggg ccc agt ttg gct gat gct ctc atc agt<br>Leu Val Thr Val Pro Pro Gly Pro Ser Leu Ala Asp Ala Leu Ile Ser<br>170                       175                    180                   185 | 699 | |
| tct ccg att ttg gct ggt gaa ggt ggt gcc atg ctg ggt ctt ggt gcc<br>Ser Pro Ile Leu Ala Gly Glu Gly Gly Ala Met Leu Gly Leu Gly Ala<br>                        190                   195                   200 | 747 | |
| agt gac ttt gaa ttt gga gta gat ccc agt gct gat cct gag ctg gcc<br>Ser Asp Phe Glu Phe Gly Val Asp Pro Ser Ala Asp Pro Glu Leu Ala<br>                        205                     210                   215 | 795 | |
| ttg gcc ctt cgt gta tct atg gaa gag cag cgg cag cgg cag gag gag<br>Leu Ala Leu Arg Val Ser Met Glu Glu Gln Arg Gln Arg Gln Glu Glu<br>       220                       225                     230 | 843 | |
| gag gcc cgg cgg gca gct gca gct tct gct gct gag gcc ggg att gct<br>Glu Ala Arg Arg Ala Ala Ala Ala Ser Ala Ala Glu Ala Gly Ile Ala<br>           235                      240                   245 | 891 | |
| acg act ggg act gaa gac tca gac gat gcc ctg ctg aag atg acc atc<br>Thr Thr Gly Thr Glu Asp Ser Asp Asp Ala Leu Leu Lys Met Thr Ile<br>250                       255                    260                   265 | 939 | |
| agc cag caa gag ttt ggc cgc act ggg ctt cct gac cta agc agt atg<br>Ser Gln Gln Glu Phe Gly Arg Thr Gly Leu Pro Asp Leu Ser Ser Met<br>                        270                   275                   280 | 987 | |
| act gag gaa gag cag att gct tat gcc atg cag atg tcc ctg cag gga<br>Thr Glu Glu Glu Gln Ile Ala Tyr Ala Met Gln Met Ser Leu Gln Gly<br>                        285                     290                   295 | 1035 | |
| gca gag ttt ggc cag gcg gaa tca gca gac att gat gcc agc tca gct<br>Ala Glu Phe Gly Gln Ala Glu Ser Ala Asp Ile Asp Ala Ser Ser Ala<br>                300                     305                   310 | 1083 | |
| atg gac aca tcc gag cca gcc aag gag gag gat gat tac gac gtg atg<br>Met Asp Thr Ser Glu Pro Ala Lys Glu Glu Asp Asp Tyr Asp Val Met<br>315                       320                    325 | 1131 | |
| cag gac ccc gag ttc ctt cag agt gtc cta gag aac ctc cca ggt gtg | 1179 | |

-continued

```
Gln Asp Pro Glu Phe Leu Gln Ser Val Leu Glu Asn Leu Pro Gly Val
330                 335                 340                 345 gat ccc aac aat gaa gcc att cga aat gct atg ggc tcc ctg gcc tcc      1227
Asp Pro Asn Asn Glu Ala Ile Arg Asn Ala Met Gly Ser Leu Ala Ser
            350                 355                 360 cag gcc acc aag gac ggc aag aag gac aag aag gag gaa gac aag aag      1275
Gln Ala Thr Lys Asp Gly Lys Lys Asp Lys Lys Glu Glu Asp Lys Lys
        365                 370                 375 tgagactgga gggaaagggt agctgagtct gcttagggac tgcatggggg aattc         1330
```

(2) INFORMATION FOR SEQ ID NO:27:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO:27:

```
Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
    210                 215                 220

Glu Glu Gln Arg Gln Arg Gln Glu Glu Ala Arg Arg Ala Ala Ala
225                 230                 235                 240

Ala Ser Ala Ala Glu Ala Gly Ile Ala Thr Thr Gly Thr Glu Asp Ser
                245                 250                 255

Asp Asp Ala Leu Leu Lys Met Thr Ile Ser Gln Gln Glu Phe Gly Arg
            260                 265                 270

Thr Gly Leu Pro Asp Leu Ser Ser Met Thr Glu Glu Gln Ile Ala
        275                 280                 285

Tyr Ala Met Gln Met Ser Leu Gln Gly Ala Glu Phe Gly Gln Ala Glu
```

|   |   |   |   |   | 290 |   |   |   | 295 |   |   | 300 |   |   |
|---|---|---|---|---|---|---|---|---|---|---|---|---|---|---|---|

Ser Ala Asp Ile Asp Ala Ser Ser Ala Met Asp Thr Ser Glu Pro Ala
305                 310                 315                 320

Lys Glu Glu Asp Asp Tyr Asp Val Met Gln Asp Pro Glu Phe Leu Gln
            325                 330                 335

Ser Val Leu Glu Asn Leu Pro Gly Val Asp Pro Asn Asn Glu Ala Ile
            340                 345                 350

Arg Asn Ala Met Gly Ser Leu Ala Ser Gln Ala Thr Lys Asp Gly Lys
            355                 360                 365

Lys Asp Lys Lys Glu Glu Asp Lys Lys
370                 375

(2) INFORMATION FOR SEQ ID NO:28:

(i) SEQUENCE CHARACTERISTICS:
        (A) LENGTH: 970 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..970
        (D) OTHER INFORMATION: /note= "Y2H9"

(xi) SEQUENCE DESCRIPTION: SEQ ID NO:28:

```
gaattcccac agataccact gctgctcccg cccctttcgct cctcggccgc gcaatgggca      60
cccgcgacga cgagtacgac tacctcttta agttgtcct tattggagat tctggtgttg      120
gaaagagtaa tctcctgtct cgatttactc gaaatgagtt taatctggaa agcaagagca     180
ccattggagt agagtttgca acaagaagca tccaggttga tggaaaaaca ataaaggcac     240
agatatggga cacagcaggg caagagcgat atcgagctat aacatcagca tattatcgtg     300
gagctgtagg tgccttattg gtttatgaca ttgctaaaca tctcacatat gaaaatgtag     360
agcgatggct gaaagaactg agagatcatg ctgatagtaa cattgttatc atgcttgtgg     420
gcaataagag tgatctacgt catctcaggg cagttcctac agatgaagca agagcttttg     480
cagaaaagaa tggtttgtca ttcattgaaa cttcggccct agactctaca aatgtagaag     540
ctgcttttca gacaattta acagagattt accgcattgt ttctcagaag caatgtcag      600
acagacgcga aaatgacatg tctccaagca acaatgtggt tcctattcat gttccaccaa     660
ccactgaaaa caagccaaag gtgcagtgct gtcagaacat ctaaggcatt tctcttctcc     720
cctagaaggc tgtgtatagt ccatttccca ggtctsasat ttaaatataw ttgtaattct     780
tgtgtcactt ttgtgttta ttacttcata cttatgaatt tttccatgtc ctaagtcttt     840
tgattttgmt ttataaaatc atccacttgt nccgaatgnc tgcagctttt tttcatgcta     900
tggcttcact agccttagtt tnataaactg aatgtttgga ttcctccccc caaaaaaaaa     960
aaaactcgag                                                            970
```

(2) INFORMATION FOR SEQ ID NO:29:

(i) SEQUENCE CHARACTERISTICS:
        (A) LENGTH: 264 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..264
        (D) OTHER INFORMATION: /note= "Y2H23b"

(xi) SEQUENCE DESCRIPTION: SEQ ID NO:29:

| | |
|---|---|
| gaattcgcgg ccgngtcgac cccccacccc cgatgccacc accccccantg ggntctcccn | 60 |
| ncccagtcat cagttcttcc atggngtncc ctggtctgcc ccctccagct cccccaggcn | 120 |
| ttctccgggt ctgncagcag ccnccagatt aactcaacag tgtcactccc tgggggtggg | 180 |
| tctggncccc ctgangatgt gaagccacca gtctnagngg tccggggtct gtactgtcca | 240 |
| cccctccag gtggacctgg cgct | 264 |

(2) INFORMATION FOR SEQ ID NO:30:

(i) SEQUENCE CHARACTERISTICS:
        (A) LENGTH: 404 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..404
        (D) OTHER INFORMATION: /note= "Y2H35"

(xi) SEQUENCE DESCRIPTION: SEQ ID NO:30:

| | |
|---|---|
| gaattcgcgg tcgcgtcgac ggttagtccc actggncgca tcgagggntt caccaacgtc | 60 |
| atggagctgt atggcangat cgccgaggtc ttccncctgc caactgccga ggtgatgttc | 120 |
| tgcaccctga ncacccacaa agtggacatn gacaagctcc tgggggggcca gatcgggctg | 180 |
| gaggacttca tcttcgccca cgtgaagggg yagcgcaagg aggtggaggt gttcawgtcg | 240 |
| gaggatgyac tcggkctcac catcacggac aacggggctg gctacgcttc catcaagcgc | 300 |
| atcaaggagg gcagcgtgat cgaccacatc cacctcatca gcgtgggcga catgatcgag | 360 |
| gccattaacg ggcagagctt cctgggctgc cggcattacg aggt | 404 |

(2) INFORMATION FOR SEQ ID NO:31:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..340
        (D) OTHER INFORMATION: /note= "Y2H27"

(xi) SEQUENCE DESCRIPTION: SEQ ID NO:31:

| | |
|---|---|
| gaattcgcgg ccgcgtcgac cgcggtcgcg tcgacctgtt gcccaggccc tagaggtcat | 60 |
| tcctcgtacc ctgatccaga actgtggggc cagcaccatc cgtctactta cctcccttcg | 120 |
| ggccaagcac acccaggaga actgtgagac ctggggtgta aatggtgaga cgggtactt | 180 |
| ggtggacatg aaggaactgg gcatatggga gccattggct gtgaagctgc agacttataa | 240 |
| gacagcagtg gagacggcag ttctgctact gcgaattgat gacatcgttt caggccacaa | 300 |
| aaagaaaggc gatgaccaga gccggcaagg cggngctcct | 340 |

(2) INFORMATION FOR SEQ ID NO:32:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ix) FEATURE:
              (A) NAME/KEY: misc_feature
              (B) LOCATION: 1..350
              (D) OTHER INFORMATION: /note= "Y2H171"

(xi) SEQUENCE DESCRIPTION: SEQ ID NO:32:

```
gaattcgcgg ccgcgtcgac aaaaaaagta aaggaactc ggcaaatctt accccgcctg      60
tttaccaaaa acatcacctc tagcatcacc agtattagag gcaccgcctg cccagtgaca    120
catgtttaac ggccgcggta ccctaaccgt gcaaaggtag cataatcact tgttccttaa    180
gtagggacct gtatgaatgg ctccacgagg gttcagctgt ctcttacttt taaccartga    240
aattgacctg cccgtgaaga ggcgggcatg acacagcaag acgagaagac cctatggagc    300
tttaatttat taatgcaaac agtacctaac aaacccacag ggtcctaaac              350
```

(2) INFORMATION FOR SEQ ID NO:33:

(i) SEQUENCE CHARACTERISTICS:
              (A) LENGTH: 3841 base pairs
              (B) TYPE: nucleic acid
              (C) STRANDEDNESS: single
              (D) TOPOLOGY: linear (ix) FEATURE:
              (A) NAME/KEY: CDS
              (B) LOCATION: 2..3121
              (D) OTHER INFORMATION: /note= "GT24"

(xi) SEQUENCE DESCRIPTION: SEQ ID NO:33:

```
ttcacagctc ccggcccgag gcacacaagc ccgagstacg ggccagagct tcagccaggg     60
cacgaccagc cgcgccggcc acctggcggg gcccgagccc gcgccgccgc cgccgccgcc   120
rccgcgggag ccgttcgcgc ccagcctggg cagcgccttc cacctgcccg acgcgccgcc   180
cgccgccgcc gccgccgcgc tctactactc cakctccacg ctgcccgcgc cgccgcgcgg   240
gggctccccg ctggccgcgc cccagggcgg ttcgcccacc aagctgcagc gcggcggctc   300
ggcccccgag ggcgccacct acgccgcgcc gcgcggctcc tcgcccaagc agtcgcccag   360
ccgcctggcc aagtcctaca gcaccagctc gcccatcaac atcgtcgtgt cctcggccgg   420
cctgtccccg atccgcgtga cctcgccccc caccgtgcag tccaccatct cctcctcgcc   480
catccaccag ctgagctcca ccatcggcac gtacgccacc ctgtcgccca ccaagcgcct   540
ggtccacgcg tccgagcagt acagcaagca ctcgcaggag ctgtatgcca cggccaccct   600
ccagaggccg ggcagcctgg cagctggttc ccgagcctca tacagcagcc agcatgggca   660
cctgggccca gagttgcggg ccctgcagtc cccagaacac cacatagatc ccatctatga   720
agaccgcgtc tatcagaagc cccctatgag gagtctcagc cagagccagg gggaccctct   780
gccgccagca cacaccggca cctaccgcac gagcacagcc ccatcttccc ctggtgtcga   840
ctccgtcccc ttgcagcgca caggcagcca gcacggccca cagaatgccg ccgcggccac   900
cttccagagg gccagctatg ccgccggccc agcctccaat tacgcggacc cctaccgaca   960
gctgcagtat tgtccctctg ttgagtctcc atacagcaaa tccggccctg ctctcccgcc  1020
tgaaggcacc ttggccaggt ccccgtccat tgatagcatt cagaaagatc ccagagaatt  1080
tggatggaga gacccggaac tgccggaagt gattcagatg ttgcagcacc agtttcctc   1140
ggtccagtct aacgcggcag cctacttgca acacctctgt tttggagaca acaaaattaa  1200
agccgagata aggagacaag gaggcatcca gctcctggtg gacctgttgg atcatcggat  1260
gaccgaagtc caccgtagtg cctgtggagc tctgagaaac ctggtgtatg ggaaggccaa  1320
cgatgataac aaaattgccc tgaaaaactg tggtggcatc ccagcactgg tgaggttact  1380
```

-continued

```
ccgcaagacg actgacctgg agatccggga gctggtcaca ggagtccttt ggaacctctc   1440
ctcatgcgat gcactcaaaa tgccaatcat ccaggatgcc ctagcagtac tgaccaacgc   1500
ggtgattatc ccccactcag gctgggaaaa ttcgcctctt caggatgatc ggaaaatca    1560 gctgcattca tcacaggtgc tgcgtaacgc caccgggtgc taaggaatg ttagttcggc    1620 cggagaggag gcccgcagaa ggatgagaga gtgtgatggg cttacggatg ccttgctgta   1680
cgtgatccag tctgcgctgg ggagcagtga gatcgatagc aagaccgttg aaaactgtgt   1740
gtgcatttta aggaacctct cgtaccggct ggcggcagaa acgtctcagg acagcacat    1800 gggcacggac gagctggacg ggctactctg tggcgaggcc aatggcaagg atgctgagag   1860
ctctgggtgc tggggcaaga agaagaagaa aagaaatcc caagatcagt gggatggagt    1920
aggacctctt ccagactgtg ctgaaccacc aaaagggatc cagatgctgt ggcacccatc   1980
aatagtcaaa ccctacctca cactgctctc tgagtgctca aatccagaca cgctggaagg   2040
ggcggcaggc gccctgcaga acttggctgc agggagctgg aagtggtcag tatatatccg   2100
agccgctgtc cgaaaagaga aaggcctgcc catcctcgtg gagctgctcc gaatagacaa   2160
tgaccgtgtg gtgtgcgcgg tggccactgc gctgcggaac atggccttgg acgtcagaaa   2220
taaggagctc atcggcaaat acgccatgcg agacctagtc cacaggcttc caggagggaa   2280
caacagcaac aacactgcaa gcaaggccat gtcggatgac acagtgacag ctgtctgctg   2340
cacactgcac gaagtgatta ccaagaacat ggagaacgcc aaggccttac gggatgccgg   2400
tggcatcgag aagttggtcg gcatctccaa aagcaaagga gataaacact ctccaaaagt   2460
ggtcaaggct gcatctcagg tcctcaacag catgtggcag taccgagatc tgaggagtct   2520
ctacaaaaag gatggatggt cacaatacca ctttgtagcc tcgtcttcaa ccatcgagag   2580
ggaccggcaa aggccctact cctcctcccg cacgccctcc atctcccctg tgcgcgtgtc   2640
tcccaacaac cgctcagcaa gtgccccagc ttcacctcgg gaaatgatca gcctcaaaga   2700
aaggaaaaca gactacgagt gcaccggcag caacgccacc taccacggag gtaaaggcga   2760
acacacttcc aggaaagatg ccatgacagc tcaaaacact ggaatttcaa cttttgtatag   2820 gaattcttat ggtgcgcccg ctgaagacat caaacacaac caggtttcag cacagccagt   2880
cccacaggag cccagcagaa aagattacga gacctaccag ccatttcaga attccacaag   2940
aaattacgat gagtccttct tcgaggacca ggtccaccat cgccctcccg ccagcgagta   3000
caccatgcac ctgggtctca gtccaccgg caactacgtt gacttctact cagctgcccg   3060
tccctacagt gaactgaact atgaaacgag ccactacccg gcctccccg actcctgggt    3120 gtgaggagca gggcacaggc gctccggaa acagtgcatg tgcatgcata ccacaagaca   3180
tttctttctg ttttggtttt tttctcctgc aaatttagtt tgttaaagcc tgttccatag   3240
gaaggctgtg ataaccagta agggaaatat taagagctat tttagaaagc taatgaatc    3300 gcaagttaac ttggaaatca gtagaaagct aaagtgatcc taaatatgac agtgggcagc   3360
acctttccta gcgtgttntg ttaggagtaa cgagaagtgc tttatactga acgtgggttg   3420
nttggtaggg tggagncgag gcattcgggc cggtggggcg taagggttat cgttaagcac   3480
aagacacaga atagtttaca cactgtgtgg gggacggctt ctcacgcttt gtttactctc   3540
ttcatccgtt gtgactctag gcttcaggtt gcattggggt tcctctgtac agcaagatgt   3600
ttcttgcctt ttgttaatgc attgttgtaa agtatttgat gtacattaca gattaaagaa   3660
gnaaagcgcg ttgtgtatat tacaccaatn ccgccgtgtt tcctcatcta tggttctaaa   3720
tattgcttca atttcnaact tttgaaagat gtatggattt ccagtttttc tttactttct   3780
```

```
cccagtatgt tttaaccnmm naaaaaaaaa aaaaaaaaaa aaaaaaaaaa aaaaactcga      3840
g                                                                     3841

(2) INFORMATION FOR SEQ ID NO:34:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..350
        (D) OTHER INFORMATION: /note= "PS1Y2H-41"

(xi) SEQUENCE DESCRIPTION: SEQ ID NO:34:

gaattcgcgg ncgcgtcgac agataatgaa aaaaccagag gttcccttct ttggtcccct       60
nnnngatggt gctattgtga atggaaaggt tctacccatt atggttagag caacagctat      120
aaatgcaagc cgtgctctga aatctctgat tccattgtat caaaacttct atgaggagag      180
agcacgatac ctgcaaacaa ttgtccagca ccacttagaa ccaacaacat ttgaagattt      240
tgnagcacag gttttttctc cagctcccta ccaccattta ccatctgatg ccgttggctc      300
ctacccagag attctaccca gtgaaaactc ccacagcaac gcaggtagga                 350

(2) INFORMATION FOR SEQ ID NO:35:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..350
        (D) OTHER INFORMATION: /note= "PS1LY2H-3-1"

(xi) SEQUENCE DESCRIPTION: SEQ ID NO:35:

gaattcgcgg ccgcgtctac gtcgacgcgg cngctggtat tggtactgtt cctgttggcc       60
gaatggagac tggtgttctc aaacccggta tggtggtcac ctttgctcca gtcaacgtta      120
caacggaagt aaaatctgtc gaaatgcacc atgaagcttt gagtgaanct cttcctgggg      180
acaatgtggg cttcaatgtc aagaatgtgt ctgtcaagga tgttcgtcgt ggcaacgttg      240
ctggtgacag caaaaatgac ccaccaatgg aagcagctgg cttcactgct caggtgatta      300
tcctgaacca tccaggccaa ataagcgccg gctatgcccc tgtattggat                 350

(2) INFORMATION FOR SEQ ID NO:36:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..400
        (D) OTHER INFORMATION: /note= "PS1LY2HEx10-6"

(xi) SEQUENCE DESCRIPTION: SEQ ID NO:36:

gaattcgcgg ccgcgtcgac cgctactgct gccggtgttt gcgtgtggca gggagccagg       60
cctggcgagc ggggtgtgtc gcgatgccgg agctggcagt gcagaaggtg gtggtccacc      120
```

```
ccctggtgct gctcagtgtg gtggatcatt tcaaccgaat cggcaacgtt ggaaaccaga      180
agcgtgttgt tggtgtgctt ttggggtcat ggcaaaagaa agtacttgat gtatcgaaca      240
gttttgcant tccttttgat gaanatgaca aacacgattc tgtatggttt ntagaccatg      300
attatttgga aaacatgtat ggaatgtnta agaaagtcca tgccagggaa agaatanttg      360
gctggtacca cncangccct aaactacaca agaatgacat                           400

(2) INFORMATION FOR SEQ ID NO:37:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..360
        (D) OTHER INFORMATION: /note= "PS1LY2HEx10-17-1"

(xi) SEQUENCE DESCRIPTION: SEQ ID NO:37:

ctcgagtttt ttttttttt ttttgtgtt gagtaanagc cacatttatt tcttaattgg       60
acanaccctc aantgcacgc acagtacagg agcctagggc taacactcgg gtgtaaaaca     120
tcgggacagg cgtcntgacg tcgggacggc agctatgaca tggggtctgg ggtgtgccca    180
cancaatcac atatntacaa gccagggacg cggcctctga gccacagggg aaaccagggg     240
acggactaac tacaggaacc acangcccan ggtaaaaacg caggtcncca canctgctgt    300
ccntctgggg gaccncncgg cccggcaccg ggggtaaggg attgtgcctt ccgtggtccc     360

(2) INFORMATION FOR SEQ ID NO:38:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..150
        (D) OTHER INFORMATION: /note= "PS1Ex10/17-1"

(xi) SEQUENCE DESCRIPTION: SEQ ID NO:38:

gaattcgcgg ccgcgtcgac agagagagag agagagagag agagagaggt cgacncggcg      60
gcgaattcgg cttcnctctc tntnntnttt ctcntctntt ttcttccctt cttnttctcn     120
cncccctccc ctctcnttct nctctctctc                                      150

(2) INFORMATION FOR SEQ ID NO:39:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..340
        (D) OTHER INFORMATION: /note= "PS1Ex10/24-1"

(xi) SEQUENCE DESCRIPTION: SEQ ID NO:39:

ctcgagtttt ttttttttt tttttntgg cgccatccag gtttgtgttt attcnataca       60
ggcccanaac ccaccctcc ttcaaaaaan tggccgagct gggggaacaa aataaataaa     120
```

```
ggccgccgag gtgtgatggg gactggacgg gccggtctgg ggcgaggcan nggtgcccag      180
naggcattga ccccaacctc agctgtccac ggctggcccc actcccagca ggctccgggg      240
gcnttgtgan cgcccacaag gagcagggct cggactcctg ccacctccaa ntcctttctt      300
ttccttcctg ccctccctct ccttcctaag gcaggtccaa                            340

(2) INFORMATION FOR SEQ ID NO:40:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..390
        (D) OTHER INFORMATION: /note= "PS1Ex10/1-2"

(xi) SEQUENCE DESCRIPTION: SEQ ID NO:40:

gaattcgcgg ccgcgtcgac gtcnacgcgg ccgcgctcga ctcttanctt gtcggggacg       60
gtaaccggga cccggtgtct gctcctgtcg ccttcgcctc ctaatcccta nccactatgc      120
gtgagtgcat ctccatccac gttggccagn ctggtgtcca cattggcaat gcctgctggg      180
agctctactg cctggaacac ngcatccagc ccnatggcca natgccaant gacnanacca      240 ttggggagg agatgactcc ttcaacncct tcttcagtga acnggcgct ggcaatcacg        300 tgccccgggc tgtgtttgta gacttggaac cacagtcntt gatgangttc gcnctggcac     360
ctaccgccca gctcttccac cctgagcagc                                       390

(2) INFORMATION FOR SEQ ID NO:41:

(i) SEQUENCE CHARACTERISTICS:
        (A) LENGTH: 2205 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..2205
        (D) OTHER INFORMATION: /note= "mutTM1-TM2"

(xi) SEQUENCE DESCRIPTION: SEQ ID NO:41:

gaattcccgg gtcgacccac gcgtccgccc acgcgtccgc ggacgcgtgg gctgcactct       60
ccccggcgcc gctctccggc cctcgccctg tccgccgcca ccgccgccgc cgccagantc      120
gccatgcaga tccgcgcgc cgctcttctc ccgctgctgc tgctgctgct ggcggcgccc       180
gcctcggcgc anctgtcccg ggccggccgc tcggcgcctt tggctgccgg ttgcccanac      240
cgctgcnagc cggcgcgctg cccgccgcag ccggaacact gtttatggcn gccnggcccn      300
ggacgcgtgc ggctgctgcg aggtgtgcgg cgcgcccgag ggcgccgcgt gcggcctgca      360
ggagggcccg tgcggcgagg ggctgcagtg cgtggtgccc ttcggggtgc cagcctcggc      420
cacggtgcgg cggcgcgcgc aggccggcct ctgtgtgtgc gccagcagcg agccggtgtg      480
cggcagcgac gccaacacct acgccaacct gtgccagctg cgcgccgcca gccgccgctc      540
cgagaggctg caccggccgc cggtcatcgt cctgcagcgc ggagcctgcg gccaagggca      600
ggaagatccc aacagtttgc gccataaata aactttatc gcggacgtgg tggagaagat       660
cgcccctgcc gtggttcata tcgaattgtt tcgcaagctt ccgttttcta aacgagaggt      720
gccggtggct agtgggtctg ggtttattgt gtcggaagat ggactgatcg tgacaaatgc      780
```

```
ccacgtggtg accaacaagc accgggtcaa agttgagctg aagaacggtg ccacttacga    840
agccaaaatc aaggatgtgg atgagaaagc agacatcgca ctcatcaaaa ttgaccacca    900
gggcaagctg cctgtcctgc tgcttggccg ctcctcagag ctgcggccgg gagagttcgt    960
ggtcgccatc ggaagcccgt tttcccttca aaacacagtc accaccggga tcgtgagcac   1020
cacccagcga ggcggcaaag agctggggct ccgcaactca gacatggact acatccagac   1080
cgacgccatc atcaactatg gaaactcggg aggcccgtta gtaaacctgg acggtgaagt   1140
gattggaatt aacactttga aagtgacagc tggaatctcc tttgcaatcc catctgataa   1200
gattaaaaag ttcctcacgg agtcccatga ccgacaggcc aaaggaaaag ccatcaccaa   1260
gaaaaagtat attggtatcc gaatgatgtc actcacgtcc agcaaagcca aagagctgaa   1320
ggaccggcac cgggacttcc cagacgtgat ctcaggagcg tatataattg aagtaattcc   1380
tgatacccca gcagaagctg gtggtctcaa ggaaaacgac gtcataatca gcatcaatgg   1440
acagtccgtg gtctccgcca atgatgtcag cgacgtcatt aaaagggaaa gcaccctgaa   1500
catggtggtc cgcaggggta atgaagatat catgatcaca gtgattcccg aagaaattga   1560
cccataggca gaggcatgag ctggacttca tgtttccctc aaagactctc ccgtggatga   1620
cggatgagga ctctgggctg ctggaatagg acactcaaga cttttgactg ccattttgtt   1680
tgttcagtgg agactccctg gccaacagaa tccttcttga tagtttgcag gcaaaacaaa   1740
tgtaatgttg cagatccgca ggcagaagct ctgcccttct gtatcctatg tatgcagtgt   1800
gcttttctt gccagcttgg gccattttg cttagacagt cagcatttgt ntcctccttt   1860
aactgagtca tcatnttagt ccaactaatg cagtcgatac aatgcgtaga tagaagaagc   1920
cccacgggag ccaggatggg actggtygtg tttgtgcttt tttccaagtc agcacccaaa   1980
ggtcaatgca cagagacccc gggtgggtga gcgctggctt ytcaaacggc cgaagttgcc   2040
tnttttagga atntntttgg aattgggagc acgatgamtt tgagtttgag ntattaaagt   2100
anttnttaca cattgaaaaa aaaaaaaaaa aaaaaaaaaa aaaaaaaaaa aaaaaaaaaa   2160
aaaaaaaaaa aaaaaagggg cggccgctct agaggatccc tcgag                   2205
```